(12) United States Patent
Yoo et al.

(10) Patent No.: US 12,186,444 B2
(45) Date of Patent: *Jan. 7, 2025

(54) APPARATUS AND METHOD FOR TREATING SHOES

(71) Applicant: LG ELECTRONICS INC., Seoul (KR)

(72) Inventors: Hyunsun Yoo, Seoul (KR); Jeong Guen Choi, Seoul (KR); Joohyeon Oh, Seoul (KR); Jae Myung Lim, Seoul (KR); Byoungjoon Han, Seoul (KR); Sang Yoon Lee, Seoul (KR); Hyunju Kim, Seoul (KR); Jeaseok Seong, Seoul (KR)

(73) Assignee: LG ELECTRONICS INC., Seoul (KR)

( * ) Notice: Subject to any disclaimer, the term of this patent is extended or adjusted under 35 U.S.C. 154(b) by 670 days.

This patent is subject to a terminal disclaimer.

(21) Appl. No.: 17/356,286

(22) Filed: Jun. 23, 2021

(65) Prior Publication Data
US 2021/0402029 A1    Dec. 30, 2021

(30) Foreign Application Priority Data

Jun. 24, 2020  (KR) ......................... 10-2020-0077410
Jun. 24, 2020  (KR) ......................... 10-2020-0077411

(Continued)

(51) Int. Cl.
*A61L 2/24*      (2006.01)
*A47B 61/04*   (2006.01)

(52) U.S. Cl.
CPC ................. *A61L 2/24* (2013.01); *A47B 61/04* (2013.01); *A61L 2202/14* (2013.01)

(58) Field of Classification Search
CPC ........ A61L 2/24; A61L 2202/14; A47B 61/04
See application file for complete search history.

(56) References Cited

U.S. PATENT DOCUMENTS

2020/0063955 A1* 2/2020 Weir .................... F21V 23/0471

FOREIGN PATENT DOCUMENTS

| CN | 104687789 A  |   | 6/2015 |
| CN | 106308112 A  | * | 1/2017 |

(Continued)

OTHER PUBLICATIONS

Korean Notice of Allowance for Korean Application No. 10-2021-0030923, dated Sep. 9, 2024.

(Continued)

*Primary Examiner* — Matthew W Ing
(74) *Attorney, Agent, or Firm* — Birch, Stewart, Kolasch & Birch, LLP

(57) ABSTRACT

A shoe treating apparatus including a shelf part including at least one shelf, a motor part configured to control tilting of the at least one shelf, a sensor part including at least one sensor, and a processor electrically connected to the motor part and the sensor part is provided. The processor may identify an approach of a user by using the at least one sensor, and, based on the identified user approach, generate a control signal for adjusting a tilt angle of the at least one shelf to adjust the tilting of the at least one shelf. A method of operating a shoe treating apparatus is also provided.

18 Claims, 76 Drawing Sheets

(30) Foreign Application Priority Data

| | | |
|---|---|---|
| Jun. 24, 2020 | (KR) | 10-2020-0077412 |
| Jun. 24, 2020 | (KR) | 10-2020-0077413 |
| Jun. 24, 2020 | (KR) | 10-2020-0077414 |
| Jun. 24, 2020 | (KR) | 10-2020-0077415 |
| Jun. 24, 2020 | (KR) | 10-2020-0077417 |
| Dec. 8, 2020 | (KR) | 10-2020-0170566 |
| Mar. 9, 2021 | (KR) | 10-2021-0030972 |

(56) References Cited

FOREIGN PATENT DOCUMENTS

| | | | | |
|---|---|---|---|---|
| CN | 208132955 | U | * | 11/2018 |
| CN | 109106086 | A | | 1/2019 |
| CN | 209171826 | U | | 7/2019 |
| CN | 111084494 | A | * | 5/2020 ............ A47B 27/02 |
| JP | 2-6543 | U | | 1/1990 |
| JP | 5-192291 | A | | 8/1993 |
| JP | 9-253595 | A | | 9/1997 |
| JP | 11-103941 | A | | 4/1999 |
| JP | 2010-119609 | A | | 6/2010 |
| KR | 20-0165450 | Y1 | | 2/2000 |
| KR | 20-0187262 | Y1 | | 7/2000 |
| KR | 20-0253977 | Y1 | | 11/2001 |
| KR | 2002-0000007 | U | | 3/2002 |
| KR | 20-0291502 | Y1 | | 10/2002 |
| KR | 20-0307594 | Y1 | | 3/2003 |
| KR | 20-0357295 | Y1 | | 7/2004 |
| KR | 10-2004-0070545 | A | | 8/2004 |
| KR | 10-2006-0060230 | A | | 6/2006 |
| KR | 20-0426182 | Y1 | | 9/2006 |
| KR | 20-0431598 | Y1 | | 11/2006 |
| KR | 10-2008-0006908 | A | | 1/2008 |
| KR | 10-2012-0059781 | A | | 6/2012 |
| KR | 10-2012-0092800 | A | | 8/2012 |
| KR | 10-2014-0106818 | A | | 9/2014 |
| KR | 10-2015-0086056 | A | | 7/2015 |
| KR | 10-2015-0117430 | A | | 10/2015 |
| KR | 10-2015-0123493 | A | | 11/2015 |
| KR | 10-2017-0024363 | A | | 3/2017 |
| KR | 10-2017-0039412 | A | | 4/2017 |
| KR | 10-1737829 | B1 | | 5/2017 |
| KR | 10-2018-0054004 | A | | 5/2018 |
| KR | 10-2019-0003274 | A | | 1/2019 |
| KR | 10-1938421 | B1 | | 1/2019 |
| KR | 10-2008104 | B1 | | 8/2019 |
| KR | 10-2020-0002725 | A | | 1/2020 |
| KR | 10-2020-0037035 | A | | 4/2020 |

OTHER PUBLICATIONS

Korean Office Action for Korean Application No. 10-2021-0030921, dated Aug. 8, 2024.
Korean Office Action for Korean Application No. 10-2021-0030922, dated Sep. 9, 2024.
Korean Office Action for Korean Application No. 10-2021-0030924, dated Sep. 9, 2024.
Korean Office Action for Korean Application No. 10-2021-0030926, dated Sep. 11, 2024.
Korean Office Action for Korean Application No. 10-2021-0030971, dated Oct. 25, 2024.
Korean Office Action for Korean Application No. 10-2021-0030973, dated Oct. 25, 2024.
Korean Notice of Allowance for Korean Application No. 10-2021-0031058, dated Nov. 6, 2024.
Korean Office Action for Korean Application No. 10-2021-0031056, dated Nov. 6, 2024.

* cited by examiner (a)

(b)

(c)

(a)

(b)

APPARATUS AND METHOD FOR TREATING SHOES

CROSS-REFERENCE TO RELATED APPLICATIONS

This application claims priority to and the benefit of Korean Patent Application No. 10-2020-0077410, filed on Jun. 24, 2020, Korean Patent Application No. 10-2020-0077411, filed on Jun. 24, 2020, Korean Patent Application No. 10-2020-77412, filed on Jun. 24, 2020, Korean Patent Application No. 10-2020-0077413, filed on Jun. 24, 2020, Korean Patent Application No. 10-2020-77414, filed on Jun. 24, 2020, Korean Patent Application No. 10-2020-0077415, filed on Jun. 24, 2020, Korean Patent Application No. 10-2020-0077417, filed on Jun. 24, 2020, Korean Patent Application No. 10-2020-0170566, filed on Dec. 8, 2020, and Korean Patent Application No. 10-2021-0030972, filed on Mar. 9, 2021, the disclosures of which are incorporated herein by reference in their entireties.

BACKGROUND OF THE INVENTION

Technical Field

The present invention relates to an apparatus and method for treating shoes.

Discussion of the Related Art

In general, a shoe cabinet stores a variety of shoes and may be placed at locations where shoes are put on or taken off, such as at homes and restaurants. The shoe cabinet may be divided into a plurality of storage areas by a multi-stage shelf to store a plurality of shoes.

However, the shoe cabinet only stores shoes and does not remove various contaminants such as foreign substances from the shoes. For this reason, the shoe cabinet may generate odors due to the shoes, and bacterial growth may occur in the shoe cabinet due to the shoes.

Also, since shelves included in the conventional shoe cabinet are fixed, the shelves do not tilt on the basis of the height of a user.

In order to address such problems, a first related art (Korean Utility Model Publication No. 2002-0000007) discloses a storage shelf being provided on a storage portion provided at a high, out-of-reach position. The storage shelf is operated by first pulling out and then lowering the shelf to draw the shelf out from the storage position. The process is reversed to move the storage shelf back into the storage position.

However, the structure disclosed in the first related art is only a structure in which a shelf is directly lowered by a user applying a physical force thereto and is not a structure in which the shelf automatically tilts on the basis of the height of the user.

Therefore, there is a need for a plurality of shelves included in a shoe cabinet to individually tilt automatically. Also, there are needs to control a tilting operation of each of the plurality of shelves on the basis of an approach of a user and to adjust a tilt angle of each of the plurality of shelves on the basis of the height of the user.

SUMMARY OF THE INVENTION

Technical Problem

In a conventional shoe treatment system, an intensive treatment zone and a normal treatment zone are not completely physically separated. Also, the conventional shoe treatment system does not treat shoes according to the material, type, function, or condition of shoes.

Also, conventionally, each of a plurality of shelves included in a shoe cabinet does not tilt automatically.

Therefore, the present invention is directed to providing an apparatus and method for treating shoes that allow each of a plurality of shelves included in a shoe cabinet to automatically tilt.

The present invention is also directed to providing an apparatus and method for treating shoes that control a tilting operation of each of the plurality of shelves on the basis of identifying the height of a user approaching the apparatus.

The present invention is also directed to providing an apparatus and method for treating shoes that identify a user and identify the position of a shoe owned by the identified user.

The present invention is also directed to providing an apparatus and method for treating shoes that display state information indicating a treatment state of at least one shoe for each user.

Objectives of the present invention are not limited to the above-mentioned objectives, and other unmentioned objectives of the present invention and advantages thereof should be understood from the following description and should be more clearly understood from embodiments of the present invention. Also, it should be easily understood that the objectives and advantages of the present invention may be realized by means shown in the claims below and combinations thereof.

Technical Solution

To achieve the above objectives, a shoe treating apparatus according to the present invention may use at least one sensor to identify an approach of a user.

Also, the shoe treating apparatus according to the present invention may identify the height of a user through at least one sensor and, on the basis of the height of the user, adjust a tilt angle of at least one shelf.

Also, the shoe treating apparatus according to the present invention may detect opening of a door through at least one sensor and may control an operation of at least one shelf that is currently tilting.

Also, the shoe treating apparatus according to the present invention may identify a position at which at least one shoe, which corresponds to a user, is placed in a shelf part and may display condition information on the at least one shoe corresponding to the position through a display part.

Also, the shoe treating apparatus according to the present invention may acquire a tilt angle of at least one shelf, which corresponds to the height of a user, from a memory and may, on the basis of the acquired tilt angle of the at least one shelf, adjust tilting of the shelf.

Also, the shoe treating apparatus according to the present invention may, in order to improve diffusion of an air flow in an upper cabinet, control a motor part so that each of a plurality of shelves included in the shelf part moves in a tilting direction different from that of another shelf disposed above or below the shelf.

Also, the shoe treating apparatus according to the present invention may acquire an image of at least one shoe stored in the shelf part through a camera and may compare the acquired image with a pre-stored image to identify a position at which at least one shoe corresponding to a user is placed.

Also, according to the present invention, whether a door of the shoe treating apparatus is opened may be identified, and whether a shoe is stored may be identified through at least one of a weight sensor, a camera, and a distance measurement sensor, which are disposed in the upper cabinet, to determine whether the shoe is a shoe corresponding to a user.

Also, according to the present invention, a first shelf among the plurality of shelves included in the shelf part may be controlled to move in a vertical direction, and a second shelf may be controlled to tilt.

Also, according to the present invention, at least one light emitting element disposed in the shoe treating apparatus may be caused to emit light on the basis of an approach of a user.

To this end, the shoe treating apparatus according to the present invention may include a shelf part including at least one shelf, a motor part configured to control tilting of the at least one shelf, a sensor part including at least one sensor, and a processor electrically connected to the motor part and the sensor part.

Also, the processor may use the at least one sensor to identify an approach of a user and may, on the basis of the identified user approach, generate a control signal for adjusting the tilting of the at least one shelf to adjust the tilting of the at least one shelf.

Also, a shoe treating method according to the present invention may include using at least one sensor to identify an approach of a user and, on the basis of the identified user approach, generating a control signal for adjusting tilting of at least one shelf included in a shelf part.

The shoe treating method may further include transmitting the generated control signal to a motor part to adjust the tilting of the at least one shelf.

Advantageous Effects

Since a shoe cabinet according to the present invention is divided into an upper cabinet and a lower cabinet, a shoe can either be intensively treated or normally treated.

Also, according to the present invention, since an approach of a user is identified using at least one sensor and, on the basis of the identified user approach, tilting of at least one shelf is adjusted, a failure of a shoe treating apparatus due to the sudden opening of a door can be prevented.

Also, according to the present invention, since the height of a user is identified and, on the basis of the identified user height, tilting of the at least one shelf is adjusted, it is possible to provide convenience in use that allows a user to easily take out a shoe placed on a shelf or easily put the shoe back on the shelf.

Also, according to the present invention, since whether a door of the shoe treating apparatus is opened is identified through at least one sensor and, on the basis of opening of the door, an operation of at least one shelf that is currently tilting is stopped, it is possible to provide convenience for a user in storing a shoe.

Also, according to the present invention, since a user is identified through at least one sensor and a position at which at least one shoe corresponding to the identified user is placed in a shelf part is identified, it is possible to provide convenience that allows a user to more easily and quickly check his or her shoe.

Also, according to the present invention, since a user is identified through at least one sensor and condition information on the at least one shoe corresponding to the identified position is displayed through a display part, the user can more easily check the current condition of his or her shoe.

Also, according to the present invention, since a tilt angle of at least one shelf, which corresponds to the height of a user, is acquired from a memory and, on the basis of the acquired tilt angle of the at least one shelf, tilting of the shelf is adjusted, it is possible to provide customized services for various users of different heights.

Also, according to the present invention, since at least one of a camera, an infrared sensor, a door open/close sensor, a knock on sensor, a weight sensor, a distance measurement sensor, and a fingerprint sensor is disposed in the shoe treating apparatus, various services, such as identifying an approach of a user, identifying the height of a user, identifying a user, and identifying whether a door is opened or closed, can be provided for each user in a customized manner.

Also, according to the present invention, since each of a plurality of shelves included in the shelf part is controlled to tilt in a direction different from a direction in which another shelf disposed above or below the shelf tilts, an air flow in the cabinet can be more effectively diffused.

Also, according to the present invention, since an image of at least one shoe is acquired through a camera and the acquired image is compared with a pre-stored image to identify a position at which at least one shoe corresponding to a user is placed, in a case in which a user approaches, the position of the corresponding shoe can be displayed through a light emitting element, and condition information on the shoe can be efficiently provided for each user.

Also, according to the present invention, since, through an identifier allocated for each of the plurality of shelves in the shelf part, a position at which at least one shoe corresponding to a user is placed is identified, and each user is notified of a position at which his or her shoe is placed, it is possible to provide various customized services for each user.

Also, according to the present invention, when a user is identified, whether a door of the shoe treating apparatus is opened is identified, and whether a shoe is stored is identified through at least one of the weight sensor, camera, and distance measurement sensor disposed in the upper cabinet, the stored shoe is determined as a shoe corresponding to the user. Thus, it is possible to easily check an owner of a shoe disposed in the cabinet, and customized service can be provided on the basis of the checking.

Also, according to the present invention, since a first shelf which is located at the lowest position among the plurality of shelves included in the shelf part is controlled to move in a vertical direction, and at least one second shelf disposed above the first shelf is controlled to tilt, it is possible to provide convenience that allows a short user to conveniently store a shoe or take out the shoe.

Also, according to the present invention, since at least one light emitting element is caused to emit light on the basis of an approach of a user, it is possible to provide convenience that allows a user to check the inside of the shoe treating apparatus even without opening a door of the shoe treating apparatus.

In addition to the above-described effects, specific effects of the present invention will be described along with specific details for practicing the invention.

BRIEF DESCRIPTION OF THE DRAWINGS

The present invention will become more fully understood from the detailed description given hereinbelow and the accompanying drawings which are given by way of illustration only, and thus are not limitative of the present invention.

DETAILED DESCRIPTION

Figure 1A:
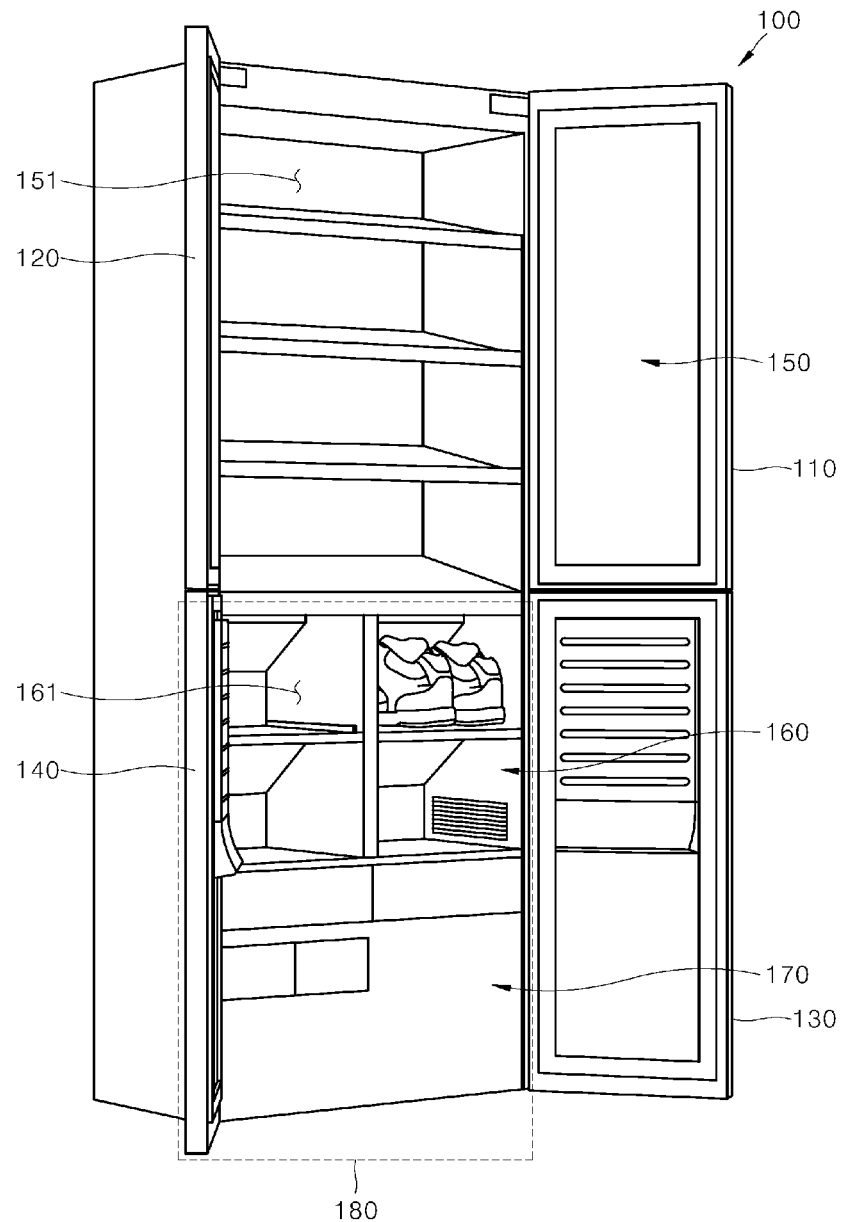
FIG. 1A is a first exemplary view illustrating a shoe cabinet including a shoe treating apparatus according to an embodiment of the present invention.

The objectives, features, and advantages will be described in detail below with reference to the accompanying drawings, and accordingly, those of ordinary skill in the art to which the present invention pertains should be able to easily practice the technical idea of the present invention. In describing the present invention, when it is determined that detailed description of a known art relating to the present invention may unnecessarily obscure the gist of the present invention, the detailed description thereof will be omitted. Hereinafter, exemplary embodiments according to the present invention will be described in detail with reference to the accompanying drawings. In the drawings, the same reference numerals are used to indicate the same or similar elements.

Although terms such as first and second are used to describe various elements, of course, the elements are not limited by the terms. The terms are only used to distinguish one element from another element, and of course, a first element may also be a second element unless otherwise stated.

Hereinafter, an apparatus and method for treating shoes according to some embodiments of the present invention will be described.

Figure 1B:
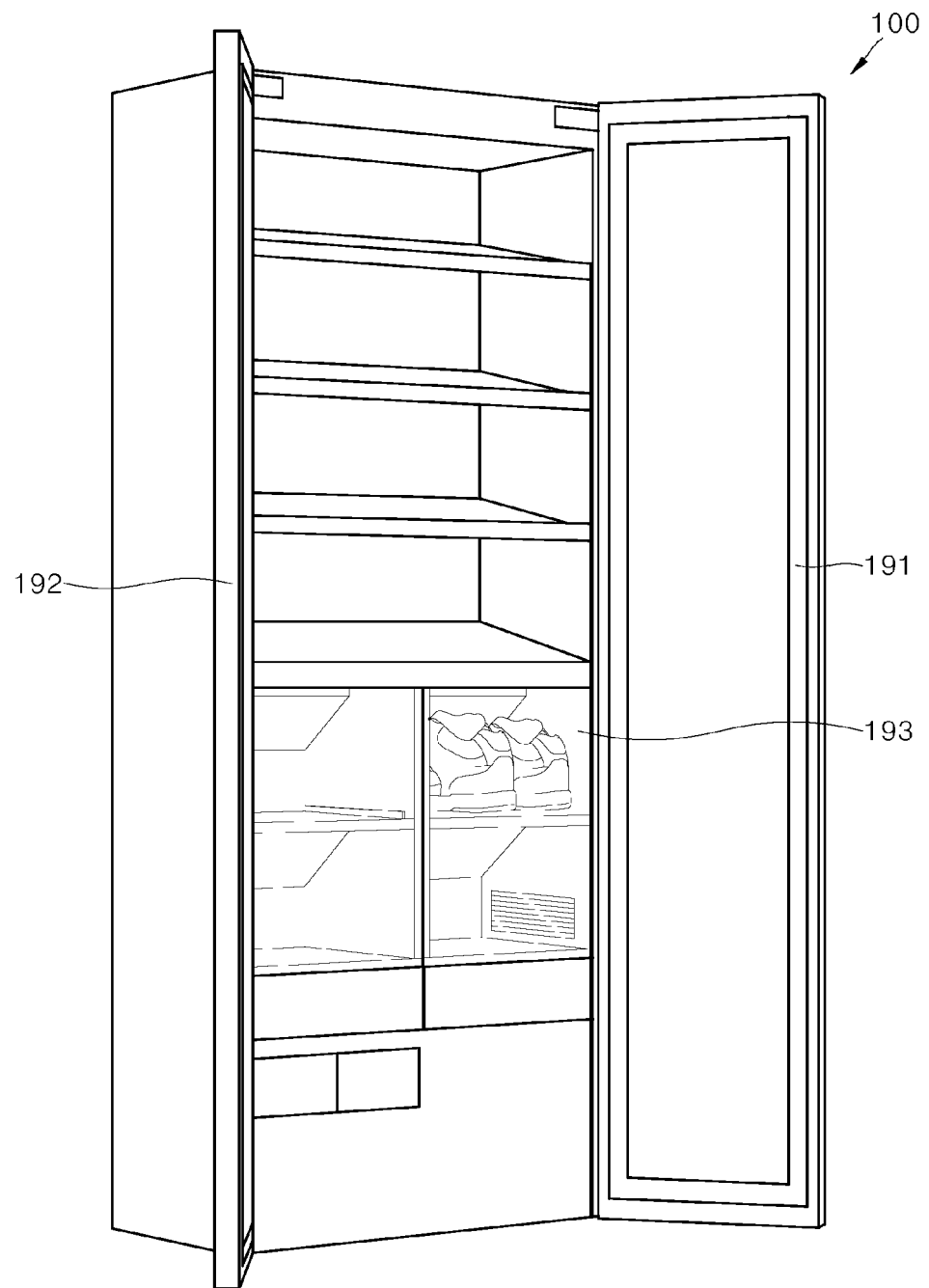
FIG. 1B is a second exemplary view illustrating a shoe cabinet including a shoe treating apparatus according to an embodiment of the present invention.

FIG. 1A is a first exemplary view illustrating a shoe cabinet including a shoe treating apparatus according to an embodiment of the present invention. FIG. 1B is a second exemplary view illustrating a shoe cabinet including a shoe treating apparatus according to an embodiment of the present invention.

Referring to FIGS. 1A and 1B, a shoe cabinet 100 according to an embodiment of the present invention may include an upper cabinet 150, a lower cabinet 160 disposed below the upper cabinet 150, and an electronic component part 170 (or electronic component compartment) disposed below the lower cabinet 160. The upper cabinet 150 includes a right door 120 and a left door 110, and the lower cabinet 160 includes a right door 140 and a left door 130.

Also, the shoe cabinet 100 according to an embodiment of the present invention may include two doors 191 and 192. Also, at least one of the upper cabinet 150 and the lower cabinet 160 of the shoe cabinet 100 according to an embodiment of the present invention may include an intermediate door 193. The intermediate door 193 may be made of a transparent material (e.g., glass, plastic, or the like) so as to be see-through.

According to an embodiment, the upper cabinet 150, the lower cabinet 160, and the electronic component part 170 may be physically coupled to each other to constitute a single shoe treating apparatus 100, or the lower cabinet 160 and the electronic component part 170 may be coupled to constitute a separate shoe treating apparatus 180. In the present invention, a way of constituting a shoe treating apparatus is not limited.

According to an embodiment, the upper cabinet 150 may include at least one storage space 151 that can store at least one shoe and may maintain the stability of the at least one shoe disposed in the storage space 151. The upper cabinet 150 may sanitize, deodorize, and dry the at least one stored shoe to provide stability that allows performance of the shoe to be maintained for a long period of time.

According to an embodiment, the lower cabinet 160 may include at least one storage space 161 that can store at least one shoe. Also, the lower cabinet 160 may intensively treat the shoe and improve performance of the shoe through removing foreign substances from the shoe, drying the shoe, dusting the shoe, moisturizing the shoe, treating the shoe to be water-repellent, and the like. The lower cabinet 160 is a cabinet that can identify at least one of the material, function, type, and condition of shoes and intensively treat the shoes.

A shoe treating apparatus according to an embodiment of the present invention may be included in the electronic component part 170 disposed below the lower cabinet 160. Alternatively, the shoe treating apparatus may be disposed on one side of the shoe cabinet 100.

Figure 2:
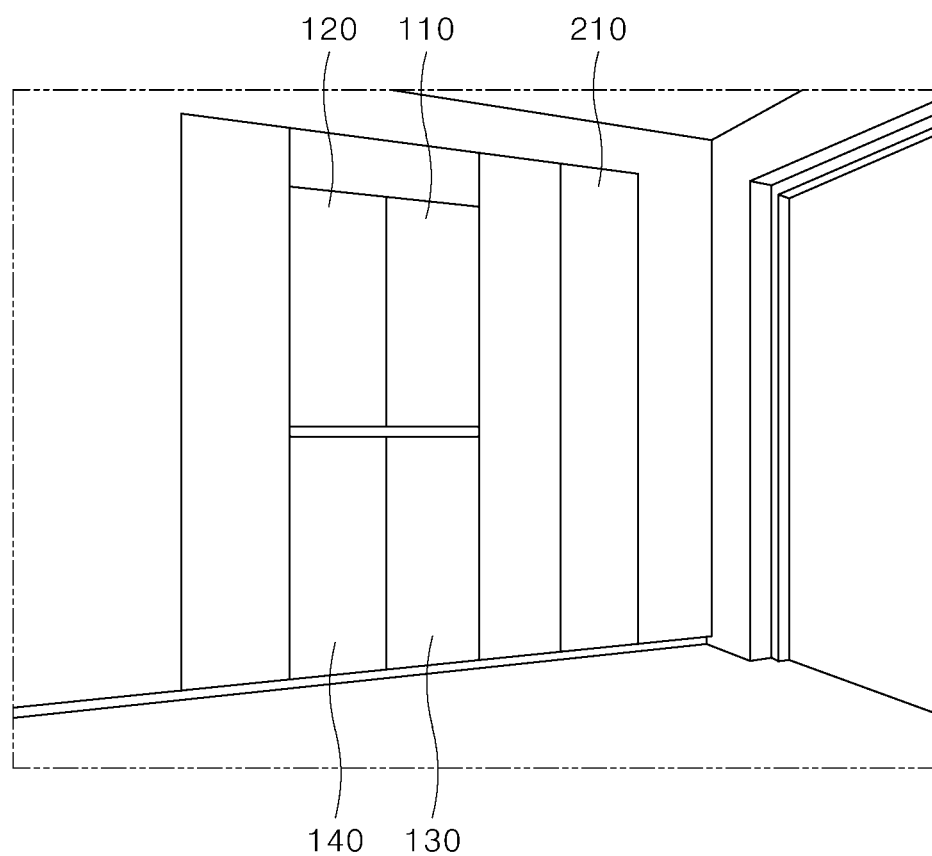
FIG. 2 is an exemplary view of a shoe cabinet embedded in a wall according to an embodiment of the present invention.

FIG. 2 is an exemplary view of a shoe cabinet embedded in a wall according to an embodiment of the present invention.

Referring to FIG. 2, a shoe cabinet 100 according to an embodiment of the present invention may be embedded (e.g., built) in an entrance wall 210. Both doors 110 and 120 of an upper cabinet 150 of the shoe cabinet 100 may be made (or formed) of a transparent material (e.g., tempered glass, transparent plastic). Also, both doors 130 and 140 of a lower cabinet 160 of the shoe cabinet 100 may be made (or formed) of an opaque material.

According to an embodiment, a display part configured to visually provide information (e.g., various pieces of information on shoe treatment, shoe condition, and user notification) to a user may be disposed on both doors 130 and 140 of the lower cabinet 160. The display part may include control circuitry for controlling display of information. The display part may include touch circuitry for detecting a touch.

According to an embodiment, the doors 130 and 140 of the lower cabinet 160 of the shoe cabinet 100 may move in the vertical direction. For example, in a case in which the doors 130 and 140 are open, a tray may be moved to the outside. Also, in a case in which a shoe is placed on the tray, the tray may be automatically moved to the inside of the lower cabinet 160 due to the weight of the shoe being detected. Also, the doors 130 and 140 may be automatically closed after the tray is moved to the inside of the lower cabinet 160.

Figure 3:
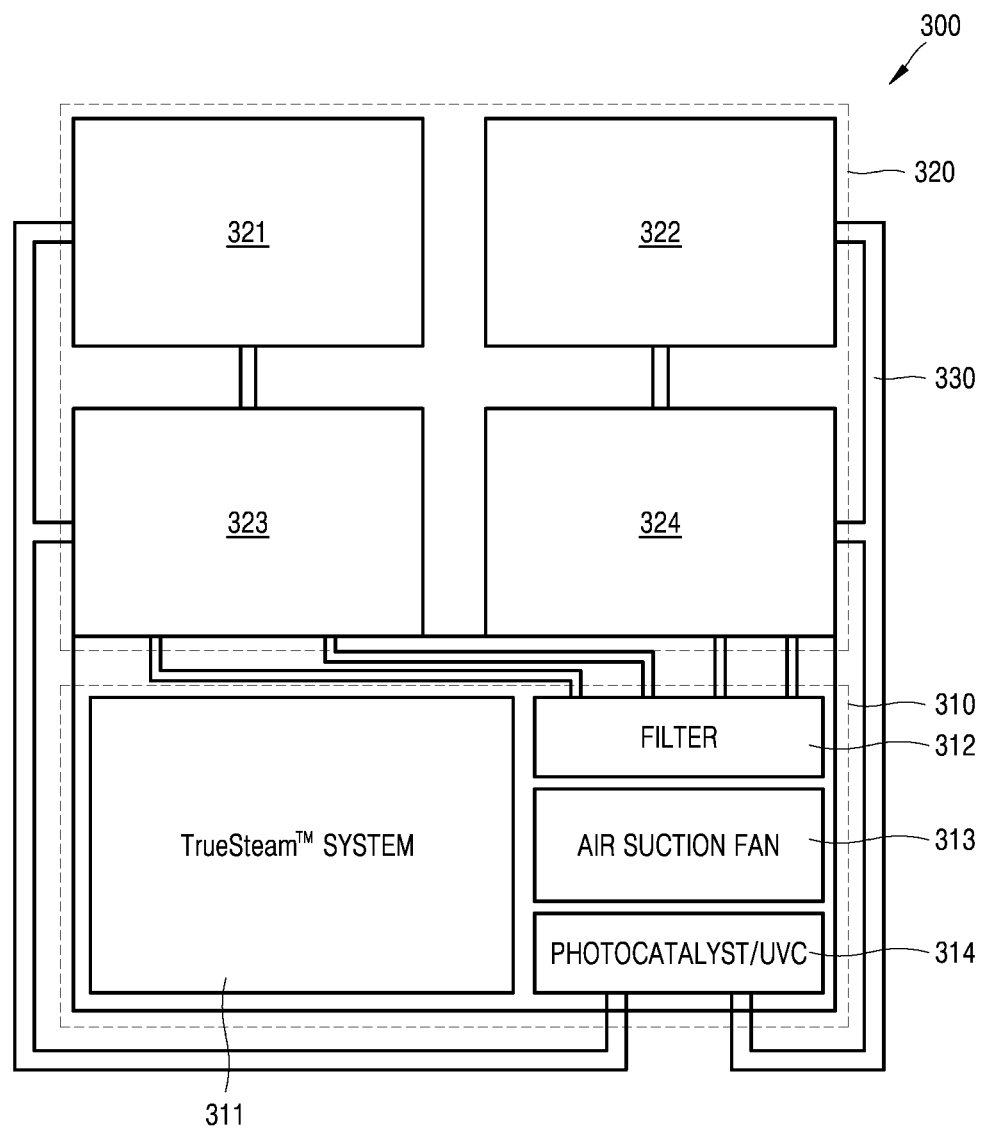
FIG. 3 is a block diagram briefly illustrating a shoe cabinet according to an embodiment of the present invention.

FIG. 3 is a block diagram briefly illustrating a shoe cabinet according to an embodiment of the present invention.

Referring to FIG. 3, a shoe cabinet 300 (e.g., a lower cabinet 160 and an electronic component part 170) according to an embodiment of the present invention may include a cabinet 320 that consists of a plurality of shoe cabinets 321, 322, 323, and 324. Also, the shoe cabinet 300 may include a shoe treating apparatus 310 (e.g., the electronic component part 170) configured to provide care for (or treat) a shoe stored in each of the plurality of shoe cabinets 321, 322, 323, and 324. The plurality of shoe cabinets 321, 322, 323, and 324 may each perform different functions to treat the shoe at a certain time.

According to an embodiment, the shoe cabinet 300 may include at least one duct 330 configured to connect each of the plurality of shoe cabinets 321, 322, 323, and 324 to the shoe treating apparatus 310. The duct 330 may be connected to each cabinet. The shoe treating apparatus 310 may include an LG TrueSteam™ system 311 configured to generate steam to treat a shoe, a filter 312 configured to filter foreign substances introduced from each of the plurality of shoe cabinets 321, 322, 323, and 324, an air suction fan 313 configured to suction air from each of the plurality of shoe cabinets 321, 322, 323, and 324, and an emitting part 314 (or emitter) configured to emit a photocatalyst/ultraviolet C (UVC).

The shoe treating apparatus 310 may be disposed below or above the cabinet 320. The filter 312, the air suction fan 313, and the emitting part 314 emitting photocatalyst/UVC may be included in a shoe treating apparatus 310 of FIG. 4.

Figure 4:
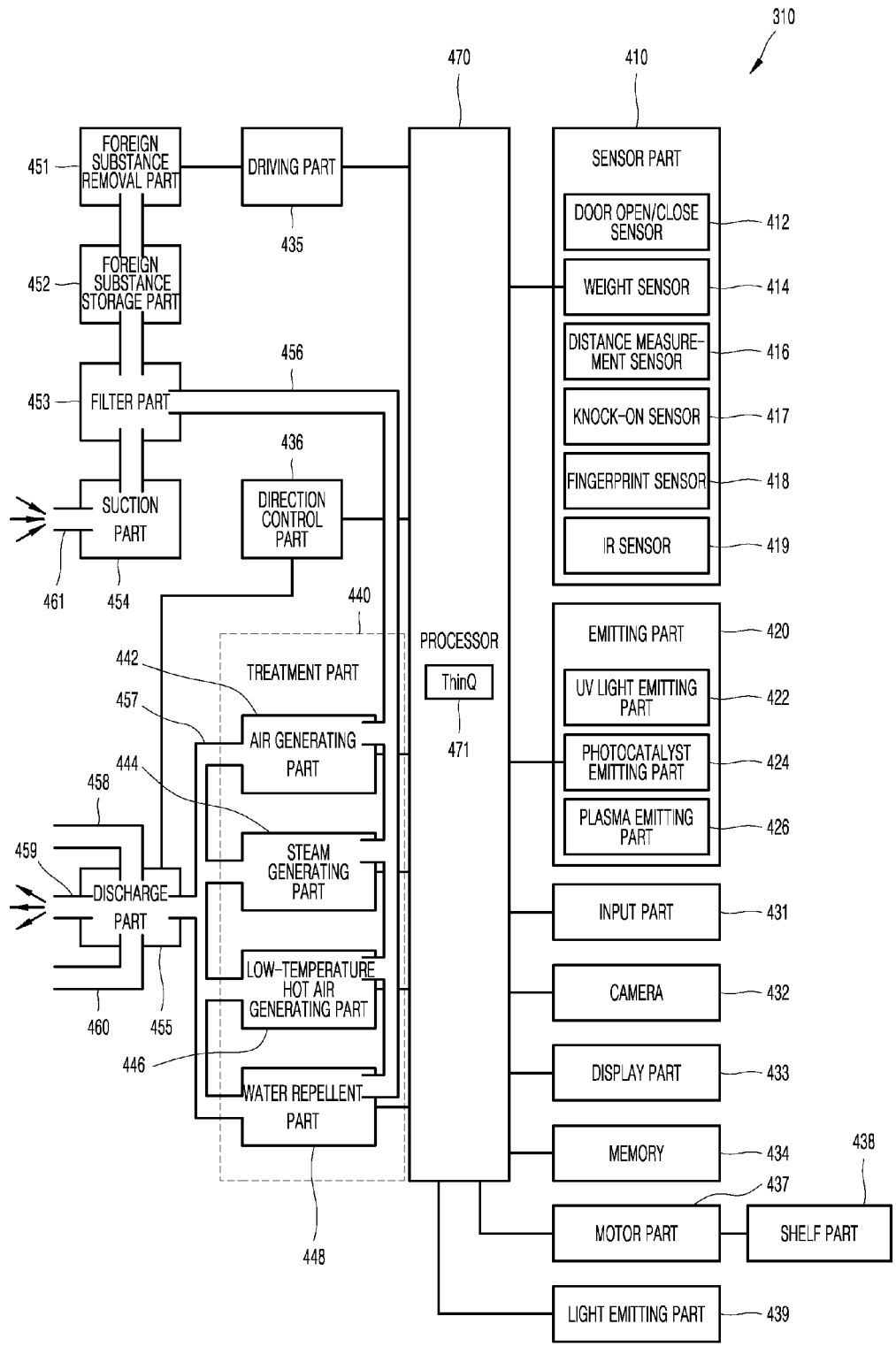
FIG. 4 is a block diagram of a shoe treating apparatus according to an embodiment of the present invention.

FIG. 4 is a block diagram of a shoe treating apparatus according to an embodiment of the present invention.

Referring to FIG. 4, the shoe treating apparatus 310 according to an embodiment of the present invention may include a sensor part 410, an emitting part 420 (or emitter), an input part 431, a camera 432, a display part 433 (or display), a memory 434, a motor part 437 (or motor), a shelf part 438 (or shelf assembly), a light emitting part 439 (or light emitter), a driving part 435 (or driver), a direction control part 436 (or direction controller), a treatment part 440, a foreign substance removal part 451, a foreign substance storage part 452 (or foreign substance storage), a filter part 453 (or filter), a suction part 454, a discharge part 455, and a processor 470.

The configuration of the shoe treating apparatus 310 illustrated in FIG. 4 is only one embodiment, and elements of the shoe treating apparatus 310 are not limited to the embodiment illustrated in FIG. 4, and some elements may be added, changed, or omitted as necessary.

According to an embodiment, the shoe treating apparatus 310 may be referred to as "shoe cabinet 100." Also, the shoe treating apparatus 310 may include an upper cabinet 150, a lower cabinet 160 disposed below the upper cabinet 150, and an electronic component part 170 configured to perform an electrical or physical operation for treatment in the upper cabinet 150 and the lower cabinet 160.

According to an embodiment, under control of the processor 470, the electronic component part 170 may be electrically or physically operated to perform a treatment function (e.g., at least one of a foreign substance removal function, a sanitizing and deodorizing function, a steaming and sanitizing function, a dehumidifying and drying function, and a nourishing and water-repellent coating function) for at least one shoe disposed in at least one storage space formed in each of the upper cabinet 150 and the lower cabinet 160.

According to an embodiment, the sensor part 410 may include a door open/close sensor 412 configured to detect opening/closing of the doors 110, 120, 130, and 140 of the shoe treating apparatus 310, a weight sensor 414 configured to detect the weight of a shoe placed in a cabinet, a distance measurement sensor 416 configured to measure a distance between the shoe and a wall (e.g., an inner wall) of each of the shoe cabinets 321, 322, 323, and 324. And, the sensor part 410 may further include a knock-on sensor 417 disposed on the doors 110, 120, 130, and 140 to detect tapping due to an external impact, a fingerprint sensor 418 configured to detect a fingerprint of a user, and an infrared (IR) sensor 419 configured to detect an approach of a user.

Also, the sensor part 410 may include a camera configured to acquire a shoe-related image.

According to an embodiment, the door open/close sensor 412 may be disposed at a position that enables opening/closing of a door to be detected (e.g., a hinge of each door) in each of the shoe cabinets 321, 322, 323, and 324. The door open/close sensor 412 may include a sensor (e.g., light sensor) configured to detect an intensity of light due to opening/closing of a door. The door open/close sensor 412 may provide a signal according to a detected result to the processor 470.

According to an embodiment, the weight sensor 414 may be disposed at a lower portion of each of the shoe cabinets 321, 322, 323, and 324 to measure the weight of a shoe. The weight sensor 414 may provide information on the measured weight of the shoe to the processor 470.

According to an embodiment, the distance measurement sensor 416 may be disposed at a position that enables a distance between a shoe and an inner wall of the shoe cabinet 320 (e.g., the lower cabinet 160) to be measured (e.g., at least one of a left surface, a right surface, a front surface, a rear surface, an upper surface, and a lower surface in each of the shoe cabinets 321, 322, 323, and 324). The distance measurement sensor 416 may be provided as a plurality of distance measurement sensors 416.

For example, the plurality of distance measurement sensors may be disposed in the horizontal direction or vertical direction on at least one of the left surface, right surface, front surface, rear surface, upper surface, and lower surface inside each of the shoe cabinets 321, 322, 323, and 324. The distance measurement sensor 416 may transmit information on a distance acquired by each distance measurement sensor (e.g., a transmission time, a reception time of a reflected signal, a distance from a shoe, and the like) to the processor 470.

Also, the processor 470 may identify the size, height, or the like of the shoe from the information on the distance received from each distance measurement sensor. Alternatively, the distance measurement sensor 416 may be disposed on the front surfaces of the doors 110, 120, 130, and 140 to measure a distance from a user according to an approach of the user.

According to an embodiment, the knock-on sensor 417 may be disposed on each of the doors 110, 120, 130, and 140 of the upper cabinet 150 and the lower cabinet 160. Also, the knock-on sensor 417 may detect vibration (or sound) due to tapping the doors 110, 120, 130, and 140. The knock-on sensor 417 may be disposed on at least one of an upper side, a lower side, a left side, and a right side of each of the doors 110, 120, 130, and 140 and may sense at least one tap.

According to an embodiment, the fingerprint sensor 418 may be disposed at a position for detecting a fingerprint of a user on a handle formed at a door to open each of the doors 110, 120, 130, and 140. Also, in this way, the fingerprint sensor 418 may acquire a fingerprint of a user opening each door and may transmit the acquired fingerprint to the processor 470.

According to an embodiment, the IR sensor 419 may be disposed on the front surface of each of the doors 110, 120, 130, and 140. Also, the IR sensor 419 may irradiate light having a certain wavelength (e.g., in a range of 700 nm to 1 mm) to detect an approach of a user toward the shoe treating apparatus 310. Also, the IR sensor 419 may measure a distance between the shoe treating apparatus 310 and the user.

According to an embodiment, the IR sensor 419 may include a plurality of IR sensors. The plurality of IR sensors may be vertically disposed in an inner wall of each cabinet to identify the height of a shoe.

According to an embodiment, the sensor part 410 may include at least one knock-on sensor 417 disposed on a door of each of the upper cabinet 150 and the lower cabinet 160, at least one fingerprint sensor 418 disposed on a handle of each of the upper cabinet 150 and the lower cabinet 160, and an IR sensor 419 disposed at one side of an exterior of the shoe treating apparatus 310. The sensor part 410 may transmit acquired information, data, or values to the processor 470.

For example, in order to detect tapping through the doors 110 and 120 of the upper cabinet 150 that are made of a transparent material (e.g., tempered glass, transparent plastic), at least one knock-on sensor 417 may be disposed on at least one of the doors 110 and 120 of the upper cabinet 150.

According to an embodiment, the fingerprint sensor 418 may acquire a digital image of a fingerprint of a user opening a door. The fingerprint sensor 418 may be disposed at a position on a handle of each door that facilitates acquisition of a digital image of a fingerprint of a user.

According to an embodiment, the sensor part 410 may include a gyro sensor. The gyro sensor may be used for zero point calibration of each shelf. The gyro sensor may be disposed at one side of each shelf and may identify whether each shelf is horizontal. The gyro sensor may periodically acquire a gyro value of each shelf and provide the acquired gyro value to the processor 470 so that the level of each shelf is maintained.

According to an embodiment, the emitting part 420 may include a UV light emitting part 422 configured to emit UVC, a photocatalyst emitting part 424 configured to emit a photocatalyst, and a plasma emitting part 426.

According to an embodiment, the UV light emitting part 422, the photocatalyst emitting part 424, and the plasma emitting part 426 may be disposed at a position that enables UV light, a photocatalyst, or plasma to be emitted to the shoe in each of the shoe cabinets 321, 322, 323, and 324 (e.g., at least one of the left surface, right surface, front surface, rear surface, upper surface, and lower surface inside the shoe cabinet). The UV light emitting part 422 may include at least one UVC light emitting diode (UVC LED).

According to an embodiment, the input part 431 may receive an input for controlling an operation or function of the shoe treating apparatus 310 from a user or an external device (e.g., a remote control device). The input part 431 (e.g., a touchscreen) may be included in the display part 433. A user may control the operation or function of the shoe treating apparatus 310 through the input part 431.

According to an embodiment, the input part 431 may receive an input of data that is input from a user and may provide various pieces of information input from the user to the processor 470. To this end, the input part 431 may include a physical manipulation member such as a switch or a button or may include an electrical manipulation member such as a touch key, a touchpad, or a touchscreen.

Alternatively, the input part 431 may further include a microphone that can receive an input of a voice signal from a user and a speaker that can output various pieces of information to a user through voice.

According to an embodiment, the camera 432 may be disposed inside each of the shoe cabinets 321, 322, 323, and 324 to identify the position, material, type, or condition of the shoe in the shoe cabinet. The camera 432 may include at least one camera (e.g., an RGB camera, a vision camera) or a reader (e.g., an optical character reader (OCR) or the like). Also, the camera 432 may acquire an image of the shoe in each of the shoe cabinets 321, 322, 323, and 324 and may transmit the acquired image to the processor 470.

According to an embodiment, the camera 432 may include at least one sensor that can acquire an image even at low brightness. The camera 432 may include at least one camera and may be included in the sensor part 410.

According to an embodiment, the camera 432 may be disposed on the front surface of the shoe treating apparatus 310. The camera 432 may be disposed on the front surface of the shoe treating apparatus 310 to identify an approach of a user toward the shoe treating apparatus 310 and to identify the user.

According to an embodiment, each camera may be disposed at one side of the doors 110, 120, 130, and 140 or may be disposed inside each cabinet. For example, by providing a camera disposed in each cabinet, the processor 470 may acquire an image for identifying the material, type, and condition of a shoe through a camera disposed on an inner wall of each shoe cabinet.

According to an embodiment, the display part 433 may display an operation of at least one of the upper cabinet 150, the lower cabinet 160, and the electronic component part 170 of the shoe treating apparatus 310. The display part 433 may include a touchscreen.

The display part 433 may display various pieces of information on the operation (e.g., a completed operation, an operation currently in progress, an operation to be performed, a time at which an operation ends, etc.) of the shoe treating apparatus 310. The display part 433 may display whether a shoe is present in each of the shoe cabinets 321, 322, 323, and 324, the type of shoe, the material of the shoe, the function of the shoe, the condition of the shoe, and an operational state or functional state of each of the shoe cabinets 321, 322, 323, and 324.

According to an embodiment, the display part 433 may display various pieces of information (e.g., multimedia data, text data, or the like). The display part 433 may display various pieces of information on a result of completed shoe treatment, the current state of treatment in progress, or treatment to be performed by the processor 470. The display part 433 may include control circuitry for controlling a display configured to visually provide information to a user.

According to an embodiment, the display part 433 may include touch circuitry configured to detect a touch or an input sensor that can measure an intensity of pressure of a touch. The display part 433 may be disposed at one side of each of the doors 110, 120, 130, and 140 of the shoe treating apparatus 310.

According to an embodiment, the display part 433 may be disposed on a transparent member (e.g., a smart mirror) of a door of the shoe treating apparatus 310. Also, the smart mirror may visually provide an operational state of the shoe treating apparatus 310 or various pieces of information (e.g., treatment-related information, information indicating the current state) on at least one shoe.

According to an embodiment, the smart mirror mounted on the door of the shoe treating apparatus 310 may be operated in any one or more modes of a first mode (e.g., a mirror mode), a second mode (e.g., a smart mirror mode), and a third mode (e.g., a display mode).

The first mode is a mode in which the smart mirror completely reflects things like a normal mirror, the second mode is a mode in which the smart mirror displays at least pieces of information on the basis of the first mode, and the third mode is a mode in which the smart mirror displays only at least pieces of information generated by the processor 470. In this way, the smart mirror may include various panels (e.g., a polarizing layer, a conductive layer, an insulating layer, a display panel, a touch sensing panel, and the like) to support such various modes.

According to an embodiment, the transmissivity and reflectivity of the smart mirror may be adjusted to allow the smart mirror to operate in various modes. For example, under control of the processor 470, the smart mirror may, in a state in which the smart mirror is able to reflect an image of a user or the like located in front of the smart mirror and display a mirror image thereof (e.g., the first mode state), be operated in a mode in which various pieces of information generated by the processor 470 (e.g., text, numbers, images, and the like) and various pieces of information received from an external device (e.g., a remote control device) (e.g., preview images, images, text, numbers, and the like) are displayed by the smart mirror (e.g., the second mode).

According to an embodiment, the memory 434 may include a volatile memory or a nonvolatile memory. For example, the memory 434 may store information, data, programs, and the like necessary for the operation of the shoe treating apparatus 310. Accordingly, the processor 470 may perform a control operation, which will be described below, by referring to the information stored in the memory 434.

According to an embodiment, the memory 434 may also store various platforms. For example, the memory 434 may include at least one type of storage medium of a flash memory type, a hard disk type, a multimedia card micro type, a card-type memory (e.g., a secure digital (SD) or extreme digital (XD) memory or the like), a random access memory (RAM), and a read-only memory (ROM) (such as an electrically erasable programmable ROM (EEPROM)).

According to an embodiment, the memory 434 may store various pieces of data acquired or used by at least one element of the shoe treating apparatus 310 (e.g., software, applications, acquired information, measured information, control signals, and the like) and instructions relating thereto.

According to an embodiment, the memory 434 may store information on the height of at least one user, an image of the user, and a fingerprint of the user and information on at least one shoe (e.g., an image according to the type of shoe, the height of the shoe, the material of the shoe, the function of the shoe, etc.).

According to an embodiment, the memory 434 may store an identifier, position information, and a tilt angle for controlling tilting of each shelf for each of a plurality of shelves included in the upper cabinet 150. Also, the memory 434 may store an identifier, position information, a tilt angle for controlling tilting of each shelf for each of a plurality of shelves included in the lower cabinet 160.

According to an embodiment, the motor part 437 may include at least one motor configured to control tilting of each of the plurality of shelves included in the upper cabinet 150. Also, the motor part 437 may include at least one motor configured to control tilting of each of the plurality of shelves included in the lower cabinet 160. At least one motor of the motor part 437 may be operated so that a shelf corresponding to control of the processor 470 tilts at the corresponding tilt angle.

According to an embodiment, the shelf part 438 may include at least one shelf included in the upper cabinet 150 and at least one shelf included in the lower cabinet 160.

According to an embodiment, the light emitting part 439 may include at least one light emitting element (e.g., an LED, a UVC LED). The at least one light emitting element may be disposed on at least one shelf included in each of the upper cabinet 150 and the lower cabinet 160. The light emitting part 439 may be disposed at various positions of the shoe cabinet 100. The light emitting part 439 may emit light under control of the processor 470. Alternatively, the light emitting part 439 may emit different colored lights under control of the processor 470.

According to an embodiment, the treatment part 440 may include an air generating part 442 configured to generate air supplied to the inside of each cabinet of the upper cabinet 150 and/or the inside of each cabinet of the lower cabinet 160, a steam generating part 444 configured to generate steam supplied to the inside of each cabinet of the upper cabinet 150 and/or the inside of each cabinet of the lower cabinet 160, a low-temperature hot air generating part 446 configured to generate low-temperature hot air supplied to the inside of each cabinet of the upper cabinet 150 and/or the inside of each cabinet of the lower cabinet 160, and a water repellent part 448 configured to generate a liquid (e.g., mist) supplied to the inside of each cabinet of the upper cabinet 150 and/or the inside of each cabinet of the lower cabinet 160.

According to an embodiment, at least one of the air generating part 442, the steam generating part 444, the low-temperature hot air generating part 446, and the water repellent part 448 in the treatment part 440 may be connected to the filter part 453 through a first duct 456. Air filtered by the filter part 453 may be supplied to at least one of the air generating part 442, the steam generating part 444, the low-temperature hot air generating part 446, and the water repellent part 448 through the first duct 456. Due to such a structure, air, steam, low-temperature hot air, and the like may circulate in the shoe cabinet 100.

According to an embodiment, at least one of the air generating part 442, the steam generating part 444, the low-temperature hot air generating part 446, and the water repellent part 448 in the treatment part 440 may be connected to the discharge part 455 through a second duct 457. The air (e.g., steam, low-temperature hot air, water repellent, or the like) discharged from at least one of the air generating part 442, the steam generating part 444, the low-temperature hot air generating part 446, and the water repellent part 448 may be delivered to the discharge part 455 through the second duct 457. The discharge part 455 may include a duct module (e.g., a duct module 5300 of FIG. 53).

According to an embodiment, the discharge part 455 may be disposed on the inner wall (e.g., at least one of the left surface, right surface, front surface, rear surface, upper surface, and lower surface) of each of the shoe cabinets. The discharge part 455 may discharge or spray at least one of air, steam, low-temperature hot air, and liquid (e.g., sprayed water) to the inside of each of the shoe cabinets. The discharge part 455 may include at least one fan (or propeller) for the discharging or spraying. Also, for the discharge, one or more third ducts 458, 459, and 460 may be disposed on the inner wall of each of the shoe cabinets.

At least part of air, steam, low-temperature hot air, and liquid (e.g., sprayed water) may be discharged or sprayed in each of the shoe cabinets through the one or more third ducts 458, 459, and 460.

For example, the discharge part 455 may include two propellers. The two propellers may each rotate in different directions coaxially. For example, in a case in which the air, steam, low-temperature hot air, and liquid (e.g., sprayed water) are intensively sprayed in a narrow area, the two propellers may simultaneously rotate in different directions (for example, a first propeller may rotate clockwise while a second propeller rotates counterclockwise).

Also, in a case in which the air, steam, low-temperature hot air, and liquid (e.g., sprayed water) are intensively sprayed in a wide area, a single propeller (e.g., a first propeller) may rotate.

According to an embodiment, the direction control part 436 may control the direction of the one or more third ducts 458, 459, and 460 so that the one or more third ducts 458, 459, and 460 face a direction toward a shoe disposed in a shoe cabinet.

According to an embodiment, the foreign substance removal part 451 may include a roller brush module (or at least one roller brush), which is configured to remove foreign substances adsorbed onto a shoe disposed in the shoe cabinet, and at least one ultrasonic vibrator.

According to an embodiment, the roller brush module may be disposed on a lower portion of each of the shoe cabinets 321, 322, 323, and 324 of the lower cabinet 160. In this way, the roller brush module may be disposed on a lower portion of the shoe cabinet so as to come in contact with the bottom of a shoe in each of the shoe cabinets 321, 322, 323, and 324. Also, the roller brush module may include a plurality of roller brushes.

According to an embodiment, the roller brush may rotate clockwise or counterclockwise to remove foreign substances (e.g., dirt, dust, or the like) attached to a shoe stored in the shoe cabinet (e.g., attached to the bottom, side, or the like of the shoe) from the shoe. The foreign substance removal part 451 may include a plurality of roller brushes according to the size of the shoe cabinet. Each roller brush may rotate independently or may rotate dependently due to a worm gear disposed between two roller brushes.

According to an embodiment, a motor and at least one vibrator may be disposed in each of the plurality of roller brushes. Also, the plurality of roller brushes may rotate independently by a rotational force of the corresponding motor.

For example, in a case in which a plurality of roller brushes are disposed on a lower portion of the shoe cabinet, a first roller brush disposed at the leftmost side (or the rightmost side) may be rotated clockwise through the driving part 435 (or the motor part 437). Also, in the case in which the first roller brush is rotated clockwise, a second roller brush disposed at the right (or left) of the first roller brush may be rotated counterclockwise on the basis of the clockwise rotation of the first roller brush.

Likewise, as the second roller brush rotates counterclockwise, a third roller brush disposed at the right (or left) of the second roller brush may be rotated clockwise.

According to an embodiment, a worm gear configured to connect rotations of roller brushes disposed on the lower portion of the shoe cabinet may be disposed between the roller brushes. Also, in a case in which a first roller brush disposed at the leftmost side (or the rightmost side) is rotated clockwise through the driving part 435, a worm gear disposed at the right (or left) of the first roller brush may be rotated counterclockwise on the basis of the clockwise rotation of the first roller brush.

Likewise, as the worm gear rotates counterclockwise, a second roller brush disposed at the right (or left) of the worm gear may be rotated clockwise. In this way, each roller brush and worm gear may rotate while being engaged with each other.

Therefore, the driving part 435 may rotate at least one roller brush disposed on the lower portion of the shoe cabinet to rotate a plurality of roller brushes.

According to an embodiment, the ultrasonic vibrator may propagate ultrasonic waves to generate vibration. The ultrasonic vibrator may be disposed on a roller brush configured to remove foreign substances adsorbed onto the lower portion of a shoe. Due to vibration of the ultrasonic vibrator, foreign substances (e.g., dirt, dust, or the like) attached to a shoe disposed in the shoe cabinet (e.g., attached to the bottom, side, or the like of the shoe) may be removed from the shoe.

According to an embodiment, the driving part 435 (or the motor part 437) may include at least one motor that can drive at least one roller brush, at least one worm gear, and at least one ultrasonic vibrator in the foreign substance removal part 451.

According to an embodiment, the suction part 454 may suction the foreign substances (e.g., dirt, dust, or the like) in each of the shoe cabinets 321, 322, 323, and 324. The suction part 454 may include a fourth duct 461 that can suction the foreign substances (e.g., dirt, dust, or the like) in the shoe cabinet. The fourth duct 461 may be disposed (or formed) toward the inside of the shoe cabinet. The fourth duct 461 may be disposed on at least one of the left surface, right surface, front surface, rear surface, upper surface, and lower surface inside the shoe cabinet.

According to an embodiment, the foreign substance removal part 451 and the foreign substance storage part 452 may be connected by a duct through which foreign substances pass.

According to an embodiment, the foreign substance storage part 452 may store foreign substances removed from a shoe. The foreign substance storage part 452 may store foreign substances separated from a shoe by at least one of rotation of at least one roller brush of the foreign substance removal part 451 and vibration of the ultrasonic vibrator of the foreign substance removal part 451. The foreign substance storage part 452 may be detachable from or attachable to a shoe cabinet and may be a container type that can store the foreign substances.

According to an embodiment, the suction part 454 may suction foreign substances in each of the shoe cabinets 321, 322, 323, and 324 through the fourth duct 461. The foreign substances (e.g., dirt, dust, or the like) suctioned through the suction part 454 pass through the filter part 453.

According to an embodiment, the suction part 454 and the filter part 453 may be connected by a duct through which foreign substances pass.

According to an embodiment, the filter part 453 may filter the foreign substances (e.g., dirt, dust, or the like) suctioned through the suction part 454. Also, the filter part 453 may store the filtered foreign substances in the foreign substance storage part 452. The filter part 453 may include a filtering member (e.g., a dust filter or the like) configured to filter the foreign substances suctioned into the suction part 454.

Also, filtered air that passed through the filter part 453 may be provided to at least one of the air generating part 442, the steam generating part 444, the low-temperature hot air generating part 446, and the water repellent part 448 in the treatment part 440 through the first duct 456.

In this way, the air provided to the treatment part 440 may be used in performing an operation according to a function of each of the air generating part 442, the steam generating part 444, the low-temperature hot air generating part 446, and the water repellent part 448.

According to an embodiment, the air generating part 442 may receive air filtered in the filter part 453 through the first duct 456. The air introduced into the air generating part 442 through the first duct 456 may be converted into air having a predetermined wind strength through the air generating part 442 and then be introduced into the discharge part 455 through the second duct 457.

Also, air introduced into the steam generating part 444 through the first duct 456 may be, together with a liquid (e.g., a spraying-type liquid), converted into a spraying-type liquid having a predetermined strength in the steam generating part 444 and then sprayed through the discharge part 455 through the second duct 457.

According to an embodiment, the steam generating part 444 may include a container that can store a liquid necessary to generate steam. The container that can store the liquid may be included in the shoe treating apparatus 310 or may be detachable from or attachable to the shoe treating apparatus 310. The steam generating part 444 (e.g., the LG TrueSteam™ system 311) may mix a heated liquid with air introduced through the first duct 456 to generate steam.

According to an embodiment, air introduced into the low-temperature hot air generating part 446 through the first duct 456 may be converted into hot air at a low temperature (e.g., 40° C.) through the low-temperature hot air generating part 446 and then introduced into the discharge part 455 through the second duct 457.

According to an embodiment, air introduced into the water repellent part 448 through the first duct 456 may be, together with a liquid (e.g., mist), converted into a spraying-type liquid having a predetermined strength in the water repellent part 448 and then introduced into the discharge part 455 through the second duct 457. Also, the spraying-type liquid introduced into the discharge part 455 may be sprayed through the one or more third ducts 458, 459, and 460.

In this way, the air, steam, low-temperature hot air, and water repellent generated by an operation of each element in the treatment part 440 may be introduced into the discharge part 455 through the second duct 457 connected to the discharge part 455.

Also, in the discharge part 455, the introduced air, steam, low-temperature hot air, and water repellent may be discharged to the inside of the shoe cabinet through the ducts 458, 459, and 460 (or a duct module) in which a discharge direction is adjusted by control of the direction control part 436.

According to an embodiment, at least one of the foreign substance removal part 451, the suction part 454, the filter part 453, and the discharge part 455 may be disposed in each of the plurality of shoe cabinets.

According to an embodiment, the foreign substance storage part 452 may be disposed outside a shoe cabinet or may be included in the shoe treating apparatus 310. Also, the foreign substance storage part 452 may be detachable from and attachable to the shoe cabinet.

According to an embodiment, the processor 470 may drive software to control at least one element connected to the processor 470 on the basis of wired communication or wireless communication. Also, the processor 470 may perform processing of various data and arithmetic operations on the basis of the wired communication or the wireless communication.

According to an embodiment, the processor 470 may load a command or data received from the memory 434, the input part 431, the camera 432, the treatment part 440, the display part 433, and the like to the memory 434 to process the command or data and may store the processed data in the memory 434. Alternatively, the processor 470 may display the processed data through the display part 433 (e.g., a touchscreen).

According to an embodiment, the processor 470 may have an artificial intelligence chip 471 (e.g., ThinQ™) embedded therein and an algorithm for the artificial intelligence chip 471 may be implemented by the processor 470. The artificial intelligence chip is a processor imitating the neural network of the human brain and may support a deep learning algorithm that analyzes, perceives, infers, and determines data by itself.

In this way, the shoe treating apparatus 310 (e.g., the processor 470) of the present invention may not only control the shoe treating apparatus 310 by artificial intelligence but also receive information acquired from at least one sensor disposed in a shoe cabinet and identify the material, function, type, and condition of the shoe stored in the shoe cabinet.

According to an embodiment, the processor 470 may detect opening/closing of a door for at least one of the upper cabinet and the lower cabinet through at least one sensor (e.g., the door open/close sensor 412) included in the sensor part 410.

According to an embodiment, the processor 470 may detect a shoe stored in a storage space of each of the upper cabinet 150 and the lower cabinet 160 through at least one sensor (e.g., the distance measurement sensor 416 and/or the weight sensor 414) included in the sensor part 410 and at least one camera 432 of the camera 432.

According to an embodiment, the processor 470 may, on the basis of opening of the door of each of the upper cabinet 150 and the lower cabinet 160 and detection of at least one shoe, control the electronic component part 170 to operate each of the upper cabinet 150 and the lower cabinet 160 in a mode for shoe treatment.

For example, the processor 470 may operate the upper cabinet 150 in a normal treatment mode and operate the lower cabinet 160 in an intensive treatment mode through the electronic component part 170. Alternatively, the processor 470 may operate the upper cabinet 150 in the normal treatment mode or may operate the lower cabinet 160 in the intensive treatment mode through the electronic component part 170.

According to an embodiment, the processor 470 may identify at least one of the material, type, and condition of at least one shoe in the upper cabinet 150 through at least one sensor (e.g., the weight sensor 414, the distance measurement sensor 416, the IR sensor 419, the camera 432).

According to an embodiment, on the basis of at least one of the material, type, and condition of at least one shoe stored in each of the plurality of storage spaces in the upper cabinet 150, the processor 470 may control at least one of the temperature and humidity inside the upper cabinet through the electronic component part 170.

According to an embodiment, on the basis of at least one of the material, type, and condition of at least one shoe disposed in each of the plurality of storage spaces included in the upper cabinet 150, the processor 470 may differently control at least one of the temperature and humidity for each of the plurality of storage spaces through the electronic component part 170 to normally treat the shoe.

The processor 470 may identify at least one of the material, type, and condition of a shoe and, on the basis of the identification, acquire information on at least one of temperature and humidity from the memory 434.

According to an embodiment, the processor 470 may perform at least one of a foreign substance removal function, a sanitizing and deodorizing function, a steaming and sanitizing function, a dehumidifying and drying function, and a nourishing and water-repellent coating function for each of the plurality of storage spaces through the electronic component part 170 to intensively treat the shoe.

Also, the processor 470 may identify at least one of the material, type, and condition of a shoe and, on the basis of the identification, acquire information (e.g., execution logic, instructions, or the like) on at least one of the foreign substance removal function, sanitizing and deodorizing function, steaming and sanitizing function, dehumidifying and drying function, and nourishing and water-repellent coating function from the memory 434.

According to an embodiment, the processor 470 may analyze an image or information of the shoe that is acquired through the camera 432 (e.g., an RGB camera, a vision camera, an OCR, or the like) to identify at least one of the material, function, type, and condition of the shoe.

According to an embodiment, the processor 470 may identify an image of the shoe and a tag attached to the shoe through the camera 432 to identify the material (or type) or the size of the shoe. Examples of the material of the shoe may include fabric, genuine leather, synthetic leather, canvas material, suede material, cork material, and the like. The type of the shoe may vary according to various purposes, and examples thereof may include, but are not limited to, heels, sneakers, slippers, hiking shoes, boots, running shoes, rain boots, soccer shoes, basketball shoes, and the like.

According to an embodiment, the processor 470 may identify whether the shoe is clean or foreign substances are adsorbed thereon through an image of the shoe and a tag attached to the shoe that are acquired by the camera 432 (e.g., an RGB camera, a vision camera) and the sensor part 410. Also, the processor 470 may identify a portion (e.g., the bottom) of the shoe where a large amount of foreign substances is adsorbed.

According to an embodiment, the processor 470 may treat a shoe through at least one of the treatment part 440 and the emitting part 420 on the basis of at least one of the material, function, type, and condition of the shoe.

Under control of the processor 470, at least one of the treatment part 440 and the emitting part 420 may execute at least one or some of a first function (e.g., a foreign substance removal function) of removing foreign substances adsorbed onto the shoe, a second function (e.g., a sanitizing and deodorizing function) of executing at least one of sanitization and deodorization of the shoe, a third function (e.g., a steaming and sanitizing function) of executing at least one of steaming and sanitization of the shoe, a fourth function (e.g., a dehumidifying and drying function) of executing at least one of dehumidification and drying of the shoe, and a fifth function (e.g., a nourishing and water-repellent coating function) of executing at least one of nourishing and water-repellent coating of the shoe.

According to an embodiment, the processor 470 may not perform at least one of the first to fifth functions according to the material of the shoe. For example, in a case in which the material of the shoe is leather, the processor 470 may not perform the third function. Alternatively, in the case in which the material of the shoe is leather, the processor 470 may not perform a steaming function in the third function.

According to an embodiment, the processor 470 may control the air generating part 442 of the treatment part 440 to generate air to be discharged to the shoe. Also, the processor 470 may control the direction control part 436 and the discharge part 455 so that the generated air is discharged toward the shoe. In this way, the first function of removing foreign substances adsorbed onto the shoe may be performed.

The processor 470 may control the direction control part 436 to adjust a discharge direction or angle of the one or more ducts 458, 459, and 460 connected to the discharge part 455. The processor 470 may control the direction control part 436 so that the discharge direction or angle of the one or more ducts 458, 459, and 460 is toward the inner side or upper of the shoe.

According to an embodiment, the first function may include discharging air to the inside of a shoe cabinet through the ducts 458, 459, and 460 of a discharge tube disposed inside each of the shoe cabinets 321, 322, 323, and 324. Also, the first function may include suctioning foreign substances dislodged due to the discharged air through at least one suction tube (e.g., the fourth duct 461) disposed inside each of the shoe cabinets 321, 322, 323, and 324.

Also, the first function may include an operation of causing foreign substances attached to the lower portion of the shoe to be dislodged therefrom through rolling of at least one rolling brush disposed at the lower portion of each of the shoe cabinets 321, 322, 323, and 324 and suctioning the foreign substances, which are dislodged from the lower portion of the shoe, through at least one suction tube (e.g., the fourth duct 461).

According to an embodiment, the second function may include emitting UV light through at least one light emitting element disposed inside each of the shoe cabinets 321, 322, 323, and 324. Alternatively, the second function may include emitting at least one of a photocatalyst and a deodorizer through at least one emitting element (e.g., the UV light emitting part 422, the photocatalyst emitting part 424, or the plasma emitting part 426) disposed inside the shoe cabinet.

Also, the second function may include sanitizing and deodorizing a shoe through a plurality of light emitting elements (e.g., ten 3 mW LEDs). By emitting UV light, a photocatalyst, and plasma based on the second function to the shoe, rapid sanitization treatment (e.g., sanitization of airborne bacteria) may be possible for the shoe. Alternatively, the second function may include sanitizing and deodorizing a shoe through negative ions.

According to an embodiment, the third function may include discharging steam through the ducts 458, 459, and 460 of the discharge tube disposed inside each of the shoe cabinets 321, 322, 323, and 324. The third function may include heating a liquid through the steam generating part 444 (e.g., the LG TrueSteam™ system 311) of the shoe treating apparatus 310 and spraying the steam due to the heated liquid through at least one duct 458, 459, and 460 of the discharge tube disposed inside each of the shoe cabinets 321, 322, 323, and 324.

Also, the third function may include performing sanitization of various bacteria (e.g., *staphylococcus*) adsorbed onto the shoe through steam at a certain temperature (e.g., 50° C.). By spraying high-temperature steam based on the third function to the shoe, rapid sanitization treatment may be possible for the shoe, moisture of the shoe may be evaporated, and the shoe may be deodorized.

According to an embodiment, the fourth function may include discharging low-temperature hot air through the at least one duct 458, 459, and 460 of the discharge tube disposed inside each of the shoe cabinets 321, 322, 323, and 324. The fourth function may include heating a liquid to a certain temperature (e.g., 40° C.) through the low-temperature hot air generating part 446 or the steam generating part 444 (e.g., the LG TrueSteam™ system 311) of the shoe treating apparatus 310 and discharging the hot air due to the heated liquid through the ducts 458, 459, and 460 of the discharge tube disposed inside each of the shoe cabinets 321, 322, 323, and 324.

Also, the fourth function may include discharging the low-temperature hot air to the shoe cabinet so that the humidity of the shoe cabinet is maintained to be constant (to be about 20% to 40%). For example, the fourth function may include providing hot air so that the humidity inside the shoe cabinet is about 20% in a case in which the material of the shoe is fiber. For example, the fourth function may include providing hot air so that the humidity inside the shoe cabinet is about 40% in a case in which the material of the shoe is leather.

According to an embodiment, the fifth function may include emitting at least one of mist and air through the ducts 458, 459, and 460 of the discharge tube disposed inside each of the shoe cabinets 321, 322, 323, and 324.

Also, the fifth function may include mixing air introduced through the first duct 456 with a liquid that supplies nourishment to the shoe and spraying the mixture through the ducts 458, 459, and 460 of the discharge tube disposed inside each of the shoe cabinets 321, 322, 323, and 324.

According to an embodiment, each of the first to fifth functions may be performed for a predetermined amount of time (or a time input by a user) under control of the processor 470. For example, the first function may be performed for about four minutes, the second function may be performed for about three minutes, and the third function may be performed for about ten minutes. Also, the fourth function may be performed for about twenty minutes, and the fifth function may be performed for about three minutes.

At least one of the time during which each function is performed and the order of performing the functions may be variably automatically set or may be operated under control of the processor 470 on the basis of at least one of the material, function, type, and condition of a shoe. Also, the order of performing the functions may be an order in which the first function to the fifth function are performed in that order under control of the processor 470. Also, at least two or more functions may be simultaneously performed under control of the processor 470.

According to an embodiment, the processor 470 may control at least one of the UV light emitting part 422, the photocatalyst emitting part 424, and the plasma emitting part 426 of the emitting part 420 to generate the UV light, a photocatalyst, or plasma and direct it toward the shoe. Also, the processor 470 may allow the generated UV light, a photocatalyst, or plasma to be discharged toward the shoe so that the second function of steaming and/or deodorizing the shoe is performed.

According to an embodiment, the processor 470 may control the steam generating part 444 of the treatment part 440 to generate steam to be directed toward the shoe. Also, the processor 470 may control the direction control part 436 and the discharge part 455 to allow the generated steam to be discharged toward the shoe so that the third function of steaming and/or sanitizing the shoe is performed.

According to an embodiment, the processor 470 may control the direction control part 436 so that the discharge direction or angle of the one or more ducts 458, 459, and 460 connected to the discharge part 455 is toward the inner side or upper of the shoe.

According to an embodiment, the processor 470 may control the steam generating part 444 so that the temperature of the discharged steam reaches a predetermined temperature (e.g., 50° C.). The processor 470 may control the steam generating part 444 to variably adjust the steam temperature according to the material and type of the shoe so that damage to the material of the shoe is prevented.

According to an embodiment, the processor 470 may adjust the temperature of air introduced through the first duct 456 through the low-temperature hot air generating part 446 of the treatment part 440 to generate low-temperature hot air. Also, the processor 470 may allow the generated hot air to be discharged toward the shoe so that the fourth function of dehumidifying and/or drying the shoe is performed.

According to an embodiment, the processor 470 may control the direction control part 436 to adjust the discharge direction or angle of the one or more ducts 458, 459, and 460 connected to the discharge part 455.

According to an embodiment, the processor 470 may control the low-temperature hot air generating part 446 so that the temperature of the discharged hot air reaches a predetermined temperature (e.g., 40° C.). The processor 470 may control the low-temperature hot air generating part 446 to variably adjust the hot air temperature according to the material and type of the shoe so that damage to the material of the shoe is prevented.

According to an embodiment, the processor 470 may control the water repellent part 448 of the treatment part 440 to generate a spraying liquid (e.g., mist) to be directed toward the shoe. Also, the processor 470 may control the direction control part 436 and the discharge part 455 to allow the generated spraying liquid to be discharged toward the shoe so that the fifth function of supplying nourishment to the shoe and/or treating the shoe to be water repellent is performed.

According to an embodiment, the processor 470 may control the water repellent part 448 of the treatment part 440 to generate the spraying liquid.

Alternatively, the processor 470 may control the direction control part 436 so that the discharge direction or angle of the one or more ducts 458, 459, and 460 is not toward the inner side of the shoe.

According to an embodiment, the processor 470 may use at least one sensor to identify an approach of a user. The processor 470 may identify an approach of a user toward the shoe treating apparatus 310 through at least one sensor (e.g., the camera 432, the distance measurement sensor 416, the IR sensor 419, or the like) disposed on the front surface of the shoe treating apparatus 310 (e.g., on the doors 110, 120, 130, and 140).

According to an embodiment, the processor 470 may cause at least one light emitting element (e.g., LED) disposed on at least one of the plurality of shelves of the upper cabinet 150 and/or at least one of the plurality of shelves of the lower cabinet 160 (e.g., disposed on the lower portion of the shelf) to emit light on the basis of the approach of the user. The processor 470 may adjust the brightness of the at least one light emitting element on the basis of a distance between the shoe treating apparatus 310 and the user.

For example, the processor 470 may cause the at least one light emitting element to emit more light as the distance between the shoe treating apparatus 310 and the user becomes shorter and may cause the at least one light emitting element to emit less light as the distance between the shoe treating apparatus 310 and the user becomes longer.

Alternatively, the processor 470 may control the at least one light emitting element so that the at least one light emitting element emits different colored lights on the basis of the distance between the shoe treating apparatus 310 and the user.

According to an embodiment, the processor 470 may generate a control signal for adjusting tilting of at least one shelf included in the upper cabinet 150 on the basis of the approach of the user.

Alternatively, the processor 470 may generate a control signal for adjusting tilting of at least one shelf included in the lower cabinet 160 on the basis of the approach of the user.

According to an embodiment, the processor 470 may identify the height of the user and, on the basis of the identified height of the user, generate a control signal for adjusting tilting of at least one shelf of the upper cabinet 150 or the lower cabinet 160.

According to an embodiment, the processor 470 may acquire information on atilt angle for each height stored in the memory 434 and, on the basis of the acquired information, generate a control signal for adjusting atilt angle of at least one shelf of the upper cabinet 150 or the lower cabinet 160. The processor 470 may adjust a tilt angle of each shelf on the basis of the height of the user.

For example, the tilt angle of the at least one shelf may be larger when the height of the user is shorter, and the tilt angle of the at least one shelf may be smaller when the height of the user is taller.

For example, a tilt angle of the highest shelf in the upper cabinet 150 may be the largest. Also, the tilt angle of a shelf progressively decreases for shelves disposed below the highest shelf.

According to an embodiment, the processor 470 may identify whether at least one of the doors 110, 120, 130, and 140 of the shoe treating apparatus 310 are open through at least one sensor (e.g., the door open/close sensor 412, the fingerprint sensor 418, and the knock-on sensor 417) and, on the basis of the opening of the door, stop an operation of at least one shelf that is currently tilting.

According to an embodiment, the processor 470 may identify a user through at least one sensor (e.g., the camera 432, the distance measurement sensor 416, the fingerprint sensor 418, and the IR sensor 419) and may identify a position on which at least one shoe corresponding to the identified user is placed on a shelf part (e.g., a shelf of the upper cabinet 150).

Also, the processor 470 may display at least part of condition information of the at least one shoe corresponding to the identified position and information on the identified position through the display part 433.

According to an embodiment, the processor 470 may display state information based on at least one of normal treatment on at least one shoe stored in the upper cabinet 150 of the shoe treating apparatus 310 and intensive treatment on at least one shoe stored in the lower cabinet 160 of the shoe treating apparatus 310 through the display part 433.

According to an embodiment, the state information may include information on a state of normally treating the at least one shoe through adjusting at least one of the temperature and humidity inside the upper cabinet 150, in which the at least one shoe is stored, on the basis of at least one of the material, type, and condition of the at least one shoe.

According to an embodiment, the state information may include information on a state of intensively treating at least one shoe inside the lower cabinet 160, in which the at least one shoe is stored, by using at least one of the foreign substance removal function, sanitizing and deodorizing function, steaming and sanitizing function, dehumidifying and drying function, and nourishing and water-repellent coating function on the basis of at least one of the material, type, and condition of the at least one shoe.

According to an embodiment, the processor 470 may acquire an image of at least one shoe stored in the shelf part (e.g., a shelf of the upper cabinet 150) through the camera 432 and may compare the acquired image with an image pre-stored in the memory 434. Also, the processor 470 may identify a position at which the at least one shoe corresponding to the identified user is placed. The memory 434 may store user information (e.g., name (for example, Gil-dong Hong etc.), relation (for example, father, mother, son, daughter, etc.), and height (for example, 170 cm, 180 cm, etc.)) for each shoe.

According to an embodiment, the processor 470 may, when the acquired image matches an image pre-stored in the memory 434 as a result of comparing the two, acquire information on a user (e.g., owner) of the shoe corresponding to the acquired image.

Therefore, the processor 470 may identify a user of each shoe and identify the position of a shoe placed on a shelf part (e.g., a shelf of the upper cabinet 150 or a shelf of the lower cabinet 160).

According to an embodiment, the processor 470 may, through an identifier allocated for each of the plurality of shelves in the shelf part (e.g., the upper cabinet 150), identify the position at which at least one shoe corresponding to the identified user is placed. The identifier may include information for distinguishing a shelf on which at least one shoe of each of a plurality of users is placed.

The memory 434 may store an identifier for each shelf of the upper cabinet 150 and each shelf of the lower cabinet 160. Also, the processor 470 may, through the identifier stored in the memory 434, identify the position at which the at least one shoe corresponding to the identified user is placed.

According to an embodiment, the processor 470 may identify the user and identify whether any one of the doors 110, 120, 130, and 140 of the shoe treating apparatus 310 is opened. Also, when any one of the doors 110, 120, 130, and 140 is identified as being opened, the processor 470 may, through at least one of the weight sensor 414, the camera 432, and the distance measurement sensor 416 disposed inside the upper cabinet of the shoe treating apparatus 310, identify whether a shoe is stored. Also, when the shoe is identified as being stored, the processor 470 may determine that the stored shoe is a shoe corresponding to the user.

According to an embodiment, the processor 470 may, when a user is identified, measure the height of the identified user and may acquire a tilt angle of the at least one shelf corresponding to the measured height from the memory 434.

The memory 434 may include information on tilt angles of shelves according to various heights. Table 1 below shows tilt angles according to the height of the user and the position of each shelf of the upper cabinet 150. For example, a first shelf is the highest shelf, a second shelf is a shelf disposed below the first shelf, and a third shelf is a shelf disposed below the second shelf

TABLE 1

| | Upper cabinet 150 | |
|---|---|---|
| 150 cm or less | First shelf | 45° |
| | Second shelf | 40° |
| | Third shelf | 35° |
| 151 cm to 160 cm | First shelf | 40° |
| | Second shelf | 35° |
| | Third shelf | 30° |
| 161 cm to 170 cm | First shelf | 35° |
| | Second shelf | 30° |
| | Third shelf | 25° |
| 171 cm to 180 cm | First shelf | 30° |
| | Second shelf | 25° |
| | Third shelf | 20° |
| 181 cm or more | First shelf | 25° |
| | Second shelf | 20° |
| | Third shelf | 15° |

Table 1 above shows tilt angles of a plurality of shelves (e.g., the first shelf, the second shelf, and the third shelf) included in the upper cabinet 150, but this is only an embodiment, and tilt angles of a plurality of shelves included in the lower cabinet 160 may be stored in the memory 434. Also, the heights and tilt angles of Table 1 above are only an embodiment, and the memory 434 may include various other tilt angles according to the user height, spacing between shelves, and the size, position, installation height, etc. of the shoe treating apparatus 310.

According to an embodiment, the processor 470 may generate a control signal on the basis of the acquired tilt angle of at least one shelf that is stored in the memory 434 and, on the basis of the generated control signal, control tilting of each of the plurality of shelves (e.g., the first shelf, the second shelf, and the third shelf) included in the upper cabinet 150.

According to an embodiment, the upper cabinet 150 may include, in addition to the plurality of shelves (e.g., the first shelf, the second shelf, and the third shelf), a shelf moving in the vertical direction (e.g., a fourth shelf).

According to an embodiment, the processor 470 may, through the motor part 437, control the fourth shelf which is the lowest among the plurality of shelves (e.g., the first shelf, the second shelf, the third shelf, and the fourth shelf) included in the upper cabinet 150 to move in the vertical direction. Also, the processor 470 may, through the motor part 437, control at least one shelf disposed above the fourth shelf (e.g., the first shelf, the second shelf, and the third shelf) to tilt.

According to an embodiment, the processor 470 may transmit a control signal to the motor part 437 to adjust the tilt speed of the at least one shelf. The processor 470 may, through the motor part 437, control the tilting direction of each of the plurality of shelves to be different from that of another shelf disposed above or below the shelf.

According to an embodiment, the processor 470 may, through at least one sensor, identify whether a door of the shoe treating apparatus 310 is opened and may, through the motor part 437, stop an operation of the at least one shelf that is currently tilting on the basis of the opening of the door.

The processor 470 may, through the at least one sensor, identify whether a door of the shoe treating apparatus 310 is closed and may, on the basis of the closing of the door, operate the upper cabinet 150 of the shoe treating apparatus 310 in the normal treatment mode again.

According to an embodiment, the processor 470 may display a screen for setting at least one tapping pattern for controlling the operation of the shoe treating apparatus 310 on the display part 433 of the shoe treating apparatus 310 or on one side of a door of the shoe treating apparatus 310 (e.g., the left and right doors 110 and 120 of the upper cabinet 150, or the left and right doors 130 and 140 of the lower cabinet 160). For example, the display part 433 may be disposed on a transparent member (e.g., a smart mirror) of a door of the upper cabinet 150 or on one side of the doors 110 and 120 of the upper cabinet 150.

According to an embodiment, the processor 470 may, on the basis of an input of a tapping pattern through the doors 110 and 120 of the upper cabinet 150, control the smart mirror disposed on the door to become transparent. A tapping pattern relating to the transparency of the smart mirror may be set or not set. For example, when a certain tap is input onto the smart mirror, the processor 470 may control the smart mirror to become transparent.

According to an embodiment, the screen may include a menu for setting at least one of opening of at least one of the doors 110 and 120 of the upper cabinet 150 of the shoe treating apparatus 310, locking of at least one of the doors 110 and 120 of the upper cabinet 150, and lighting control of at least one light emitting element disposed on at least one shelf of the upper cabinet 150 or deleting settings.

Also, the screen may include a menu for setting at least one of opening of at least one of the doors 130 and 140 of the lower cabinet 160 of the shoe treating apparatus 310, locking of at least one of the doors 130 and 140 of the lower cabinet 160, lighting control of at least one light emitting element disposed on at least one shelf of the lower cabinet 160, and lighting control of at least one shelf on which a shoe is placed for each user or deleting settings.

According to an embodiment, the processor 470 may identify at least one tapping pattern corresponding to at least one function of the shoe treating apparatus 310 through the sensor part 410 (e.g., the knock-on sensor 417).

According to an embodiment, the processor 470 may, through the sensor part 410 (e.g., the knock-on sensor 417), identify time intervals between taps of the tapping pattern and the intensity of each tap.

According to an embodiment, the sensor part 410 (e.g., the knock-on sensor 417) may include a microphone configured to detect a sound wave signal due to the tapping pattern and convert the detected sound wave signal to an electrical signal, an amplifier configured to amplify the converted signal, and a filter configured to remove noise from the amplified signal.

Also, the sensor part 410 (e.g., the knock-on sensor 417) may include a microcontroller (MiCom) configured to, on the basis of the signal from which noise is removed, determine whether a tapping pattern has been input and configured to, when it is determined that the tapping pattern has been input, transmit time intervals between taps and the intensity of each tap according to the tapping pattern to the processor 470.

According to an embodiment, the processor 470 may match the tapping pattern to a function of the shoe treating apparatus 310. For example, the processor 470 may, when a tapping pattern is input after a function to be set by a user is selected among a plurality of functions displayed on the screen, match the input tapping pattern to the selected function. The matching is to, for example, in a case in which a user wants to control an operation of the shoe treating apparatus 310, allow the user to control the corresponding function by inputting a predetermined tapping pattern.

According to an embodiment, the processor 470 may store the matched result (e.g., information on a function to be executed on the basis of each time interval and each intensity) in the memory 434. The processor 470 may set a certain margin for each time interval and each intensity. The margin is a certain range of each time interval and a certain range of each intensity, and in a case in which the time interval and the intensity are included in the margin, the processor 470 may recognize an input tapping pattern as a tapping pattern for executing the corresponding function.

According to an embodiment, the processor 470 may, on the basis of an input of a tapping pattern (e.g., a first tapping pattern) by tapping a door of the shoe treating apparatus 310 (e.g., the left and right doors 110 and 120 of the upper cabinet 150 or the left and right doors 130 and 140 of the lower cabinet 160), compare the input tapping pattern with at least one tapping pattern matched and stored in the memory 434.

For example, the processor 470 may, through time intervals between taps of a first tapping pattern and a sound wave intensity of each tap, identify a tapping pattern identical (or similar within a margin range) to the first tapping pattern among a plurality of tapping patterns pre-stored in the memory 434.

According to an embodiment, the processor 470 may identify whether the first tapping pattern corresponds to a second tapping pattern among one or more tapping patterns stored in the memory 434. Also, the processor 470 may, when the input first tapping pattern corresponds to the second tapping pattern, execute a function matched to the second tapping pattern (e.g., a function set in the second tapping pattern).

According to an embodiment, the memory 434 may, on the basis of tapping patterns, store information on time intervals between taps of at least one tapping pattern controlling an operation of the shoe treating apparatus 310 and information on the intensity of each tap.

According to an embodiment, the processor 470 may identify whether a user touches a handle of a door of the shoe treating apparatus. The processor 470 may identify whether a user touches a handle of a door of the shoe treating apparatus through fingerprint information acquired by the fingerprint sensor 418 which is disposed on inner sides of the doors 110 and 120 of the upper cabinet 150 of the shoe treating apparatus 310 or disposed on inner sides of the doors 130 and 140 of the lower cabinet 160 of the shoe treating apparatus 310.

Alternatively, the processor 470 may identify whether a user touches a handle of a door of the shoe treating apparatus through at least one sensor of the sensor part 410.

According to an embodiment, the processor 470 may adjust a strength of sanitization, which uses at least one first light emitting element of the light emitting part 439, to be different for each user (e.g., father, mother, son, daughter, etc.) touching a handle of the upper cabinet 150 or a handle of the lower cabinet 160.

For example, in a case in which a user touching a handle of the upper cabinet 150 or a handle of the lower cabinet 160 is a father who frequently goes out, the processor 470 may adjust the strength of sanitization using at least one first light emitting element of the light emitting part 439 to "high" to sanitize the handle.

For example, in a case in which a user touching a handle of the upper cabinet 150 or a handle of the lower cabinet 160 is a mother who does not go out frequently, the processor 470 may adjust the strength of sanitization using at least one first light emitting element of the light emitting part 439 to "low" to sanitize the handle.

In this way, the processor 470 may adjust the strength of sanitizing a handle on the basis of the degree of contamination of the user's hands, outgoing time, or the frequency of going out.

According to an embodiment, in a case in which a handle is currently being sanitized, the processor 470 may cause at least one second light emitting element of the light emitting part 439 to emit light to indicate that the handle is being sanitized. For example, the first light emitting element may include an LED, and the second light emitting element may include a UVC LED.

For example, one or more first light emitting elements and one or more second light emitting elements may be alternately disposed on an inner side of a door of the upper cabinet of the shoe treating apparatus.

According to an embodiment, the lower cabinet 160 of the shoe treating apparatus 310 may further include a reflective plate configured to reflect light emitted from the second light emitting element. Light reflected through the reflective plate may be reflected to a handle portion of each of the upper cabinet 150 and the lower cabinet 160 to sanitize the handle portion.

According to an embodiment, the processor 470 may store the number of times each user has touched a handle and a time window in which the user has touched the handle in the memory 434.

According to an embodiment, on the basis of the number of times each user has touched a handle and a time window in which the touch occurred, the processor 470 may display a notification message that induces hand washing for each user through the display part 433. The notification message may include various pieces of information on contamination of hands such as the importance of hand washing and a method of hand washing. The display part 433 may be disposed on the doors 110 and 120 (e.g., smart mirrors 3510 and 3520) of the upper cabinet 150 or disposed on lower portions of the doors 110 and 120.

According to an embodiment, the processor 470 may set the strength of sanitizing a handle (e.g., high, intermediate, low) on the basis of at least some of the identified user, the number of times the user has touched the handle, and a time window in which the user has touched the handle. For example, in a case in which the current time reaches the time window, the processor 470 may sanitize the handle on the basis of the set sanitization strength.

According to an embodiment, when it is identified through the sensor part 410 that a shoe is stored in a state in which a shelf is folded, the processor 470 may identify the height of the shoe through a first sensor disposed at the highest position inside the cabinet in which the shoe is stored and one or more second sensors sequentially disposed below the first sensor to acquire a distance value. A plurality of sensors for measuring the height (or length) of a shoe may be vertically disposed on an inner wall of a cabinet (e.g., each cabinet of the lower cabinet 160) of the shoe treating apparatus 310. The distance value may include, for example, a value of a distance between a sensor and a shoe or a value of a distance between a sensor and an inner wall (e.g., a second inner wall) that faces the above inner wall (e.g., a first inner wall).

For example, in a case in which a distance value acquired by the sensor disposed at the highest position (e.g., the first sensor) and a distance value acquired by the second sensor disposed right below the first sensor are the same (e.g., the same within a range that ignores error), it can be seen that the height of a shoe is lower than the height at which the second sensor is disposed inside the cabinet.

For example, in a case in which a distance value acquired by a third sensor disposed right below the second sensor is less than the distance value acquired by the second sensor by a predetermined value (e.g., 5 cm) or more, it can be seen that the height of a shoe is the same as (or similar to) the height at which the third sensor is disposed inside the cabinet.

In this way, the processor 470 may acquire distance values measured by the first sensor and one or more second sensors vertically disposed below the first sensor and may identify one or more third sensors that measured distance values different from the acquired distance values.

Also, the processor 470 may identify that the height of a sensor disposed at the highest position among the identified one or more third sensors is the height of the shoe.

According to an embodiment, on the basis of a comparison between the height of the identified shoe and a predetermined height, the processor 470 may generate a control signal for controlling unfolding or folding of a shelf in the cabinet in which the identified shoe is stored. The predetermined height may include a height from the bottom of a single shoe cabinet to a shelf disposed thereabove.

According to an embodiment, the height from the bottom of the shoe cabinet to a shelf disposed thereabove may vary according to manufacture of the shoe treating apparatus. For example, the height from the bottom of the shoe cabinet to a shelf disposed thereabove may be about 20 cm. Alternatively, the height from the bottom of the shoe cabinet to a shelf disposed thereabove may be less than or greater than about 20 cm. The height may be variably adjusted.

For example, in a case in which the height of the identified shoe is not greater than the predetermined height, the processor 470 may generate a control signal for controlling a motor physically connected to the shelf so that a shelf disposed above the cabinet in which the shoe is stored is unfolded.

For example, in a case in which the height of the identified shoe is greater than the predetermined height, the processor 470 may not control the motor physically connected to the shelf so that the shelf disposed above the cabinet in which the shoe is stored maintains a folded state.

In this way, in a case in which the height of the shoe is less than the predetermined height, the processor 470 may generate a control signal for controlling the corresponding motor so that the shelf is unfolded and may transmit the generated control signal to the corresponding motor to control an operation so that the shelf is unfolded.

Alternatively, in a case in which the height of the shoe is not less than the predetermined height, the processor 470 may control the corresponding motor so that the shelf maintains a folded state.

According to an embodiment, at least one shelf of a shoe cabinet (e.g., the lower cabinet 160) of the shoe treating apparatus 310 may be formed in a structure that is folded or unfolded on the basis of the height of a shoe. Also, portions where the shelf is folded may be connected to each other through a hinge.

Also, in order to prevent at least part of air, steam, low-temperature hot air, and water repellent from leaking through portions where the at least one shelf is folded, rubber packing may be formed on the portions. Thus, in a case in which the shelf is unfolded, at least part of air, steam, low-temperature hot air, and water repellent may not leak.

According to an embodiment, the processor 470 may, on the basis of detecting a shoe (or detecting the type of shoe) in a storage space (e.g., at least one storage space 4810 of the lower cabinet 160), rotate a rotatable duct part toward the inside of the detected shoe. The rotatable duct part may be disposed on an upper portion of each storage space. Also, the rotatable duct part may be embedded in an upper portion of each storage space and may protrude by rotating toward the inside of the storage space.

According to an embodiment, the processor 470 may, on the basis of identification of the type of shoe, determine whether to rotate the rotatable duct part. The processor 470 may, on the basis of the type (or height) of the identified shoe, determine whether to rotate the rotatable duct part toward the inside of the storage space.

According to an embodiment, when it is determined on the basis of the type (or height) of the identified shoe that the height of the shoe is a first predetermined height or less, the processor 470 may rotate the rotatable duct part. The first predetermined height may be a height at which the height of the shoe does not interfere with rotation of the rotatable duct part.

According to an embodiment, in a case in which the height of the shoe is a second predetermined height or less, the processor 470 may rotate the rotatable duct part and expand an expandable duct part formed in the rotatable duct part toward the inside of the shoe. The second predetermined height may be the same as or less than the first predetermined height.

According to an embodiment, in a case in which, on the basis of the type (or height) of the identified shoe, the height of the shoe exceeds the first predetermined height, the processor 470 may not rotate the rotatable duct part.

For example, in a case in which, when the height of the storage space is 50 cm and the length of the rotatable duct part is 10 cm, the height of the identified shoe is greater than a first predetermined height (e.g., a height obtained by subtracting the length of the rotatable duct part from the height of the storage space (e.g., 40 cm)), the processor 470 may not rotate the rotatable duct part. Also, the processor 470 may, through the display part 433, display information indicating that the shoe has a height that makes it impossible to treat the shoe.

For example, the values of the height of the storage space, the height of the shoe, the first predetermined height, and the second predetermined height are only an embodiment, and the present invention may also be applied to storage spaces and shoes having various other height values.

According to an embodiment, the expandable duct part may be connected to the rotatable duct part (e.g., a lower portion of the rotatable duct part) and may extend downward (or toward the inside of the shoe) from the rotatable duct part which is rotated toward the inside of the storage space (or the inside of the shoe).

According to an embodiment, the expandable duct part may include a second duct connected to a first duct formed in the rotatable duct part. For example, the first duct and the second duct may constitute a single duct. The first duct and the second duct may be formed in the rotatable duct part and the expandable duct part to discharge at least part of air, steam, low-temperature hot air, and water repellent, which are introduced through the first duct, to the inside of the shoe through the second duct.

According to an embodiment, the expandable duct part may be formed to include an upper duct part, a variable duct part which is connected to a lower side of the upper duct part and has a shape that may be changed by an external force, and a lower duct part which is connected to a lower side of the variable duct part and has a roller brush disposed on a lower portion. The upper duct part and the lower duct part may be coupled through the variable duct part whose shape may be changed by an external force.

Also, a roller for reducing friction against the bottom of a shoe may be disposed on the lower portion of the lower duct part. For example, in a case in which the expandable duct part expands toward the inside of a shoe, the lower portion of the lower duct part may come in contact with the bottom of the shoe.

In this state, in a case in which the expandable duct part continues to expand to the inside of the shoe, due to the roller disposed at the lower portion of the lower duct part and the variable duct part, an expanding direction of the lower duct part may be a direction different from an expanding direction of the upper duct part.

According to an embodiment, the processor 470 may control a motor in the rotatable duct part to allow the expandable duct part to repeatedly perform expansion to the outside of the rotatable duct part and insertion into the rotatable duct part on the basis of the height of a shoe in the storage space. The processor 470 may allow the expandable duct part to repeatedly perform the expansion and insertion during a shoe treatment process to thoroughly treat the inside of the shoe.

According to an embodiment, when the identified shoe is determined as a type having a height greater than a predetermined height (e.g., boots, rain boots, or the like), the processor 470 may control the motor in the rotatable duct part to allow the expandable duct part to repeatedly perform expansion to the outside of the rotatable duct part and insertion into the rotatable duct part.

According to an embodiment, the processor 470 may control treatment on the detected shoe through the rotatable duct part which is rotated toward the inside of the detected shoe. The processor 470 may discharge at least part of air, steam, low-temperature hot air, and water repellent, which are generated in the treatment part 440, to the inside of the shoe through a duct in the rotatable duct part to treat the inside of the shoe.

According to an embodiment, the processor 470 may treat the inside of the shoe through at least one light emitting element disposed on a lower portion of the rotatable duct part. The light emitting element may include a UVC LED. The light emitting element may be disposed on the lower portion of the rotatable duct part.

According to an embodiment, the processor 470 may identify whether treatment (e.g., intensive treatment) on the shoe has ended. Also, on the basis of an end of treatment on the detected shoe, the processor 470 may control the motor in the rotatable duct part to rotate the rotatable duct part toward an upper portion of the storage space. The processor 470 may embed the rotatable duct part in the upper portion of the storage space so that the shoe returns to a state before the shoe is detected.

According to an embodiment, the rotatable duct part may be the ducts 458, 459, and 460 of FIG. 4.

According to an embodiment, the processor 470 may, on the basis of the material, type, and condition of the shoe, set the rotational speed, operation time, and rotational direction of one or more rolling brushes of a rolling brush module 6300 disposed on the lower portion of the storage space and may operate the one or more rolling brushes on the basis of the set rotational speed, operation time, and rotational direction.

According to an embodiment, the rolling brush module 6300 may be detached from or attached to the shoe treating apparatus 310 (e.g., the lower cabinet 160).

According to an embodiment, the rolling brush module 6300 may include a wireless charging module configured to wirelessly receive power, a battery configured to store the received power, a holder coupled to the rolling brush module 6300 to prevent falling of a shoe due to an operation of a rolling brush, and a tray detachably mounted on a lower portion of the rolling brush module 6300 to store foreign substances that are dislodged from the shoe.

According to an embodiment, the rolling brush may include at least one brush configured to remove foreign substances adsorbed onto the lower portion of a shoe, a brush body configured to fix the at least one brush, at least one light emitting element coupled to the brush body to sanitize the lower portion of the shoe, a motor configured to rotate the rolling brush, and a vibrator configured to vibrate the rolling brush.

The rolling brush module 6300 will be described in detail below with reference to FIGS. 63, 64, and 65.

According to an embodiment, the processor 470 may, on the basis of the material (e.g., leather, fabric, rubber, or the like), type (e.g., sneakers, heels, or the like), and condition (e.g., cleanliness) of a shoe, set the rotational speed (e.g., revolutions per minute (RPM)), operation time (e.g., ten minutes), and rotational direction (e.g., clockwise/counterclockwise rotation) of the one or more rolling brushes.

Also, the processor 470 may operate the one or more rolling brushes on the basis of the set rotational speed, operation time, and rotational direction.

According to an embodiment, the processor 470 may, on the basis of the position of the identified shoe, rotate the one or more rolling brushes in the same direction (e.g., clockwise or counterclockwise) so that the identified shoe is moved to a position (e.g., a position at which at least part of air, steam, low-temperature hot air, and water repellent are discharged from a discharge tube) that corresponds to the position of the discharge tube (e.g., the ducts 458, 459, and 460) formed in the storage space.

Also, when the shoe is moved to the position (e.g., the position at which at least part of air, steam, low-temperature hot air, and water repellent are discharged from the discharge tube) that corresponds to the position of the discharge tube (e.g., the ducts 458, 459, and 460), the processor 470 may stop rotation of the one or more rolling brushes.

According to an embodiment, in a case in which the amount of foreign substances adsorbed onto a shoe (e.g., the bottom of the shoe) is large, the processor 470 may set the operation time of the one or more rolling brushes as a first time (e.g., ten minutes).

For example, in a case in which the amount of foreign substances adsorbed onto a shoe (e.g., the bottom of the shoe) is not large, the processor 470 may set the operation time of the one or more rolling brushes as a second time (e.g., five minutes) which is less than the first time (e.g., ten minutes). The time may be variably adjusted according to the amount of foreign substances adsorbed onto the shoe, the material of the shoe, and the type of the shoe.

According to an embodiment, through the weight of a shoe acquired through at least one weight sensor 414, the processor 470 may identify one or more rolling brushes on which the shoe is placed.

Also, the processor 470 may operate a motor (e.g., a motor of the motor part 437) coupled to each of the identified one or more rolling brushes to cause the rolling brush to rotate (e.g., clockwise and/or counterclockwise).

According to an embodiment, the processor 470 may rotate the rolling brush (e.g., a first rolling brush) in a direction (e.g., counterclockwise) that is opposite to a rotational direction (e.g., clockwise) of another rolling brush (e.g., a second rolling brush) adjacent to the rolling brush (e.g., the first rolling brush).

For example, the processor 470 may rotate the first rolling brush clockwise and rotate the second rolling brush, which is adjacent to the first rolling brush, counterclockwise. Also, the processor 470 may rotate a third rolling brush, which is adjacent to the second rolling brush, clockwise. In this way, the processor 470 may rotate a rolling brush in a direction opposite to a rotational direction of other rolling brushes adjacent to the rolling brush.

According to an embodiment, in a state in which the one or more rolling brushes are rotating or not rotating, the processor 470 may vibrate at least one vibrator disposed at one side of the rolling brush module 6300 to vibrate the one or more rolling brushes.

According to an embodiment, the processor 470 may treat a shoe on the basis of at least one of the first to fifth functions during an operation time which is set according to the condition, type, and material of the shoe. Also, when the set operation time has elapsed, the processor 470 may rotate the corresponding rolling brush through the motor coupled to each rolling brush and may cause at least one light emitting element disposed in the rolling brush (e.g., a rolling body) to emit light to sanitize the bottom of the shoe.

Hereinafter, shoe treatment of the shoe treating apparatus 310 will be described.

[Shoe Treatment]

Figure 5:
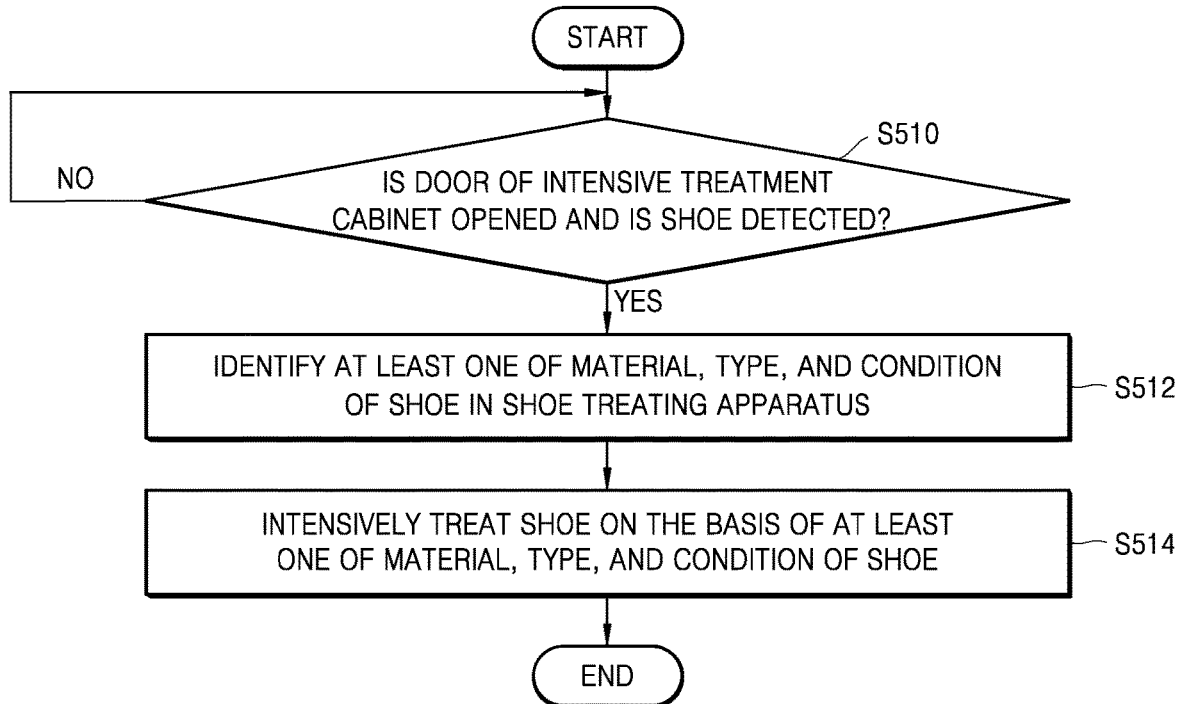
FIG. 5 is a flowchart illustrating a shoe treating process according to an embodiment of the present invention.
Figure 6:
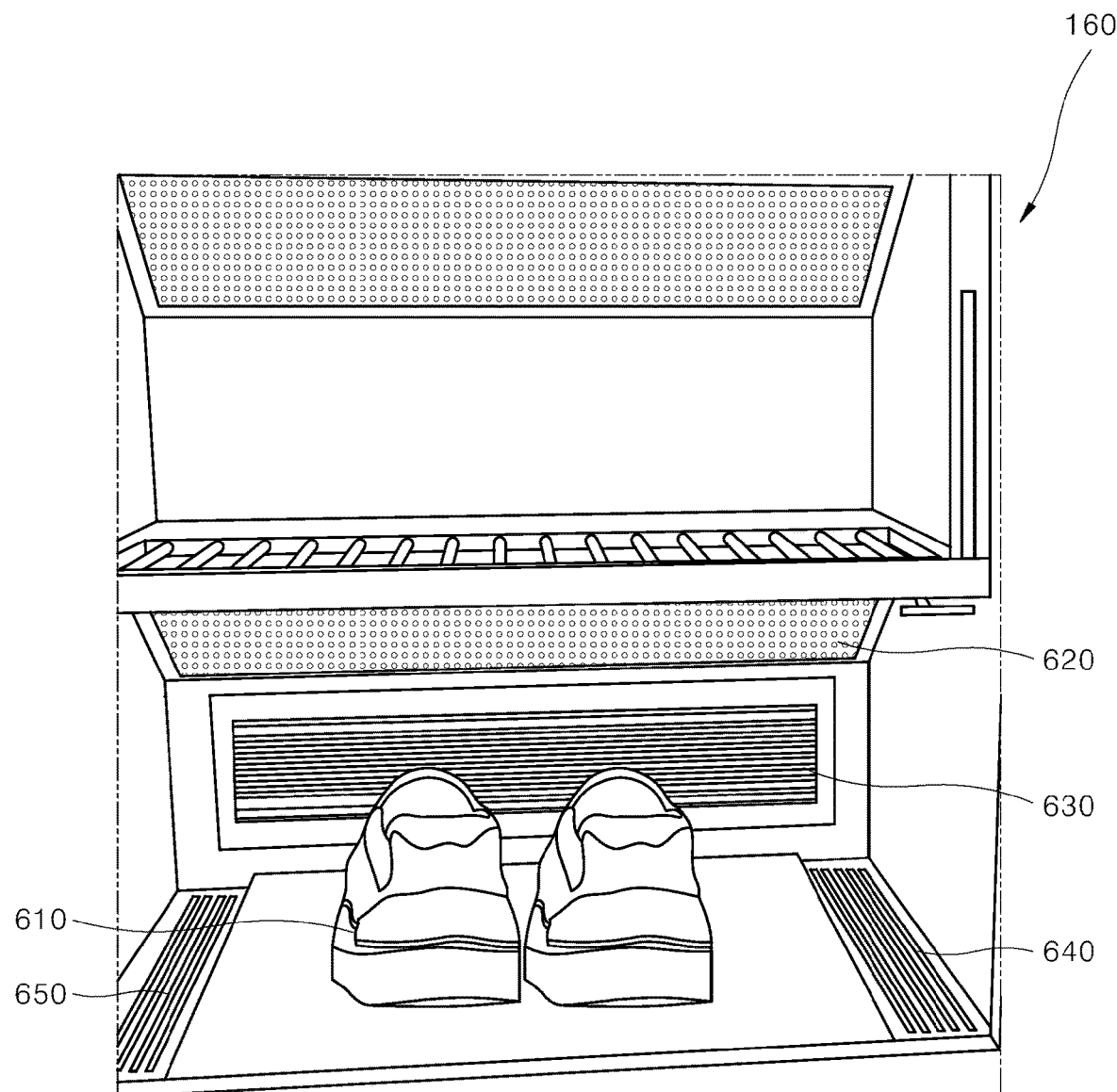
FIG. 6 is an exemplary view illustrating a storage space of a lower cabinet according to an embodiment of the present invention.

FIG. 5 is a flowchart illustrating a process of intensively treating a shoe according to an embodiment of the present invention. FIG. 6 is an exemplary view illustrating a storage space of a lower cabinet according to an embodiment of the present invention.

Hereinafter, the process of intensively treating a shoe according to an embodiment of the present invention will be described in detail with reference to FIGS. 5 and 6.

According to an embodiment, the processor 470 of the shoe treating apparatus 310 may identify whether a door of an intensive treatment cabinet (e.g., the lower cabinet 160) is opened and/or whether a shoe is present in the lower cabinet 160 (S510). The processor 470 may receive a signal according to whether the door is opened or closed from the door open/close sensor 412 and may detect whether the door is opened or closed.

According to an embodiment, the processor 470 may, through at least one of the camera 432 (e.g., an RGB camera, a vision camera) and the weight sensor 414 disposed on the lower portion of the lower cabinet 160, identify whether a shoe is present in the lower cabinet 160.

According to an embodiment, the processor 470 may identify at least one of the material, function, type, and condition of the shoe in the lower cabinet 160 (S512). The processor 470 may identify at least one of the material, function, type, and condition of the shoe in the lower cabinet 160 through at least one of the sensor part 410 and the camera 432. The weight sensor 414 may be disposed at the center of the bottom of the lower cabinet 160.

For example, for a shoe made of a genuine leather material (e.g., leather, suede), it is important that the shoe does not become wet and the humidity of the shoe is maintained at 40%. Therefore, preferably, a shoe made of a genuine leather material should be stored in a well-ventilated place that absorbs foot sweat well.

Preferably, a shoe made of a genuine leather material should be dusted using a brush or an air brush and should be hydrated and maintained in that state. Also, preferably, a shoe made of a genuine leather material should be managed at a certain temperature (e.g., 45° C.) or below.

For example, for a shoe made of a synthetic leather material (e.g., general fiber), care should be taken since adhesion may be weakened due to a high temperature, and it is preferable that the shoe is stored at a certain temperature (e.g., 60° C.) or below.

For example, for a shoe made of a functional material (e.g., hiking shoes, running shoes, soccer shoes, and the like), care should be taken since adhesion may be weakened due to a high temperature, and it is preferable that the shoe is stored at a certain temperature (e.g., 45° C.) or below.

According to an embodiment, the memory 434 of the shoe treating apparatus 310 stores data relating to the temperature, humidity, degree of ventilation, and the like according to the material, function, type, and condition of the shoe. Also, the processor 470 may acquire the corresponding data according to the material, function, type, and condition of the shoe from the memory 434.

According to an embodiment, the processor 470 may intensively treat the shoe on the basis of at least one of the material, function, type, and condition of the shoe (S514). The processor 470 may intensively treat the shoe (e.g., perform at least one or some of foreign substance removal, sanitization/deodorization, steaming/sanitization, dehumidification/drying, and nourishing/water-repellent coating) through at least one element of the shoe treating apparatus 310.

According to an embodiment, the processor 470 may execute at least one of the first function of removing foreign substances adsorbed onto the shoe, the second function of executing at least one of sanitization and deodorization of the shoe, the third function of executing at least one of steaming and sanitization of the shoe, the fourth function of executing at least one of dehumidification and drying of the shoe, and the fifth function of executing at least one of nourishing and water-repellent coating of the shoe.

According to an embodiment, the processor 470 may perform the first to fifth functions for a predetermined amount of time (about forty minutes).

According to an embodiment, the processor 470 may control the direction control part 436 and the discharge part 455 to allow air to be discharged toward a shoe 610 through one or more ventilation parts 620, 630, 640, and 650. In this way, the first function of removing foreign substances adsorbed onto the shoe may be performed. For example, as illustrated in FIGS. 5 and 6, air, steam, or the like discharged through the one or more ducts 458, 459, and 460 connected to the discharge part 455 is sprayed toward the shoe 610 through the one or more ventilation parts 620, 630, 640, and 650.

According to an embodiment, through the one or more ventilation parts 620, 630, 640, and 650, at least one of air, steam, and liquid for treating the shoe may be discharged, or foreign substances due to a shoe in the lower cabinet 160 may be suctioned. The ventilation part may be disposed at an arbitrary position in the lower cabinet 160. Also, the one or more ventilation parts 620, 630, 640, and 650 may be connected to at least one of the ducts 461, 458, 459, and 460.

According to an embodiment, the processor 470 may emit at least one of a photocatalyst and a deodorizer through at least one emitting element (e.g., the UV light emitting part 422, the photocatalyst emitting part 424, the plasma emitting part 426) disposed inside the lower cabinet 160 to perform the second function of sanitizing and/or deodorizing the shoe.

According to an embodiment, the processor 470 may perform the third function of discharging steam through a duct of the discharge tube disposed inside the lower cabinet 160.

According to an embodiment, the processor 470 may perform the fourth function of discharging low-temperature hot air through a duct of the discharge tube disposed inside the lower cabinet 160.

According to an embodiment, the processor 470 may perform the fifth function of emitting at least one of mist and air through a duct of the discharge tube disposed inside the lower cabinet 160.

According to an embodiment, the processor 470 may sequentially perform the functions or simultaneously perform at least two or more functions.

Figure 7:
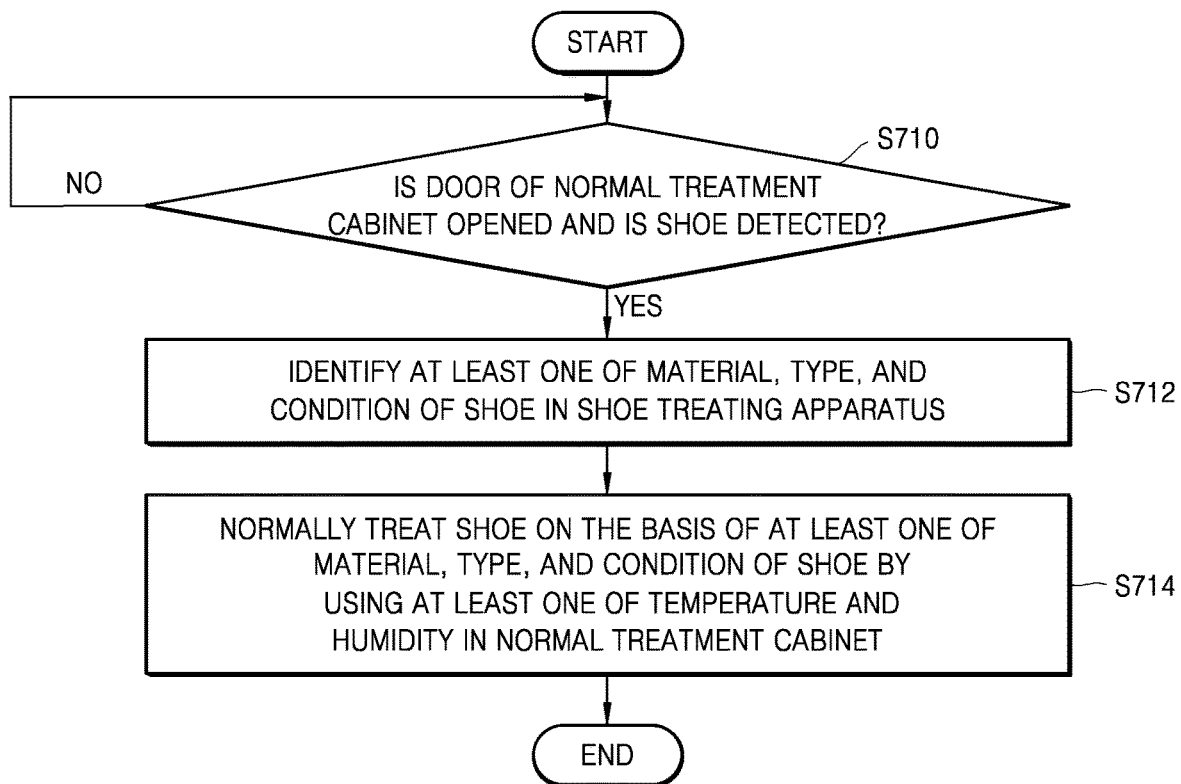
FIG. 7 is a flowchart illustrating a process of normally treating a shoe according to an embodiment of the present invention.
Figure 8:
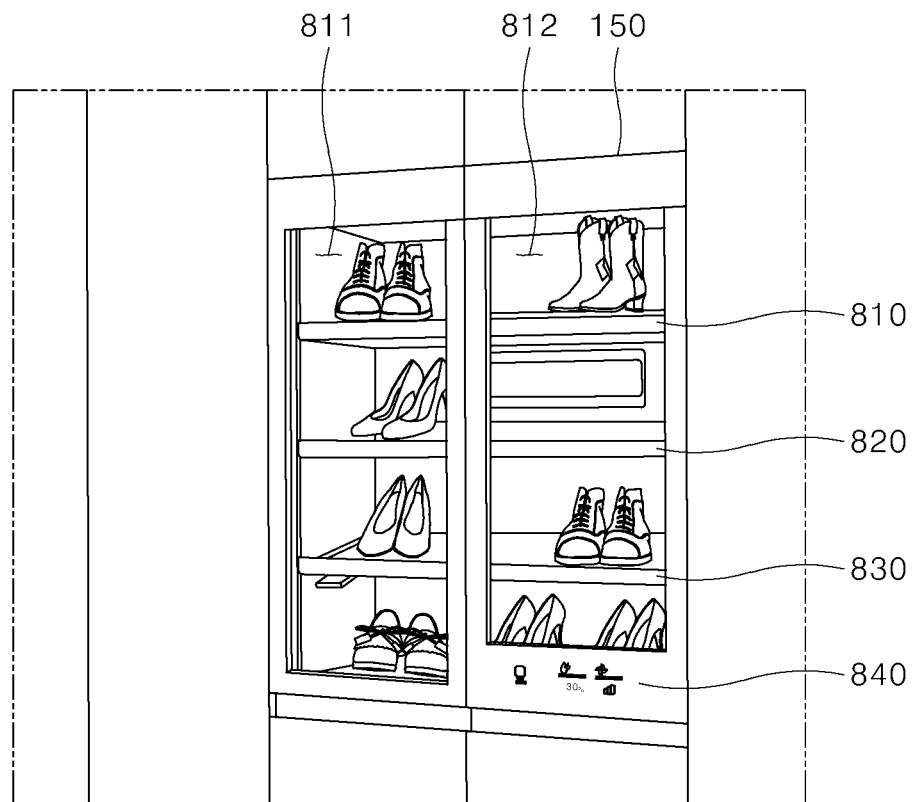
FIG. 8 is an exemplary view of an upper cabinet according to an embodiment of the present invention.
Figure 9:
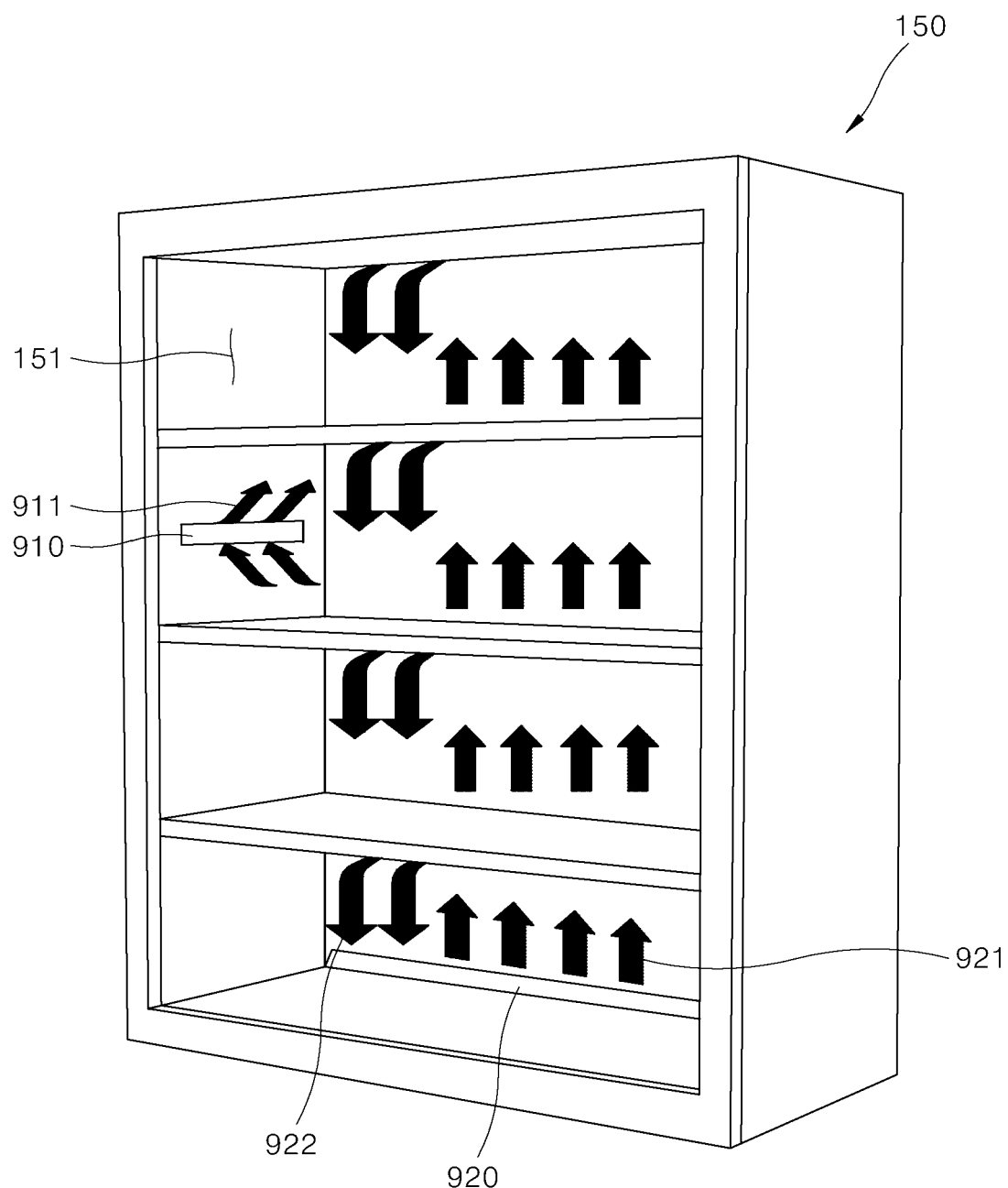
FIG. 9 is an exemplary view illustrating an air flow in a plurality of storage spaces of the upper cabinet according to an embodiment of the present invention.

FIG. 7 is a flowchart illustrating a process of normally treating a shoe according to an embodiment of the present invention. FIG. 8 is an exemplary view of an upper cabinet according to an embodiment of the present invention. FIG. 9 is an exemplary view illustrating an air flow in a plurality of storage spaces of the upper cabinet according to an embodiment of the present invention.

Hereinafter, the process of normally treating a shoe according to an embodiment of the present invention will be described in detail with reference to FIGS. 7, 8, and 9.

According to an embodiment, the processor 470 of the shoe treating apparatus 310 may identify whether a door of a normal treatment cabinet (e.g., the upper cabinet 150) is opened (or opening) and/or whether a shoe is present in the upper cabinet 150 (S710). The process (S710) may include at least one function or operation performed in FIG. 5 (e.g., the process (S510)).

According to an embodiment, the processor 470 may identify at least one of the material, function, type, and condition of the shoe in the upper cabinet 150 (S712). The process (S712) may include at least one function or operation performed in FIG. 5 (e.g., the process (S512)).

According to an embodiment, the processor 470 may normally treat the shoe on the basis of at least one of the material, function, type, and condition of the shoe (S714). The processor 470 may normally treat the shoe (e.g., adjust at least one of the temperature and humidity) through at least one element (e.g., the steam generating part 444, the low-temperature hot air generating part 446) of the shoe treating apparatus 310.

Alternatively, the processor 470 may normally treat a shoe in the upper cabinet 150 through at least one of the UV light emitting part 422, the photocatalyst emitting part 424, and the plasma emitting part 426.

Referring to FIG. 8, the upper cabinet 150 according to an embodiment of the present invention may have both doors 110 and 120 formed of a transparent material (e.g., tempered glass, transparent plastic). Also, the upper cabinet 150 may be formed of multiple layers through a plurality of shelves 810, 820, and 830. Also, storage spaces 811 and 812 may be formed by the plurality of shelves 810, 820, and 830.

According to an embodiment, a display part 840 (or the display part 433 of FIG. 4) for an operational state of the upper cabinet 150 and operation control thereof may be disposed at one side of the upper cabinet 150. The display part 840 may be disposed at one side of one of the upper cabinet 150 and the lower cabinet 160, and may display an operational state of the upper cabinet 150 or the lower cabinet 160 and operation control thereof.

Referring to FIG. 9, the upper cabinet 150 according to an embodiment of the present invention may be formed of a plurality of storage spaces 151, and each of the plurality of storage spaces 151 may be sealed from each other to be airtight or may not be sealed to allow ventilation.

According to an embodiment, a discharge part 920 (or the discharge part 455 of FIG. 4) formed in a storage space disposed on the lower portion of the upper cabinet 150 may discharge air 921 upward. The air 921 discharged upward may flow upward along a wall of the upper cabinet 150 and be introduced into each storage space. Alternatively, a portion 922 of the air 921 discharged upward may be introduced into a storage space disposed at a lower portion.

According to an embodiment, a discharge part 910 (or the discharge part 455 of FIG. 4) formed in a storage space disposed on an intermediate portion of the upper cabinet 150 may discharge air 911 upward. The air 911 discharged upward may flow upward along a wall of a shelf and be suctioned into the discharge part 910 (or the suction part 454 of FIG. 4). The discharge part 910 may perform both discharge and suction of air.

Figure 10:
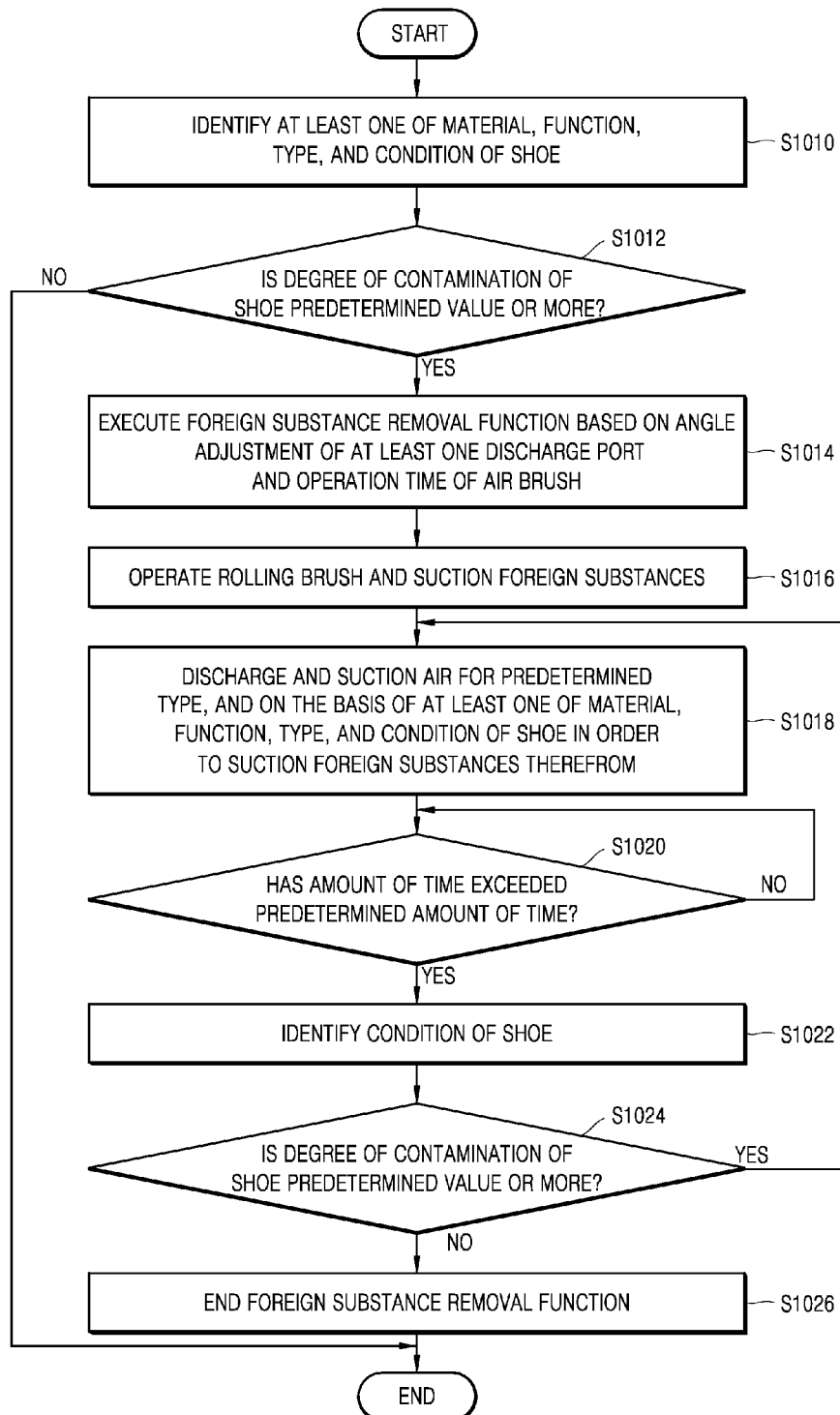
FIG. 10 is a flowchart illustrating a process of removing foreign substances from a shoe according to an embodiment of the present invention.
Figure 11A:
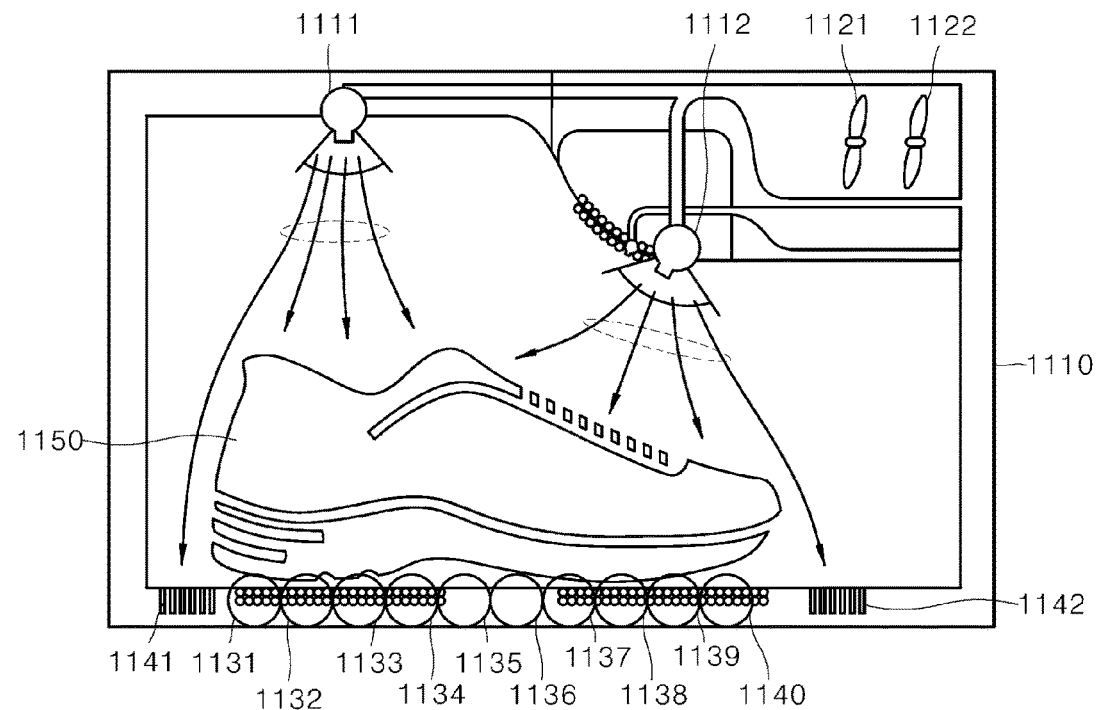
FIG. 11A is a first exemplary view of removing foreign substances from a shoe according to an embodiment of the present invention.
Figure 11B:
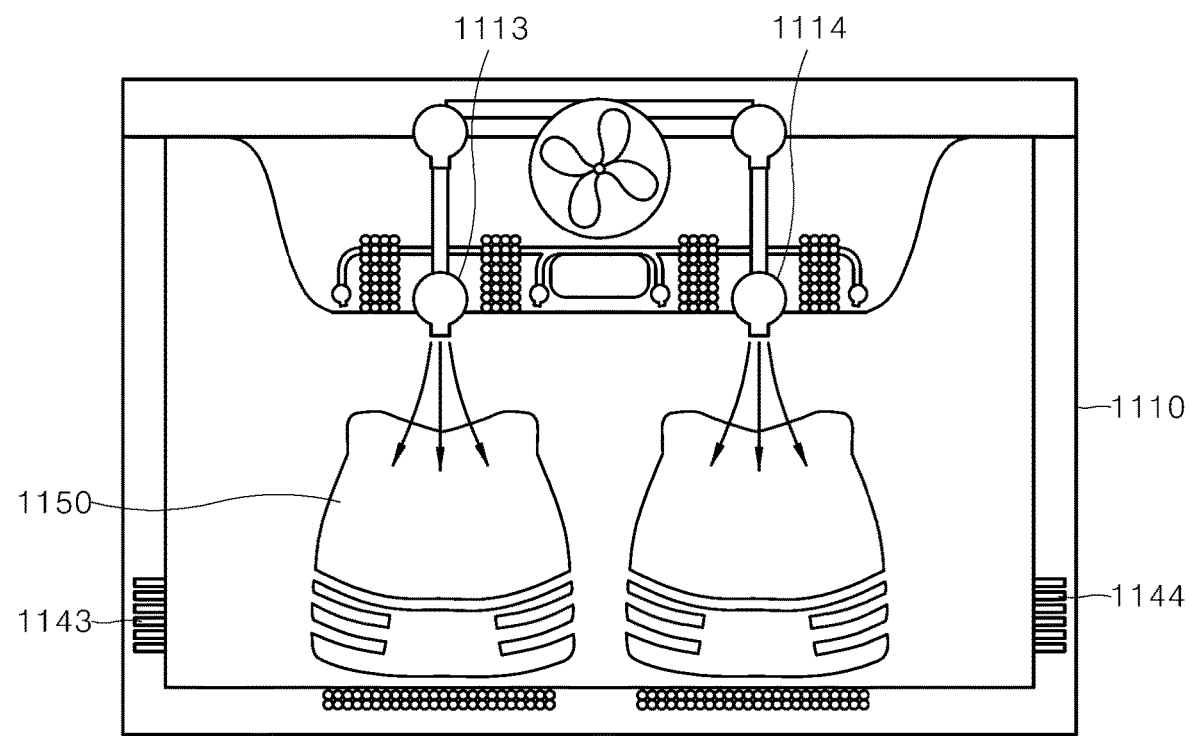
FIG. 11B is a second exemplary view of removing foreign substances from a shoe according to an embodiment of the present invention.

FIG. 10 is a flowchart illustrating a process of removing foreign substances from a shoe according to an embodiment of the present invention. FIG. 11A is a first exemplary view of removing foreign substances from a shoe according to an embodiment of the present invention. FIG. 11B is a second exemplary view of removing foreign substances from a shoe according to an embodiment of the present invention.

Hereinafter, the process of removing foreign substances from a shoe according to an embodiment of the present invention will be described in detail with reference to FIGS. 10, 11A, and 11B.

According to an embodiment, the processor 470 of the shoe treating apparatus 310 may identify at least one of the material, function, type, and condition of shoes in the shoe cabinets 150 and 160 (S1010). The processor 470 may identify at least one of the material, function, type, and condition of a shoe in the shoe cabinet 320 through at least one of the sensor part 410 and the camera 432.

According to an embodiment, the process (S1010) may include at least one operation or function of the processes (S510 and S512) of FIG. 5.

According to an embodiment, the processor 470 may identify whether a degree of contamination of a shoe 1150 is a predetermined value or more (S1012). The processor 470 may, on the basis of at least one of the material, function, type, and condition of the shoe 1150 identified by the process (S1010), identify whether the degree of contamination of the shoe 1150 is the predetermined value or more.

For example, in a case in which the degree of contamination of the shoe 1150 is less than the predetermined value, the processor 470 may not perform a function of removing foreign substances attached to the shoe 1150. Alternatively, the processor 470 may perform the function of removing foreign substances attached to the shoe 1150 even in the case in which the degree of contamination of the shoe 1150 is less than the predetermined value.

According to an embodiment, the processor 470 may execute a foreign substance removal function based on angle adjustment of at least one discharge port and operation time of an air brush (S1014). The processor 470 may, when the degree of contamination of the shoe 1150 is determined as being the predetermined value or more, adjust an angle of one or more discharge ports 1111, 1112, 1113, and 1114 of the shoe treating apparatus 310.

Also, the processor 470 may control the air generating part 442 of the shoe treating apparatus 310 to generate air and may discharge the generated air through the one or more discharge ports 1111, 1112, 1113, and 1114.

The strength of the discharged air may be proportional to the rotational speed of one or more fans (or propellers) 1121 and 1122. The processor 470 may control the rotational speed of the one or more fans (or propellers) 1121 and 1122 to discharge air through the one or more discharge ports 1111, 1112, 1113, and 1114.

According to an embodiment, foreign substances adsorbed onto the shoe 1150 may be removed from the shoe 1150 by the air discharged through the one or more discharge ports 1111, 1112, 1113, and 1114. Also, the foreign substances removed from the shoe 1150 may be suctioned through one or more suction ports 1141, 1142, 1143, and 1144. The processor 470 may control the strength of suction force of the one or more suction ports 1141, 1142, 1143, and 1144 to be proportional to the strength of air discharged through the one or more discharge ports 1111, 1112, 1113, and 1114.

Alternatively, the processor 470 may control the strength of suction force so that the suction force of the one or more suction ports 1141, 1142, 1143, and 1144 is greater than the strength of air discharged through the one or more discharge ports 1111, 1112, 1113, and 1114. The positions of the one or more suction ports 1141, 1142, 1143, and 1144 may be variably changed inside a shoe cabinet 1110.

According to an embodiment, foreign substances suctioned through the one or more suction ports 1141, 1142, 1143, and 1144 may be filtered by passing through the filter part 453 of the shoe treating apparatus 310, and the foreign substances filtered by the filter part 453 may be stored in the foreign substance storage part 452.

Also, air that has passed through the filter part 453 may be delivered to at least one of the air generating part 442, the steam generating part 444, the low-temperature hot air generating part 446, and the water repellent part 448 through the first duct 456.

According to an embodiment, the processor 470 may operate a rolling brush and suction foreign substances (S1016). One or more rolling brushes 1131, 1132, 1133, 1134, 1135, 1136, 1137, 1138, 1139, and 1140 may be provided on a lower portion of at least one shoe cabinet 1110.

Also, the rolling brushes may be connected to a worm gear so as to rotate while being engaged with each other. A worm gear may be disposed between the rolling brushes.

According to an embodiment, a worm gear may not be disposed between the rolling brushes, and the rolling brushes may independently rotate through a motor.

According to an embodiment, the processor 470 may identify the condition (e.g., the degree of contamination, foreign substance adsorption state, or the like) of the shoe 1150 in the shoe cabinet 1110. The processor 470 may operate the one or more rolling brushes 1131, 1132, 1133, 1134, 1135, 1136, 1137, 1138, 1139, and 1140 on the basis of the condition of the shoe 1150.

Also, the processor 470 may, on the basis of the operation of the one or more rolling brushes, control the suction part 454 to suction the foreign substances dislodged from the shoe 1150 through the one or more suction ports 1141, 1142, 1143, and 1144.

According to an embodiment, the processor 470 may identify the one or more rolling brushes 1131, 1132, 1133, 1134, 1135, 1136, 1137, 1138, 1139, and 1140 that correspond to the position or size of the shoe 1150 and may control the rotational direction (e.g., counterclockwise) of the identified one or more rolling brushes. The one or more rolling brushes may rotate in the same direction (e.g., counterclockwise) due to a worm gear disposed therebetween.

The processor 470 may adjust the position of the shoe 1150 to correspond to the direction of the one or more discharge ports 1111, 1112, 1113, and 1114. Alternatively, the processor 470 may adjust the direction or angle of the one or more discharge ports 1111, 1112, 1113, and 1114 to correspond to the position of the shoe 1150.

When the degree of contamination of the shoe is determined as being the predetermined value or more in the process (S1012), the processor 470 may simultaneously perform the processes (S1014 and S1016).

According to an embodiment, the processor 470 may discharge and suction air for a predetermined amount of time on the basis of at least one of the material, function, type, and condition of the shoe in order to suction foreign substances therefrom (S1018). The processor 470 may identify at least one of the material, function, type, and condition of the shoe in the shoe cabinet 320 through at least one of the sensor part 410 and the camera 432 of the shoe treating apparatus 310.

According to an embodiment, the processor 470 may identify the time during which air is discharged and suctioned on the basis of at least one of the material, function, type, and condition of the identified shoe. The time may be set to different amounts of time according to at least one of the material, function, type, and condition of the shoe.

When at least one of the material, function, type, and condition of the shoe is identified, the processor 470 may identify a predetermined amount of time according thereto.

According to an embodiment, the processor 470 may discharge air through the one or more discharge ports 1111, 1112, 1113, and 1114 for a predetermined amount of time to remove foreign substances from the shoe 1150.

Also, the processor 470 may suction the foreign substances, which are separated from the shoe 1150 through the discharged air, through the one or more suction ports 1141, 1142, 1143, and 1144. The processor 470 may discharge air and then suction the discharged air to execute the first function of removing foreign substances adsorbed onto the shoe 1150.

According to an embodiment, the first function may include an operation of causing foreign substances attached to the lower portion of the shoe 1150 to be dislodged through rolling of one or more rolling brushes disposed on the lower portion of the shoe cabinet 1110 and suctioning the foreign substances dislodged from the lower portion of the shoe 1150 through the one or more suction ports 1141, 1142, 1143, and 1144.

Also, the first function may include an operation of discharging air through the one or more discharge ports 1111, 1112, 1113, and 1114 disposed inside the shoe cabinet 1110 and suctioning the foreign substances dislodged from the shoe 1150 due to the discharged air through the one or more suction ports 1141, 1142, 1143, and 1144.

The angle or direction of the one or more discharge ports 1111, 1112, 1113, and 1114 may be adjusted through the processor 470 on the basis of the position or direction of the shoe.

According to an embodiment, the processor 470 may, while the air is being discharged through the one or more discharge ports 1111, 1112, 1113, and 1114, acquire an image showing the condition of the shoe 1150 through the camera 432 of the shoe treating apparatus 310 at least one time.

While the air is being discharged through the one or more discharge ports 1111, 1112, 1113, and 1114, the processor 470 may, on the basis of the acquired image, adjust the angle of the one or more discharge ports 1111, 1112, 1113, and 1114 toward a portion where a large amount of foreign substances is present.

According to an embodiment, the processor 470 may identify whether an amount of time has exceeded a predetermined amount of time (S1020). The processor 470 may identify whether the time during which the processes (S1014, S1016, and S1018) are performed has exceeded the predetermined amount of time.

The predetermined amount of time may be determined as different amounts of time according to at least one of the material, function, type, and condition of the shoe 1150. Alternatively, the predetermined amount of time may be adjusted on the basis of a user input.

According to an embodiment, the processor 470 may identify the condition of the shoe (S1022). In a case in which the total time during which the processes (S1014, S1016, and S1018) are performed has exceeded the predetermined amount of time, the processor 470 may identify the condition of the shoe 1150 on the basis of the operation (S1010).

According to an embodiment, the processor 470 may identify the condition of the shoe 1150 on the basis of the operation (S1010) at predetermined time intervals.

According to an embodiment, the processor 470 may identify whether the degree of contamination of the shoe is the predetermined value or more (S1024). When the degree of contamination of the shoe 1150 is determined as being the predetermined value or more, the processor 470 may, as described above in relation to the process (S1018), discharge and suction air for a predetermined amount of time on the basis of at least one of the material, function, type, and condition of the shoe 1150.

Also, the processor 470 may suction the foreign substances dislodged from the shoe 1150 due to the discharge of air through the suction part 454.

According to an embodiment, the processor 470 may end the foreign substance removal function (S1026). When the degree of contamination of the shoe 1150 is identified as not exceeding the predetermined value in the process (S1024), the processor 470 may end the foreign substance removal function.

According to an embodiment, the processor 470 may display information on the operation, result, or the like of each process illustrated in FIG. 10 through the display part 433 of the shoe treating apparatus 310.

Figure 12:
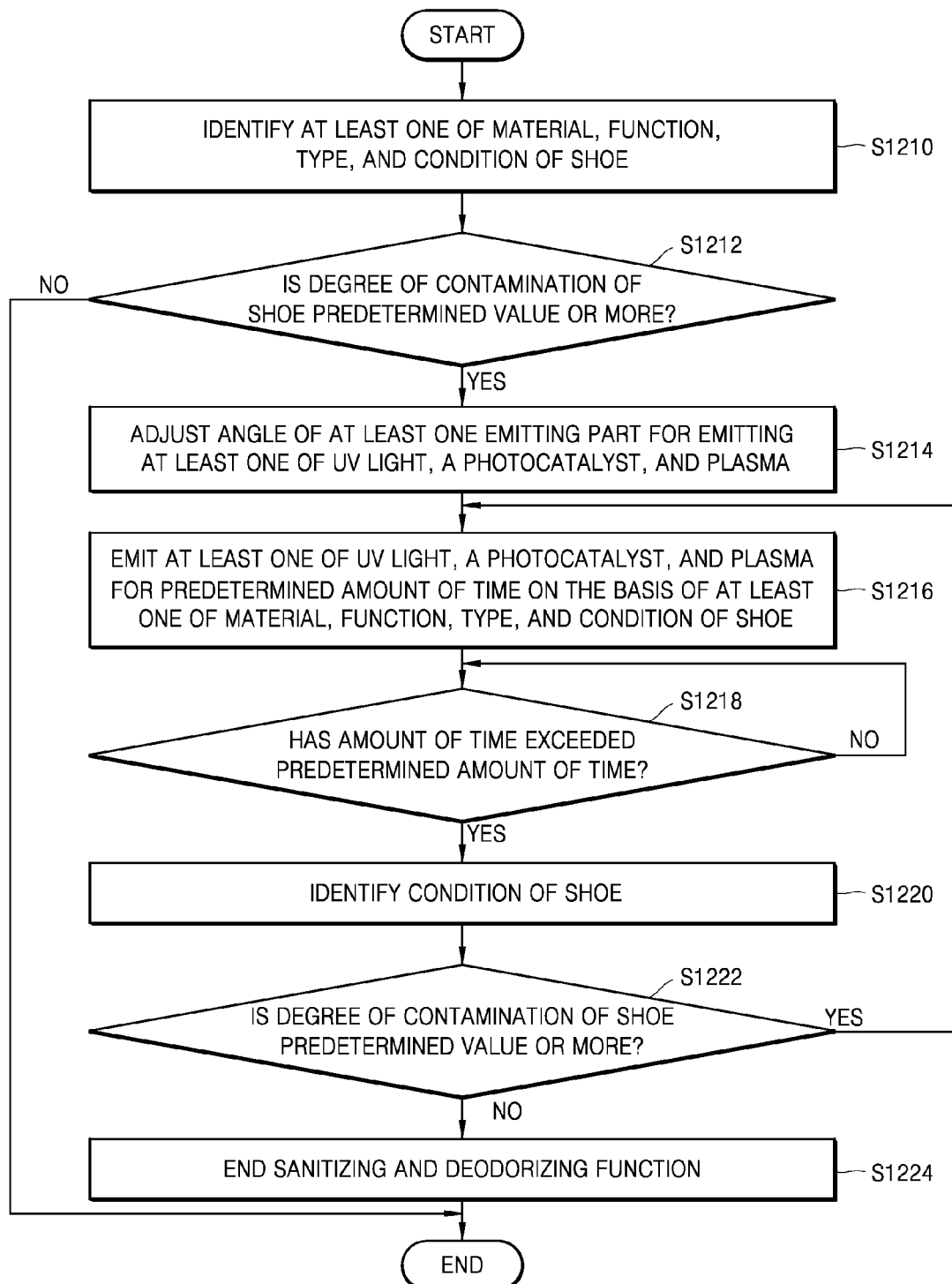
FIG. 12 is a flowchart illustrating a process of sanitizing and deodorizing a shoe according to an embodiment of the present invention.
Figure 13A:
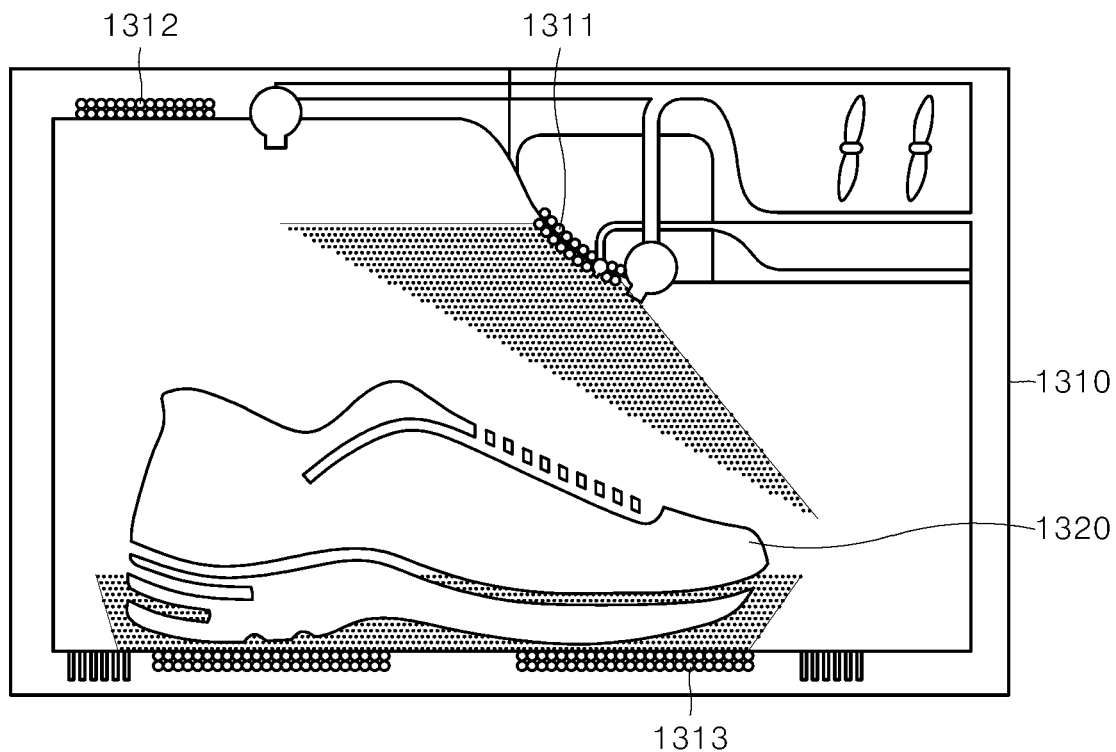
FIG. 13A is a first exemplary view of sanitizing and deodorizing a shoe according to an embodiment of the present invention.
Figure 13B:
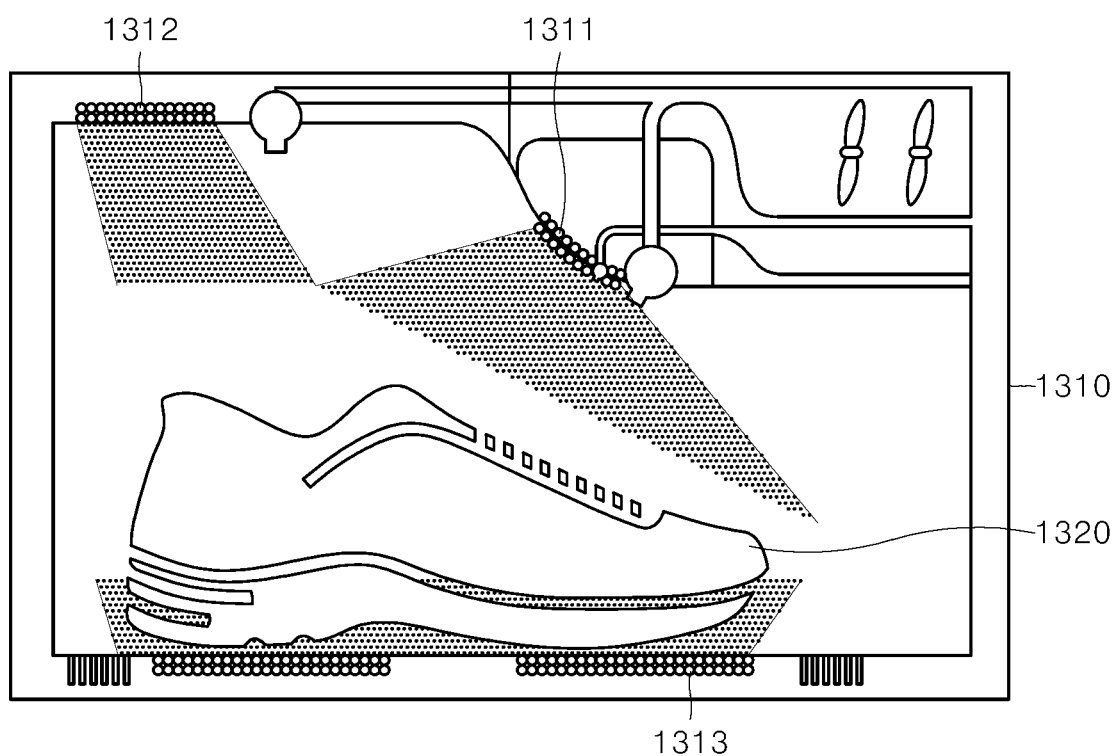
FIG. 13B is a second exemplary view of sanitizing and deodorizing a shoe according to an embodiment of the present invention.

FIG. 12 is a flowchart illustrating a process of sanitizing and deodorizing a shoe according to an embodiment of the present invention. FIG. 13A is a first exemplary view of sanitizing and deodorizing a shoe according to an embodiment of the present invention. FIG. 13B is a second exemplary view of sanitizing and deodorizing a shoe according to an embodiment of the present invention.

Hereinafter, the process of sanitizing and deodorizing a shoe according to an embodiment of the present invention will be described in detail with reference to FIGS. 12, 13A, and 13B.

According to an embodiment, the processor 470 of the shoe treating apparatus 310 may identify at least one of the material, function, type, and condition of a shoe 1320 (S1210). The process (S1210) may include at least one operation or function of the process (S1010) of FIG. 10. Also, the process (S1210) may include at least one operation or function of the processes (S710 and S712) of FIG. 7.

According to an embodiment, the processor 470 may identify whether the degree of contamination of the shoe 1320 is a predetermined value or more (S1212). The process (S1212) may include at least one operation or function of the process (S1012) of FIG. 10.

According to an embodiment, the processor 470 may adjust an angle of at least one emitting part for emitting at least one of UV light, a photocatalyst, and plasma (S1214). In a case in which the degree of contamination of the identified shoe 1320 is the predetermined value or more, the processor 470 may adjust an angle of one or more emitting parts 1311, 1312, and 1313 for emitting at least one of UV light, a photocatalyst, and plasma.

Alternatively, the processor 470 may adjust the angle of the one or more emitting parts 1311, 1312, and 1313 so that at least one of the UV light, a photocatalyst, and plasma is first emitted to a portion where the degree of contamination of the shoe 1320 is high.

According to an embodiment, the one or more emitting parts 1311, 1312, and 1313 may be disposed on at least one of a left surface, a right surface, a front surface, a rear surface, an upper surface, and a lower surface inside a shoe cabinet 1310.

According to an embodiment, in a state of being disposed on an inner wall of the shoe cabinet 1310, the one or more emitting parts 1311, 1312, and 1313 may emit at least one of the UV light, a photocatalyst, and plasma generated by at least one of the UV light emitting part 422, the photocatalyst emitting part 424, and the plasma emitting part 426 of the emitting part 420.

According to an embodiment, the processor 470 may emit at least one of the UV light, a photocatalyst, and plasma for a predetermined amount of time on the basis of at least one of the material, function, type, and condition of the shoe (S1216). The processor 470 may emit at least one of the UV light, a photocatalyst, and plasma to the shoe for a predetermined amount of time to start the function of sanitizing and deodorizing the shoe. The predetermined amount of time (e.g., three minutes) may be variably adjusted.

The processor 470 may emit at least one of the UV light, a photocatalyst, and plasma to the inner side, outer side, and bottom of the shoe for a predetermined amount of time on the basis of at least one of the material, function, type, and condition of the shoe.

According to an embodiment, a first emitting part 1311 among the plurality of emitting parts 1311, 1312, and 1313 disposed on the inner wall of the shoe cabinet 1310 may be disposed to face the front of the shoe 1320, and a second emitting part 1312 among the plurality of emitting parts 1311, 1312, and 1313 may be disposed to face the inside of the shoe 1320. Also, a third emitting part 1313 among the plurality of emitting parts 1311, 1312, and 1313 may be disposed to face the bottom of the shoe 1320 at the lower portion of the shoe cabinet 1310.

According to an embodiment, the processor 470 may identify the time during which at least one of the UV light, a photocatalyst, and plasma is emitted on the basis of at least one of the material, function, type, and condition of the shoe 1320. The time may be set to different amounts of time according to at least one of the material, function, type, and condition of the shoe 1320.

When at least one of the material, function, type, and condition of the shoe 1320 is identified, the processor 470 may identify a predetermined amount of time according thereto.

According to an embodiment, the processor 470 may identify whether an amount of time has exceeded a predetermined amount of time (S1218). The processor 470 may identify whether the time during which the process (S1216) is performed has exceeded the predetermined amount of time. The predetermined amount of time may be determined as different amounts of time according to at least one of the material, function, type, and condition of the shoe 1320. Alternatively, the predetermined amount of time may be adjusted on the basis of a user input.

According to an embodiment, the processor 470 may identify the condition of the shoe (S1220). In a case in which the total time during which the process (S1216) is performed has exceeded the predetermined amount of time (e.g., three minutes), the processor 470 may identify the condition of the shoe 1320 on the basis of the operation (S1210). The processor 470 may identify the condition of the shoe 1320 on the basis of the operation (S1210) at predetermined time intervals.

According to an embodiment, the processor 470 may identify whether the degree of contamination of the shoe is the predetermined value or more (S1222). When the degree of contamination of the shoe 1320 is determined as being the predetermined value or more, the processor 470 may, as described above in relation to the process (S1216), emit at least one of the UV light, a photocatalyst, and plasma for a predetermined amount of time on the basis of at least one of the material, function, type, and condition of the shoe 1320 to sanitize and deodorize the shoe 1320.

According to an embodiment, the processor 470 may end the sanitizing and deodorizing function (S1224). When the degree of contamination of the shoe 1320 is identified as not exceeding the predetermined value in the process (S1222), the processor 470 may end the sanitizing and deodorizing function.

Figure 14:
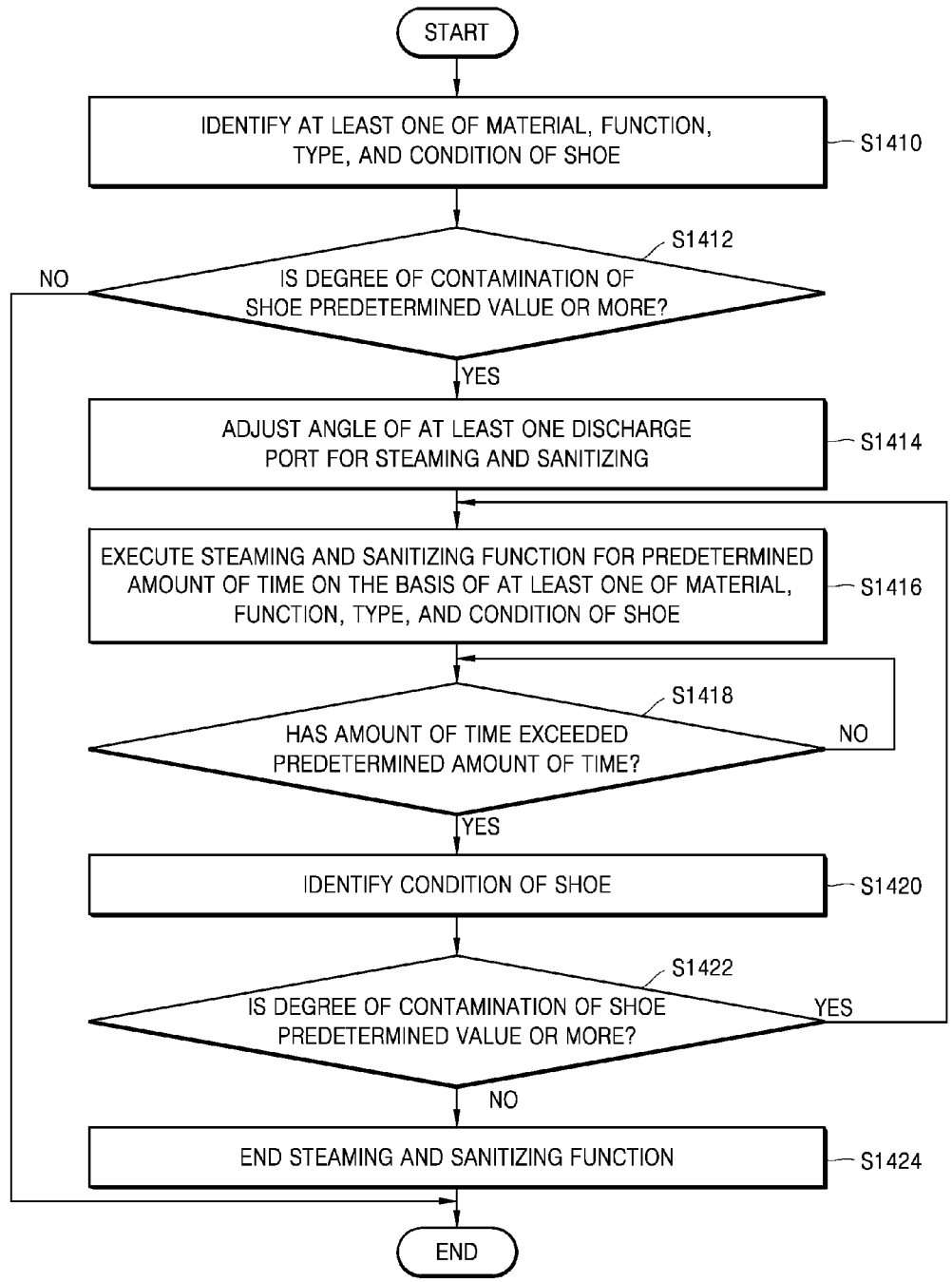
FIG. 14 is a flowchart illustrating a process of steaming and sanitizing a shoe according to an embodiment of the present invention.
Figure 15:
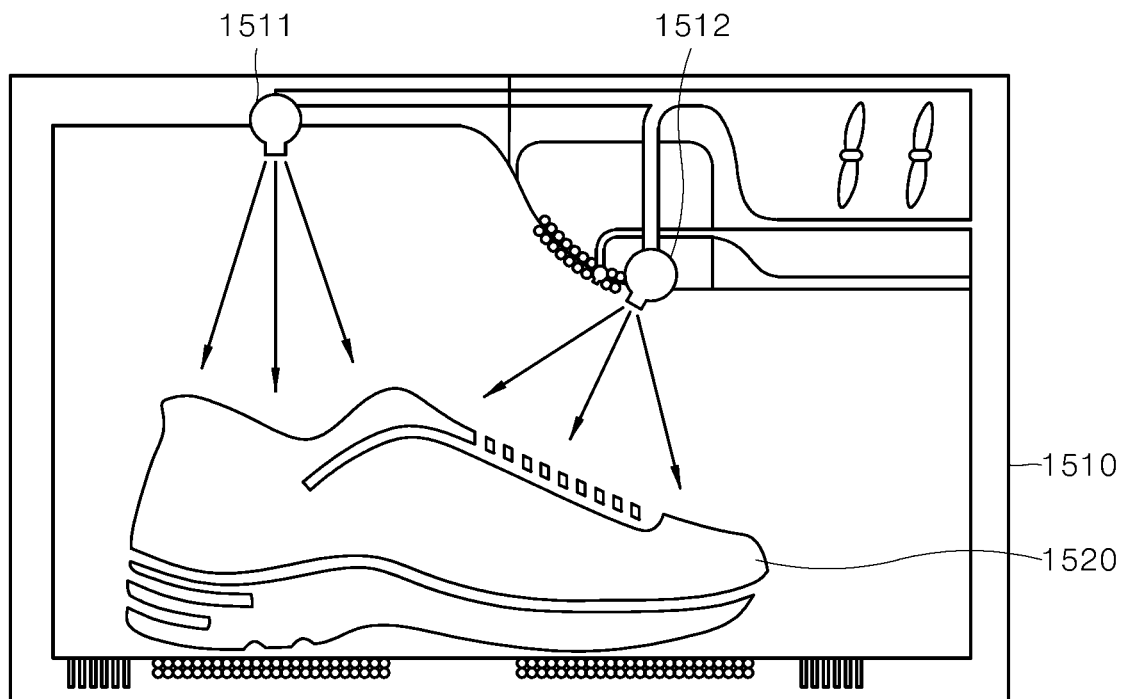
FIG. 15 is a first exemplary view of steaming and sanitizing a shoe according to an embodiment of the present invention.

FIG. 14 is a flowchart illustrating a process of steaming and sanitizing a shoe according to an embodiment of the present invention. FIG. 15 is a first exemplary view of steaming and sanitizing a shoe according to an embodiment of the present invention.

Hereinafter, the process of steaming and sanitizing a shoe according to an embodiment of the present invention will be described in detail with reference to FIGS. 14 and 15.

According to an embodiment, the processor 470 of the shoe treating apparatus 310 may identify at least one of the material, function, type, and condition of a shoe 1520 (S1410). The process (S1410) may include an operation or function in at least one of the process (S1010) of FIG. 10 and the process (S1210) of FIG. 12. Also, the process (S1410) may include at least one operation or function of the processes (S710 and S712) of FIG. 7.

According to an embodiment, the processor 470 may identify whether the degree of contamination of the shoe 1520 is a predetermined value or more (S1412). The process (S1412) may include at least one operation or function of the process (S1012) of FIG. 10 and the process (S1212) of FIG. 12.

According to an embodiment, the processor 470 may adjust an angle of at least one discharge port for steaming and sanitizing (S1414). In a case in which the degree of contamination of the shoe 1520 is the predetermined value or more, the processor 470 may adjust an angle of one or more discharge ports 1511 and 1512 for emitting steam through the steam generating part 444 of the shoe treating apparatus 310.

The processor 470 may adjust the angle of the one or more discharge ports 1511 and 1512 so that steam is first emitted to a portion where the degree of contamination of the shoe 1520 is high.

According to an embodiment, the one or more discharge ports 1511 and 1512 may be disposed on at least one of a left surface, a right surface, a front surface, a rear surface, an upper surface, and a lower surface inside a shoe cabinet 1510.

According to an embodiment, in a state of being disposed on an inner wall of the shoe cabinet 1510, the one or more discharge ports 1511 and 1512 may emit steam generated by the steam generating part 444 toward the shoe 1520. According to an embodiment, the steam may also be discharged through a discharge port through which air is discharged.

According to an embodiment, the processor 470 may execute the steaming and sanitizing function for a predetermined amount of time on the basis of at least one of the material, function, type, and condition of the shoe (S1416). The processor 470 may emit steam to the shoe 1520 for a predetermined amount of time (e.g., ten minutes) to start steaming and sanitization of the shoe 1520. The predetermined amount of time (e.g., ten minutes) may be variably adjusted.

The processor 470 may emit steam to at least one of the inner side, outer side, and bottom of the shoe 1520 for a predetermined amount of time on the basis of at least one of the material, function, type, and condition of the shoe 1520. The temperature of the emitted steam may be a predetermined temperature (e.g., 50° C.) or lower. The steam temperature (e.g., 50° C.) may be a suitable temperature that does not cause damage to the material of the shoe 1520.

According to an embodiment, a first discharge port 1511 among the plurality of discharge ports 1511 and 1512 disposed on the inner wall of the shoe cabinet 1510 may be disposed to face the inside of the shoe 1520. Also, a second discharge port 1512 among the plurality of discharge ports 1511 and 1512 may be disposed to face the front of the shoe 1520.

According to an embodiment, the processor 470 may identify the time during which steam is emitted on the basis of at least one of the material, function, type, and condition of the shoe 1520. The time may be set to different amounts of time according to at least one of the material, function, type, and condition of the shoe 1520. When at least one of the material, function, type, and condition of the shoe 1520 is identified, the processor 470 may identify a predetermined amount of time according thereto.

According to an embodiment, the processor 470 may identify whether an amount of time has exceeded a predetermined amount of time (S1418). The processor 470 may identify whether the time during which the process (S1416) is performed has exceeded the predetermined amount of time (e.g., ten minutes). The predetermined amount of time may be determined as different amounts of time according to at least one of the material, function, type, and condition of the shoe 1520. Alternatively, the predetermined amount of time may be adjusted on the basis of a user input.

According to an embodiment, the processor 470 may identify the condition of the shoe (S1420). In a case in which the total time during which the process (S1416) is performed has exceeded the predetermined amount of time (e.g., ten minutes), the processor 470 may identify the condition of the shoe 1520 on the basis of the operation (S1410). According to an embodiment, the processor 470 may identify the condition of the shoe 1520 on the basis of the operation (S1410) at predetermined time intervals.

According to an embodiment, the processor 470 may identify whether the degree of contamination of the shoe is the predetermined value or more (S1422). When the degree of contamination of the shoe 1520 is determined as being the predetermined value or more, the processor 470 may, as described above in relation to the process (S1416), emit steam for a predetermined amount of time on the basis of at least one of the material, function, type, and condition of the shoe 1520 to steam and sanitize the shoe 1520.

According to an embodiment, the processor 470 may end the steaming and sanitizing function (S1424). When the degree of contamination of the shoe 1520 is identified as not exceeding the predetermined value in the process (S1422), the processor 470 may end the steaming and sanitizing function.

Figure 16:
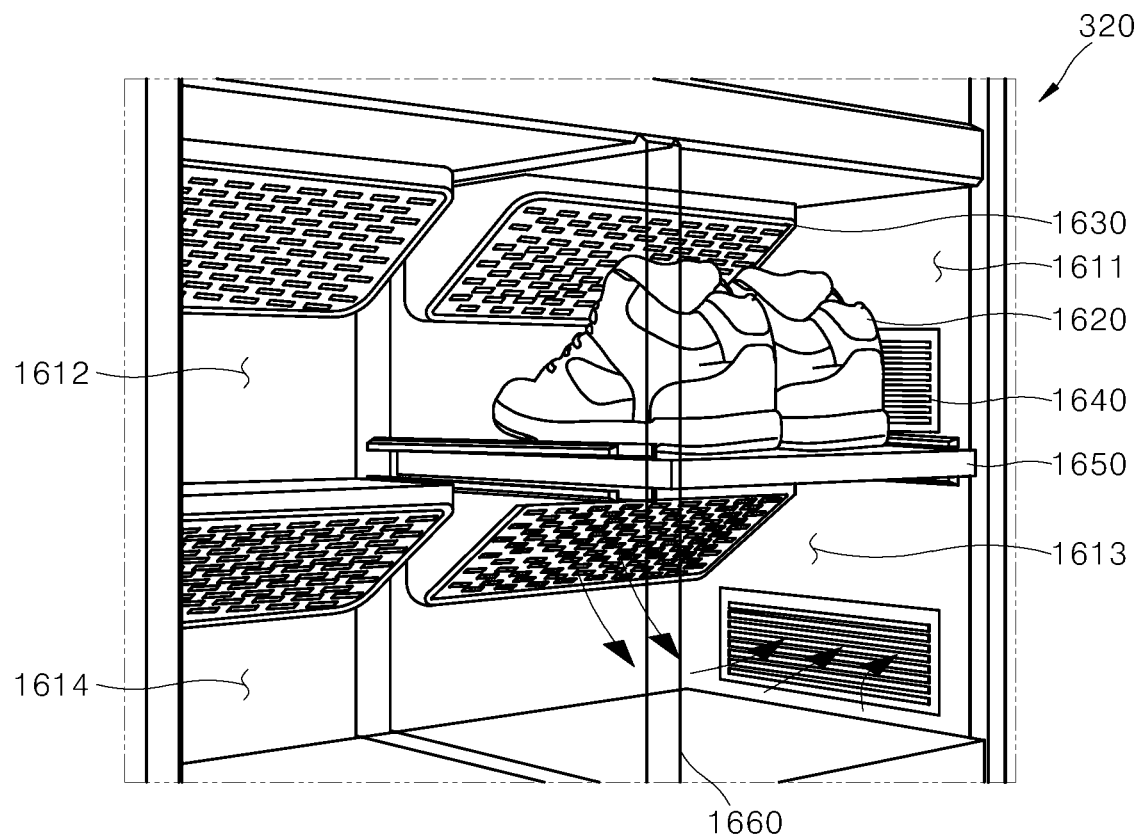
FIG. 16 is a second exemplary view of steaming and sanitizing a shoe according to an embodiment of the present invention.

FIG. 16 is a second exemplary view of steaming and sanitizing a shoe according to an embodiment of the present invention.

Referring to FIG. 16, a cabinet 320 may include a plurality of shoe cabinets 1611, 1612, 1613, and 1614. A first partition member 1660 may be disposed in a first shoe cabinet 1611 and a second shoe cabinet 1612 among the plurality of shoe cabinets 1611, 1612, 1613, and 1614. The first partition member 1660 may include plastic or glass made of a transparent material.

According to an embodiment, a second partition member 1650 may be disposed between the first shoe cabinet 1611 and the second shoe cabinet 1612, which is disposed below the first shoe cabinet 1611, among the plurality of shoe cabinets 1611, 1612, 1613, and 1614. The second partition member 1650 may move upward or downward according to the size of a shoe 1620.

According to an embodiment, a display part configured to display various pieces of information on an operational state of any one of the first shoe cabinet 1611 and the second shoe cabinet 1612 may be disposed at one side (e.g., a front surface) of the second partition member 1650.

According to an embodiment, each of the plurality of shoe cabinets 1611, 1612, 1613, and 1614 may include at least one ventilation part 1630 through which steam is emitted. The steam discharged through the at least one ventilation part 1630 may be suctioned through a suction part 1640.

Figure 17:
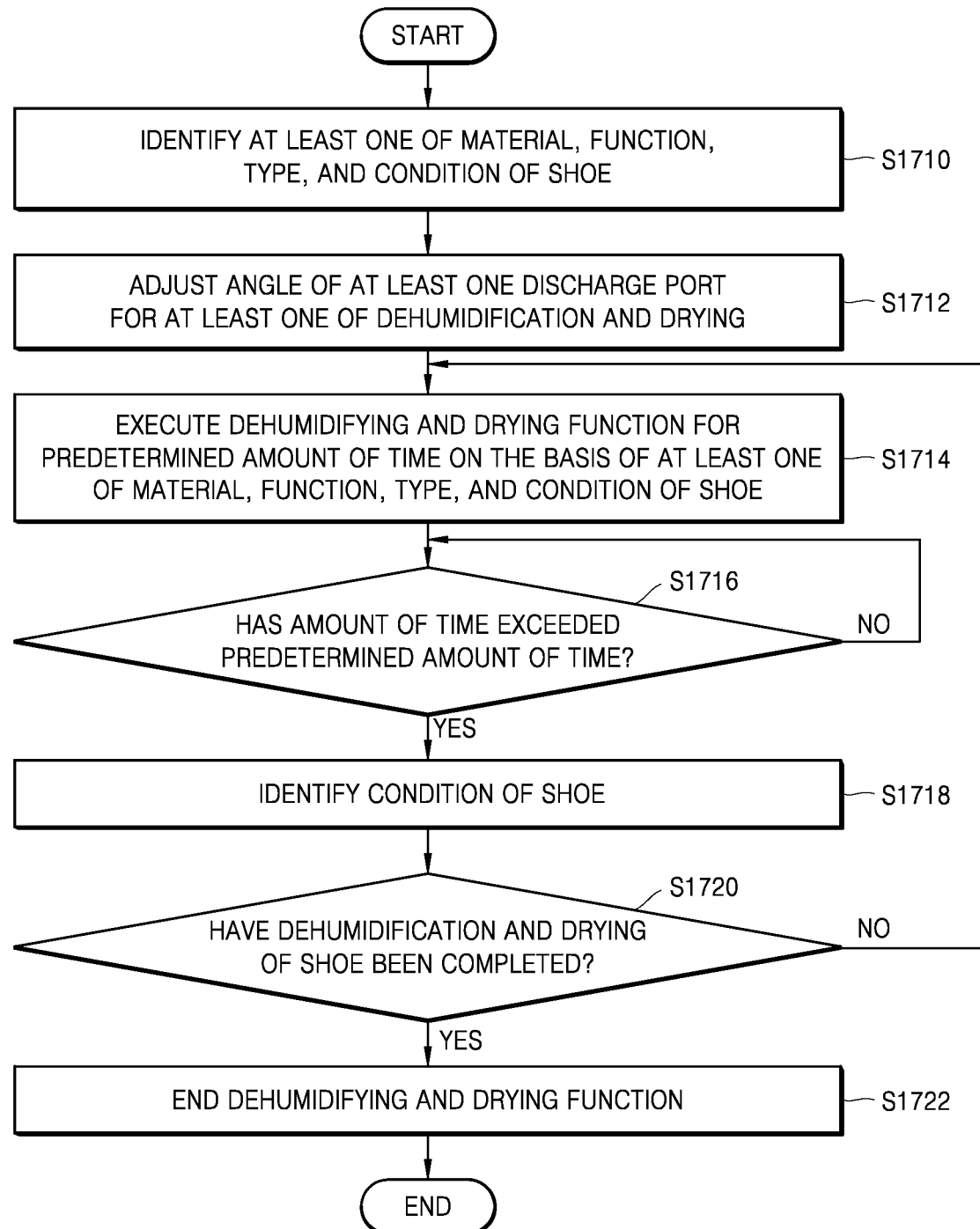
FIG. 17 is a flowchart illustrating a process of dehumidifying and drying a shoe according to an embodiment of the present invention.
Figure 18:
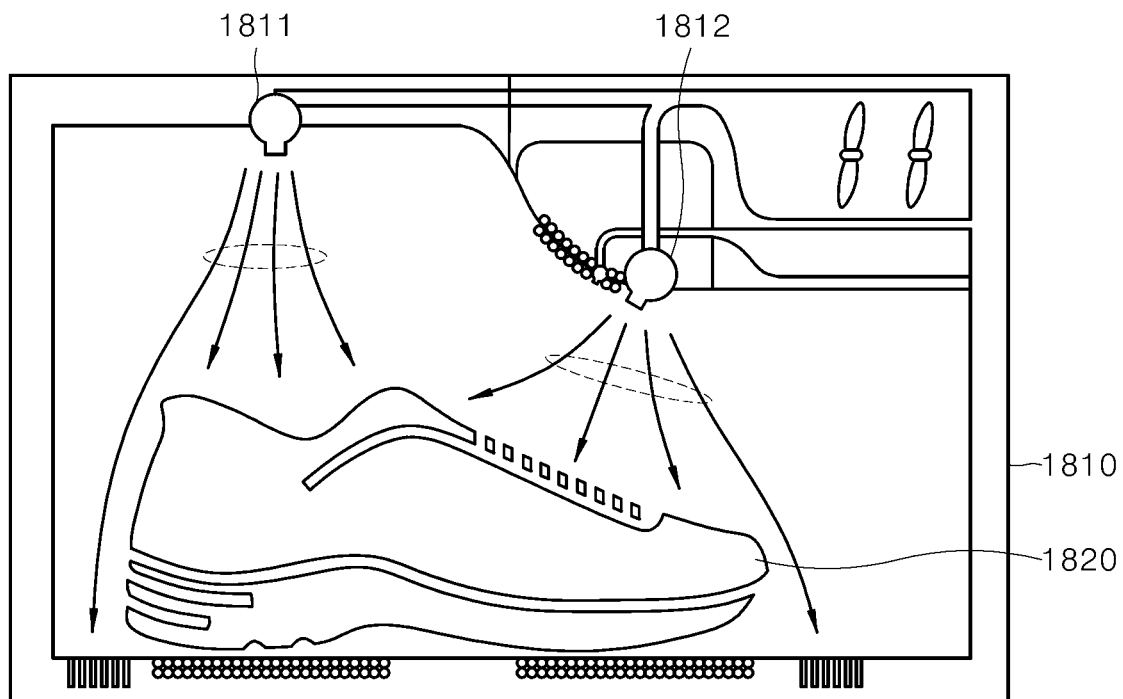
FIG. 18 is an exemplary view of dehumidifying and drying a shoe according to an embodiment of the present invention.

FIG. 17 is a flowchart illustrating a process of dehumidifying and drying a shoe according to an embodiment of the present invention. FIG. 18 is an exemplary view of dehumidifying and drying a shoe according to an embodiment of the present invention.

According to an embodiment, the processor 470 of the shoe treating apparatus 310 may identify at least one of the material, function, type, and condition of a shoe 1820 (S1710). The process (S1710) may include an operation or function in at least one of the process (S1010) of FIG. 10, the process (S1210) of FIG. 12, and the process (S1410) of FIG. 14. Also, the process (S1710) may include at least one operation or function of the processes (S710 and S712) of FIG. 7.

According to an embodiment, the processor 470 may adjust an angle of at least one discharge port for at least one of dehumidification and drying (S1712). The processor 470 may identify the material, function, type, and condition of the shoe 1820 and then adjust an emission angle of one or more discharge ports 1811 and 1812 for emitting low-temperature hot air through the low-temperature hot air generating part 446 of the shoe treating apparatus 310. The processor 470 may adjust the angle of the one or more discharge ports 1811 and 1812 so that low-temperature hot air is first emitted to a portion of the shoe 1820 where dehumidification or drying is required.

According to an embodiment, in a state of being disposed on an inner wall of a shoe cabinet 1810, the one or more discharge ports 1811 and 1812 may emit hot air generated by the low-temperature hot air generating part 446 toward the shoe 1820.

According to an embodiment, the hot air may also be discharged through a discharge port through which air is discharged or a discharge port through which steam is discharged. A duct through which the hot air passes may be dried due to the hot air.

According to an embodiment, the processor 470 may execute the dehumidifying and drying function for a predetermined amount of time on the basis of at least one of the material, type, and condition of the shoe 1820 (S1714). The processor 470 may emit low-temperature hot air to the shoe 1820 for a predetermined amount of time (e.g., twenty minutes) to start dehumidification or drying of the shoe 1820. The predetermined amount of time (e.g., twenty minutes) may be variably adjusted.

The processor 470 may emit hot air to at least one of the inner side, outer side, and bottom of the shoe 1820 for a predetermined amount of time on the basis of at least one of the material, function, type, and condition of the shoe 1820. The temperature of the emitted hot air may be a predetermined temperature (e.g., 40° C.) or lower. The hot air temperature (e.g., 40° C.) may be a temperature that increases efficiency of dehumidification or drying on the basis of the material of the shoe 1820.

According to an embodiment, a first discharge port 1811 among the plurality of discharge ports 1811 and 1812 disposed on the inner wall of the shoe cabinet 1810 may be disposed to face the inside of the shoe 1820. Also, a second discharge port 1812 among the plurality of discharge ports 1811 and 1812 may be disposed to face the front of the shoe 1820.

According to an embodiment, the processor 470 may identify the time during which hot air is to be emitted on the basis of at least one of the material, function, type, and condition of the shoe 1820. The time may be set to different amounts of time according to at least one of the material, function, type, and condition of the shoe 1820. When at least one of the material, function, type, and condition of the shoe 1820 is identified, the processor 470 may identify a predetermined amount of time according thereto.

According to an embodiment, the processor 470 may identify whether an amount of time has exceeded a predetermined amount of time (S1716). The processor 470 may identify whether the time during which the process (S1714) is performed has exceeded the predetermined amount of time (e.g., twenty minutes). The predetermined amount of time may be determined as different amounts of time according to at least one of the material, function, type, and condition of the shoe 1820. Alternatively, the predetermined amount of time may be adjusted on the basis of a user input.

According to an embodiment, the processor 470 may identify the condition of the shoe (S1718). In a case in which the total time during which the process (S1714) is performed has exceeded the predetermined amount of time (e.g., twenty minutes), the processor 470 may identify the condition of the shoe 1820 on the basis of the operation (S1710). The processor 470 may identify the condition of the shoe 1820 on the basis of the operation (S1710) at predetermined time intervals.

According to an embodiment, the processor 470 may identify whether dehumidification and drying of the shoe have been completed (S1720). The processor 470 may acquire information on the humidity of the shoe cabinet 1810, in which the shoe 1820 is stored, through a humidity sensor included in the sensor part 410 of the shoe treating apparatus 310.

The processor 470 may, on the basis of the acquired information, determine the dehumidification or drying of the shoe 1820. When the dehumidification and drying of the shoe 1820 are identified as not having been completed, the processor 470 may, as described above in relation to the process (S1714), emit hot air for a predetermined amount of time on the basis of at least one of the material, function, type, and condition of the shoe 1820 to dehumidify and dry the shoe 1820.

According to an embodiment, the processor 470 may end the dehumidifying and drying function (S1722). When the dehumidification and drying of the shoe 1820 are identified as having been completed in the process (S1720), the processor 470 may end the dehumidifying and drying function.

Figure 19:
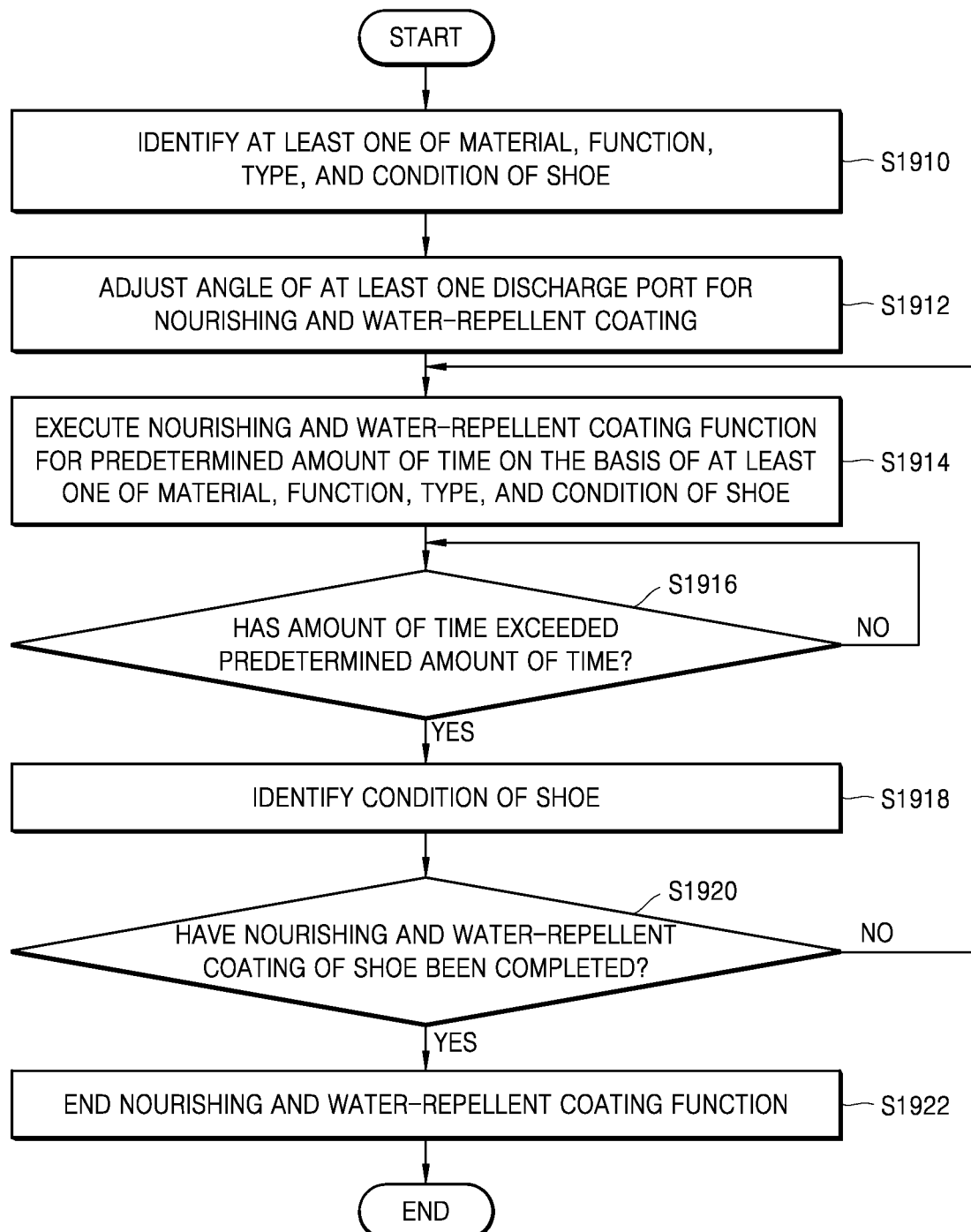
FIG. 19 is a flowchart illustrating a process of nourishing a shoe and coating the shoe to be water-repellent according to an embodiment of the present invention.
Figure 20:
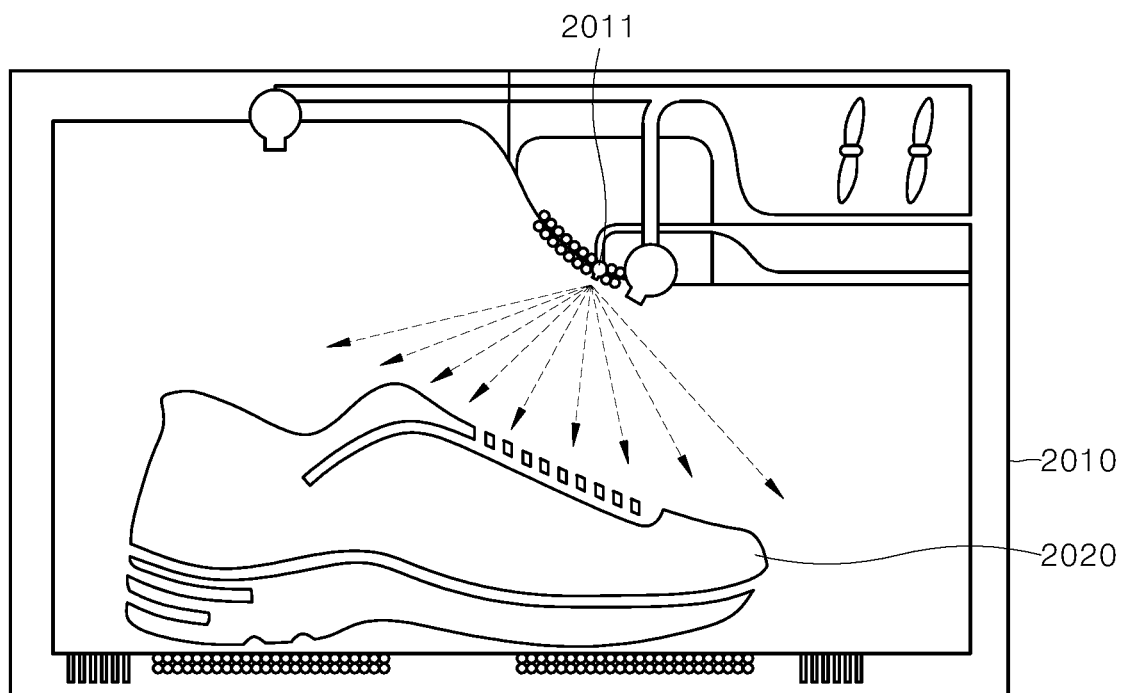
FIG. 20 is an exemplary view of nourishing a shoe and coating the shoe to be water-repellent according to an embodiment of the present invention.

FIG. 19 is a flowchart illustrating a process of nourishing a shoe and coating the shoe to be water-repellent according to an embodiment of the present invention. FIG. 20 is an exemplary view of nourishing a shoe and coating the shoe to be water-repellent according to an embodiment of the present invention.

Hereinafter, the process of nourishing a shoe and coating the shoe to be water-repellent according to an embodiment of the present invention will be described in detail with reference to FIGS. 19 and 20.

According to an embodiment, the processor 470 of the shoe treating apparatus 310 may identify at least one of the material, function, type, and condition of a shoe 2020 (S1910). The process (S1910) may include an operation or function in at least one of the process (S1010) of FIG. 10, the process (S1210) of FIG. 12, the process (S1410) of FIG. 14, and the process (S1710) of FIG. 17. Also, the process (S1910) may include at least one operation or function of the processes (S710 and S712) of FIG. 7.

According to an embodiment, the processor 470 may adjust an angle of at least one discharge port for nourishing and water-repellent coating (S1912). The processor 470 may identify the material, function, type, and condition of the shoe 2020 and then generate a spraying liquid (e.g., mist) through the water repellent part 448 of the shoe treating apparatus 310.

The processor 470 may adjust a discharge angle of at least one discharge port 2011 through which a spraying liquid for nourishing or water-repellent coating is discharged. The processor 470 may adjust the angle of the at least one discharge port 2011 so that the spraying liquid is first emitted to a portion of the shoe 2020 where at least one of nourishing and water-repellent coating is required.

According to an embodiment, in a state of being disposed on an inner wall of a shoe cabinet 2010, the at least one discharge port 2011 may spray the liquid generated by the water repellent part 448 toward the shoe 2020. The liquid may include a chemical component for supplying nourishment to the shoe 2020 or moisturizing the shoe 2020.

According to an embodiment, the liquid may also be discharged through a discharge port through which air is discharged, a discharge port through which steam is discharged, or a discharge port through which low-temperature hot air is discharged. A duct through which the liquid passes may be moisturized due to the liquid.

According to an embodiment, the processor 470 may execute the nourishing and water-repellent coating function for a predetermined amount of time on the basis of at least one of the material, type, and condition of the shoe (S1914). The processor 470 may spray the liquid toward the shoe 2020 for a predetermined amount of time (e.g., three minutes) to supply nourishment to the shoe 2020 or moisturize the shoe 2020.

The predetermined amount of time (e.g., three minutes) may be variably adjusted. The processor 470 may spray the liquid toward at least one of the inner side, outer side, and bottom of the shoe 2020 for a predetermined amount of time on the basis of at least one of the material, function, type, and condition of the shoe 2020. Also, the processor 470 may identify the time during which the liquid is sprayed. The time may be set to different amounts of time according to at least one of the material, function, type, and condition of the shoe 2020.

According to an embodiment, the processor 470 may identify whether an amount of time has exceeded a predetermined amount of time (S1916). The processor 470 may identify whether the time during which the process (S1914) is performed has exceeded the predetermined amount of time (e.g., three minutes). The predetermined amount of time may be determined as different amounts of time according to at least one of the material, function, type, and condition of the shoe 2020. Alternatively, the predetermined amount of time may be adjusted on the basis of a user input.

According to an embodiment, the processor 470 may identify the condition of the shoe (S1918). In a case in which the total time during which the process (S1914) is performed has exceeded the predetermined amount of time (e.g., three minutes), the processor 470 may identify the condition of the shoe 2020 on the basis of the operation (S1910). The processor 470 may identify the condition of the shoe 2020 on the basis of the operation (S1910) at predetermined time intervals.

According to an embodiment, the processor 470 may identify whether nourishing and water-repellent coating of the shoe have been completed (S1920). The sensor part 410 of the shoe treating apparatus 310 may include a sensor that can identify a moisturizing condition or a nourishing condition of the shoe. The processor 470 may acquire information on the moisturizing condition or nourishing condition of the shoe 2020 through the sensor part 410.

The processor 470 may, on the basis of the acquired information, determine the moisturizing condition or nourishing condition of the shoe 2020. In a case in which the moisturizing or nourishing condition of the shoe 2020 is a reference value or less, the processor 470 may, as described above in relation to the process (S1914), spray a liquid for a predetermined amount of time on the basis of at least one of the material, function, type, and condition of the shoe 2020 to supply nourishment to the shoe 2020.

According to an embodiment, the processor 470 may end the nourishing and water-repellent coating function (S1922). When the nourishing and water-repellent coating of the shoe 2020 are identified as having been completed in the process (S1920), the processor 470 may end the nourishing and water-repellent coating function.

Figure 21:
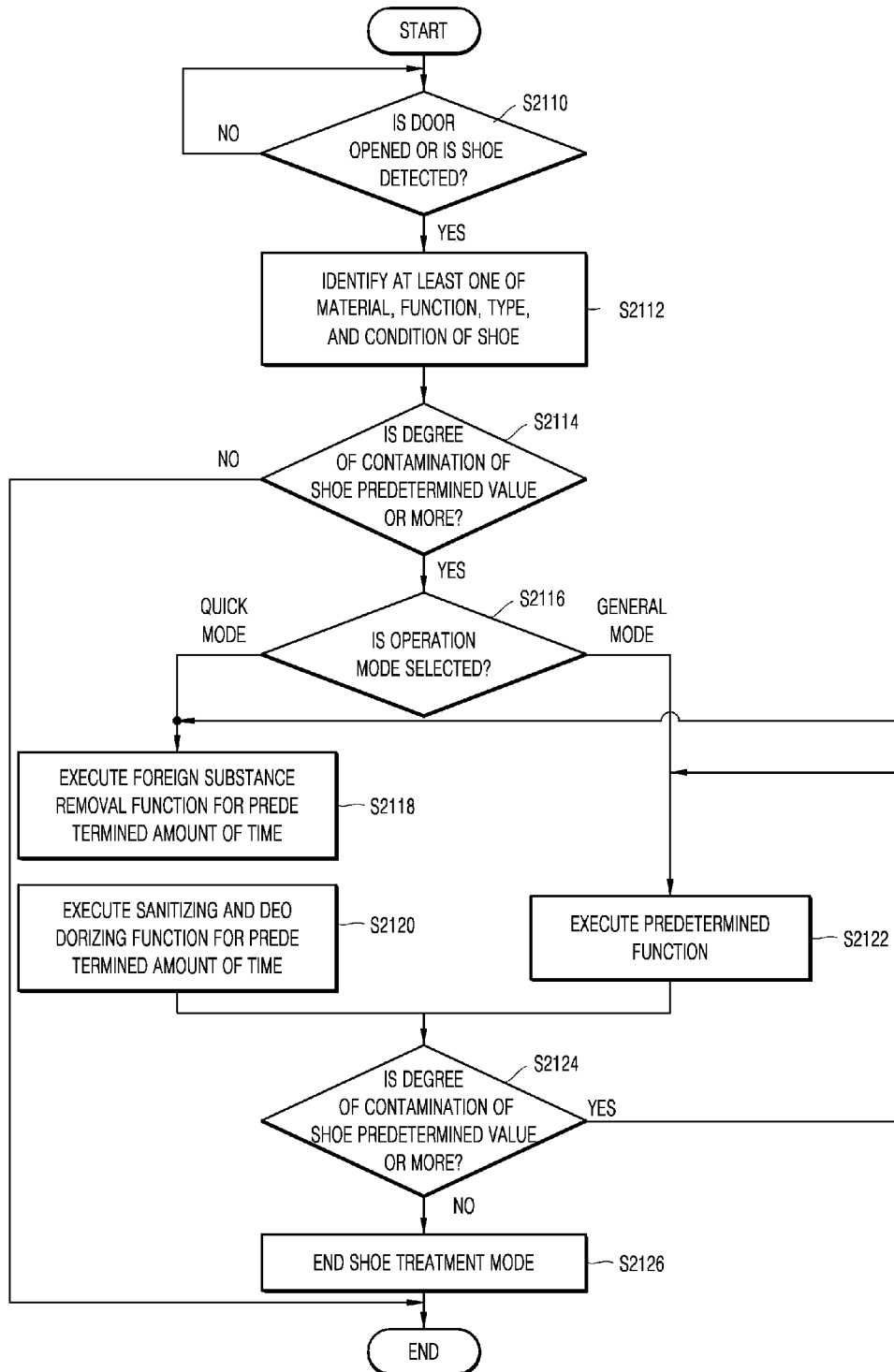
FIG. 21 is a flowchart illustrating a process of treating a shoe according to operation modes for treating shoes according to an embodiment of the present invention.

FIG. 21 is a flowchart illustrating a process of treating a shoe according to operation modes for treating shoes according to an embodiment of the present invention.

Hereinafter, the process of treating a shoe according to operation modes for treating shoes according to an embodiment of the present invention will be described in detail with reference to FIG. 21.

According to an embodiment, the processor 470 of the shoe treating apparatus 310 may identify whether a door of a shoe cabinet is opened or whether a shoe is present in the shoe cabinet (S2110). The process (S2110) may include at least one operation or function in the process (S510) of FIG. 5 and the process (S710) of FIG. 7.

According to an embodiment, the processor 470 may identify at least one of the material, function, type, and condition of the shoe (S2112). The process (S2112) may include at least one operation or at least one function performed in at least one of the process (S512) of FIG. 5, the process (S712) of FIG. 7, the process (S1010) of FIG. 10, the process (S1210) of FIG. 12, the process (S1410) of FIG. 14, the process (S1710) of FIG. 17, and the process (S1910) of FIG. 19. According to an embodiment, the processor 470 may identify whether the degree of contamination of the shoe is a predetermined value or more (S2114). The process (S2114) may include at least one operation or at least one function performed in at least one of the process (S1024) of FIG. 10, the process (S1222) of FIG. 12, and the process (S1422) of FIG. 14.

According to an embodiment, a shoe treating function of removing foreign substances attached to the shoe may also be performed even when the degree of contamination of the shoe does not exceed the predetermined value.

According to an embodiment, the processor 470 may select an operation mode of the shoe treating apparatus 310 (S2116). The operation mode may be selected through a result identified through the process (S2114). Alternatively, the operation mode may be selected by a user's selection. The operation mode may be classified into a quick mode and a general mode.

Alternatively, the operation mode may include various modes according to the effects of weather such as snow and rain. Alternatively, the operation mode may include a selection mode in which at least one of first to fifth functions selected by a user is performed. Alternatively, the operation mode may include a fiber/synthetic leather mode, a genuine leather mode, an enhanced function mode, a rapid sanitizing/deodorizing mode, a low-temperature hot air mode, an air brush mode, and the like. A selection relating to the operation mode may be input through the display part 433 or the input part 431 of the shoe treating apparatus 310.

According to an embodiment, the quick mode may include a first function of removing foreign substances adsorbed onto the shoe for a predetermined amount of time (e.g., four minutes) and a second function of executing at least one of sanitization and deodorization of the shoe for a predetermined amount of time (e.g., three minutes).

According to an embodiment, the quick mode may be a mode in which the first function is executed and then the second function is executed. Alternatively, the quick mode may be a mode in which the second function is executed and then the first function is executed. The time corresponding to the first function (e.g., four minutes) and the time corresponding to the second function (e.g., three minutes) may be variably changed by control of the processor 470 according to the degree of contamination of the shoe or may be changed by a user's settings.

According to an embodiment, the general mode may include the first function of removing foreign substances adsorbed onto the shoe for a predetermined amount of time (e.g., four minutes), the second function of executing at least one of sanitization and deodorization of the shoe for a predetermined amount of time (e.g., three minutes), a third function of executing at least one of steaming and sanitization of the shoe for a predetermined amount of time (e.g., ten minutes), a fourth function of executing at least one of dehumidification and drying of the shoe for a predetermined amount of time (e.g., twenty minutes), and a fifth function of executing at least one of nourishing and water-repellent coating of the shoe for a predetermined amount of time (e.g., three minutes).

According to an embodiment, the general mode may be a mode in which the first mode, the second mode, the third mode, the fourth mode, and the fifth mode are executed in that order. Alternatively, the general mode may be a mode in which the first to fifth modes are randomly executed. The amounts of time corresponding to the first to fifth functions may be variably changed by control of the processor 470 according to the degree of contamination of the shoe or may be changed by a user's settings.

According to an embodiment, the processor 470 may execute a foreign substance removal function for a predetermined amount of time (S2118). In a case in which an operation mode selected in the process (S2116) is the quick mode, the processor 470 may execute the function (e.g., the first function) of removing foreign substances adsorbed onto the shoe for a predetermined amount of time (e.g., four minutes).

According to an embodiment, in the quick mode, the processor 470 may, for a predetermined amount of time (e.g., four minutes), discharge air to the shoe through at least one discharge port disposed in the shoe cabinet in order to remove foreign substances from the shoe. Also, the processor 470 may suction the foreign substances separated from the shoe due to the discharged air through at least one suction port disposed in the shoe cabinet. The processor 470 may, after discharging the air, suction the air from inside the shoe cabinet in order to suction the foreign substances dislodged from the shoe due to the discharged air.

According to an embodiment, the processor 470 may adjust the angle or direction of the at least one discharge port to face a portion of the shoe where a large amount of foreign substances is adsorbed.

According to an embodiment, the processor 470 may execute a sanitizing and deodorizing function for a predetermined amount of time (S2120). In the quick mode, the processor 470 may emit at least one of UV light, a photocatalyst, and plasma in predetermined sizes to the shoe for a predetermined amount of time (e.g., three minutes) to execute the function of sanitizing and deodorizing the shoe (e.g., the second function).

According to an embodiment, the processor 470 may execute a predetermined function (S2122). In a case in which an operation mode selected in the process (S2116) is the general mode, the processor 470 may execute predetermined functions (e.g., the first to fifth functions in that order). The processor 470 may perform the first function of removing foreign substances adsorbed onto the shoe for a predetermined amount of time (e.g., four minutes), the second function of executing at least one of sanitization and deodorization of the shoe for a predetermined amount of time (e.g., three minutes), the third function of executing at least one of steaming and sanitization of the shoe for a predetermined amount of time (e.g., ten minutes), the fourth function of executing at least one of dehumidification and drying of the shoe for a predetermined amount of time (e.g., twenty minutes), and the fifth function of executing at least one of nourishing and water-repellent coating of the shoe for a predetermined amount of time (e.g., three minutes).

According to an embodiment, the first function may include at least one operation or function in FIGS. 10, 11A, and 11B. The second function may include at least one operation or function in FIGS. 12, 13A, and 13B.

The third function may include at least one operation or function in FIGS. 14, 15, 16A, and 16B. The fourth function may include at least one operation or function in FIGS. 17 and 18. Also, the fifth function may include at least one operation or function in FIGS. 19 and 20.

According to an embodiment, the processor 470 may identify whether the degree of contamination of the shoe is a predetermined value or more (S2124). The process (S2124) may include at least one operation or at least one function performed in at least one of the process (S1024) of FIG. 10, the process (S1222) of FIG. 12, the process (S1422) of FIG. 14, and the process (S2114) of FIG. 21.

According to an embodiment, in a case in which the selected mode is the quick mode, when the degree of contamination is identified as being the predetermined value or more, the processor 470 may perform the process (S2118).

According to an embodiment, in a case in which the selected mode is the general mode, when the degree of contamination is identified as being the predetermined value or more, the processor 470 may perform the process (S2122).

According to an embodiment, in a case in which the degree of contamination of the shoe is not the predetermined value or more in the process (S2124), the processor 470 may end the shoe treatment mode (S2126). According to an embodiment, in a case in which the degree of contamination of the shoe is not the predetermined value or more, the processor 470 may end the execution of the first to fifth functions.

Figure 22:
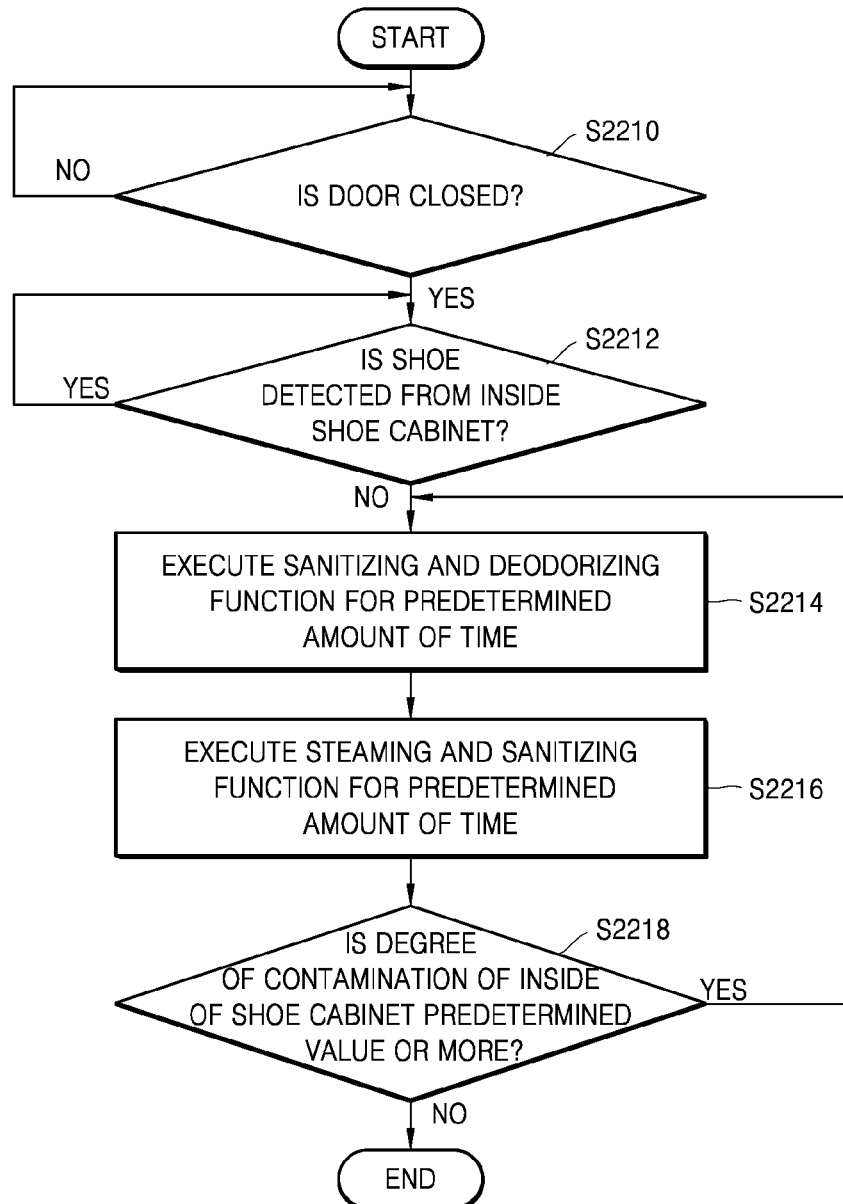
FIG. 22 is a flowchart illustrating a process of disinfecting a shoe treating apparatus according to an embodiment of the present invention.

FIG. 22 is a flowchart illustrating a process of disinfecting a shoe treating apparatus according to an embodiment of the present invention.

Hereinafter, the process of disinfecting a shoe treating apparatus according to an embodiment of the present invention will be described in detail with reference to FIG. 22.

According to an embodiment, the processor 470 of the shoe treating apparatus 310 may identify whether a door of a shoe cabinet is closed (S2210). The processor 470 may receive a signal according to closing of the door from the door open/close sensor 412 and may detect the closing of the door through the received signal.

According to an embodiment, the processor 470 may detect a shoe in the shoe cabinet (S2212). The processor 470 may, through at least one of the camera 432 and the weight sensor 414 disposed on the lower portion of the shoe cabinet, identify whether a shoe is present in the shoe cabinet 320.

According to an embodiment, the processor 470 may execute a sanitizing and deodorizing function for a predetermined amount of time (S2214). When a shoe is not detected from the shoe cabinet, the processor 470 may determine that a shoe is not present in the shoe cabinet. When it is determined that a shoe is not present in the shoe cabinet, the processor 470 may emit at least one of UV light, a photocatalyst, and plasma to the shoe cabinet at a predetermined intensity (e.g., the maximum intensity) for a predetermined amount of time to execute a function of sanitizing and deodorizing the shoe cabinet.

In a case in which a shoe is not detected from inside the shoe cabinet, the processor 470 may, in order to disinfect the inside of the shoe cabinet, execute the second and third functions with a higher intensity than the second and third functions in a case in which a shoe is detected. For example, in a case in which a shoe is not detected from inside the shoe cabinet, the processor 470 may emit at least one of the UV light, a photocatalyst, and plasma with the maximum intensity.

According to an embodiment, the processor 470 may execute a steaming and sanitizing function for a predetermined amount of time (S2216). The processor 470 may, after performing the process (S2214), emit steam to the shoe cabinet at a predetermined intensity (e.g., the maximum intensity) for a predetermined amount of time to steam and sanitize the shoe cabinet. For example, in a case in which a shoe is not detected from inside the shoe cabinet, the processor 470 may spray steam with the maximum intensity.

According to an embodiment, the processor 470 may identify whether the degree of contamination of the inside of the shoe cabinet is a predetermined value or more (S2218). The processor 470 may perform the processes (S2214 and S2216) to perform sanitization, deodorization, and disinfection of the shoe cabinet. The processor 470 may identify the degree of contamination of the shoe cabinet and determine whether the identified degree of contamination is the predetermined value or more.

For example, when the degree of contamination of the shoe cabinet is identified as being the predetermined value or more, the processor 470 may restart the processes (S2214 and S2216). For example, when the degree of contamination of the shoe cabinet is determined as not being the predetermined value or more, the processor 470 may end the sanitization, deodorization, and disinfection of the shoe cabinet.

Hereinafter, movement control of each of a plurality of shelves of a cabinet (e.g., the upper cabinet 150) of the shoe treating apparatus 310 will be described.

[Shelf Angle Adjustment According to User Identification]

Figure 23:
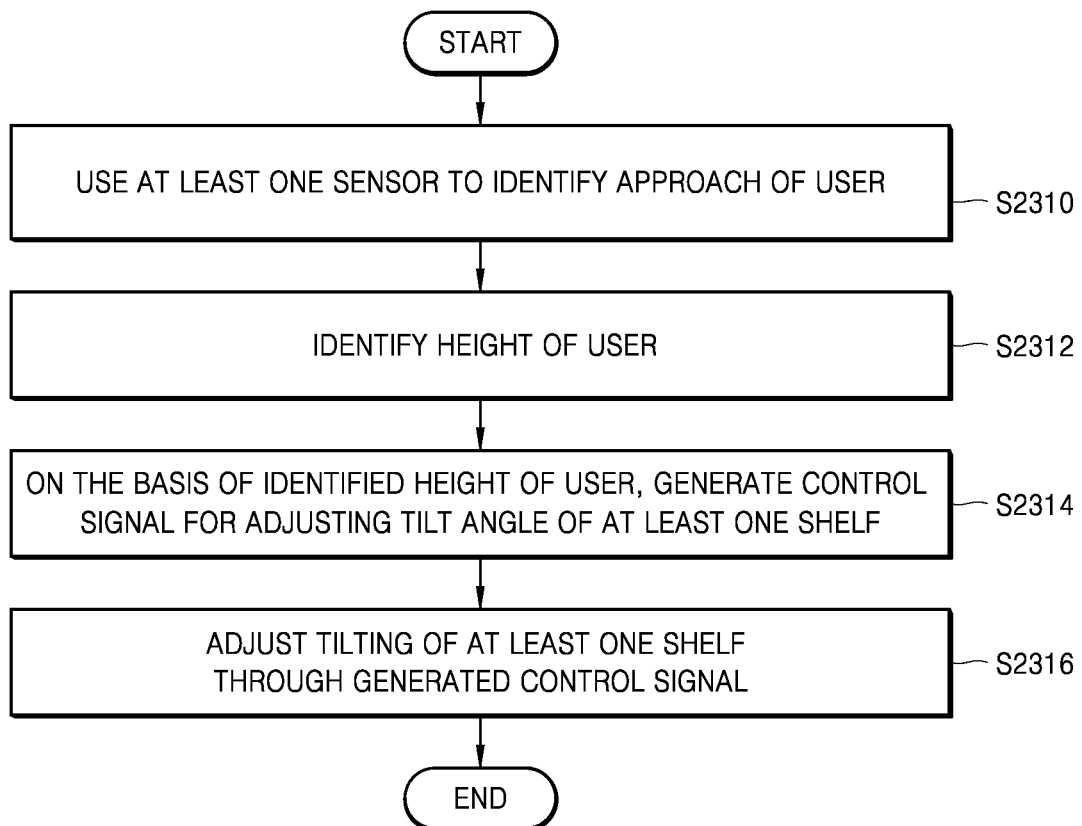
FIG. 23 is a flowchart illustrating a process of controlling tilting of a shelf of an upper cabinet of a shoe treating apparatus according to an embodiment of the present invention.
Figure 24A:
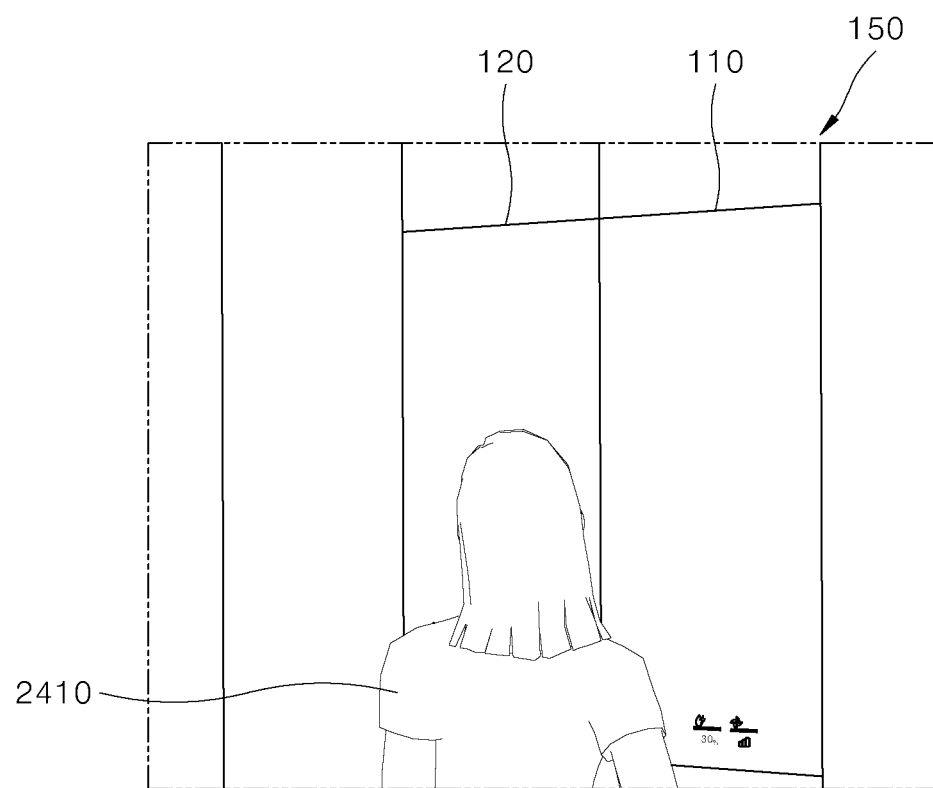
FIG. 24A is an exemplary view illustrating a user approaching a shoe treating apparatus according to an embodiment of the present invention.
Figure 24B:
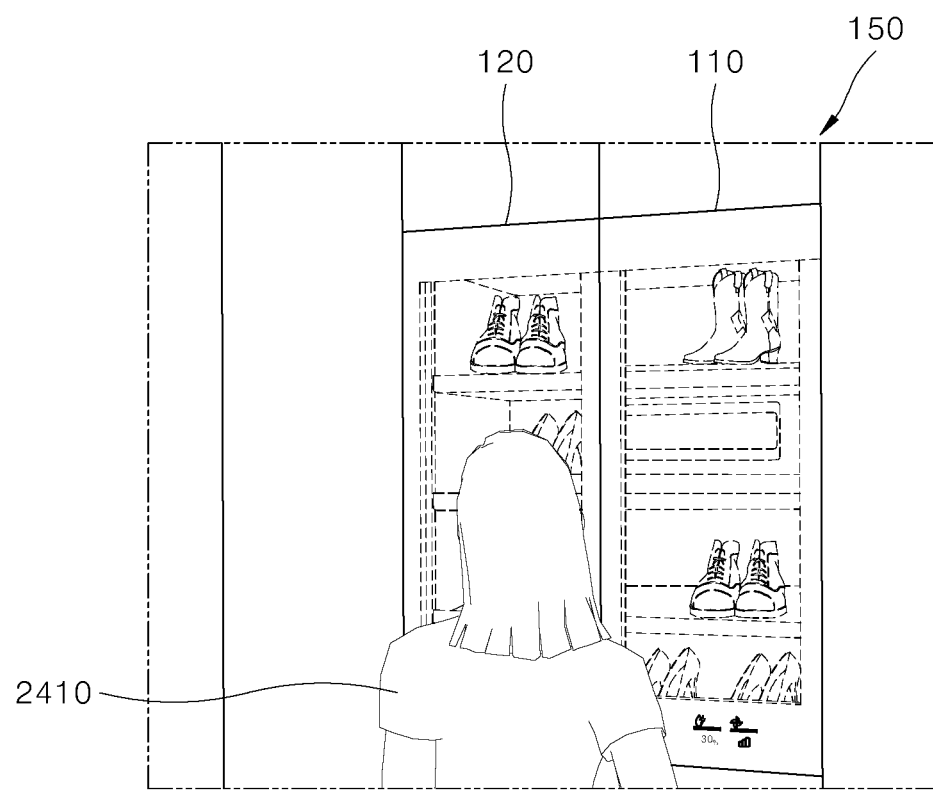
FIG. 24B is an exemplary view illustrating a state of the shoe treating apparatus in a case in which a user approaches the shoe treating apparatus according to an embodiment of the present invention.
Figure 25A:
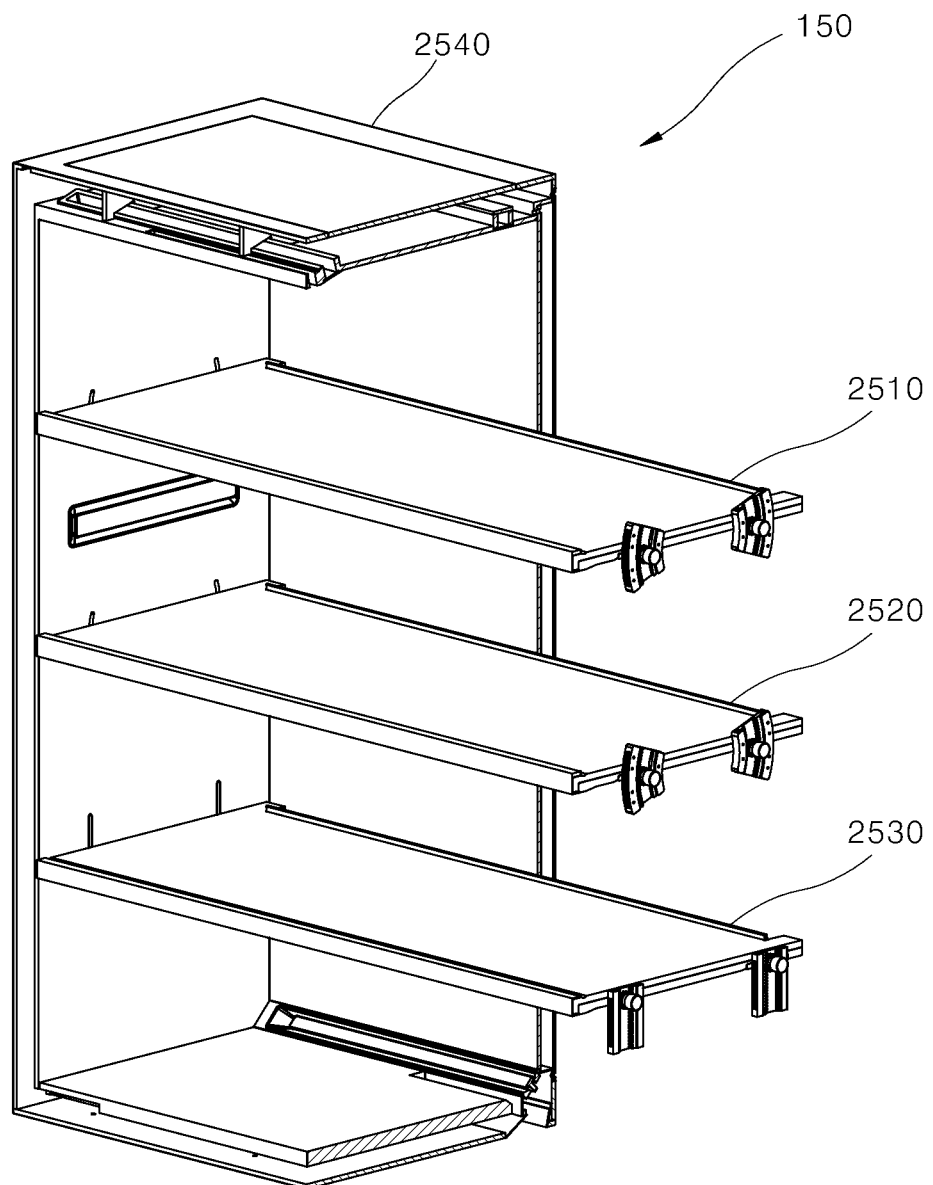
FIG. 25A is an exemplary view of a plurality of shelves disposed in the upper cabinet according to an embodiment of the present invention.
Figure 25B:
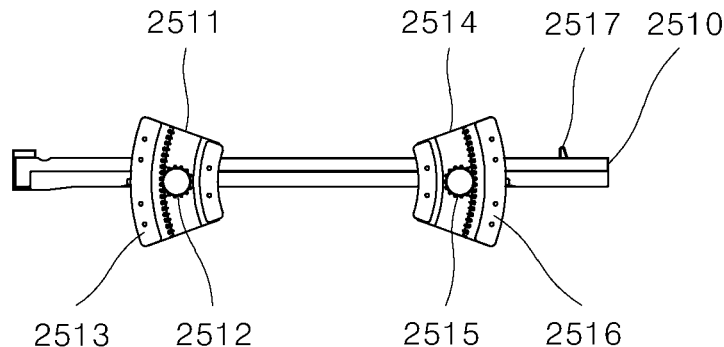
FIG. 25B is an exemplary view illustrating coupling members allowing each of the plurality of shelves disposed in the upper cabinet to be attached to an inner wall of the shoe treating apparatus according to an embodiment of the present invention.
Figure 25B:
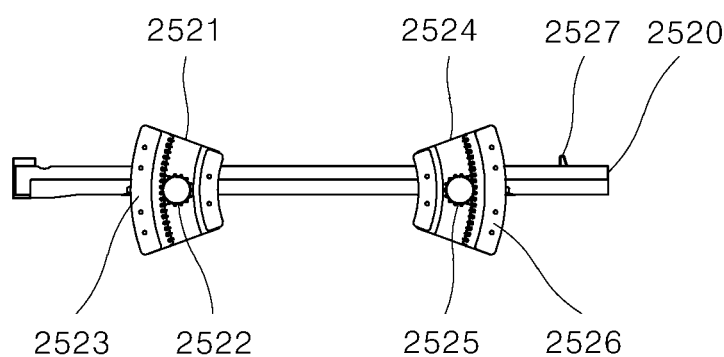
Figure 25B:
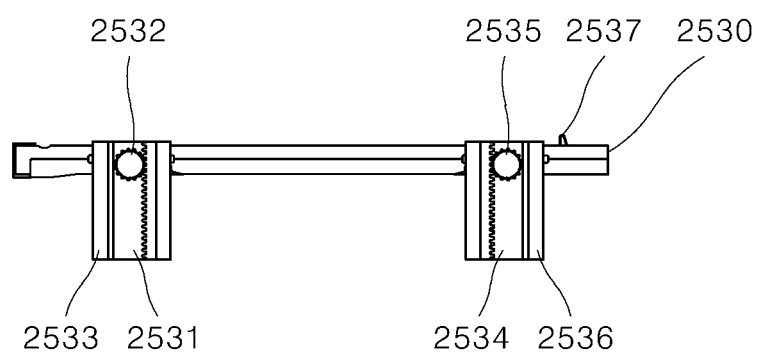
Figure 26A:
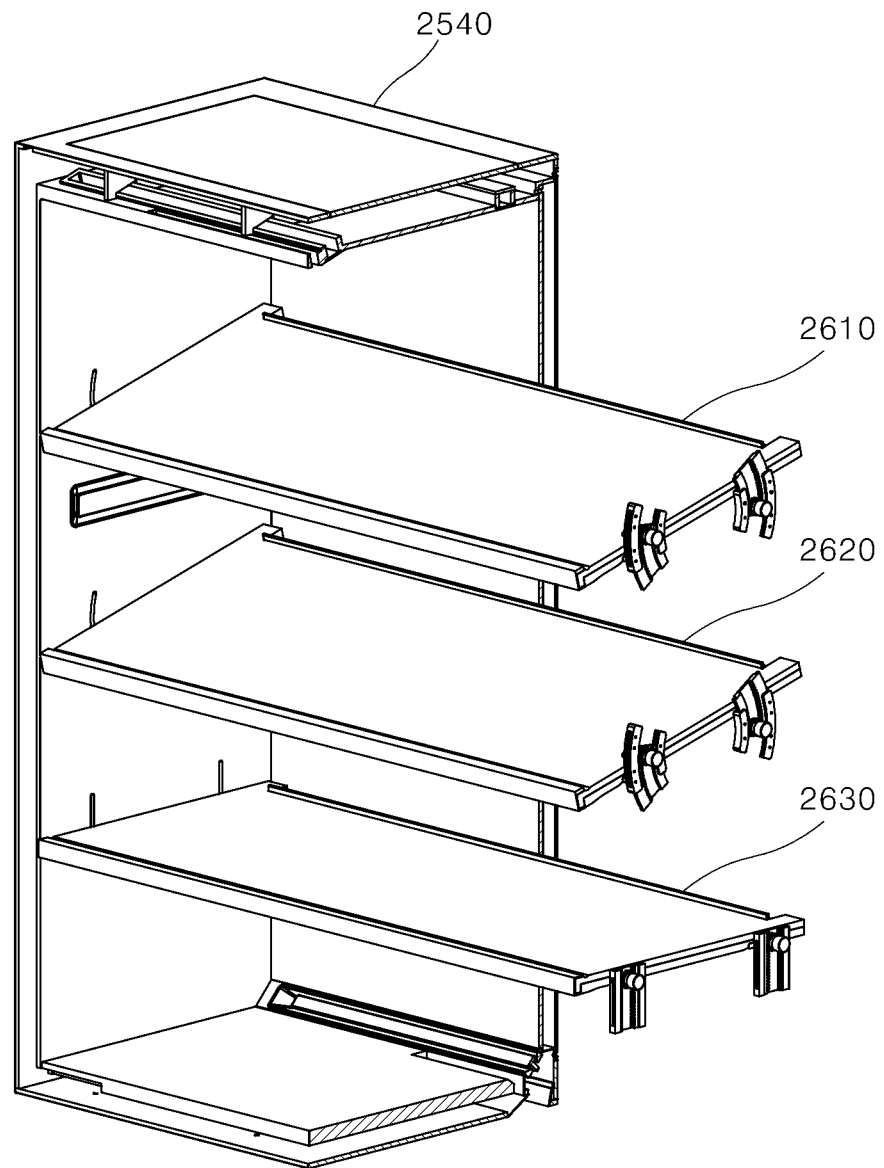
FIG. 26A is an exemplary view of a plurality of shelves tilting in the same direction in an upper cabinet according to an embodiment of the present invention.
Figure 26B:
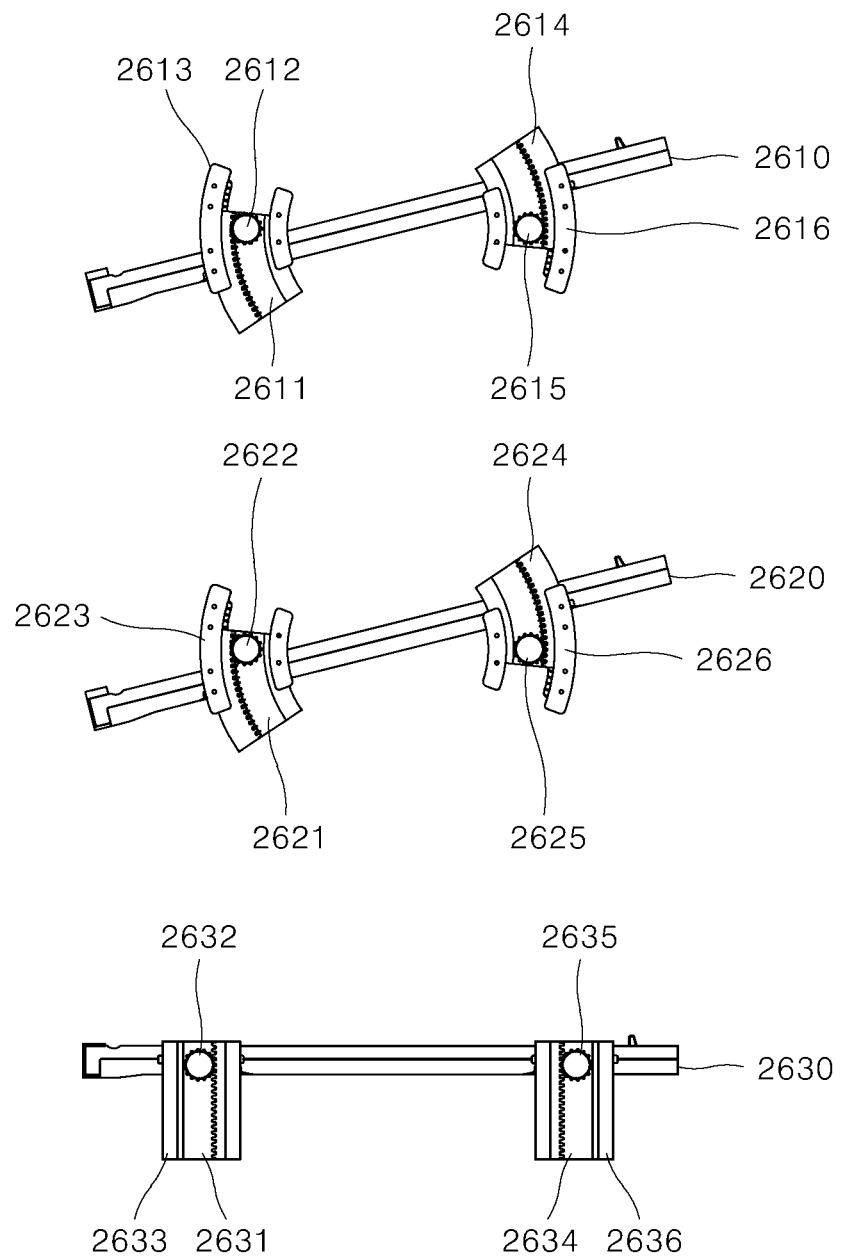
FIG. 26B is an exemplary view illustrating coupling members in a case in which the plurality of shelves disposed in the upper cabinet tilt in the same direction according to an embodiment of the present invention.
Figure 27A:
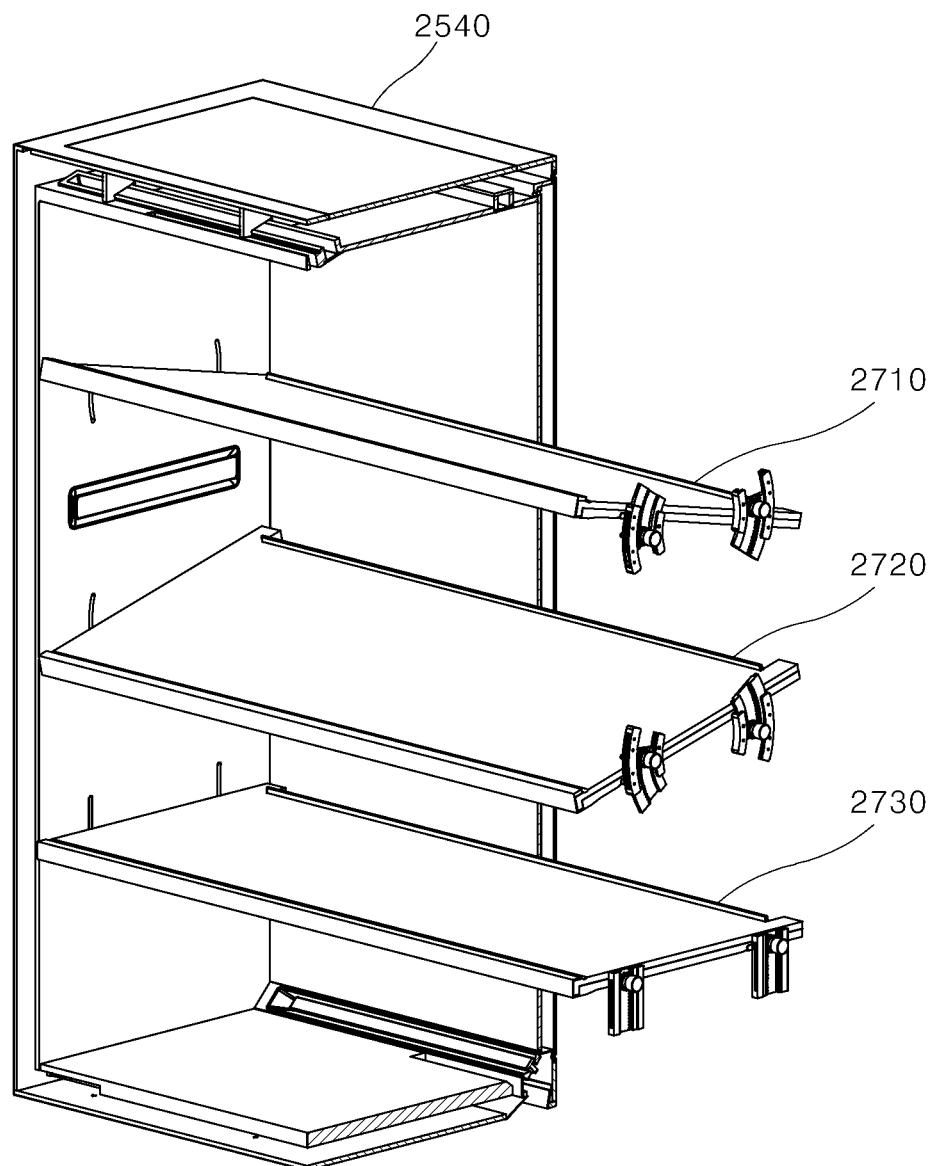
FIG. 27A is an exemplary view of a plurality of shelves tilting in different directions in an upper cabinet according to an embodiment of the present invention.
Figure 27B:
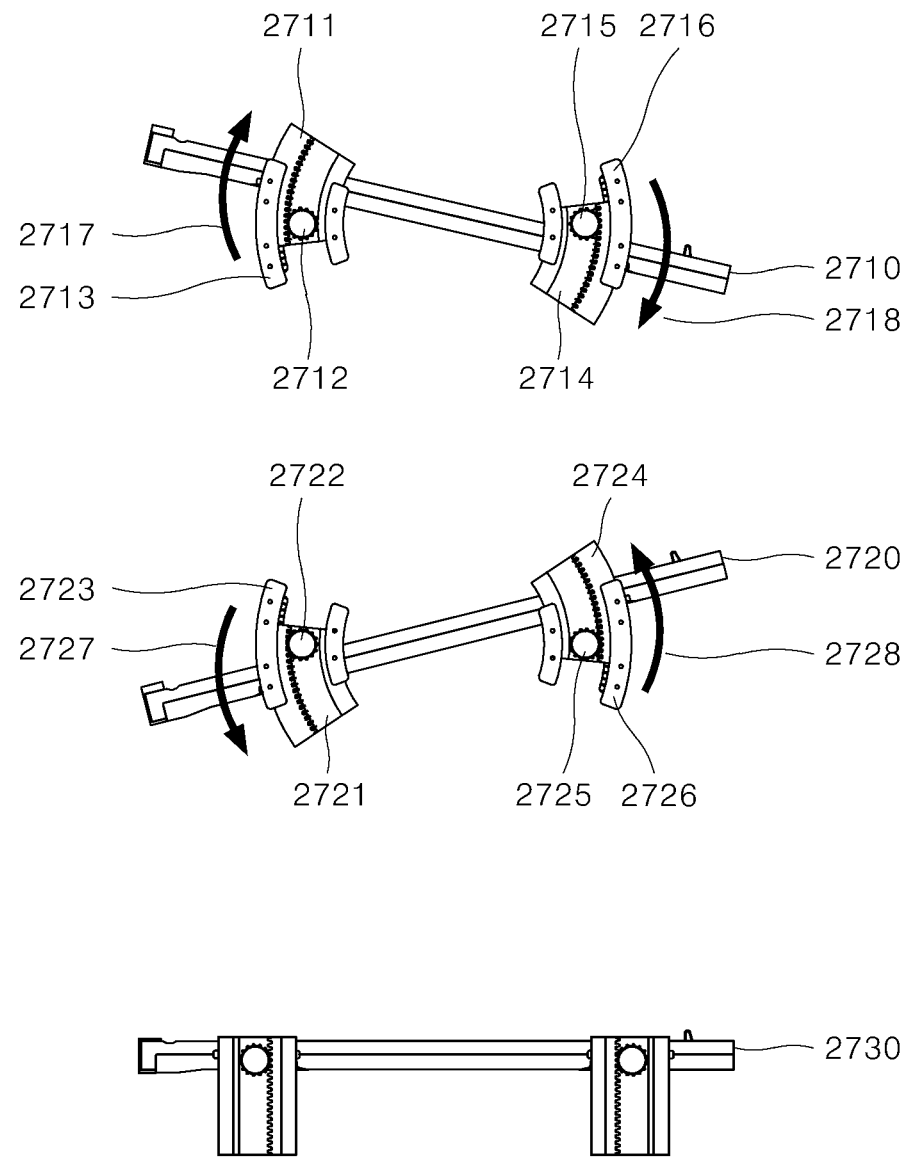
FIG. 27B is an exemplary view illustrating coupling members in a case in which the plurality of shelves disposed in the upper cabinet tilt in different directions according to an embodiment of the present invention.
Figure 28A:
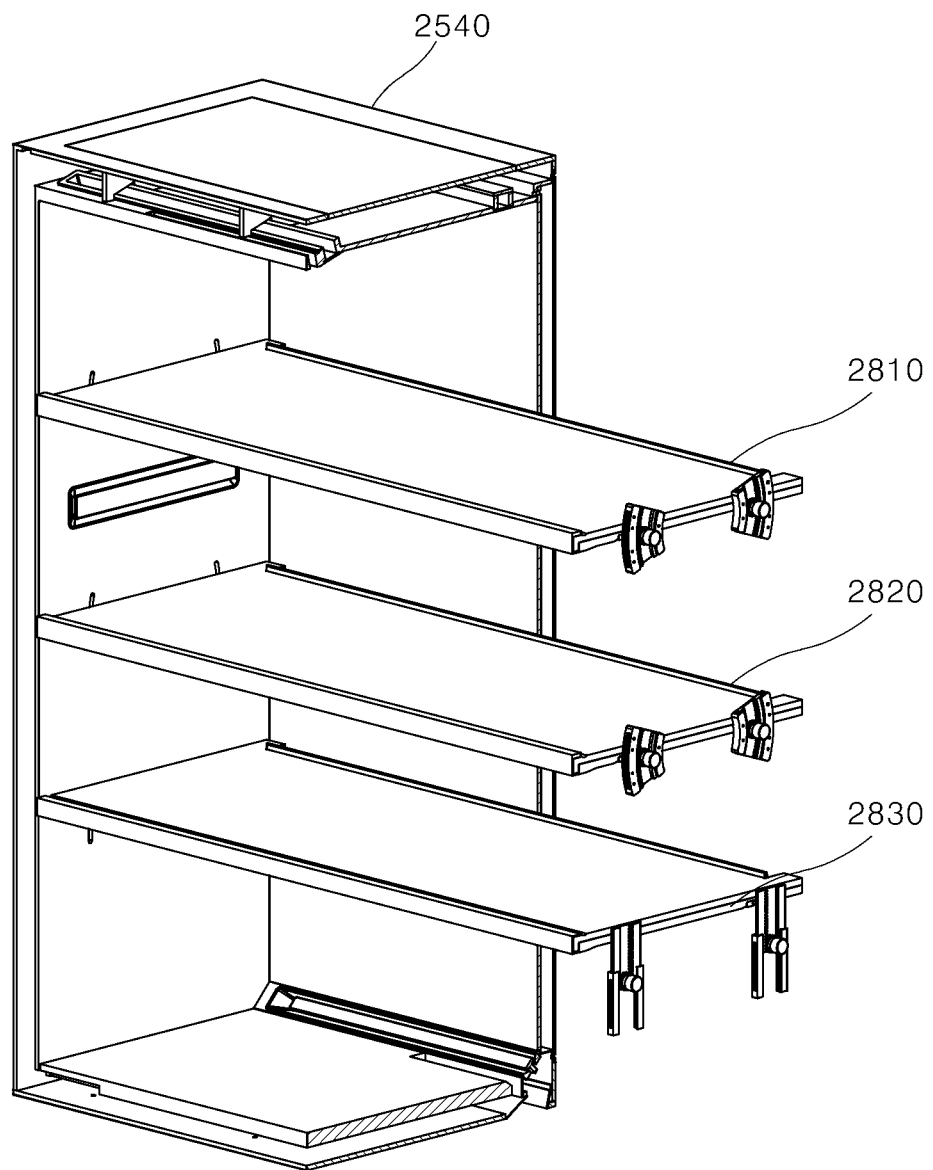
FIG. 28A is an exemplary view of a state in which the lowest shelf of a plurality of shelves moves upward in an upper cabinet according to an embodiment of the present invention.
Figure 28B:
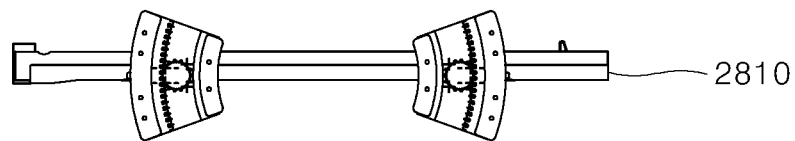
FIG. 28B is an exemplary view illustrating coupling members in a case in which the lowest shelf of the plurality of shelves disposed in the upper cabinet moves upward according to an embodiment of the present invention.
Figure 28B:
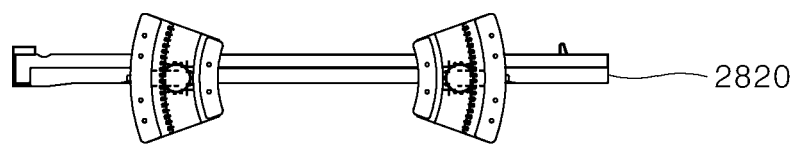
Figure 28B:
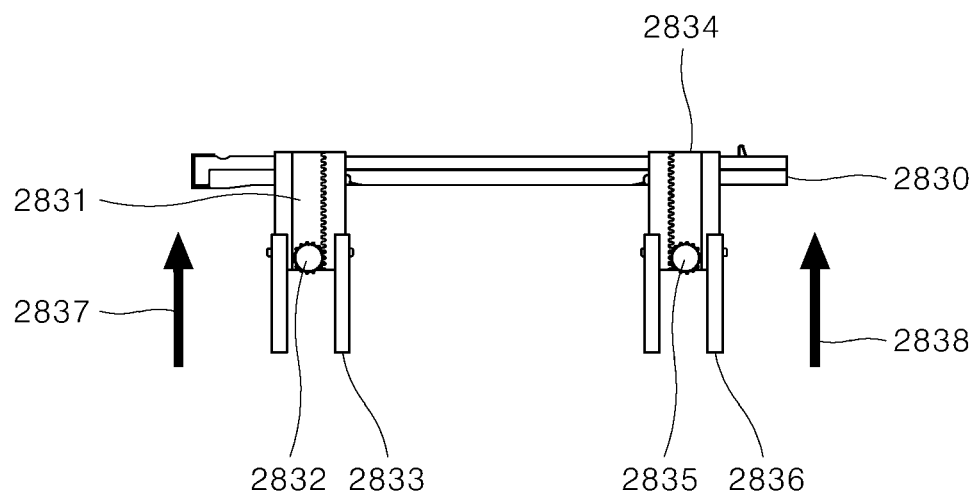

FIG. 23 is a flowchart illustrating a process of controlling tilting of a shelf of an upper cabinet of a shoe treating apparatus according to an embodiment of the present invention. FIG. 24A is an exemplary view illustrating a user approaching a shoe treating apparatus according to an embodiment of the present invention. FIG. 24B is an exemplary view illustrating a state of the shoe treating apparatus in a case in which a user approaches the shoe treating apparatus according to an embodiment of the present invention. FIG. 25A is an exemplary view of a plurality of shelves disposed in the upper cabinet according to an embodiment of the present invention. FIG. 25B is an exemplary view illustrating coupling members allowing each of the plurality of shelves disposed in the upper cabinet to be attached to an inner wall of the shoe treating apparatus according to an embodiment of the present invention. FIG. 26A is an exemplary view of a plurality of shelves tilting in the same direction in an upper cabinet according to an embodiment of the present invention. FIG. 26B is an exemplary view illustrating coupling members in a case in which the plurality of shelves disposed in the upper cabinet tilt in the same direction according to an embodiment of the present invention. FIG. 27A is an exemplary view of a plurality of shelves tilting in different directions in an upper cabinet according to an embodiment of the present invention. FIG. 27B is an exemplary view illustrating coupling members in a case in which the plurality of shelves disposed in the upper cabinet tilt in different directions according to an embodiment of the present invention. FIG. 28A is an exemplary view of a state in which the lowest shelf of a plurality of shelves moves upward in an upper cabinet according to an embodiment of the present invention. FIG. 28B is an exemplary view illustrating coupling members in a case in which the lowest shelf of the plurality of shelves disposed in the upper cabinet moves upward according to an embodiment of the present invention.

Hereinafter, the process of controlling tilting of a shelf of an upper cabinet of a shoe treating apparatus according to an embodiment of the present invention will be described in detail with reference to FIGS. 23 to 28B.

According to an embodiment, the processor 470 may use at least one sensor to identify an approach of a user (S2310). Through at least one sensor (e.g., the camera 432, the distance measurement sensor 416, the IR sensor 419, or the like) disposed at one side (e.g., the upper side, lower side, left side, or right side) of the front surface (e.g., the doors 110, 120, 130, and 140) of the shoe treating apparatus 310, the processor 470 may identify a user approaching the shoe treating apparatus 310.

Referring to FIG. 24A, through at least one sensor (e.g., the camera 432, the distance measurement sensor 416, the IR sensor 419, or the like), the processor 470 may detect a user 2410 approaching the shoe treating apparatus 310. The at least one sensor (e.g., the camera 432, the distance measurement sensor 416, the IR sensor 419, or the like) may be disposed at one side (e.g., the upper side, lower side, left side, or right side) of the doors 110 and 120 of the upper cabinet 150 of the shoe treating apparatus 310.

According to an embodiment, the processor 470 may identify the height of the user (S2312). When the user is identified as approaching, the processor 470 may cause at least one light emitting element disposed on at least one of a plurality of shelves of the upper cabinet 150 and/or at least one of a plurality of shelves of the lower cabinet 160 (for example, disposed on the lower portion of the shelf) to emit light.

At least one light emitting element may be disposed on a bottom surface of each of the plurality of shelves included in each of the upper cabinet 150 and the lower cabinet 160.

According to an embodiment, the processor 470 may, on the basis of a distance between the shoe treating apparatus 310 and the user, adjust the brightness of at least one light emitting element disposed on the bottom surface of each shelf.

For example, the processor 470 may cause the at least one light emitting element to emit more light as the distance between the shoe treating apparatus 310 and the user becomes shorter and may cause the at least one light emitting element to emit less light as the distance between the shoe treating apparatus 310 and the user becomes longer. Alternatively, the processor 470 may control the at least one light emitting element so that the at least one light emitting element emits different colored lights on the basis of the distance between the shoe treating apparatus 310 and the user.

Referring to FIG. 24B, when the approach of the user 2410 is identified, the processor 470 may cause all light emitting elements disposed on the lower surface of each shelf of the upper cabinet 150 to emit light. Alternatively, the processor 470 may identify a certain shelf of the upper cabinet 150 on which a shoe of the identified user is stored and may cause at least one light emitting element disposed on the bottom surface of the identified shelf to emit light.

Referring to FIG. 23, the processor 470 may, on the basis of the identified height of the user, generate a control signal for adjusting a tilt angle of at least one shelf (S2314). The processor 470 may, on the basis of the approach of the user 2410, identify the height of the user and then generate a control signal for adjusting tilting of at least one shelf included in the upper cabinet 150.

Alternatively, the processor 470 may, on the basis of the approach of the user 2410, generate a control signal for adjusting tilting of at least one shelf included in the lower cabinet 160.

According to an embodiment, the processor 470 may adjust tilting of at least one shelf through the generated control signal (S2316). The processor 470 may acquire information on atilt angle for each height (e.g., Table 1) that is stored in the memory 434 and may, on the basis of the acquired information, adjust tilting of at least one shelf of the upper cabinet 150 or the lower cabinet 160.

Also, the processor 470 may provide a control signal to a motor of the corresponding shelf to adjust tilting of each shelf.

In this way, the processor 470 may adjust tilting of each shelf by referring to Table 1 so that it is easy for the user to see a shoe disposed on each shelf.

Referring to FIG. 25A, the upper cabinet 150 according to an embodiment of the present invention may include a plurality of shelves 2510, 2520, and 2530. Each of the plurality of shelves 2510, 2520, and 2530 may be coupled to an inner wall of a frame 2540 of the upper cabinet 150. Among the plurality of shelves 2510, 2520, and 2530, a first shelf 2510 may be disposed at the highest position, a second shelf 2520 may be disposed below the first shelf 2510, and a third shelf 2530 may be disposed below the second shelf 2520.

According to an embodiment, the upper cabinet 150 may include more or fewer shelves instead of including the first to third shelves.

Referring to FIG. 25B, each of both side surfaces of each shelf may be coupled to the inner wall of the frame 2540 of the upper cabinet 150. Also, two coupling members may be formed on each of both side surfaces of each shelf. For example, a first coupling member and a second coupling member may be formed on a right side surface of each shelf.

Also, a groove for gathering foreign substances adsorbed onto a shoe and dislodged therefrom may be formed in each shelf, and at least one light emitting element may be formed on the bottom surface of each shelf. Also, protrusions 2517, 2527, and 2537 configured to support sliding of a shoe may be formed on a flat surface of each shelf. The protrusions 2517, 2527, and 2537 may be disposed on a front side of each shelf.

For example, a first coupling member formed on a right side surface of the first shelf 2510 may include a first inner member 2511, a first rotary member 2512, and a first outer member 2513. The first inner member 2511 may be coupled to be fixed to the first shelf 2510, and the first rotary member 2512 may move according to control of the motor part 437 in the first inner member 2511 and may be coupled to the inner wall of the frame 2540. Also, the first outer member 2513 may be formed to surround the first rotary member 2512 and the first inner member 2511 and may be coupled to the inner wall of the frame 2540. One side of the first inner member 2511 may be coupled to the first rotary member 2512 and may be formed in the shape of a sawtooth to rotate according to rotation of the first rotary member 2512.

For example, a second coupling member formed on the right side surface of the first shelf 2510 may include a second inner member 2514, a second rotary member 2515, and a second outer member 2516. The second inner member 2514 may be coupled to be fixed to the first shelf 2510, and the second rotary member 2515 may move according to control of the motor part 437 in the second inner member 2514 and may be coupled to the inner wall of the frame 2540. Also, the second outer member 2516 may be formed to surround the second rotary member 2515 and the second inner member 2514 and may be coupled to the inner wall of the frame 2540. One side of the second inner member 2514 may be coupled to the second rotary member 2515 and may be formed in the shape of a sawtooth to rotate according to rotation of the second rotary member 2515.

For example, the second shelf 2520 may be disposed below the first shelf 2510. A third coupling member formed on a right side surface of the second shelf 2520 may include a third inner member 2521, a third rotary member 2522, and a third outer member 2523. The third inner member 2521 may be coupled to be fixed to the second shelf 2520, and the third rotary member 2522 may move according to control of the motor part 437 in the third inner member 2521 and may be coupled to the inner wall of the frame 2540. Also, the third outer member 2523 may be formed to surround the third rotary member 2522 and the third inner member 2521 and may be coupled to the inner wall of the frame 2540. One side of the third inner member 2521 may be coupled to the third rotary member 2522 and may be formed in the shape of a sawtooth to rotate according to rotation of the third rotary member 2522.

For example, a fourth coupling member formed on the right side surface of the second shelf 2520 may include a fourth inner member 2524, a fourth rotary member 2525, and a fourth outer member 2526. The fourth inner member 2524 may be coupled to be fixed to the second shelf 2520, and the fourth rotary member 2525 may move according to control of the motor part 437 in the fourth inner member 2524 and may be coupled to the inner wall of the frame 2540. Also, the fourth outer member 2526 may be formed to surround the fourth rotary member 2525 and the fourth inner member 2524 and may be coupled to the inner wall of the frame 2540. One side of the fourth inner member 2524 may be coupled to the fourth rotary member 2525 and may be formed in the shape of a sawtooth to rotate according to rotation of the fourth rotary member 2525.

For example, the third shelf 2530 may be disposed below the second shelf 2520. A fifth coupling member formed on a right side surface of the third shelf 2530 may include a fifth inner member 2531, a fifth rotary member 2532, and a fifth outer member 2533. The fifth inner member 2531 may be coupled to be fixed to the third shelf 2530, and the fifth rotary member 2532 may move according to control of the motor part 437 in the fifth inner member 2531 and may be coupled to the inner wall of the frame 2540. Also, the fifth outer member 2533 may be formed to surround the fifth rotary member 2532 and the fifth inner member 2531 and may be coupled to the inner wall of the frame 2540. One side of the fifth inner member 2531 may be coupled to the fifth rotary member 2532 and may be formed in the shape of a sawtooth to move upward or downward according to rotation of the fifth rotary member 2532.

For example, a sixth coupling member formed on the right side surface of the third shelf 2530 may include a sixth inner member 2534, a sixth rotary member 2535, and a sixth outer member 2536. The sixth inner member 2534 may be coupled to be fixed to the third shelf 2530, and the sixth rotary member 2535 may move according to control of the motor part 437 in the sixth inner member 2534 and may be coupled to the inner wall of the frame 2540. Also, the sixth outer member 2536 may be formed to surround the sixth rotary member 2535 and the sixth inner member 2534 and may be coupled to the inner wall of the frame 2540. One side of the sixth inner member 2534 may be coupled to the sixth rotary member 2535 and may be formed in the shape of a sawtooth to move upward or downward according to rotation of the sixth rotary member 2535.

In this way, each shelf may tilt or vertically move on the basis of rotation of a rotary member connected to each shelf.

Referring to FIG. 26A, each of a plurality of shelves 2610, 2620, and 2630 included in the upper cabinet 150 according to an embodiment of the present invention may tilt. Each of the plurality of shelves 2610, 2620, and 2630 may tilt in a state of being coupled to the inner wall of the frame 2540 of the upper cabinet 150.

For example, among the plurality of shelves 2610, 2620, and 2630, a first shelf 2610 and a second shelf 2620 may tilt so that the front and rear thereof move in different directions. Among the plurality of shelves 2610, 2620, and 2630, the first shelf 2610 and the second shelf 2620 may tilt in the same direction. Also, a third shelf 2630 may move upward or downward.

Referring to FIG. 26B, a plurality of shelves disposed in the upper cabinet according to an embodiment of the present invention may tilt in the same direction.

For example, as a first rotary member 2612 of a first coupling member formed on a right side surface of the first shelf 2610 rotates counterclockwise, a first inner member 2611 connected to the first rotary member 2612 may move downward. Also, on the basis of the downward movement of the first inner member 2611, the front of the first shelf 2610, which is coupled to the first inner member 2611, may tilt downward.

Also, as a second rotary member 2615 of a second coupling member formed on the right side surface of the first shelf 2610 rotates counterclockwise, a second inner member 2614 connected to the second rotary member 2615 may move upward. Also, on the basis of the upward movement of the second inner member 2614, the rear of the first shelf 2610, which is coupled to the second inner member 2614, may tilt upward. The rotational directions of the first rotary member 2612 and the second rotary member 2615 may be the same.

For example, as a third rotary member 2622 of a third coupling member formed on a right side surface of the second shelf 2620 rotates counterclockwise, a third inner member 2621 connected to the third rotary member 2622 may move downward. Also, on the basis of the downward movement of the third inner member 2621, the front of the second shelf 2620, which is coupled to the third inner member 2621, may tilt downward.

Also, as a fourth rotary member 2625 of a fourth coupling member formed on the right side surface of the second shelf 2620 rotates counterclockwise, a fourth inner member 2624 connected to the fourth rotary member 2625 may move upward. Also, on the basis of the upward movement of the fourth inner member 2624, the rear of the second shelf 2620, which is coupled to the fourth inner member 2624, may tilt upward. For example, the rotational directions of the third rotary member 2622 and the fourth rotary member 2625 may be the same.

For example, as a fifth rotary member 2632 of a fifth coupling member formed on a right side surface of the third shelf 2630 rotates counterclockwise, a fifth inner member 2631 connected to the fifth rotary member 2632 may move upward. Also, on the basis of the upward movement of the fifth inner member 2631, the third shelf 2630 may move upward.

Also, as a sixth rotary member 2635 of a sixth coupling member formed on the right side surface of the third shelf 2630 rotates counterclockwise, a sixth inner member 2634 connected to the sixth rotary member 2635 may move downward. Also, on the basis of the downward movement of the sixth inner member 2634, the third shelf 2630 may move downward.

For example, for the third shelf 2630 to move upward, the processor 470 may control the motor part 437 to perform at least one of counterclockwise rotation of the fifth rotary member 2632 and clockwise rotation of the sixth rotary member 2635.

Alternatively, for the third shelf 2630 to move downward, the processor 470 may control the motor part 437 to perform at least one of clockwise rotation of the fifth rotary member 2632 and counterclockwise rotation of the sixth rotary member 2635.

Referring to FIG. 27A, each of a plurality of shelves 2710, 2720, and 2730 included in the upper cabinet 150 according to an embodiment of the present invention may tilt. Each of the plurality of shelves 2710, 2720, and 2730 may tilt in a state of being coupled to the inner wall of the frame 2540 of the upper cabinet 150.

For example, among the plurality of shelves 2710, 2720, and 2730, a first shelf 2710 and a second shelf 2720 may tilt to move in different directions. For example, the front portion of the first shelf 2710 may move upward, and the front portion of the second shelf 2720 may move downward.

In this way, the first shelf 2710 and the second shelf 2720 among the plurality of shelves 2710, 2720, and 2730 may tilt in different directions each other. Also, a third shelf 2730 may move upward or downward.

Referring to FIG. 27B, a plurality of shelves disposed in the upper cabinet according to an embodiment of the present invention may tilt in different directions.

For example, as a first rotary member 2712 of a first coupling member formed on a right side surface of the first shelf 2710 rotates clockwise, a first inner member 2711 connected to the first rotary member 2712 may move upward. Also, on the basis of the upward movement of the first inner member 2711, the front of the first shelf 2710, which is coupled to the first inner member 2711, may tilt in an upward direction 2717.

Also, as a second rotary member 2715 of a second coupling member formed on the right side surface of the first shelf 2710 rotates clockwise, a second inner member 2714 connected to the second rotary member 2715 may move downward. Also, on the basis of the downward movement of the second inner member 2714, the rear of the first shelf 2710, which is coupled to the second inner member 2714, may tilt in a downward direction 2718. The rotational directions of the first rotary member 2712 and the second rotary member 2715 may be the same.

For example, as a third rotary member 2722 of a third coupling member formed on a right side surface of the second shelf 2720 rotates counterclockwise, a third inner member 2721 connected to the third rotary member 2722 may move downward. Also, on the basis of the downward movement of the third inner member 2721, the front of the second shelf 2720, which is coupled to the third inner member 2721, may tilt in a downward direction 2727.

Also, as a fourth rotary member 2725 of a fourth coupling member formed on the right side surface of the second shelf 2720 rotates counterclockwise, a fourth inner member 2724 connected to the fourth rotary member 2725 may move upward. Also, on the basis of the upward movement of the fourth inner member 2724, the rear of the second shelf 2720, which is coupled to the fourth inner member 2724, may tilt in an upward direction 2728. The rotational directions of the third rotary member 2722 and the fourth rotary member 2725 may be the same.

For example, the third shelf 2730 may move upward or may be maintained in a non-moving state.

Referring to FIG. 28A, among a plurality of shelves 2810, 2820, and 2830 included in the upper cabinet 150 according to an embodiment of the present invention, first and second shelves 2810 and 2820 may not tilt, and a third shelf 2830 may move upward. For example, all of the first and second shelves 2810 and 2820 and the third shelf 2830 may move.

Alternatively, the first and second shelves 2810 and 2820 may tilt, and the third shelf 2830 may not move. Alternatively, the first and second shelves 2810 and 2820 may not move, and the third shelf 2830 may move upward or downward.

Referring to FIG. 28B, among a plurality of shelves disposed in the upper cabinet according to an embodiment of the present invention, the lowest shelf may move upward.

For example, for the third shelf 2830 to move upward, the processor 470 may control the motor part 437 to perform at least one of counterclockwise rotation of a fifth rotary member 2832 and clockwise rotation of a sixth rotary member 2835.

In this way, in a case in which the fifth rotary member 2832 rotates counterclockwise or the sixth rotary member 2835 rotates clockwise, the third shelf 2830 moves in upward directions 2837 and 2838.

For example, for the third shelf 2830 to move downward, the processor 470 may control the motor part 437 to perform at least one of clockwise rotation of the fifth rotary member 2832 and counterclockwise rotation of the sixth rotary member 2835.

In this way, in a case in which the fifth rotary member 2832 rotates clockwise or the sixth rotary member 2835 rotates counterclockwise, the third shelf 2830 moves upward.

As described above, according to the present invention, the tilting or height of at least one shelf may be adjusted on the basis of the height of the user.

Figure 29:
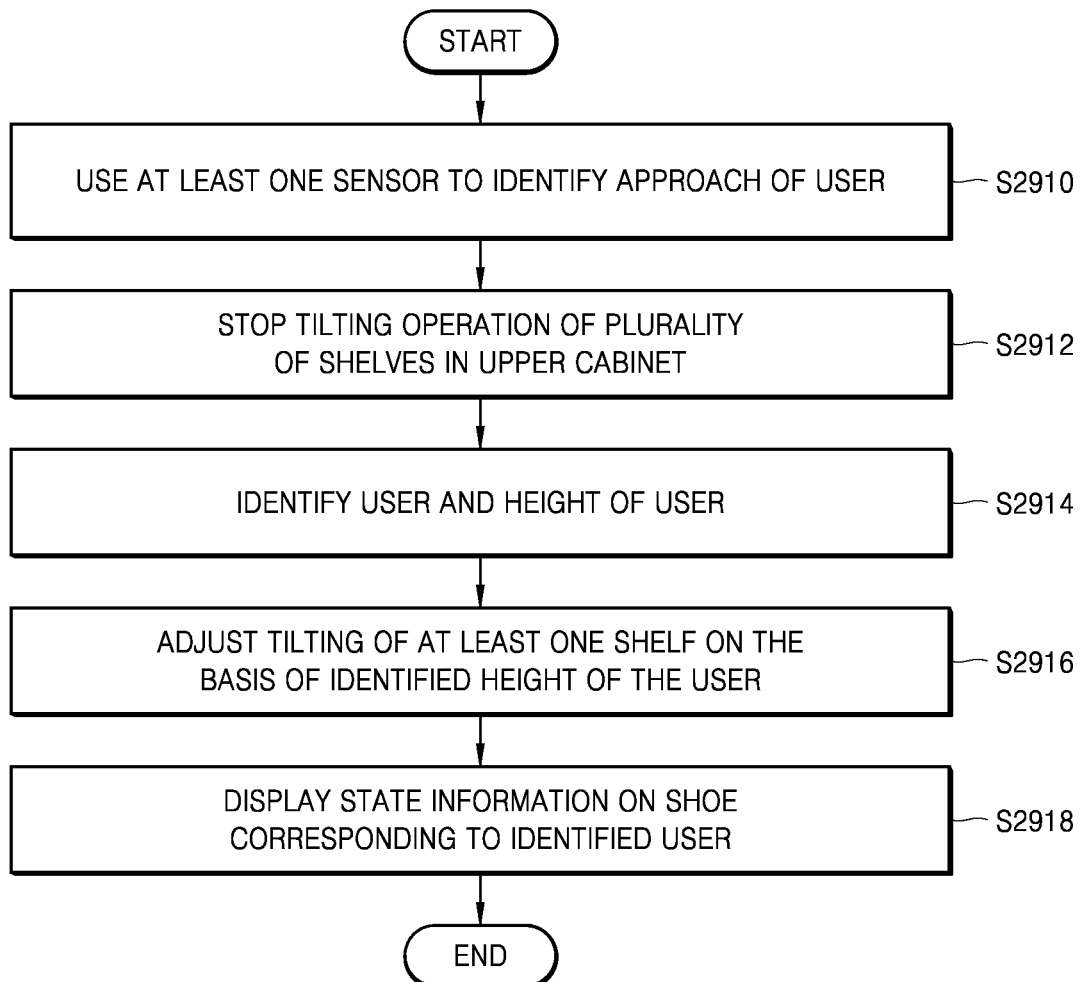
FIG. 29 is a flowchart illustrating a process of controlling tilting of a shelf of an upper cabinet of a shoe treating apparatus according to another embodiment of the present invention.
Figure 30:
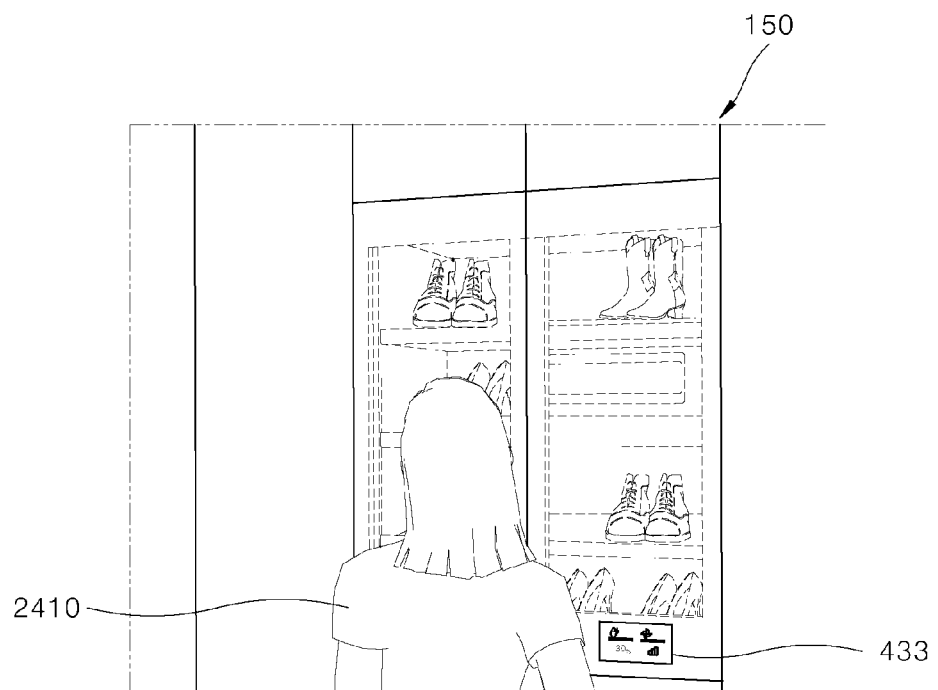
FIG. 30 is an exemplary view of displaying condition information of a shoe that corresponds to a user approaching a shoe treating apparatus according to another embodiment of the present invention.

FIG. 29 is a flowchart illustrating a process of controlling tilting of a shelf of an upper cabinet of a shoe treating apparatus according to another embodiment of the present invention. FIG. 30 is an exemplary view of displaying condition information of a shoe that corresponds to a user approaching a shoe treating apparatus according to another embodiment of the present invention.

Hereinafter, the process of controlling tilting of a shelf of an upper cabinet of a shoe treating apparatus according to another embodiment of the present invention will be described in detail with reference to FIGS. 29 and 30.

According to an embodiment, the processor 470 may use at least one sensor to identify an approach of a user (S2910). The process (S2910) may include at least one operation or at least one function performed in the process (S2310) of FIG. 23.

Referring to FIG. 30, through at least one sensor (e.g., the camera 432, the distance measurement sensor 416, the IR sensor 419, or the like), the processor 470 may detect a user 2410 approaching the shoe treating apparatus 310.

According to an embodiment, the processor 470 may stop a tilting operation of a plurality of shelves in the upper cabinet (S2912). The processor 470 may, through at least one sensor (e.g., the door open/close sensor 412, the fingerprint sensor 418, and the knock-on sensor 417), identify whether at least one of the doors 110, 120, 130, and 140 of the shoe treating apparatus 310 is opened and may, on the basis of the opening of the door, stop (or pause) an operation of at least one shelf that is currently tilting.

According to an embodiment, when the approach of the user 2410 is identified through at least one sensor (e.g., the camera 432, the distance measurement sensor 416, the IR sensor 419, or the like), the processor 470 may stop an operation of at least one shelf that is currently tilting.

According to an embodiment, the processor 470 may identify a user and the height of the user (S2914). The process (S2914) may include at least one operation or at least one function performed in the process (S2312) of FIG. 23.

According to an embodiment, the processor 470 may adjust tilting (or swing angle) of at least one shelf on the basis of the identified height of the user (S2916). The process (S2916) may include at least one function or at least one operation performed in the processes (S2314 and S2316) of FIG. 23.

According to an embodiment, the processor 470 may display state information on a shoe corresponding to the identified user (S2918). The processor 470 may display at least part of state information on at least one shoe corresponding to the identified user and the position of the at least one shoe through the display part 433.

Referring to FIG. 30, the state information displayed through the display part 433 by the processor 470 may include a state in which, on the basis of at least one of the material, type, and condition of at least one shoe, the at least one shoe is normally treated through adjusting at least one of the temperature and humidity inside the upper cabinet 150 in which the at least one shoe is stored.

Hereinafter, adjusting a tilt speed of a shelf will be described.

[Shelf Tilt Speed Adjustment]

Figure 31:
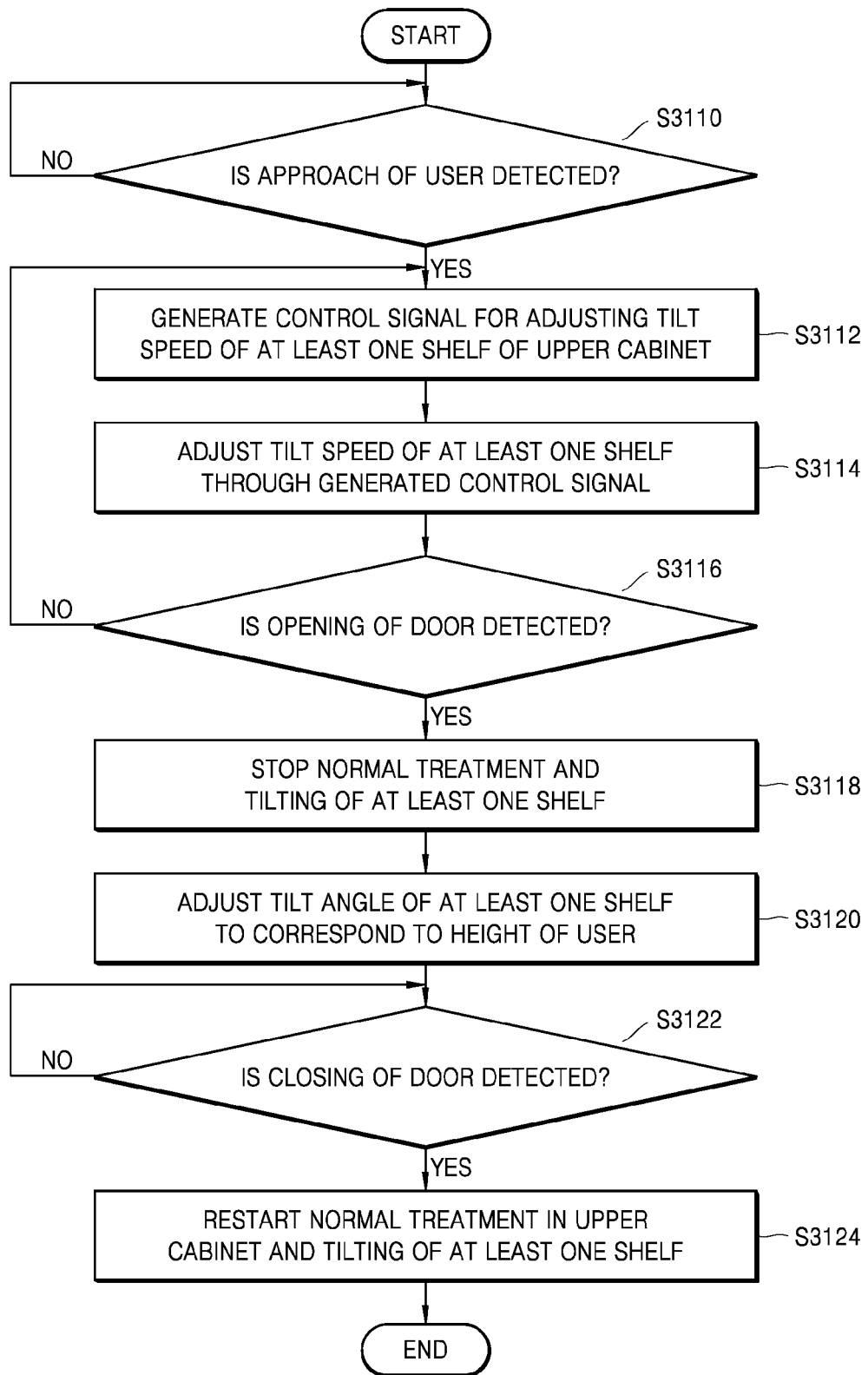
FIG. 31 is a flowchart illustrating a normal treatment process of a shoe treating apparatus according to opening and closing of a door according to an embodiment of the present invention.
Figure 32A:
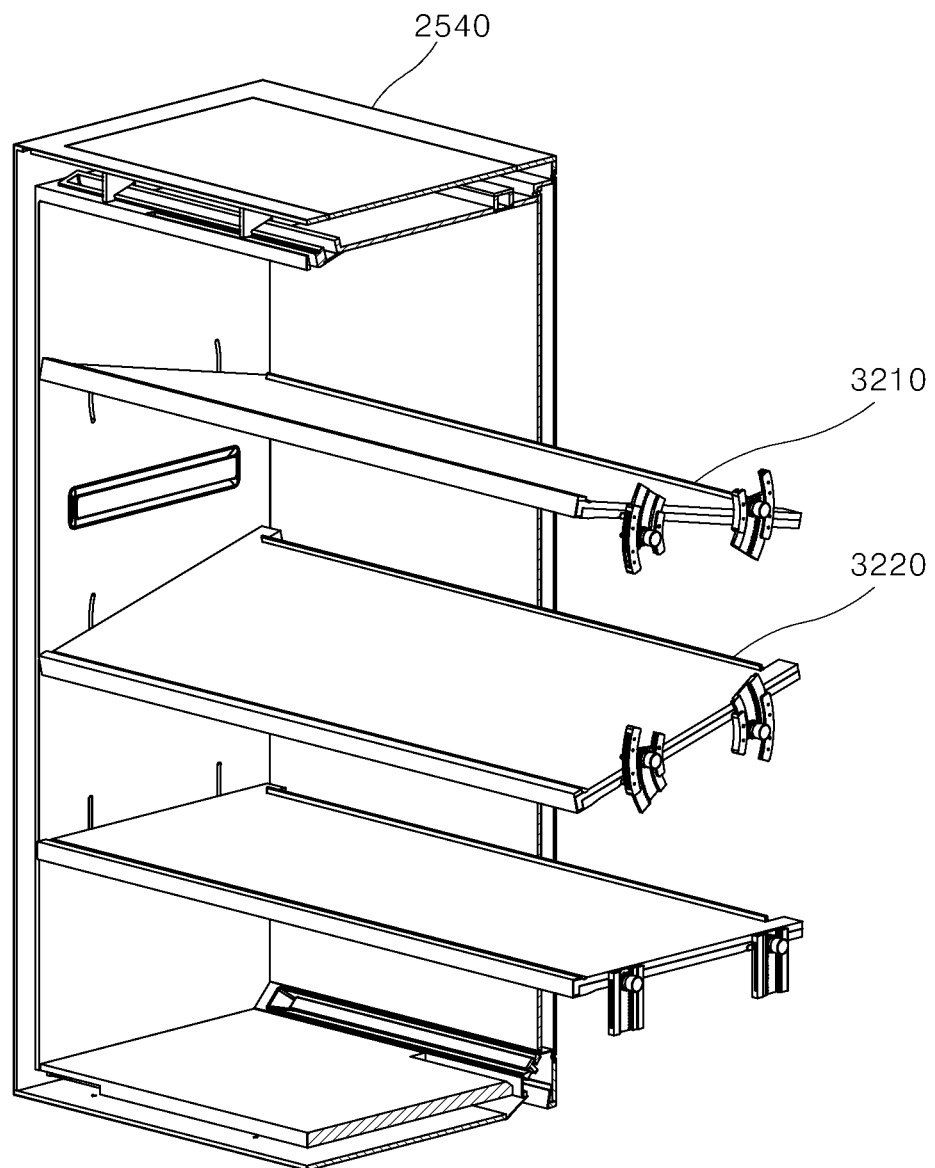
FIG. 32A is an exemplary view illustrating a plurality of shelves included in an upper cabinet according to an embodiment of the present invention.
Figure 32B:
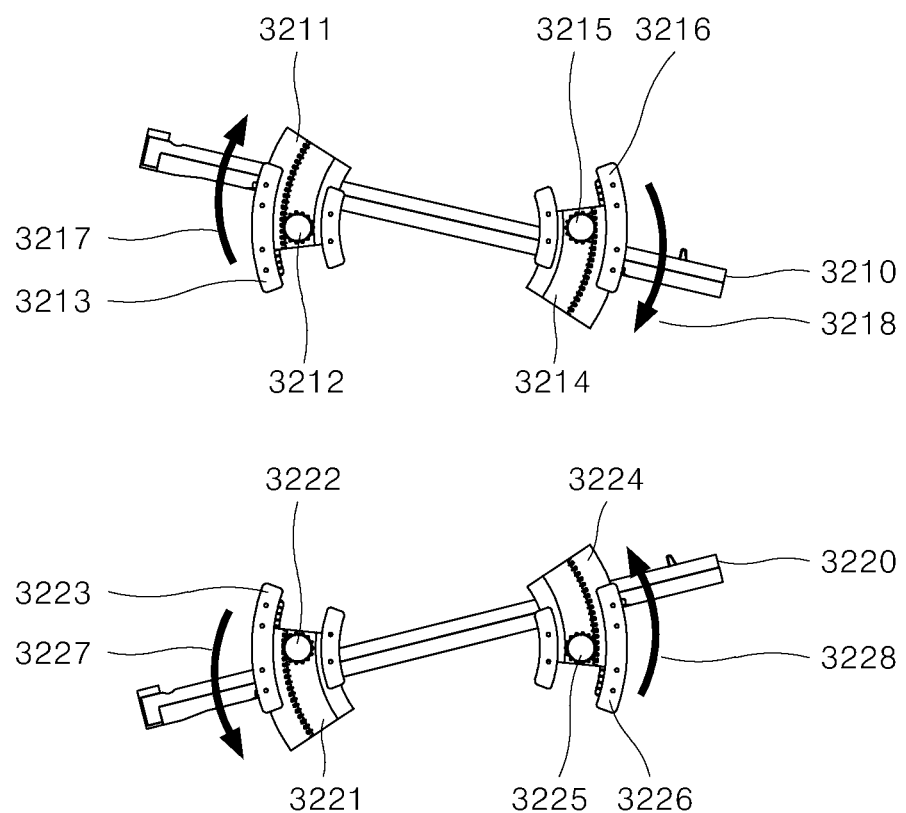
FIG. 32B is an exemplary view of the plurality of shelves tilting on the basis of normal treatment according to an embodiment of the present invention.
Figure 33:
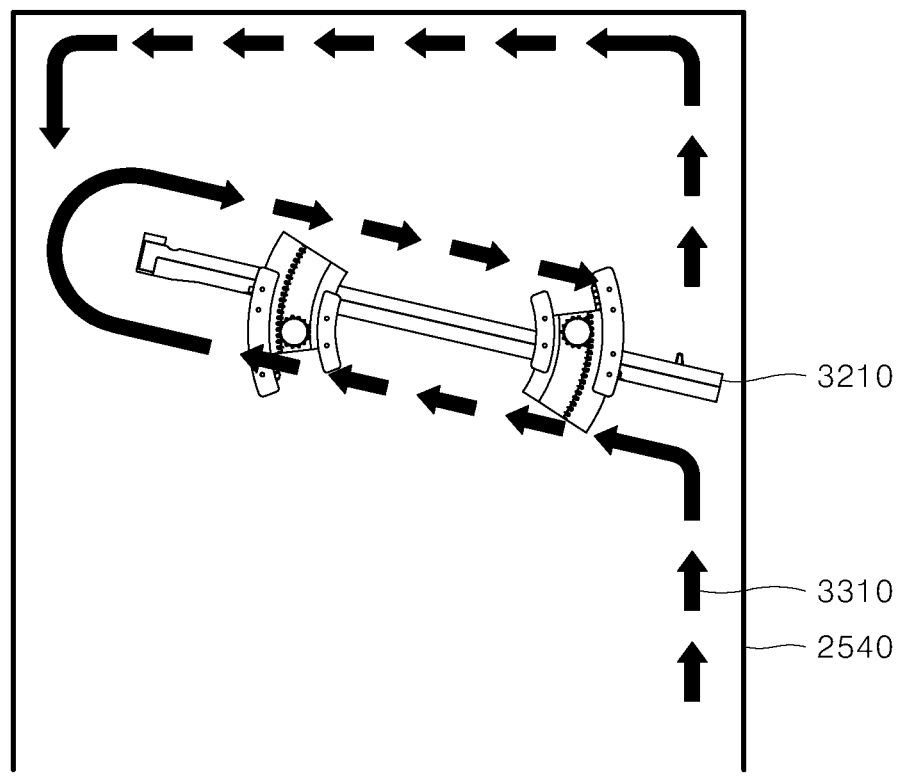
FIG. 33 is an exemplary view illustrating an air flow in an upper cabinet on the basis of normal treatment according to an embodiment of the present invention.

FIG. 31 is a flowchart illustrating a normal treatment process of a shoe treating apparatus according to opening and closing of a door according to an embodiment of the present invention. FIG. 32A is an exemplary view illustrating a plurality of shelves included in an upper cabinet according to an embodiment of the present invention. FIG. 32B is an exemplary view of the plurality of shelves tilting on the basis of normal treatment according to an embodiment of the present invention. FIG. 33 is an exemplary view illustrating an air flow in an upper cabinet on the basis of normal treatment according to an embodiment of the present invention.

Hereinafter, the normal treatment process of a shoe treating apparatus according to opening and closing of a door according to an embodiment of the present invention will be described in detail with reference to FIGS. 31, 32A, 32B, and 33.

According to an embodiment, the processor 470 may detect whether a user is approaching (S3110). The process (S3110) may include at least one function or at least one operation performed in the process (S2310) of FIG. 23.

According to an embodiment, the processor 470 may generate a control signal for adjusting the tilt speed of at least one shelf of the upper cabinet (S3112). When an approach of a user is detected, the processor 470 may generate a control signal for adjusting the tilt speed of at least one shelf included in the upper cabinet 150 at least one time.

According to an embodiment, the processor 470 may generate at least one control signal on the basis of a distance value between the shoe treating apparatus 310 and the user.

For example, the processor 470 may generate at least one control signal for gradually reducing the tilt speed of at least one shelf as the distance between the shoe treating apparatus 310 and the user decreases.

According to an embodiment, the processor 470 may generate a control signal for each shelf or may generate a single control signal for controlling the tilt speed of each of the plurality of shelves. The processor 470 may, on the basis of a speed at which the distance between the shoe treating apparatus 310 and the user decreases, determine a control signal generation cycle.

According to an embodiment, the processor 470 may adjust the tilt speed of at least one shelf through the generated control signal (S3114). The processor 470 may acquire information on a tilt speed for each distance between the shoe treating apparatus 310 and the user that is pre-stored in the memory 434 and may adjust the tilt speed of at least one shelf of the upper cabinet 150 on the basis of the acquired information.

For example, the processor 470 may provide the control signal to the corresponding motor of each shelf to adjust the tilt speed of each shelf.

According to an embodiment, the processor 470 may gradually reduce the tilt speed of the at least one shelf as the distance between the shoe treating apparatus 310 and the user decreases and may improve the tilt speed of the at least one shelf as the distance increases. Table 2 below shows tilt speeds of shelves according to the distance between the shoe treating apparatus 310 and the user.

TABLE 2

| Distance (cm) | Speed (RPM) |
|---|---|
| 20 cm or less | 0 |
| 21 cm to 40 cm | 2 |
| 41 cm to 60 cm | 4 |
| 61 cm to 80 cm | 6 |
| 81 cm or more | 8 |

Referring to Table 2, for example, in a case in which the distance between the shoe treating apparatus 310 and the user is 20 cm or less, the processor 470 may not tilt the at least one shelf.

Also, in a case in which the distance between the shoe treating apparatus 310 and the user is 21 cm to 40 cm, the processor 470 may rotate the at least one shelf at a tilt speed of 2 RPM. Also, in a case in which the distance between the shoe treating apparatus 310 and the user is 41 cm to 60 cm, the processor 470 may rotate the at least one shelf at a tilt speed of 4 RPM.

Alternatively, in a case in which the distance between the shoe treating apparatus 310 and the user is 61 cm to 80 cm, the processor 470 may rotate the at least one shelf at a tilt speed of 6 RPM, and in a case in which the distance between the shoe treating apparatus 310 and the user is 81 cm or more, the processor 470 may rotate the at least one shelf at a tilt speed of 8 RPM. The above distance and speed values are only an embodiment, and the present invention is not limited thereto and may include various other distances and various other speeds.

According to an embodiment, the processor 470 may detect whether a door is opened (S3116). The processor 470 may, through at least one sensor (e.g., the door open/close sensor 412, the knock-on sensor 417, and the fingerprint sensor 418), detect whether a door of the shoe treating apparatus 310 is opened.

According to an embodiment, the processor 470 may stop normal treatment and tilting of at least one shelf (S3118). When it is identified through the at least one sensor that at least one of the doors 110, 120, 130, and 140 of the shoe treating apparatus 310 is being opened, the processor 470 may stop normal treatment that is currently being performed in the upper cabinet of the shoe treating apparatus 310.

Also, the processor 470 may stop a tilting operation of at least one shelf that tilts during the normal treatment. For example, in a case in which the distance between the shoe treating apparatus 310 and the user is within 20 cm before at least one of the doors 110, 120, 130, and 140 is opened, the processor 470 may stop the normal treatment and stop the tilting operation of at least one shelf.

According to an embodiment, the processor 470 may adjust the tilt angle of at least one shelf to correspond to the height of the user (S3120). The processor 470 may measure the height of the user through at least one sensor (e.g., the camera 432, the distance measurement sensor 416, the IR sensor 419, or the like) or may identify the height of the user through user information (e.g., name, relation, height, weight, and the like) pre-stored in the memory 434. The memory 434 may include information on tilt angles of a shelf according to various heights as in Table 1.

According to an embodiment, the process (S3120) may include at least one function or at least one operation performed in the process (S2916) of FIG. 29. The processor 470 may generate a control signal on the basis of the tilt angle of at least one shelf that is stored in the memory 434 and may, on the basis of the generated control signal, adjust the tilt angle of each of the plurality of shelves (e.g., the first shelf, second shelf, and third shelf) included in the upper cabinet 150.

According to an embodiment, the processor 470 may detect whether a door is closed (S3122). The processor 470 may, through at least one sensor (e.g., the door open/close sensor 412, the knock-on sensor 417, and the fingerprint sensor 418), detect whether a door of the shoe treating apparatus 310 is closed.

Alternatively, when a knock on an open door is detected through the knock-on sensor 417, the processor 470 may control the open door to be closed.

According to an embodiment, the processor 470 may restart the normal treatment in the upper cabinet and tilting of at least one shelf (S3124). The processor 470 may, through at least one element (e.g., the steam generating part 444, the low-temperature hot air generating part 446) of the shoe treating apparatus 310, normally treat (e.g., adjust at least one of the temperature and humidity of) at least one shoe stored in the upper cabinet 150.

Alternatively, the processor 470 may normally treat at least one shoe in the upper cabinet 150 through at least one of the UV light emitting part 422, the photocatalyst emitting part 424, and the plasma emitting part 426.

According to an embodiment, the processor 470 may tilt the at least one shelf to correspond to the normal treatment. The processor 470 may tilt the at least one shelf on the basis of the tilt speed corresponding to the normal treatment.

For example, the processor 470 may restart the tilting of the at least one shelf on the basis of an environment (e.g., tilt speed, shoe treatment environment (e.g., temperature, humidity, or the like)) similar to the normal treatment before the approach of the user is detected in the process (S3110).

Referring to FIG. 32A, a plurality of shelves 3210 and 3220 included in the upper cabinet 150 according to an embodiment of the present invention may tilt at different speeds (or different direction) or at the same speed. Each of the plurality of shelves 3210 and 3220 may tilt in a state of being coupled to the inner wall of the frame 2540 of the upper cabinet 150.

For example, a first shelf 3210 and a second shelf 3220 of the plurality of shelves 3210 and 3220 may tilt to move at the same speed (or at different speeds) in different directions.

For example, the front portion of the first shelf 3210 may swing upward, and the front portion of the second shelf 3220 may swing downward. In this way, the first shelf 3210 and the second shelf 3220 of the plurality of shelves 3210 and 3220 may tilt at the same speed (or at different speeds) in different directions.

Referring to FIG. 32B, a plurality of shelves disposed in the upper cabinet according to an embodiment of the present invention may tilt at different speeds in different directions.

For example, as a first rotary member 3212 of a first coupling member formed on a right side surface of the first shelf 3210 rotates clockwise, a first inner member 3211 connected to the first rotary member 3212 may move upward, and on the basis of the upward movement of the first inner member 3211, the front of the first shelf 3210, which is coupled to the first inner member 3211, may tilt in an upward direction 3217.

Also, as a second rotary member 3215 of a second coupling member formed on the right side surface of the first shelf 3210 rotates clockwise, a second inner member 3214 connected to the second rotary member 3215 may move downward, and on the basis of the downward movement of the second inner member 3214, the rear of the first shelf 3210, which is coupled to the second inner member 3214, may tilt in a downward direction 3218. The rotational directions of the first rotary member 3212 and the second rotary member 3215 may be the same.

According to an embodiment, the processor 470 may adjust the rotational speeds of the first rotary member 3212 and the second rotary member 3215 through the motor part 437. The tilt speed of the first shelf 3210 may be adjusted on the basis of the rotational speeds of the first rotary member 3212 and the second rotary member 3215.

The processor 470 may determine the rotational speeds of the first rotary member 3212 and the second rotary member 3215 on the basis of the distance between the shoe treating apparatus 310 and the user and may use the determined rotational speeds to operate the motor part 437. In this way, the first rotary member 3212 and the second rotary member 3215 which are physically connected to the motor part 437 may rotate.

As a result, the first rotary member 3212 and the second rotary member 3215 rotate according to the determined rotational speeds, and the first shelf 3210 rotates according to the rotational speeds of the first rotary member 3212 and the second rotary member 3215.

For example, as a third rotary member 3222 of a third coupling member formed on a right side surface of the second shelf 3220 rotates counterclockwise, a third inner member 3221 connected to the third rotary member 3222 may move downward. Also, on the basis of the downward movement of the third inner member 3221, the front of the second shelf 3220, which is coupled to the third inner member 3221, may tilt in a downward direction 3227.

Also, as a fourth rotary member 3225 of a fourth coupling member formed on the right side surface of the second shelf 3220 rotates counterclockwise, a fourth inner member 3224 connected to the fourth rotary member 3225 may move upward. Also, on the basis of the upward movement of the fourth inner member 3224, the rear of the second shelf 3220, which is coupled to the fourth inner member 3224, may tilt in an upward direction 3228. The rotational directions of the third rotary member 3222 and the fourth rotary member 3225 may be the same.

According to an embodiment, the processor 470 may adjust the rotational speeds of the third rotary member 3222 and the fourth rotary member 3225 through the motor part 437. The tilt speed of the second shelf 3220 may be adjusted on the basis of the rotational speeds of the third rotary member 3222 and the fourth rotary member 3225.

The processor 470 may determine the rotational speeds of the third rotary member 3222 and the fourth rotary member 3225 on the basis of the distance between the shoe treating apparatus 310 and the user and may use the determined rotational speeds to operate the motor part 437. In this way, the third rotary member 3222 and the fourth rotary member 3225 which are physically connected to the motor part 437 may rotate.

As a result, the third rotary member 3222 and the fourth rotary member 3225 rotate according to the determined rotational speeds, and the second shelf 3220 rotates according to the rotational speeds of the third rotary member 3222 and the fourth rotary member 3225.

According to an embodiment, the processor 470 may control the motor part 437 so that the tilt speeds of the first and second rotary members 3212 and 3215 are the same as the tilt speeds of the third and fourth rotary members 3222 and 3225.

Alternatively, the processor 470 may control the motor part 437 so that the tilt speeds of the first and second rotary members 3212 and 3215 are different from the tilt speeds of the third and fourth rotary members 3222 and 3225. The tilt speed of the one or more shelves 3210 and 3220 may be determined on the basis of the distance between the shoe treating apparatus 310 and the user.

Referring to FIG. 33, a discharge part (the discharge part 920 of FIG. 9) may be formed on a lower portion of the shoe treating apparatus 310 (e.g., the upper cabinet 150). Air 3310 discharged through the discharge part (the discharge part 920 of FIG. 9) may flow upward along the inner wall of the frame 2540 of the upper cabinet 150.

The discharged air 3310 may be diffused in the upper cabinet 150 due to the tilting operation of each shelf (e.g., the first shelf 3210). For example, the air flow in the upper cabinet 150 may be diffused more rapidly as the tilt speed of each shelf (e.g., the first shelf 3210 and the second shelf 3220 of FIG. 32) becomes higher. In this way, as the air flow is diffused, at least one of the temperature and humidity in the upper cabinet 150 may be efficiently maintained to be uniform.

Hereinafter, the input, setting, and operation control of a tapping pattern for controlling at least one function or operation of the shoe treating apparatus 310 will be described.

[Control of Shoe Treating Apparatus Through Tapping Pattern]

Figure 34:
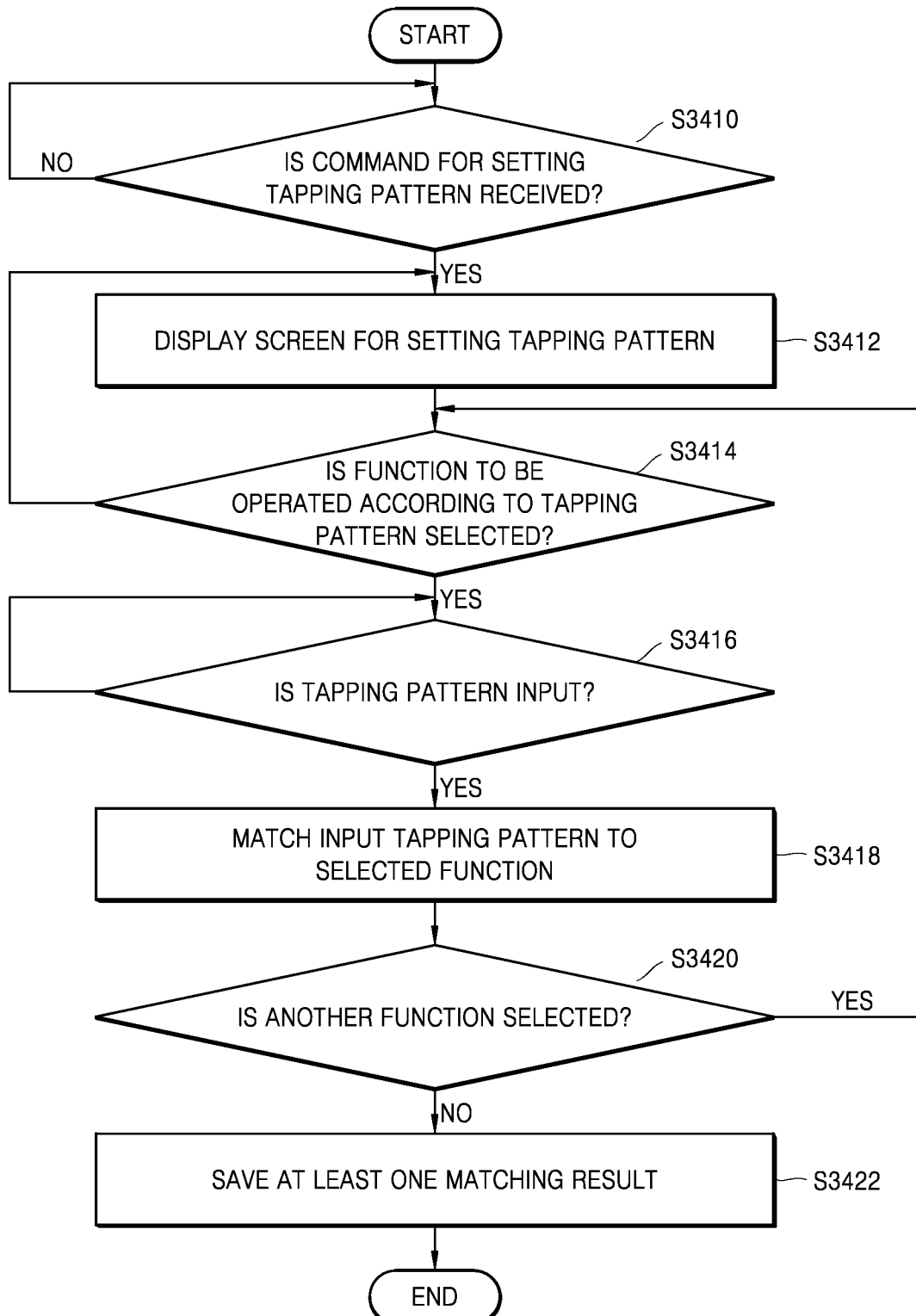
FIG. 34 is a flowchart illustrating a process of setting a tapping pattern for controlling a shoe treating apparatus according to an embodiment of the present invention.
Figure 35:
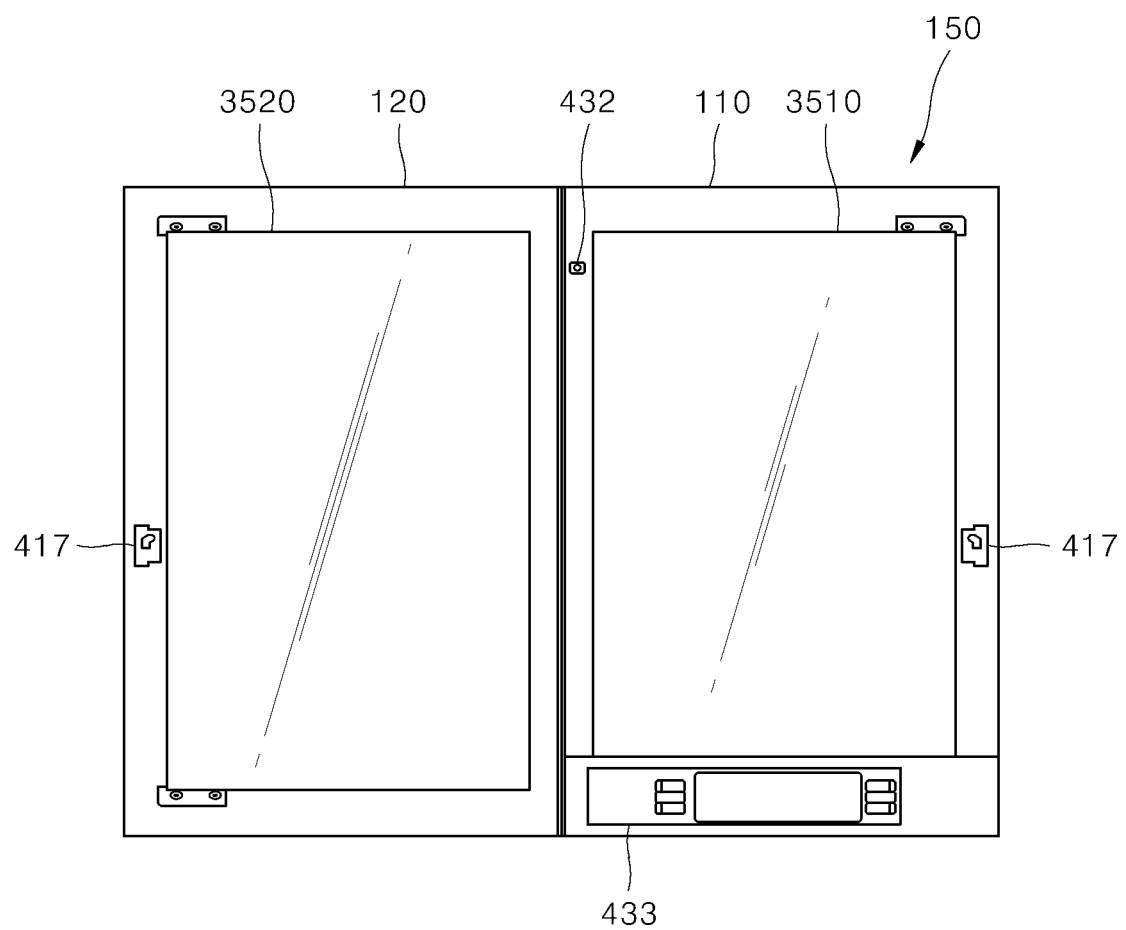
FIG. 35 is an exemplary view illustrating a door of an upper cabinet according to an embodiment of the present invention.
Figure 36:
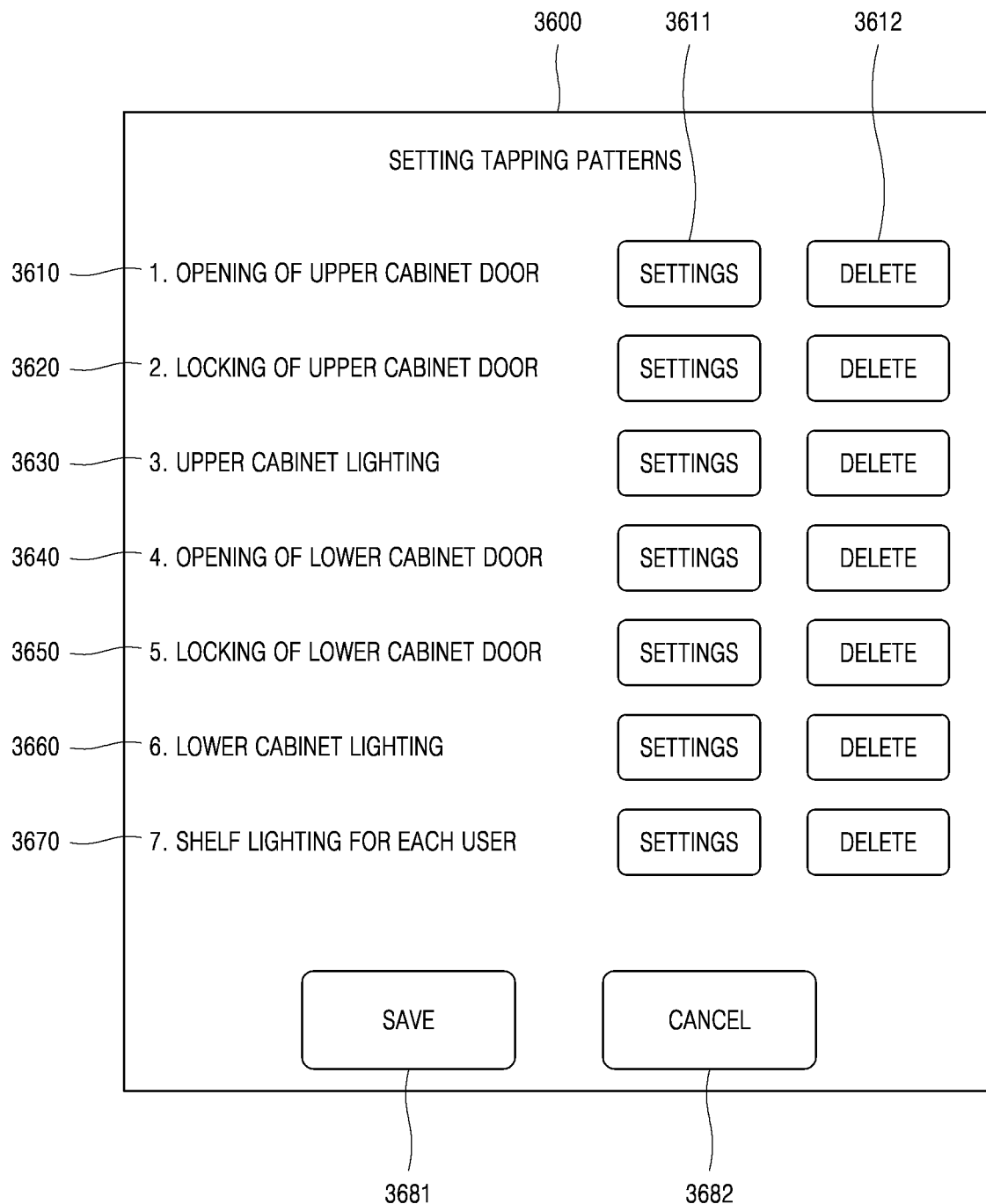
FIG. 36 is an exemplary view illustrating a screen for setting a tapping pattern for controlling an operation of a shoe treating apparatus according to an embodiment of the present invention.
Figure 37:
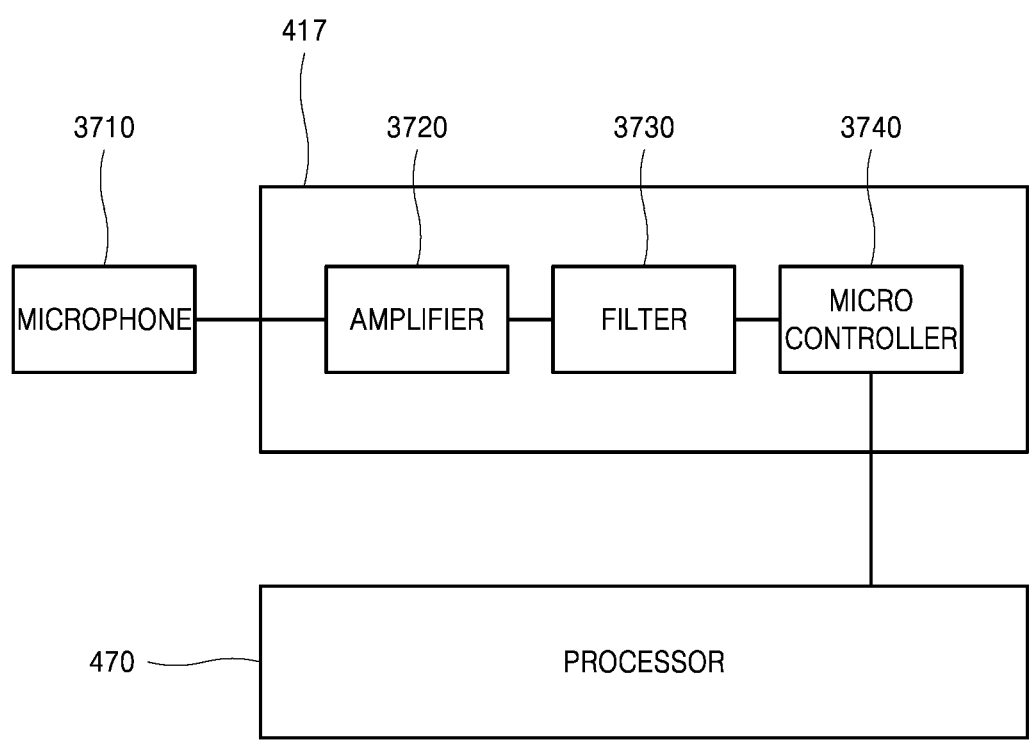
FIG. 37 is a block diagram of a knock on sensor according to an embodiment of the present invention.
Figure 38:
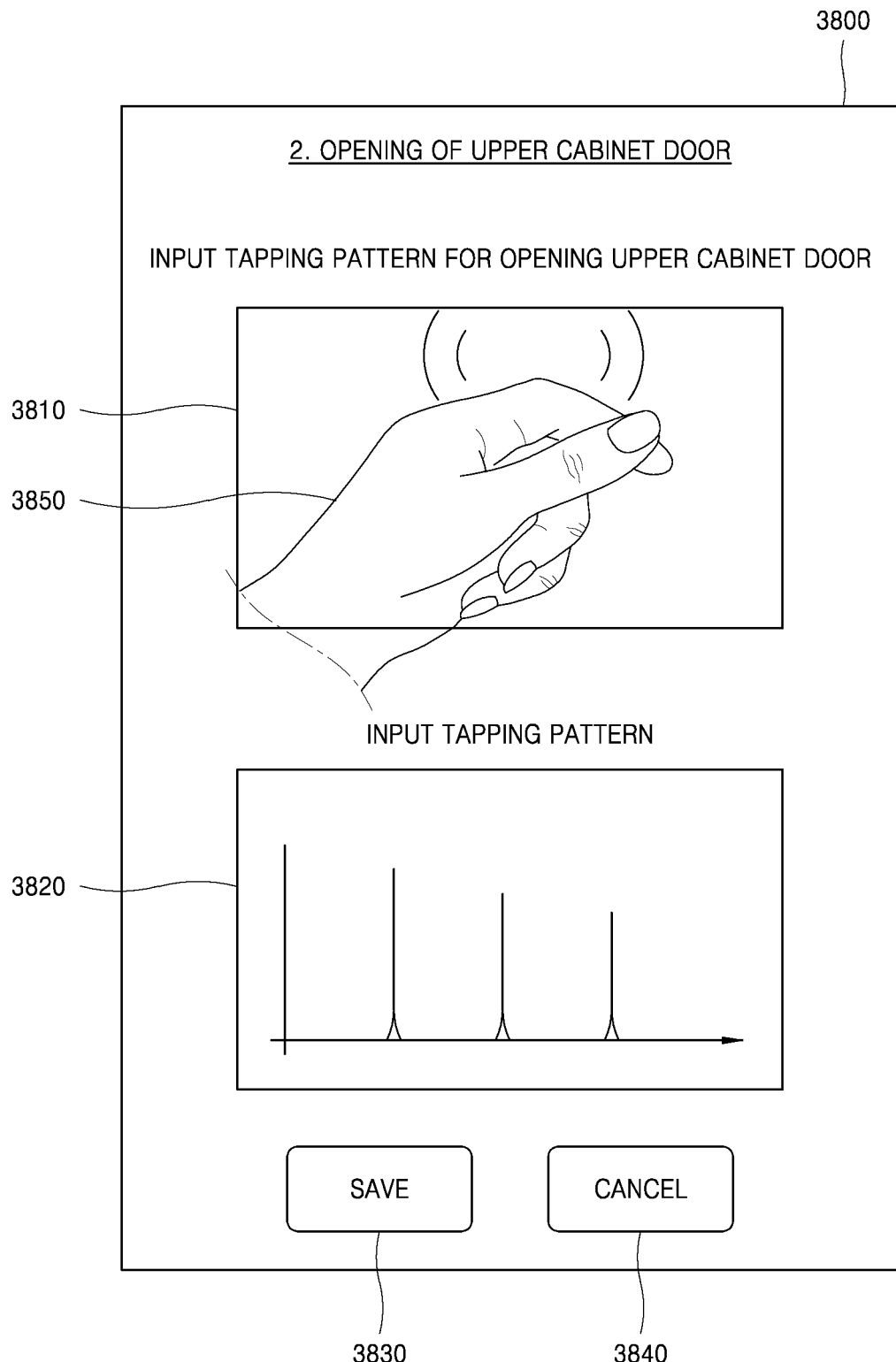
FIG. 38 is an exemplary view of receiving an input of a tapping pattern according to an embodiment of the present invention.
Figure 39:
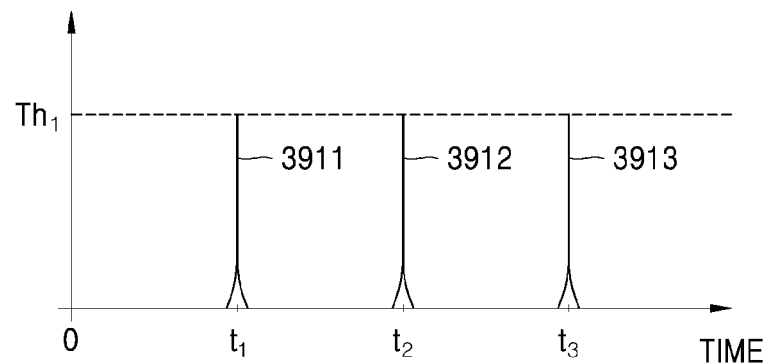
FIG. 39 is an exemplary view illustrating time intervals and sound wave intensities of taps of each tapping pattern according to an embodiment of the present invention.
Figure 39:
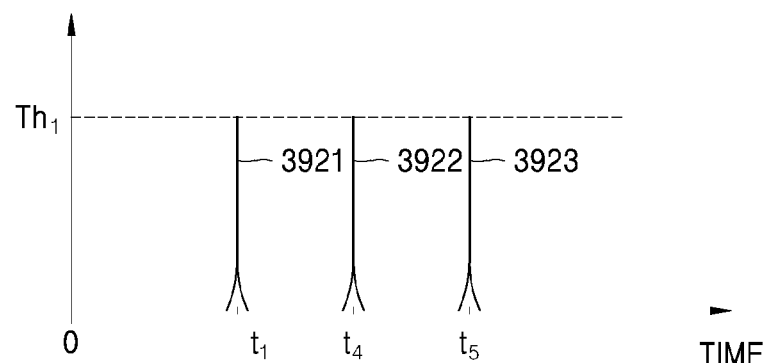
Figure 39:
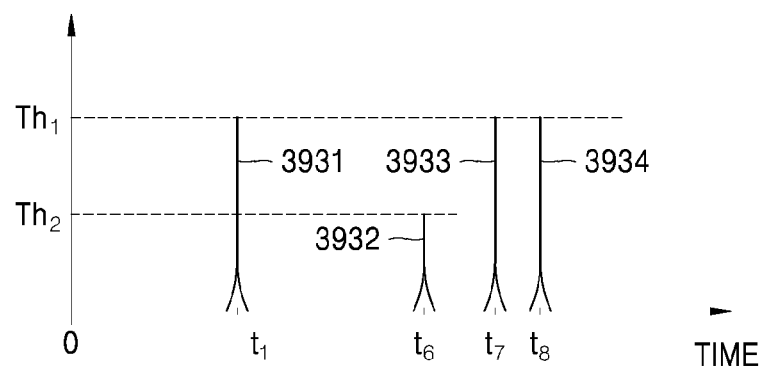

FIG. 34 is a flowchart illustrating a process of setting a tapping pattern for controlling a shoe treating apparatus according to an embodiment of the present invention. FIG. 35 is an exemplary view illustrating a door of an upper cabinet according to an embodiment of the present invention. FIG. 36 is an exemplary view illustrating a screen for setting a tapping pattern for controlling an operation of a shoe treating apparatus according to an embodiment of the present invention. FIG. 37 is a block diagram of a knock-on sensor according to an embodiment of the present invention. FIG. 38 is an exemplary view of receiving an input of a tapping pattern according to an embodiment of the present invention. FIG. 39 is an exemplary view illustrating time intervals and sound wave intensities of taps of each tapping pattern according to an embodiment of the present invention.

Hereinafter, the process of setting a tapping pattern for controlling a shoe treating apparatus according to an embodiment of the present invention will be described in detail with reference to FIGS. 34 to 39.

According to an embodiment, the processor 470 may identify whether a command for setting a tapping pattern is received (S3410). The processor 470 may identify whether a command to display a screen for controlling each function of the shoe treating apparatus 310 using a tapping pattern (e.g., a tapping pattern setting command) is input.

According to an embodiment, the processor 470 may display a screen for setting a tapping pattern (S3412). The processor 470 may, on the basis of an input of the command to display a screen for controlling each function of the shoe treating apparatus 310 using a tapping pattern (e.g., the tapping pattern setting command), display the screen on the doors 110 and 120 (e.g., smart mirrors) of the upper cabinet 150.

Alternatively, the processor 470 may, on the basis of an input of the command to display a screen for controlling each function of the shoe treating apparatus 310 using a tapping pattern (e.g., the tapping pattern setting command), display the screen through the display part 433 disposed at one side of the upper cabinet 150.

Referring to FIG. 35, the upper cabinet 150 according to an embodiment of the present invention may include the left door 110 and the right door 120. For example, the smart mirror 3510 may be disposed on the left door 110 of the upper cabinet 150. Also, the smart mirror 3520 may be disposed on the right door 120 of the upper cabinet 150.

Also, the at least one knock-on sensor 417 may be disposed at one side of each of the doors 110 and 120. Also, the display part 433 may be disposed on one side of the left door 110 of the upper cabinet 150. The display part 433 may be disposed at one side of any one of the left door 110 and right door 120 of the upper cabinet 150. Also, the camera 432 configured to detect a user may be disposed at one side of the left door 110.

According to an embodiment, the smart mirrors 3510 and 3520 mounted on the doors of the shoe treating apparatus 310 may be operated in a mirror mode in which the smart mirror completely reflects things like a normal mirror, a smart mirror mode in which the smart mirror displays at least pieces of information on the basis of the mirror mode, and a display mode in which the smart mirror displays only at least pieces of information generated by the processor 470.

Referring to FIG. 36, in order to control the shoe treating apparatus 310 on the basis of a tapping pattern, the processor 470 may generate a screen relating to a tapping pattern. The screen may include information on at least one function or operation provided by the shoe treating apparatus 310 and information (e.g., a menu) that indicates setting or deletion of a tapping pattern to be set for each function. Also, the processor 470 may display the generated screen on the smart mirrors 3510 and 3520. Alternatively, the processor 470 may display the generated screen on the display part 433.

For example, a screen 3600 may include information on door opening of the upper cabinet 150 (3610), door locking of the upper cabinet 150 (3620), and lighting control of the upper cabinet 150 (3630). Also, the screen 3600 may include information (e.g., an operation name) on at least one of door opening of the lower cabinet 160 (3640), door locking of the lower cabinet 160 (3650), lighting control of the lower cabinet 160 (3660), and lighting control of shelves of the upper cabinet 150 (or the lower cabinet 160) on which at least one shoe is placed for each user (3670).

Also, the screen 3600 may include a Settings menu 3611 and a Delete menu 3612 for each function. For example, the screen 3600 may also include information on various functions provided by the shoe treating apparatus 310 other than the above-described various functions and include a Settings menu or a Delete menu therefor.

According to an embodiment, the processor 470 may identify whether a function to be operated according to a tapping pattern is selected (S3414). The processor 470 may identify whether at least one function included in the screen 3600 of FIG. 36 is selected.

For example, the processor 470 may identify whether a user has selected the Settings menu 3611 relating to the upper cabinet door opening (3610) to input opening of the doors 110 and 120 of the upper cabinet 150 using a tapping pattern.

According to an embodiment, the processor 470 may identify whether a tapping pattern is input (S3416). The processor 470 may identify a tapping pattern input through the doors 110 and 120 of the upper cabinet 150 after the Settings menu 3611 relating to the upper cabinet door opening (3610) is selected.

According to an embodiment, the processor 470 may identify a tapping pattern through the knock-on sensor 417 disposed at one side of the doors 110 and 120 of the upper cabinet 150.

Referring to FIG. 37, the knock-on sensor 417 according to an embodiment of the present invention may include an amplifier 3720 configured to amplify an electrical signal transmitted through a microphone 3710, a filter 3730 configured to remove noise from the amplified signal, and a microcontroller 3740 configured to, on the basis of the signal from which noise is removed, identify time intervals between taps included in a tapping pattern and the sound wave intensity of each tap.

The microphone 3710 may be disposed at a position where it is easy to acquire a sound wave due to tapping in the upper cabinet 150 (or the lower cabinet 160). The microcontroller 3740 may transmit a signal from which noise is removed to the processor 470 or may transmit time intervals between taps and a sound wave intensity of each tap to the processor 470.

Referring to FIG. 38, in a case in which the Settings menu 3611 relating to the upper cabinet door opening (3610) is selected in FIG. 36, the processor 470 may display a screen 3800 for receiving an input of a tapping pattern according to the upper cabinet door opening (3610) on the smart mirror (or the display part 433).

The screen 3800 may include a first area 3810 configured to receive an input of a tapping pattern and a second area 3820 configured to display sound wave intensities according to time of the tapping pattern input to the first area 3810. Also, the screen 3800 may include a Save menu 3830 for saving the input tapping pattern and a Cancel menu 3840 for cancelling the input tapping pattern.

For example, in a case in which the Settings menu 3611 relating to the upper cabinet door opening (3610) is selected in FIG. 36 and, in a state in which the screen 3800 is displayed, a tapping pattern is input by a user through apart of the body (e.g., a hand 3850) or through an object (e.g., a pen or the like) that can transmit tapping, the processor 470 may display sound wave intensities of the input tapping pattern on the second area 3820.

The tapping pattern may be input through at least one of the left door 110 and the right door 120 of the upper cabinet 150. Alternatively, the tapping pattern may be input through at least one of the left door 130 and the right door 140 of the lower cabinet 160. The tapping pattern may be alternately input through the left doors 110 and 130 and the right doors 120 and 140. The processor 470 may identify a tapping pattern input for each door.

Referring to FIG. 39, various tapping patterns may be set according to each function of the shoe treating apparatus 310. For example, (a) of FIG. 39 shows a tapping pattern according to the upper cabinet door opening (3610), (b) of FIG. 39 shows a tapping pattern according to the upper cabinet door locking (3620), and (c) of FIG. 39 shows a tapping pattern according to the lighting of shelves for each user (3670).

For example, as illustrated in (a) of FIG. 39, the tapping pattern according to the door opening of the upper cabinet 150 (3610) may include a first tap 3911 having a first sound wave intensity $Th_1$ at a first time $t_1$, a second tap 3912 having the first sound wave intensity $Th_1$ at a second time $t_2$, and a third tap 3913 having the first sound wave intensity $Th_1$ at a third time $t_3$. A time difference between the first time $t_1$ and the second time $t_2$ may be the same (or the same within a range having a negligible error) as a time difference between the second time $t_2$ and the third time $t_3$.

For example, as illustrated in (b) of FIG. 39, the tapping pattern according to the door locking of the upper cabinet 150 (3620) may include a first tap 3921 having the first sound wave intensity $Th_1$ at the first time $t_1$, a second tap 3922 having the first sound wave intensity $Th_1$ at a second time $t_4$, and a third tap 3923 having the first sound wave intensity $Th_1$ at a third time $t_5$. A time difference between the first time $t_1$ and the second time $t_4$ may be the same (or the same within a range having a negligible error) as a time difference between the second time $t_4$ and the third time $t_5$.

For example, the time difference in (a) of FIG. 39 may be different from the time difference in (b) of FIG. 39. The processor 470 may identify time intervals between taps and the sound wave intensity of each tap to set a function or determine whether a matching pattern is present.

For example, as illustrated in (c) of FIG. 39, the tapping pattern according to the lighting of shelves of the upper cabinet 150 for each user (3670) may include a first tap 3931 having the first sound wave intensity $Th_1$ at the first time $t_1$, a second tap 3932 having a second sound wave intensity $Th_2$ at a second time $t_6$, a third tap 3933 having the first sound wave intensity $Th_1$ at a third time $t_7$, and a fourth tap 3934 having the first sound wave intensity $Th_1$ at a fourth time $t_8$. A time difference between the first time $t_1$ and the second time $t_U$ may be different from a time difference between the second time $t_6$ and the third time $t_7$.

Also, the time difference between the second time $t_6$ and the third time $t_7$ may be the same (or the same within a range having a negligible error) as a time difference between third time $t_7$ and the fourth time $t_8$.

In this way, since time intervals between taps included in a single tapping pattern and the sound wave intensity of each tap may vary, the processor 470 may set a function or determine whether a matching pattern is present through at least one of the time intervals between taps and the sound wave intensity of each tap.

According to an embodiment, the number of taps included in each tapping pattern may be at least one or plural.

According to an embodiment, the processor 470 may match the input tapping pattern to the selected function (S3418). The processor 470 may identify time intervals between taps included in each tapping pattern and the intensity of each tap and may match the identified time intervals between the taps and the intensity of each tap to the corresponding function (e.g., a function selected on the screen 3600 of FIG. 36).

According to an embodiment, the processor 470 may set a certain margin to each time interval and each intensity, or may receive the margin from a user. The margin may be variably adjusted.

According to an embodiment, the processor 470 may identify whether another function is selected (S3420). When it is identified that another function is selected through the screen 3600 of FIG. 36, the processor 470 may perform the processes (S3416 and S3418). The processor 470 may set a tapping pattern for at least one function through the processes (S3412 to S3418).

According to an embodiment, the processor 470 may save at least one matching result (S3422). The processor 470 may save a result of matching each tapping pattern (e.g., information on a function to be executed based on each time interval and each intensity) in the memory 434. The matching result may include at least one instruction for executing a function according to an input tapping pattern.

The matching result may include information on each time interval, information on each sound wave intensity, a door identifier (that is, door identifier information to determine whether a tap is input through the left door or a tap is input through the right door), and information on a function to be executed on the basis of the input of the tap.

Figure 40:
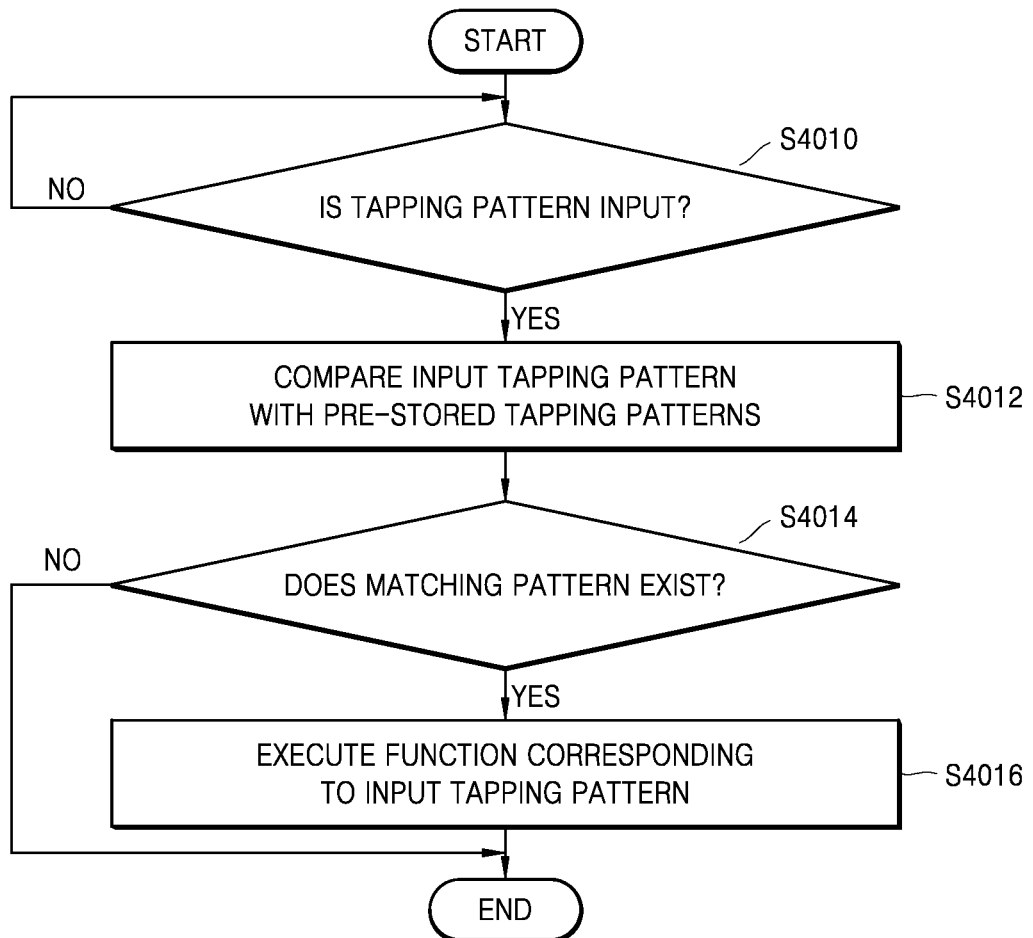
FIG. 40 is a flowchart illustrating a process of executing a function according to an input of a tapping pattern according to an embodiment of the present invention.

FIG. 40 is a flowchart illustrating a process of executing a function according to an input of a tapping pattern according to an embodiment of the present invention.

Hereinafter, the process of executing a function according to an input of a tapping pattern according to an embodiment of the present invention will be described in detail with reference to FIG. 40.

According to an embodiment, the processor 470 may identify whether a tapping pattern is input (S4010). The processor 470 may identify whether a tapping pattern is input through a door (e.g., the doors 110 and 120 of the upper cabinet 150 or the doors 130 and 140 of the lower cabinet 160) of the shoe treating apparatus 310.

According to an embodiment, the processor 470 may compare the input tapping pattern with pre-stored tapping patterns (S4012). The processor 470 may compare the input tapping pattern with at least one tapping pattern stored in the memory 434.

For example, the processor 470 may compare time intervals and sound wave intensities relating to each tap of the input tapping pattern with time intervals and sound wave intensities relating to each tap of at least one tapping pattern stored in the memory 434.

The processor 470 may identify whether time intervals and sound wave intensities relating to each tap of a tapping pattern that are the same as (or similar within a margin range) the time intervals and sound wave intensities relating to each tap of the input tapping pattern are stored in the memory 434.

According to an embodiment, the processor 470 may identify whether a tapping pattern matching the input tapping pattern exists (S4014). The processor 470 may identify whether a pattern identical to the input tapping pattern (or similar patterns within a certain range with negligible errors) is present among one or more tapping patterns stored in the memory 434.

The processor 470 may identify whether time intervals and sound wave intensities that are the same as those of the input tapping pattern are present among time intervals and sound wave intensities of one or more tapping patterns stored in the memory 434.

According to an embodiment, the processor 470 may execute a function corresponding to the input tapping pattern (S4016). When it is identified that a pattern which is the same as the input tapping pattern is present among one or more tapping patterns stored in the memory 434, the processor 470 may execute a function corresponding to the input tapping pattern.

When it is identified that time intervals and sound wave intensities that are the same as those of the input tapping pattern are present among time intervals and sound wave intensities of one or more tapping patterns stored in the memory 434, the processor 470 may execute a function corresponding to the input tapping pattern.

According to an embodiment, the function may include at least one of door opening of the upper cabinet 150 of the shoe treating apparatus 310, door locking of the upper cabinet 150, and lighting control of the upper cabinet 150. Also, the function may include at least one of door opening of the lower cabinet 160 of the shoe treating apparatus 310, door locking of the lower cabinet 160, lighting control of the lower cabinet 160, and lighting control of at least one shelf for each user.

Hereinafter, sanitizing a door handle will be described.
[Sanitizing Door Handle]

Figure 41:
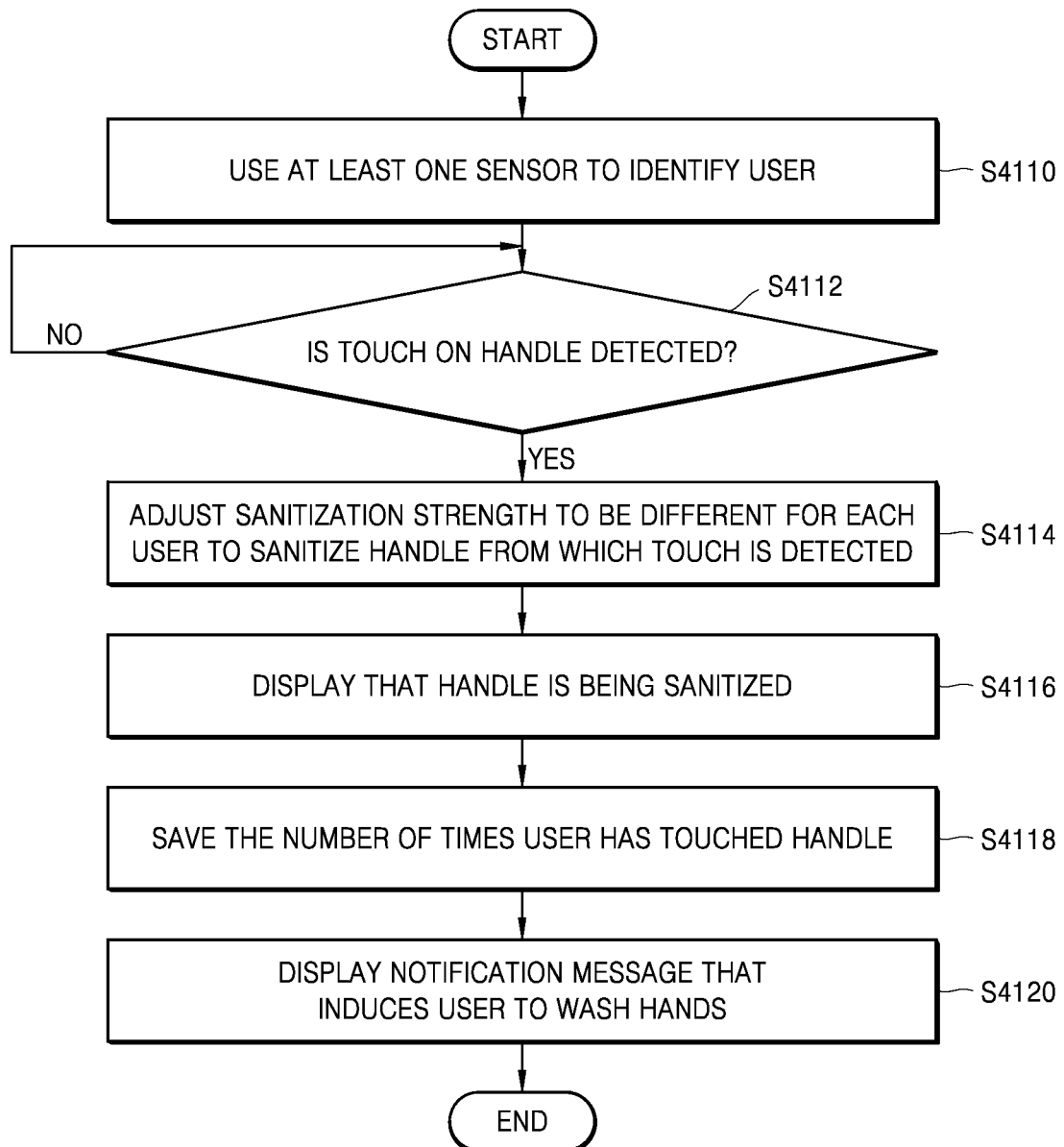
FIG. 41 is a flowchart illustrating a process of sanitizing a handle of a shoe treating apparatus according to an embodiment of the present invention.
Figure 42A:
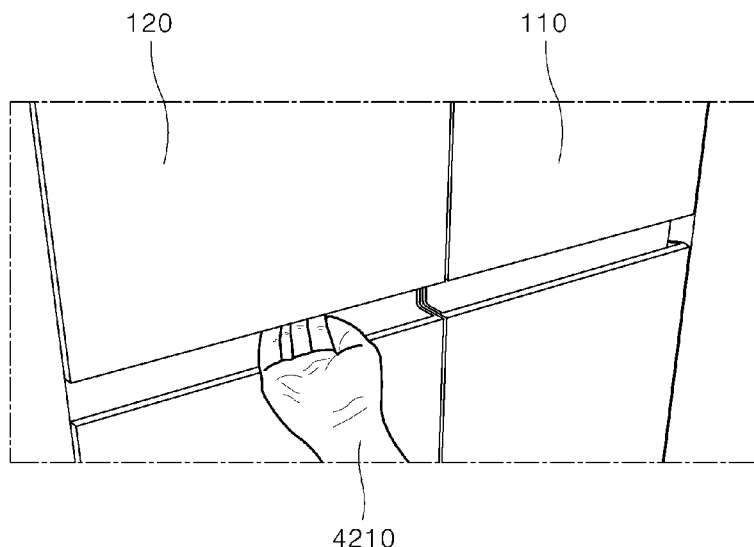
FIG. 42A is an exemplary view of touching a handle of a shoe treating apparatus according to an embodiment of the present invention.
Figure 42B:
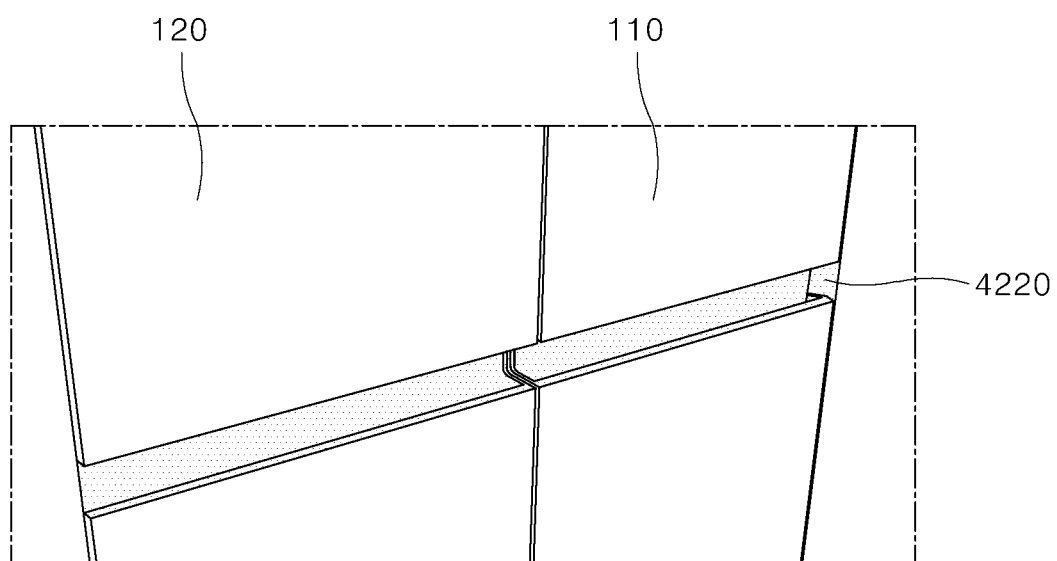
FIG. 42B is an exemplary view of sanitizing a handle of a shoe treating apparatus according to an embodiment of the present invention.
Figure 43A:
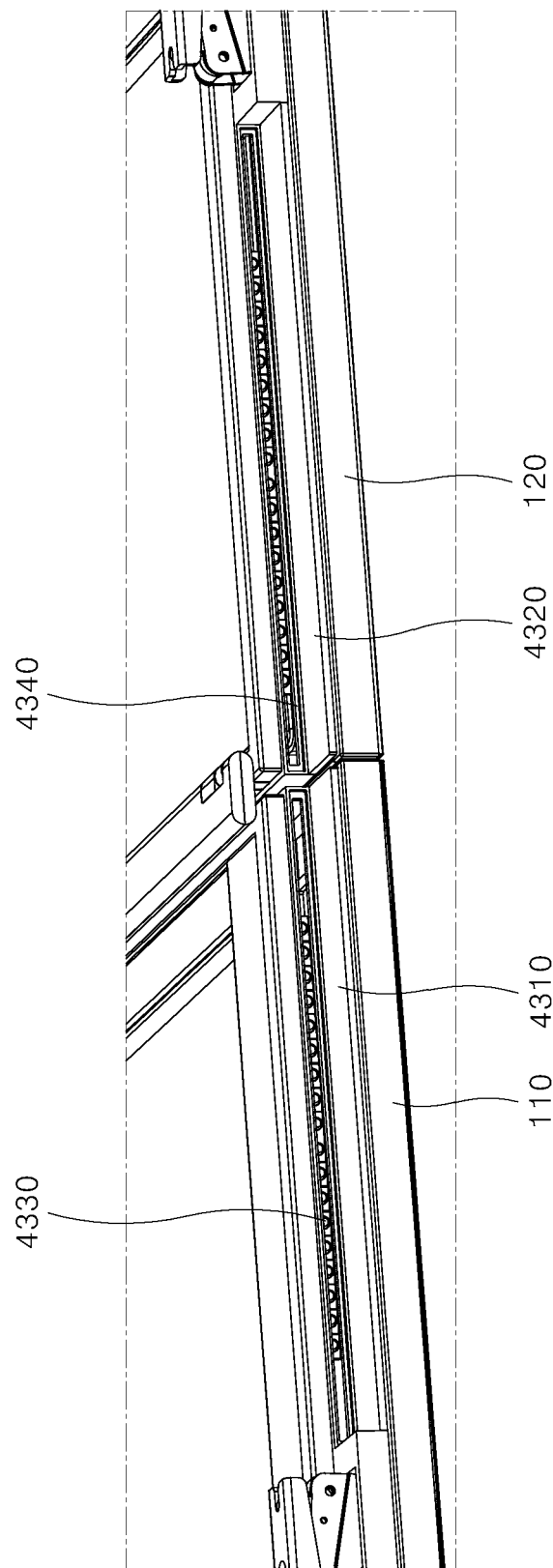
FIG. 43A is an exemplary view illustrating a bottom surface of an upper cabinet door according to an embodiment of the present invention.
Figure 43B:
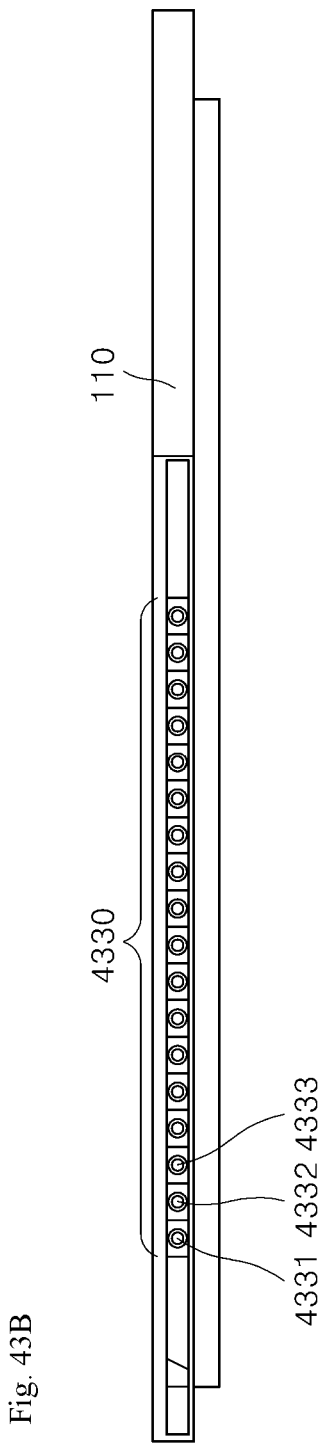
FIG. 43B is an exemplary view illustrating arrangement of a plurality of light emitting elements of a sensor part according to an embodiment of the present invention.
Figure 44:
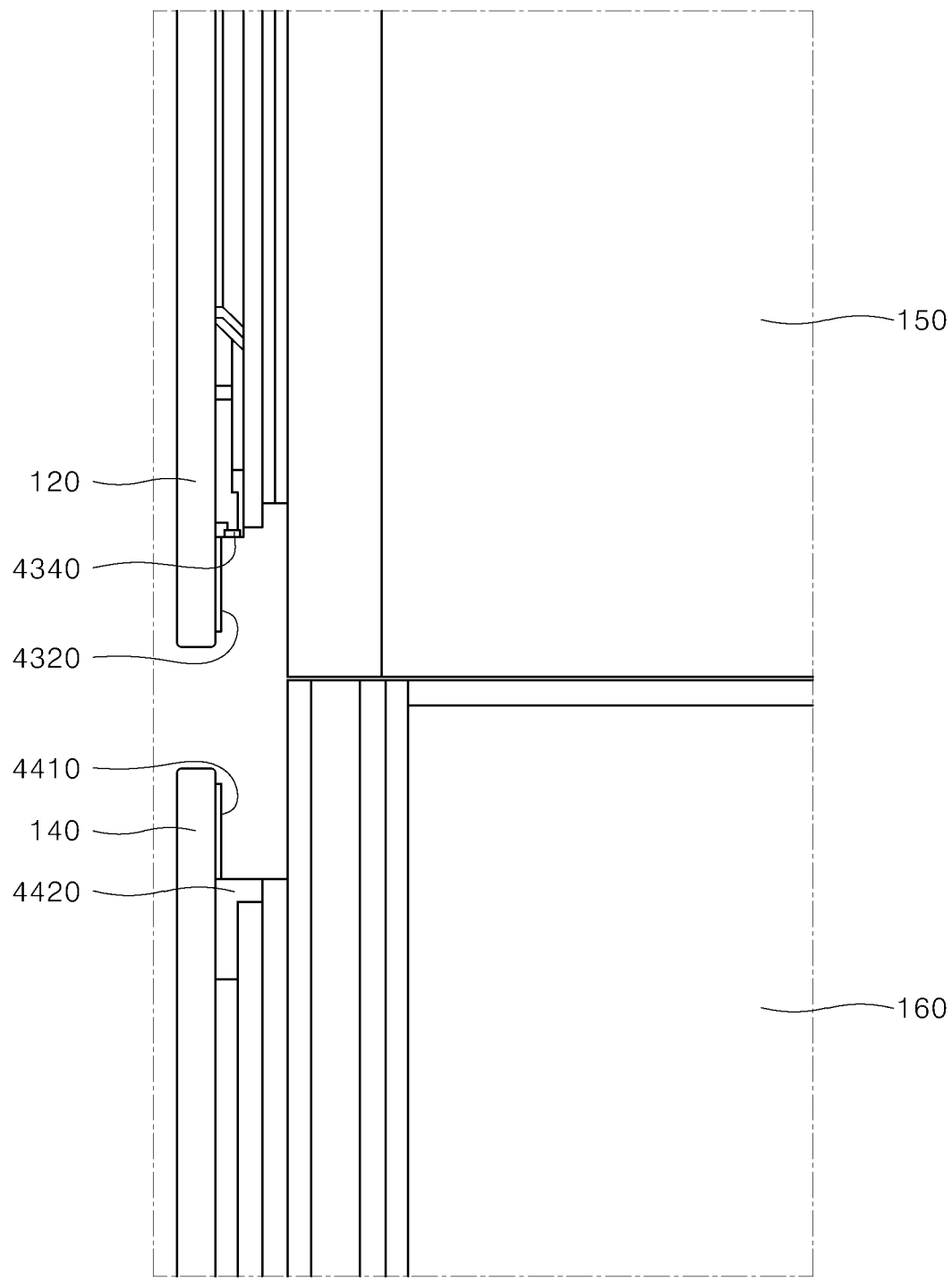
FIG. 44 is an exemplary view illustrating a side surface of a shoe treating apparatus according to an embodiment of the present invention.
Figure 45:
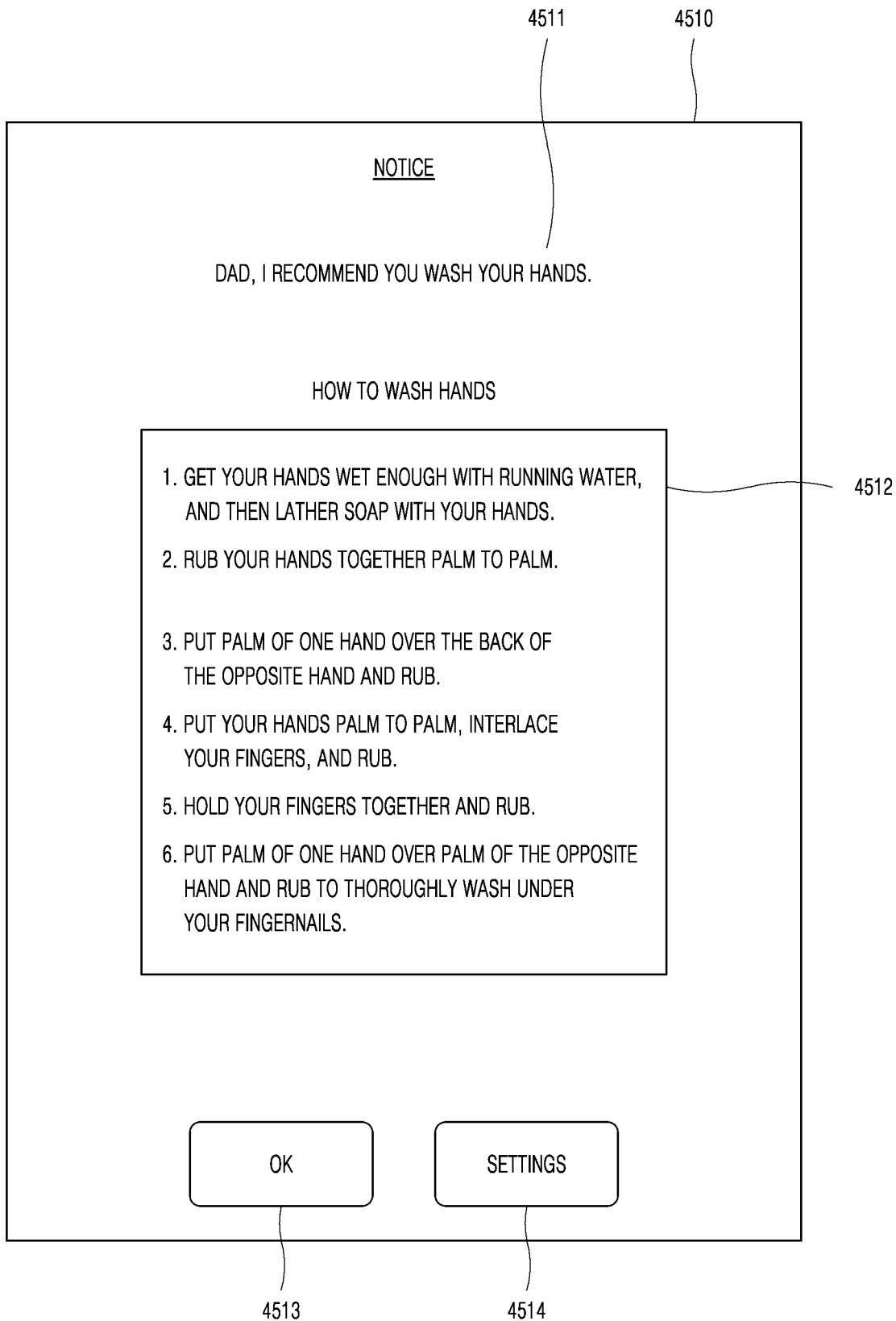
FIG. 45 is an exemplary view illustrating a notification message that induces hand washing according to an embodiment of the present invention.

FIG. 41 is a flowchart illustrating a process of sanitizing a handle of a shoe treating apparatus according to an embodiment of the present invention. FIG. 42A is an exemplary view of touching a handle of a shoe treating apparatus according to an embodiment of the present invention. FIG. 42B is an exemplary view of sanitizing a handle of a shoe treating apparatus according to an embodiment of the present invention. FIG. 43A is an exemplary view illustrating a bottom surface of an upper cabinet door according to an embodiment of the present invention. FIG. 43B is an exemplary view illustrating arrangement of a plurality of light emitting elements of a sensor part according to an embodiment of the present invention. FIG. 44 is an exemplary view illustrating a side surface of a shoe treating apparatus according to an embodiment of the present invention. FIG. 45 is an exemplary view illustrating a notification message that induces hand washing according to an embodiment of the present invention.

The process of sanitizing a handle of a shoe treating apparatus according to an embodiment of the present invention will be described in detail with reference to FIGS. 41, 42A, 42B, 43A, 43B, and 44.

According to an embodiment, the processor 470 may identify a user by using at least one sensor (S4110). The process (S4110) may include at least one function or at least one operation performed in at least one of the processes (S2310 and S2312) of FIG. 23.

According to an embodiment, the processor 470 may detect a touch on a handle (S4112). The processor 470 may identify a user through the fingerprint sensor 418 disposed at inner sides of the doors 110 and 120 of the upper cabinet 150 of the shoe treating apparatus 310 or inner sides of the doors 130 and 140 of the lower cabinet 160. The fingerprint sensor 418 may be disposed on a portion (e.g., the part where the fingerprint of the finger touches) of the door that is grasped by a user.

Referring to FIG. 42A, lower portions of the doors 110 and 120 of the upper cabinet 150 of the shoe treating apparatus 310 and upper portions of the doors 130 and 140 of the lower cabinet 160 may be formed in a shape of being concave inward to facilitate grasping. For example, in a case in which a user 4210 wants to open the right door 120 of the upper cabinet 150, the user 4210 may pull the right door 120 of the upper cabinet 150 while grasping the right door 120.

In such a case in which the user 4210 has grasped the right door 120 of the upper cabinet 150, the fingerprint sensor 418 provided at the inner side of the right door 120 may acquire fingerprint information of the user and transmit the acquired fingerprint information to the processor 470.

Referring to FIG. 43A, a fingerprint sensor 4310 and a plurality of light emitting elements 4330 may be disposed at the inner side of the left door 110 of the upper cabinet 150. Also, a fingerprint sensor 4320 and a plurality of light emitting elements 4340 may be disposed at the inner side of the right door 120 of the upper cabinet 150. The plurality of light emitting elements 4330 may include one or more first light emitting elements (e.g., LEDs) and one or more second light emitting elements (e.g., UVC LEDs).

Also, the first light emitting element and the second light emitting element may be disposed at the inner side of the left door 110 of the upper cabinet 150 and/or the inner side of the right door 120.

Referring to FIG. 43B, the plurality of light emitting elements 4330 may be disposed at the lower portion of the inner side of the left door 110 of the upper cabinet 150. The first light emitting elements (e.g., LEDs) and the second light emitting elements (e.g., UVC LEDs) among the plurality of light emitting elements 4330 may be alternately disposed.

For example, a first light emitting element 4331 (e.g., LED) may be disposed, and a second light emitting element 4332 (e.g., UVC LED) may be disposed beside the first light emitting element 4331 (e.g., LED). Also, a third light emitting element 4333 (e.g., LED) may be disposed beside the second light emitting element 4332 (e.g., UVC LED).

Referring to FIG. 44, the fingerprint sensor 4320 and the light emitting part 4340 are disposed at an inner side of a lower portion of a door (e.g., the right door 120) of the upper cabinet 150. Also, in the light emitting part 4340, as illustrated in FIG. 43B, the first light emitting elements (e.g., LEDs) and the second light emitting elements (e.g., UVC LEDs) may be alternately disposed.

Also, the fingerprint sensor 4310 and a reflective plate 4420 are disposed at an inner side of a lower portion of a door (e.g., the right door 140) of the lower cabinet 160. The reflective plate 4420 may reflect light emitted from the second light emitting element, and the light reflected through the reflective plate 4420 may be reflected toward a handle portion of each of the upper cabinet 150 and the lower cabinet 160 to overall sanitize the handle portion.

According to an embodiment, the processor 470 may adjust a sanitization strength to be different for each user to sanitize a handle from which a touch is detected (S4114). The processor 470 may adjust the strength of sanitization using one or more first light emitting elements of the light emitting part 439 to be different for each user (e.g., father, mother, son, daughter, etc.) touching the handle of the upper cabinet 150 or the handle of the lower cabinet 160.

Referring to FIG. 42B, after the user 4210 grasps a handle portion of the door 120 in FIG. 42A, when the hand of the user 4210 is determined as having been removed from the handle portion, the processor 470 may adjust the strength of sanitization using one or more UVC LEDs of the light emitting part 4340 to be different on the basis of at least some of the identification of the user 4210, the number of times the user has touched the handle, and a time window in which the user has touched the handle and may sanitize the handle on the basis of the adjusted sanitization strength.

Also, the processor 470 may cause one or more LEDs of the light emitting part 4340 to emit light to indicate that the handle is being sanitized so as to indicate that the handle portion is currently being sanitized (4220).

According to an embodiment, the processor 470 may display that a handle is being sanitized (S4116). In a case in which the handle is currently being sanitized, the processor 470 may cause one or more second light emitting elements of the light emitting part 439 to emit light to indicate that the handle is being sanitized.

According to an embodiment, the one or more first light emitting elements (e.g., LEDs) and the one or more second light emitting elements (e.g., UVC LEDs) may be alternately disposed at the inner sides of the doors 110 and 120 of the upper cabinet 150. Alternatively, the one or more first light emitting elements (e.g., LEDs) and the one or more second light emitting elements (e.g., UVC LEDs) may be alternately disposed at the inner sides of the doors 130 and 140 of the lower cabinet 160.

According to an embodiment, the processor 470 may add up the number of times a user has touched a handle (S4118). The processor 470 may save the number of times each user has touched a handle and a time window in which the user has touched the handle in the memory 434.

According to an embodiment, the processor 470 may display a notification message that induces a user to wash his or her hands (S4120). On the basis of the number of times each user has touched a door handle and a time window in which the user has touched the door handle, the processor 470 may display a notification message inducing hand washing for each user through the display part 433.

The notification message may include various pieces of information on contamination of hands such as the importance of hand washing and a method of hand washing. The display part 433 may be disposed on the doors 110 and 120 (e.g., the smart mirrors 3510 and 3520) of the upper cabinet 150 or disposed on lower portions of the doors 110 and 120.

Referring to FIG. 45, the processor 470 may, on the basis of identifying a user who has touched a handle, display a notification message 4510 through the display part 433 to make the corresponding user wash hands. The notification message 4510 may include a hand washing recommendation message 4511 and a hand washing method 4512 for each user. The hand washing recommendation message 4511 may include various pieces of information from which a user may be identified, such as the name, relation, and position of the identified user. Also, the notification message 4510 may include various pieces of information that show the importance of hand washing.

Also, when an OK menu 4513 is selected, the display of the notification message 4510 may end. For example, in a case in which a user does not want the notification message 4510 to be displayed, the user may go to a Settings menu 4514 to stop the displaying of the notification message.

Figure 46:
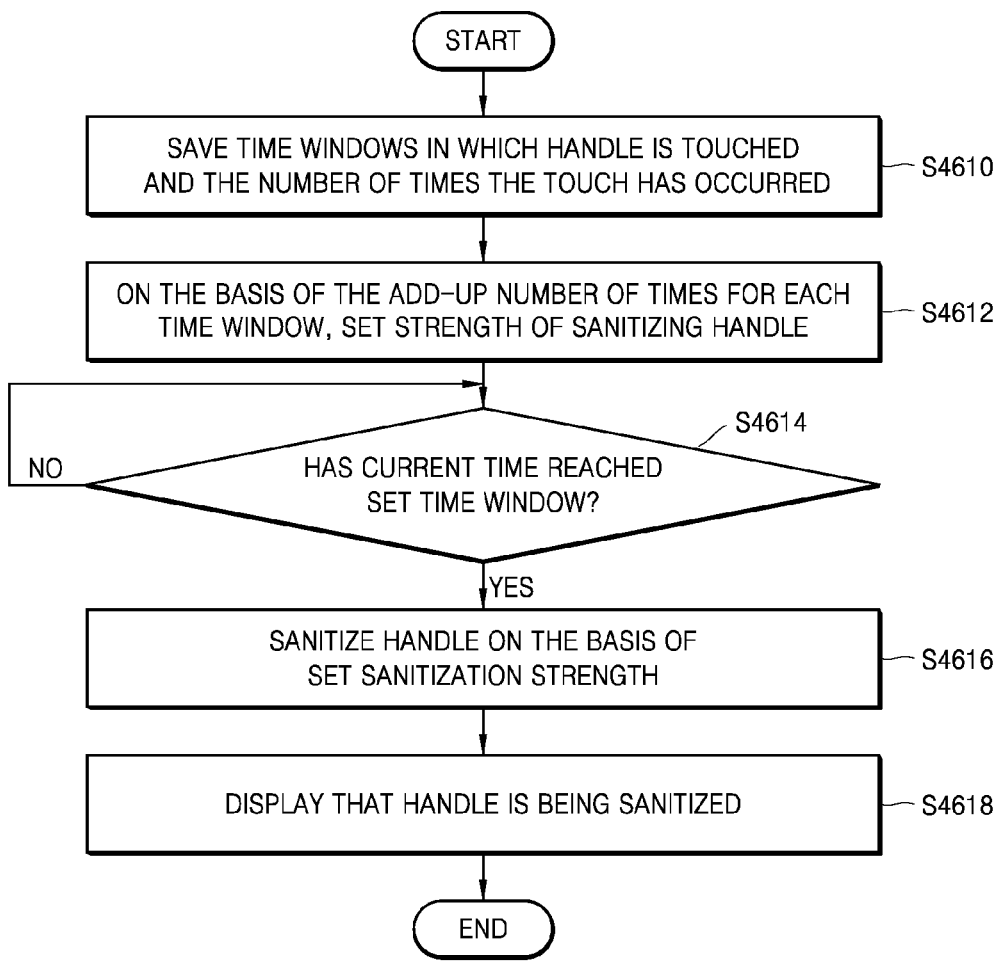
FIG. 46 is an exemplary view illustrating a process in which a shoe treating apparatus sanitizes a handle in each time window according to an embodiment of the present invention.

FIG. 46 is an exemplary view illustrating a process in which a shoe treating apparatus sanitizes a handle in each time window according to an embodiment of the present invention.

Hereinafter, the process in which a shoe treating apparatus sanitizes a handle in each time window according to an embodiment of the present invention will be described in detail with reference to FIG. 46.

According to an embodiment, the processor 470 may save time windows in which a handle is touched and the number of times the touch occurs (S4610). The processor 470 may store the number of times each user has touched a handle and time windows in which each user has touched the handle in the memory 434. By storing the above, the processor 470 may identify a time window in which the handle is frequently touched, who often touches the handle, and when.

According to an embodiment, the processor 470 may, on the basis of the add-up number of times for each time window, set the strength of sanitizing a handle (S4612). The processor 470 may, for each user (e.g., father, mother, son, daughter, etc.) touching the handle, add up the number of times the user has touched the handle in the memory 434.

Also, the processor 470 may add up the number of times the handle is touched in each time window in the memory 434. Through the result of adding up, the processor 470 may differently set the strength of sanitization using one or more first light emitting elements of the light emitting part 439.

For example, for a time window in which the number of times the handle is touched is large, the processor 470 may set the sanitization strength to "high." Alternatively, for a time window in which the number of times the handle is touched is small, the processor 470 may set the sanitization strength to "low."

According to an embodiment, the processor 470 may identify whether the current time has reached a set time window (S4614). The processor 470 may identify whether the current time (e.g., 5:59 pm) has reached a set time window (e.g., 6 pm to 7 pm). For example, in a case in which the current time (e.g., 5:59 pm) has not reached a set time window (e.g., 6 pm to 7 pm), the processor 470 may not perform sanitization through the light emitting part 439.

According to an embodiment, the processor 470 may sanitize the handle on the basis of a set sanitization strength (S4616). For example, in a case in which the current time (e.g., 6:00 pm) has reached a set time window (e.g., 6 pm to 7 pm), the processor 470 may start sanitization through the light emitting part 439 while the sanitization strength is set to "high." The processor 470 may perform sanitization for a predetermined amount of time (e.g., three minutes).

According to an embodiment, the processor 470 may display that the handle is being sanitized (S4618). In a case in which the handle is currently being sanitized, the processor 470 may cause one or more LEDs of the light emitting part 439 to emit light to indicate that the handle is currently being sanitized. For example, through a speaker, the processor 470 may output a voice indicating that the handle portion is currently being sanitized.

Hereinafter, folding or unfolding of each shelf disposed in a shoe cabinet will be described.

[Shelf Control]

Figure 47:
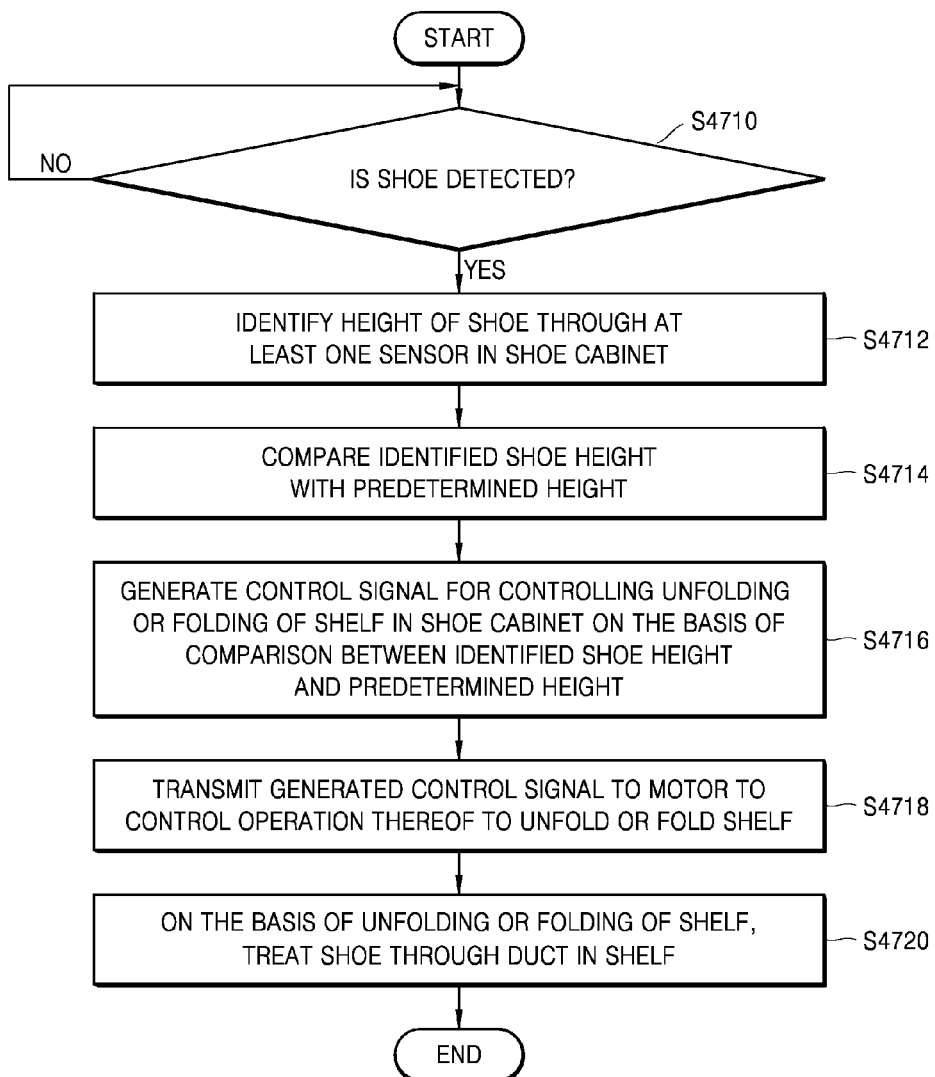
FIG. 47 is a flowchart illustrating a process of controlling folding or unfolding of a shelf of a shoe cabinet according to an embodiment of the present invention.
Figure 48:
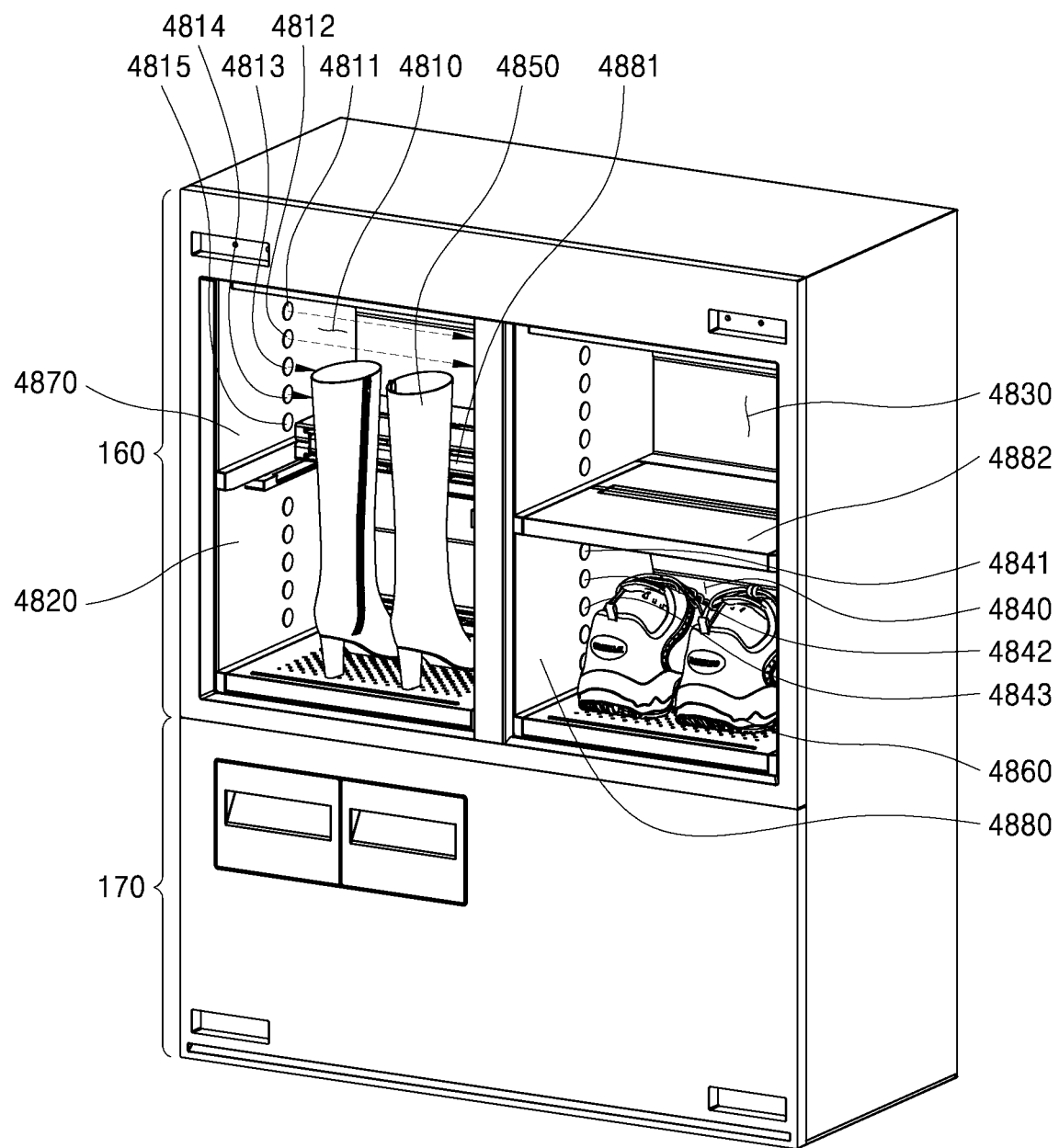
FIG. 48 is a perspective view of a shoe cabinet according to an embodiment of the present invention.
Figure 49:
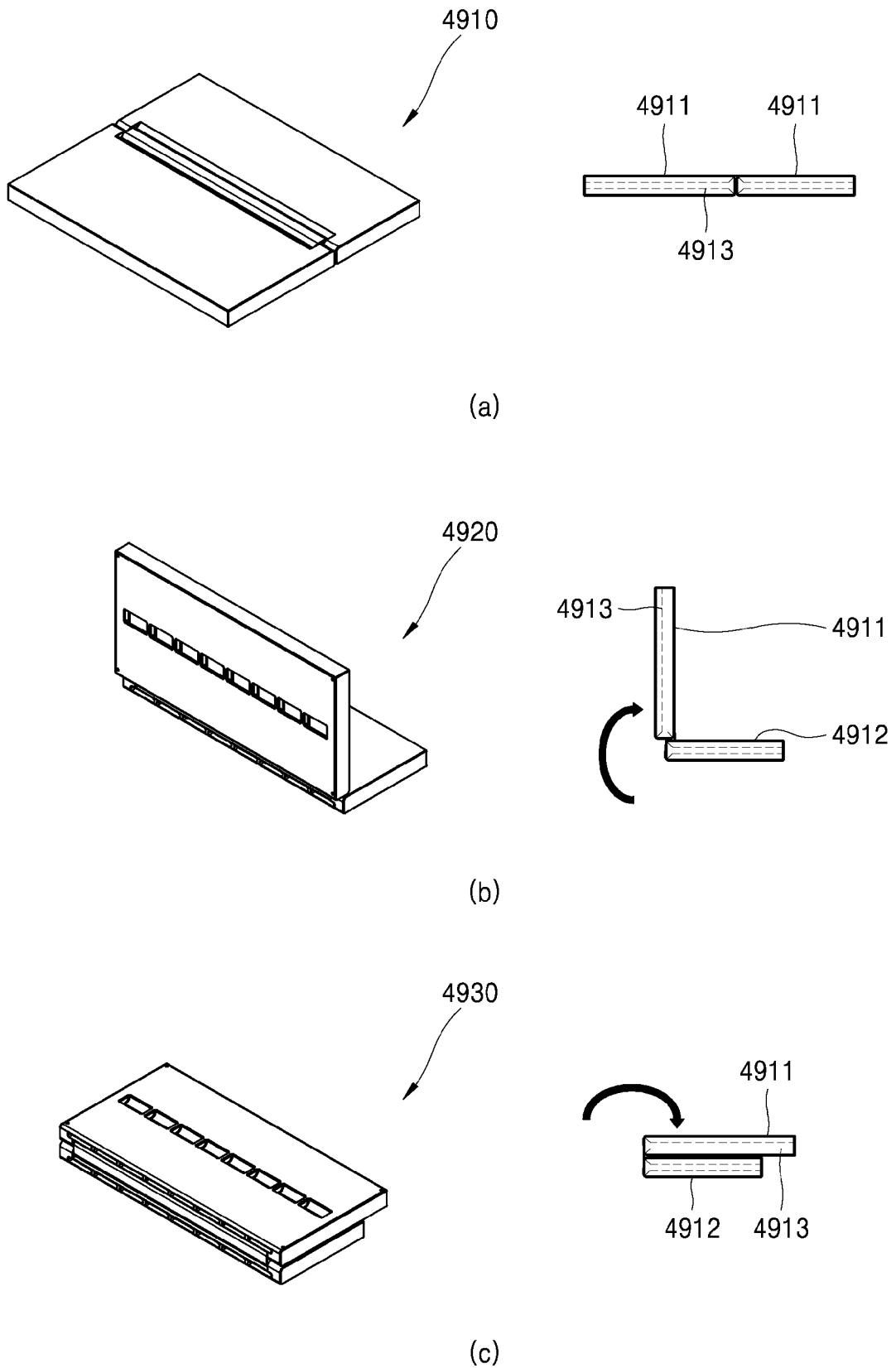
FIG. 49 is an exemplary view illustrating an operation relating to folding or unfolding of a shelf according to an embodiment of the present invention.

FIG. 47 is a flowchart illustrating a process of controlling folding or unfolding of a shelf of a shoe cabinet according to an embodiment of the present invention. FIG. 48 is a perspective view of a shoe cabinet according to an embodiment of the present invention. FIG. 49 is an exemplary view illustrating an operation relating to folding or unfolding of a shelf according to an embodiment of the present invention.

Hereinafter, the process of controlling folding or unfolding of a shelf of a shoe cabinet according to an embodiment of the present invention will be described in detail with reference to FIGS. 47, 48, and 49.

According to an embodiment, the processor 470 may detect whether a shoe is stored in a shoe cabinet (S4710). The process (S4710) may include at least one function or at least one operation performed in at least one of the process (S510) of FIG. 5 and the process (S710) of FIG. 7.

According to an embodiment, the processor 470 may identify the height of a shoe through at least one sensor in the shoe cabinet (S4712). The processor 470 may identify the height of the shoe placed in the shoe treating apparatus 310 through at least one sensor (e.g., the distance measurement sensor 416, the IR sensor 419, and/or the camera 432) included in the sensor part 410.

For example, in a case in which distance values measured by a plurality of sensors are the same or are within a negligible error range, the processor 470 may determine that the height of the shoe is lower than the position of a sensor located at the lowest position among the plurality of sensors that acquired the same distance values.

According to an embodiment, the processor 470 may identify a sensor that measures a distance value different from distance values (e.g., the distance between the sensor and the shoe or the distance between the sensor and the inner wall at the other side) measured by each of a plurality of sensors vertically disposed on the inner wall of the shoe cabinet (e.g., the lower cabinet 160). Also, the processor 470 may identify the height of the shoe on the basis of identifying the sensor that measures a different distance value (e.g., identifying the height of the sensor).

Referring to FIG. 48, the shoe cabinet (e.g., the lower cabinet 160) may be formed to have first to fourth storage spaces 4810, 4820, 4830, and 4840. Also, the electronic component part 170 may be disposed on the lower portion of the shoe cabinet (e.g., the lower cabinet 160).

For example, a first shelf 4881 may be disposed between the first storage space 4810 and the second storage space 4820. Also, a second shelf 4882 may be disposed between the third storage space 4830 and the fourth storage space 4840.

According to an embodiment, at least one of the first shelf 4881 and the second shelf 4882 may have a coupling member (e.g., a motor or the like) formed at an intermediate portion to fold or unfold the shelf. Also, at least one of the first shelf 4881 and the second shelf 4882 may be folded or unfolded through the coupling member (e.g., a motor or the like).

For example, in a case in which the first shelf 4881 is folded, a shoe 4850 (e.g., boots) may be stored in the first storage space 4810 and the second storage space 4820. Also, in a case in which the second shelf 4882 is unfolded, a shoe 4860 (e.g., sneakers) may be stored in each of the third storage space 4830 and the fourth storage space 4840. For example, a plurality of sensors 4841, 4842, 4843, etc. may be disposed at predetermined intervals on an inner wall 4880 of the fourth storage space 4840.

According to an embodiment, a plurality of sensors (e.g., a first sensor 4811, a second sensor 4812, a third sensor 4813, a fourth sensor 4814, and a fifth sensor 4815) may be vertically disposed at predetermined intervals on a first inner wall 4870 of the first storage space 4810.

According to an embodiment, the processor 470 may identify whether a shoe is present and the height of a shoe through at least one of a plurality of sensors (e.g., the distance measurement sensor 416, the IR sensor 419, and the like) vertically disposed on an inner wall of each storage space of the shoe cabinet (e.g., the lower cabinet 160). Also, the processor 470 may, on the basis of the height of the shoe, determine whether to fold or unfold the corresponding shelf.

For example, in a case in which the shoe 4860 (e.g., sneakers) is stored in the fourth storage space 4840, the processor 470 may identify the height of the shoe 4860 (e.g., sneakers) through the one or more sensors 4841, 4842, 4843, etc.

Also, the processor 470 may, on the basis of the identified height of the shoe 4860 (e.g., sneakers), generate a control signal that causes the second shelf 4882 to be unfolded and may transmit the generated control signal to a motor disposed at the second shelf 4882 to unfold the shelf.

According to an embodiment, the processor 470 may compare the identified shoe height with a predetermined height (S4714). The memory 434 of the shoe treating apparatus 310 may store information on the size, design, width, and height of various shoes. Through the information on various shoes that is stored in the memory 434, the processor 470 may identify the type, size, height, and the like of the shoe. The processor 470 may identify the exact height of the shoe on the basis of the identified shoe height and the information on various shoes that is stored in the memory 434.

The predetermined height may include the height from the bottom of the shoe cabinet to a shelf disposed thereabove. The height from the bottom of the shoe cabinet to a shelf disposed thereabove may vary according to a method of manufacturing the shoe treating apparatus.

For example, the height from the bottom of the shoe cabinet to a shelf disposed thereabove may be about 20 cm. Alternatively, the height from the bottom of the shoe cabinet to a shelf disposed thereabove may be higher than about 20 cm or may not be higher than about 20 cm. The height may be variably adjusted.

According to an embodiment, on the basis of the comparison between the identified shoe height and the predetermined height, the processor 470 may generate a control signal for controlling unfolding or folding of a shelf in the shoe cabinet (S4716). For example, in a case in which the identified shoe height is not greater than the predetermined height, the processor 470 may generate a control signal for controlling folding of a shelf, which is disposed above a cabinet storing the shoe, so that the shelf is unfolded. The control signal is a signal for controlling an operation of a motor that allows the shelf to be unfolded.

For example, in a case in which the identified shoe height is greater than the predetermined height, the processor 470 may not generate a control signal for controlling folding of the shelf, which is disposed above the cabinet storing the shoe, so that the shelf maintains a folded state.

According to an embodiment, the processor 470 may transmit the generated control signal to a motor to control an operation of the motor to unfold or fold the shelf (S4718). In a case in which the identified shoe height is not greater than the predetermined height, the processor 470 may, to the corresponding motor, transmit a control signal generated to control folding of the shelf, which is disposed above the cabinet storing the shoe, so that the shelf is unfolded.

Alternatively, in a case in which the identified shoe height is not greater than the predetermined height, the processor 470 may, to the corresponding motor, not transmit a control signal for controlling folding of the shelf, which is disposed above the cabinet storing the shoe, so that the shelf maintains a folded state.

Referring to FIG. 49, a shelf according to an embodiment of the present invention may be folded or unfolded.

Referring to (a) of FIG. 49, a shelf 4910 according to an embodiment of the present invention may be unfolded at a predetermined angle (e.g., 180°). For example, the shelf 4910 may have a first member 4911 and a second member 4912 coupled through a connecting member. Also, the movement of the first member 4911 and the second member 4912 may be controlled through the corresponding motor of the motor part 437.

Also, a duct 4913 may be formed inside the first member 4911 and the second member 4912. At least part of air, steam, low-temperature hot air, and water repellent may flow through the duct 4913.

Referring to (b) of FIG. 49, a shelf 4920 according to an embodiment of the present invention may be folded at a predetermined angle (e.g., 90°). For example, the shelf 4920 may have a first member 4911 and a second member 4912 coupled through a connecting member. Also, a duct 4913 may be formed inside the first member 4911 and the second member 4912. At least part of air, steam, low-temperature hot air, and water repellent may flow through the duct 4913.

However, in a case in which the first member 4911 and the second member 4912 are formed at a predetermined angle to each other as in FIG. 49B instead of being parallel to each other, at least part of air, steam, low-temperature hot air, and water repellent may flow through any one (e.g., the second member 4912) of the first member 4911 and the second member 4912 and be discharged to the inside of the storage space 4840 of the shoe cabinet (e.g., the lower cabinet 160).

Referring to (c) of FIG. 49, a shelf 4930 according to an embodiment of the present invention may be folded completely (e.g., at 00). For example, the shelf 4930 may have a first member 4911 and a second member 4912 coupled through a connecting member, and the first member 4911 may be folded through the connecting member so as to be parallel to the second member 4912. Also, a duct 4913 may be formed inside the first member 4911 and the second member 4912.

At least part of air, steam, low-temperature hot air, and water repellent may flow through the duct 4913. In the above case in which the first member 4911 and the second member 4912 are completely folded, at least part of air, steam, low-temperature hot air, and water repellent may flow through any one (e.g., the second member 4912) of the first member 4911 and the second member 4912 and be discharged to the inside of the storage space 4840 of the shoe cabinet (e.g., the lower cabinet 160).

Referring to FIG. 47, the processor 470 may, on the basis of the unfolding or folding of the shelf, treat the shoe through the duct in the shelf (S4720). The processor 470 may discharge at least part of air, steam, low-temperature hot air, and water repellent through the duct formed in the unfolded shelf.

Alternatively, the processor 470 may discharge at least part of air, steam, low-temperature hot air, and water repellent through the duct formed in the folded shelf. For example, in a case in which the shelf is unfolded, ducts formed in the shelf may be coupled to each other, and at least part of air, steam, low-temperature hot air, and water repellent may flow therethrough. In order to prevent this, rubber packing may be formed on portions where the at least one shelf is folded in order to prevent at least part of air, steam, low-temperature hot air, and water repellent from leaking through the portions.

Figure 50:
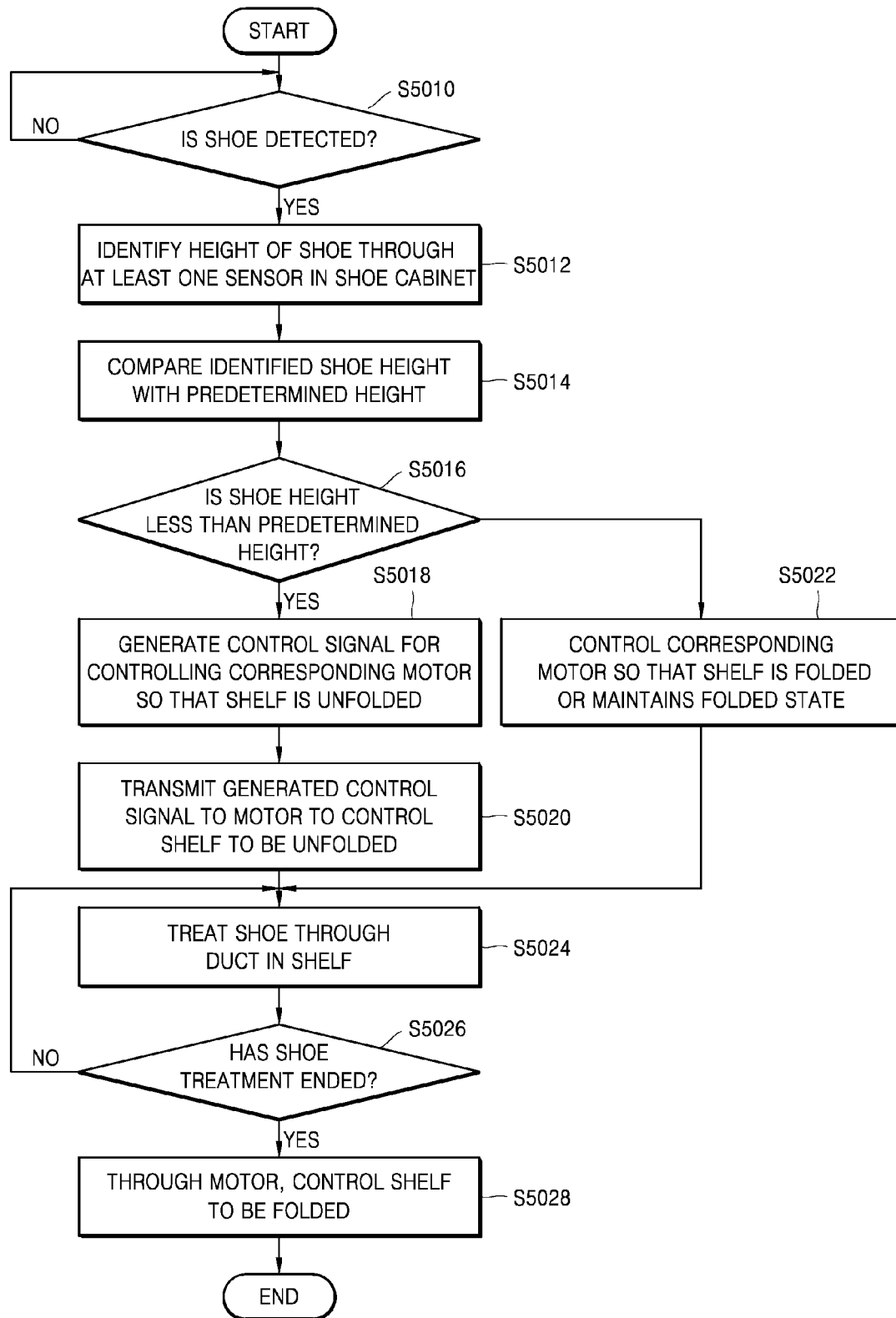
FIG. 50 is a flowchart illustrating a process of controlling folding or unfolding of a shelf of a shoe cabinet according to another embodiment of the present invention.
Figure 51:
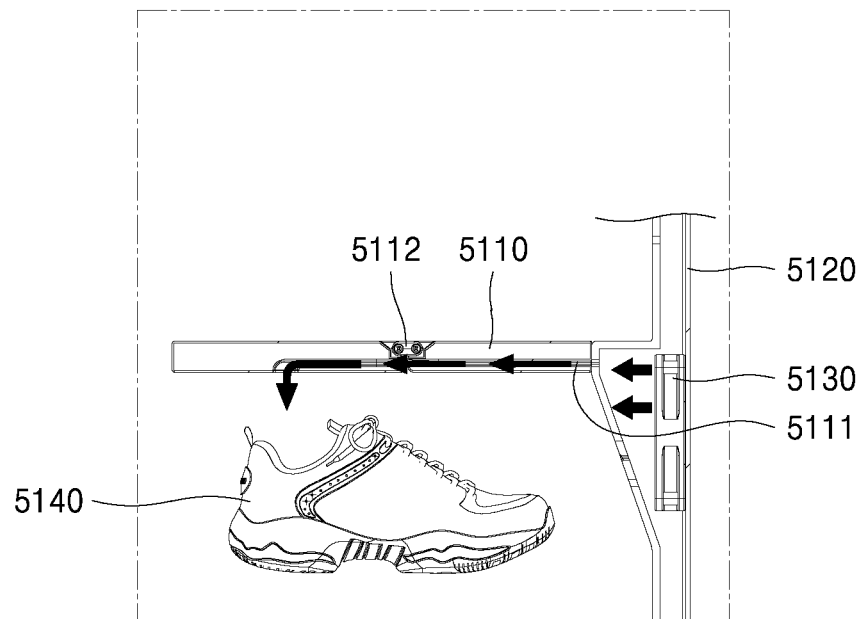
FIG. 51 is an exemplary view illustrating unfolded and folded states of a shelf according to the height of a shoe according to an embodiment of the present invention.
Figure 51:
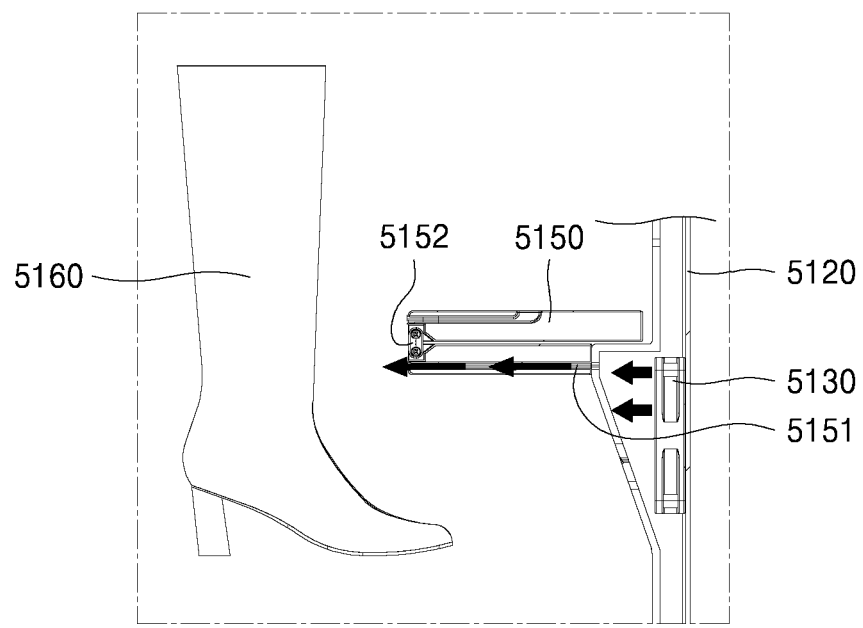

FIG. 50 is a flowchart illustrating a process of controlling folding or unfolding of a shelf of a shoe cabinet according to another embodiment of the present invention. FIG. 51 is an exemplary view illustrating unfolded and folded states of a shelf according to the height of a shoe according to an embodiment of the present invention.

Hereinafter, the process of controlling folding or unfolding of a shelf of a shoe cabinet according to another embodiment of the present invention will be described in detail with reference to FIGS. 50 and 51.

According to an embodiment, the processor 470 may detect whether a shoe is stored in a shoe cabinet (S5010). The process (S5010) may include at least one function or at least one operation performed in the process (S4710) of FIG. 47.

According to an embodiment, the processor 470 may identify the height of a shoe through at least one sensor in the shoe cabinet (S5012). The process (S5012) may include at least one function or at least one operation performed in the process (S4712) of FIG. 47. According to an embodiment, the processor 470 may compare the identified shoe height with a predetermined height (S5014). The process (S5014) may include at least one function or at least one operation performed in the process (S4714) of FIG. 47.

According to an embodiment, the processor 470 may identify whether the shoe height is smaller than the predetermined height (S5016). The processor 470 may compare the shoe height with a predetermined height (e.g., the height of a cabinet (e.g., each cabinet of the lower cabinet 160) storing the shoe).

For example, the height from the bottom of the shoe cabinet to a shelf disposed thereabove may be about 20 cm. The height may be variably adjusted.

According to an embodiment, the processor 470 may generate a control signal for controlling the corresponding motor so that the shelf is unfolded (S5018). When the shoe height acquired in the process (S5012) is identified as being smaller than a predetermined cabinet height, the processor 470 may generate a control signal for controlling the corresponding motor so that the shelf is unfolded.

In a case in which the shoe height is smaller than the predetermined cabinet height, the processor 470 may determine that a storage space is sufficient to store the shoe. Also, the processor 470 may generate a control signal for unfolding the shelf to allow the shoe to be stored in a storage space disposed above the storage space in which the shoe is stored.

According to an embodiment, the processor 470 may transmit the generated control signal to a motor to control the shelf to be unfolded (S5020). In a case in which the shoe height is not greater than the predetermined height, the processor 470 may, to the corresponding motor, transmit a control signal generated to control tilting of the shelf, which is disposed above the cabinet storing the shoe, so that the shelf is unfolded.

Referring to FIG. 51, a shelf may be unfolded or folded according to the height of a shoe stored in a storage space.

Referring to (a) of FIG. 51, in a case in which the height of a shoe 5140 is low (e.g., sneakers, loafers, slippers, or the like), the processor 470 may identify the height of the shoe 5140 and, to cause a shelf 5110 to be unfolded, control a motor 5112 corresponding thereto.

Also, the processor 470 may operate a fan 5130 disposed at an inner wall 5120 of a storage space to discharge at least part of air, steam, low-temperature hot air, and water repellent, which are supplied from the fan 5130, to the inside of the shoe 5140 through a duct 5111 formed inside the shelf 5110.

Referring to (b) of FIG. 51, in a case in which the height of a shoe 5160 is high (e.g., boots, rain boots, or the like), the processor 470 may identify the height of the shoe 5160 and, to cause a shelf 5150 to be folded, control a motor 5152 corresponding thereto.

Also, the processor 470 may operate a fan 5130 disposed at an inner wall 5120 of a storage space to discharge at least part of air, steam, low-temperature hot air, and water repellent, which are supplied from the fan 5130, to the storage space through a duct 5152 formed in the shelf 5150.

According to an embodiment, the processor 470 may control the corresponding motor so that the shelf is folded (S5022). When the shoe height acquired in the process (S5012) is identified as not being smaller than the predetermined cabinet height, the processor 470 may generate a control signal for controlling the corresponding motor so that the shelf is folded.

Alternatively, the processor 470 may not generate a control signal for controlling the corresponding motor so that the shelf maintains a folded state.

In a case in which the shoe height is greater than the predetermined height, the processor 470 may, to the corresponding motor, transmit a control signal generated to control tilting of the shelf, which is disposed above the cabinet storing the shoe, so that the shelf is folded. The processor 470 may, to a motor corresponding to the shelf to be folded, provide a control signal that causes the shelf to be folded (e.g., a torque value of the corresponding motor).

According to an embodiment, the processor 470 may treat a shoe through a duct in the shelf (S5024). The processor 470 may discharge at least part of air, steam, low-temperature hot air, and water repellent through a duct formed in the unfolded shelf to treat a shoe.

For example, the processor 470 may treat a shoe through an intensive treatment function (e.g., at least one or some of foreign substance removal, sanitization/deodorization, steaming/sanitization, dehumidification/drying, and nourishing/water-repellent coating) of the shoe treating apparatus 310.

According to an embodiment, the processor 470 may identify whether shoe treatment has ended (S5026). The processor 470 may perform the intensive treatment function for a predetermined amount of time (about forty minutes). Also, the processor 470 may determine whether the time during which intensive treatment is performed on the shoe has exceeded the predetermined amount of time (e.g., forty minutes).

Alternatively, the processor 470 may determine whether the intensive treatment function on the shoe has ended. The intensive treatment function may end according to various conditions such as a user command or exceeding a predetermined amount of time.

According to an embodiment, the processor 470 may, through a motor corresponding to a shelf, control the shelf to be folded (S5028). When a shoe treatment mode is identified as having ended, the processor 470 may control the shelf to be folded through the motor corresponding to the shelf.

Alternatively, when the shoe treatment mode is identified as having ended, the processor 470 may control the corresponding motor so that the shelf maintains an unfolded state.

Hereinafter, controlling an operation of a rotatable duct part disposed in at least one storage space of a lower cabinet of the present invention will be described.

[Control of Rotatable Duct Part]

Figure 52:
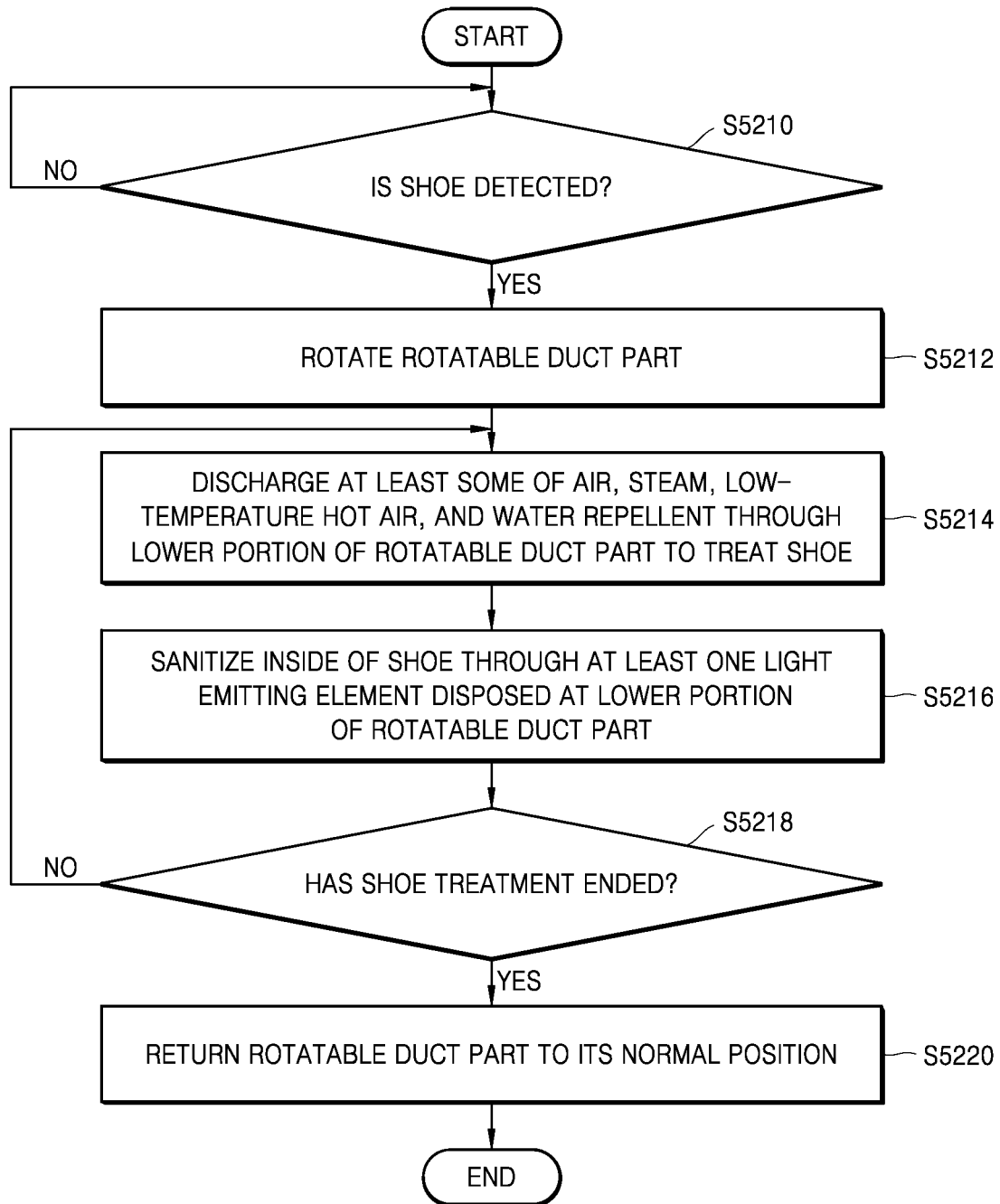
FIG. 52 is a flowchart illustrating a process of controlling an operation of a rotatable duct part disposed in a storage space according to an embodiment of the present invention.
Figure 53:
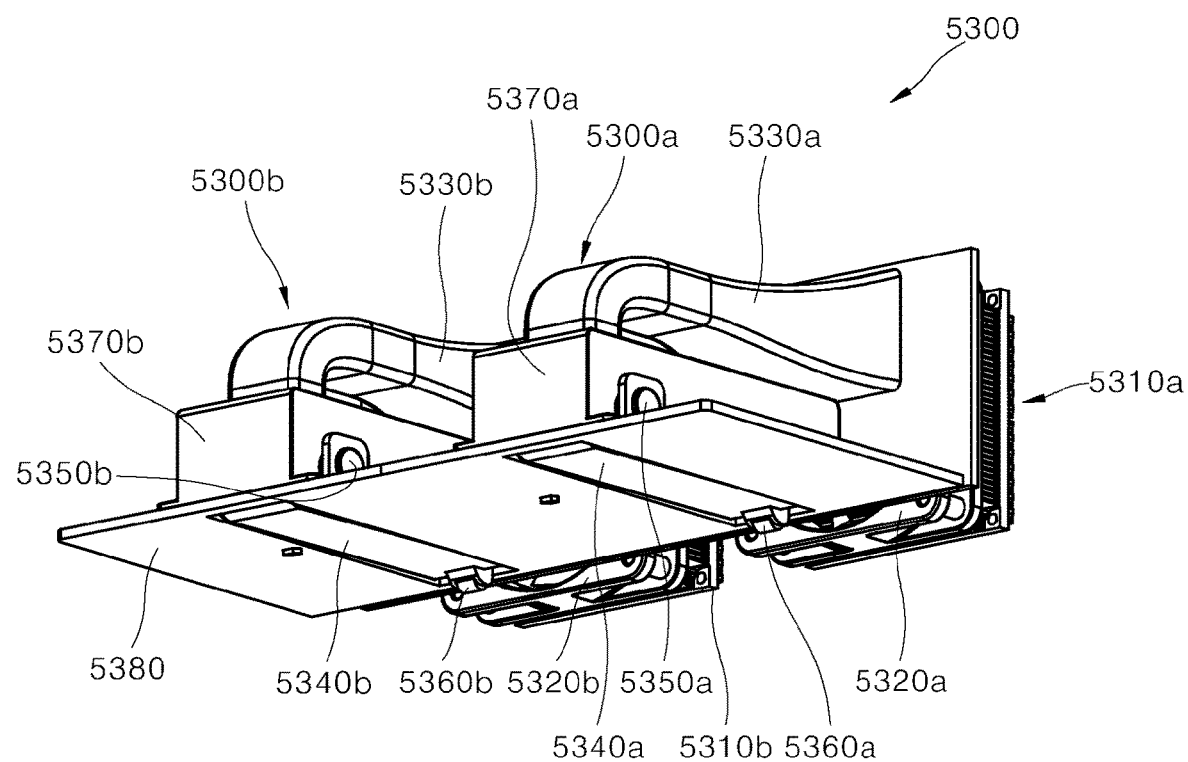
FIG. 53 is a perspective view illustrating a state in which a rotatable duct part is folded upward according to an embodiment of the present invention.
Figure 54:
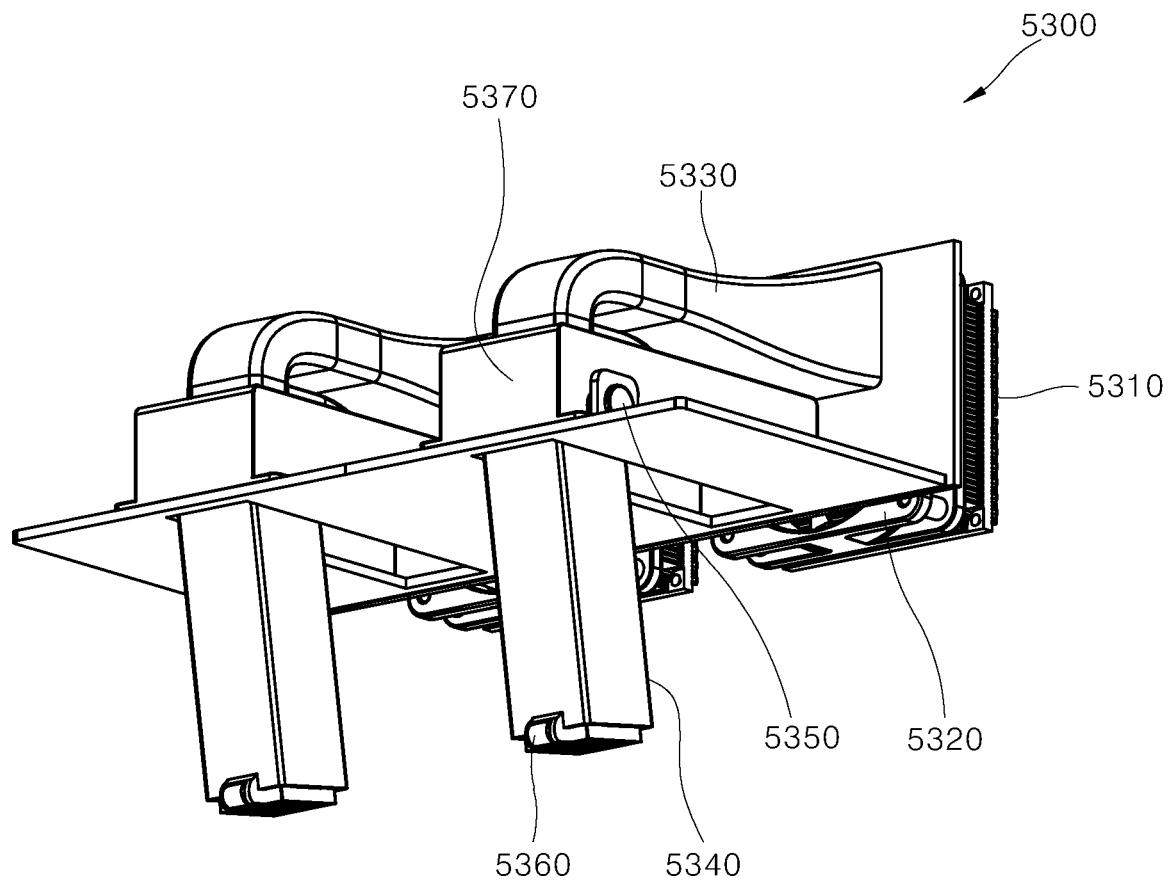
FIG. 54 is a perspective view illustrating a state in which a rotatable duct part is rotated downward according to an embodiment of the present invention.
Figure 55:
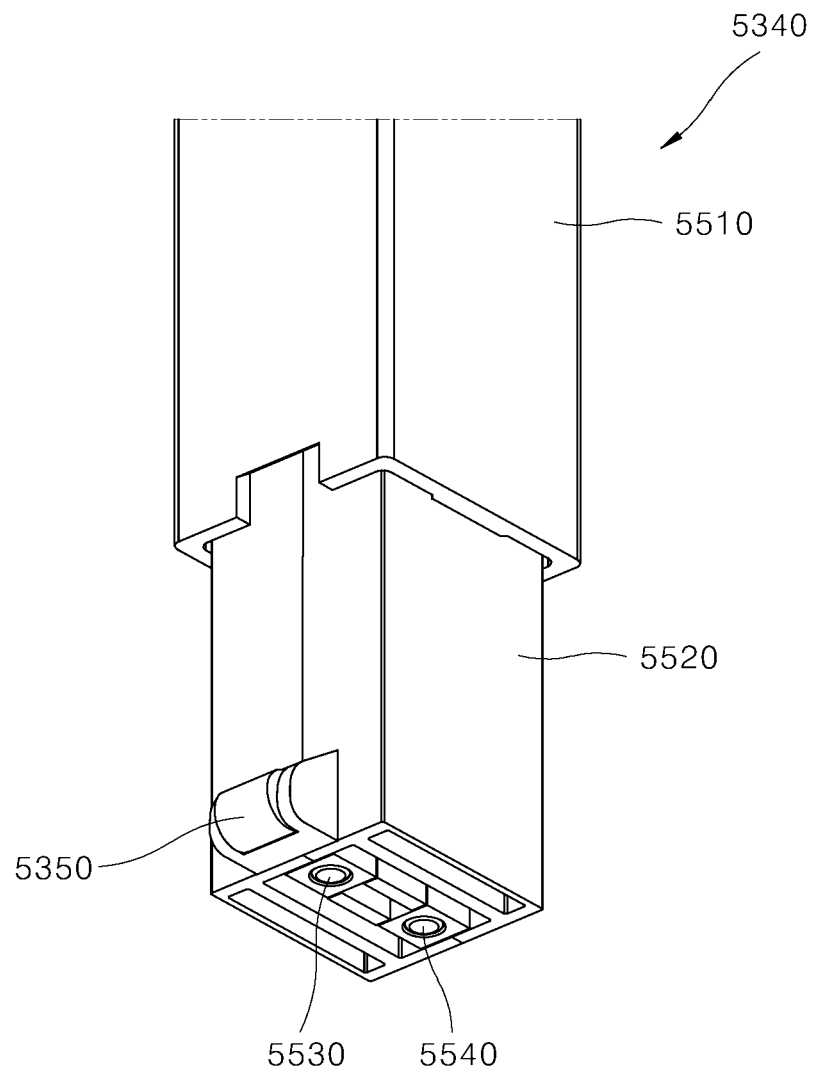
FIG. 55 is a perspective view illustrating a state in which an expandable duct part in a rotatable duct part is expanded downward according to an embodiment of the present invention.

FIG. 52 is a flowchart illustrating a process of controlling an operation of a rotatable duct part disposed in a storage space according to an embodiment of the present invention. FIG. 53 is a perspective view illustrating a state in which a rotatable duct part is folded upward according to an embodiment of the present invention. FIG. 54 is a perspective view illustrating a state in which a rotatable duct part is rotated downward according to an embodiment of the present invention. FIG. 55 is a perspective view illustrating a state in which an expandable duct part in a rotatable duct part is expanded downward according to an embodiment of the present invention.

Hereinafter, the process of controlling an operation of a rotatable duct part disposed in a storage space according to an embodiment of the present invention will be described in detail with reference to FIGS. 52, 53, 54, and 55.

According to an embodiment, the processor 470 may identify whether a shoe is detected (S5210). The process (S5210) may include at least one function or at least one operation performed in the process (S4710) of FIG. 47.

According to an embodiment, the processor 470 may rotate a rotatable duct part (S5212). When a shoe is identified as being stored in a storage space of a shoe cabinet (e.g., the lower cabinet 160), the processor 470 may rotate a rotatable duct part of a duct module toward where the shoe is located (e.g., downward).

According to an embodiment, the processor 470 may, on the basis of identifying the type of shoe, determine whether to rotate a rotatable duct part. The processor 470 may, on the basis of the identified type (or height) of shoe, determine whether to rotate the rotatable duct part toward the inside of the storage space.

According to an embodiment, the rotatable duct part may be disposed on an upper portion of each storage space. Also, the rotatable duct part may be embedded in the upper portion of each storage space and may be formed in a structure that may protrude by rotating toward the inside of the storage space.

According to an embodiment, in a case in which, on the basis of the type (or height) of the shoe, the height of the shoe is less than or equal to a first predetermined height, the processor 470 may rotate the rotatable duct part. The first predetermined height may be a height at which the height of the shoe does not interfere with rotation of the rotatable duct part.

Alternatively, in a case in which the height of the shoe is less than or equal to a second predetermined height, the processor 470 may rotate the rotatable duct part and expand an expandable duct part, which is formed in the rotatable duct part, toward the inside of the shoe. The second predetermined height may be less than or equal to the first predetermined height.

For example, in a case in which, when the height of the storage space is 50 cm and the length of the rotatable duct part is 10 cm, the identified height of the shoe is 38 cm, that is, not greater than a first predetermined height (e.g., a height obtained by subtracting the length of the rotatable duct part from the height of the storage space (e.g., 40 cm)), the processor 470 may rotate the rotatable duct part. Also, the processor 470 may expand the expandable duct part formed in the rotatable duct part toward the inside of the shoe.

For example, in a case in which, when the height of the storage space is 50 cm and the length of the rotatable duct part is 10 cm, the identified height of the shoe is 30 cm, that is, not greater than a second predetermined height (e.g., a height obtained by subtracting the length of the rotatable duct part from the height of the storage space (e.g., 40 cm)), the processor 470 may rotate the rotatable duct part. Also, the processor 470 may expand the expandable duct part formed in the rotatable duct part toward the inside of the shoe.

Referring to FIGS. 53 and 54, the rotatable duct part according to an embodiment of the present invention may be embedded in the duct module 5300 in a state of being folded upward or may rotate downward.

According to an embodiment, the duct module 5300 may be formed in a form in which two duct modules 5300a and 5300b are coupled. A first duct module 5300a may include a first heat exchange part 5310a, a first fan 5320a, a first duct part 5330a, and a first rotatable duct part 5340a. Also, a second duct module 5300b may include a second heat exchange part 5310b, a second fan 5320b, a second duct part 5330b, and a second rotatable duct part 5340b. First motor 5350a and second motor 5350b are provided to rotate the first rotatable duct part 5340a and the second rotatable duct part 5340b, respectively. First roller 5360a and second roller 5360b are provided near the ends of the first rotatable duct part 5340a and the second rotatable duct part 5340b, respectively.

According to an embodiment, each duct module may operate together or operate independently of each other. For example, in a case in which a pair of shoes is present in a storage space, the first and second duct modules 5300a and 5300b may operate together.

Alternatively, in a case in which a single shoe, instead of a pair of shoes, is present in a storage space, only one of the first and second duct modules 5300a and 5300b that corresponds to the position at which the single shoe is placed may operate.

Although the term "first" or "second" is omitted (for example, the first duct module 5300a and the second duct module 5300b are referred to as "duct module 5300") in the following description with respect to FIG. 54, the corresponding element may be interpreted as including at least one of "first" and "second."

According to an embodiment, the heat exchange part 5310 may be installed continuously with the fan 5320, and the heat exchange part 5310 may include various types of heat exchange devices within the technical idea that the heat exchange device exchanges heat with air introduced into the fan 5320.

According to an embodiment, the heat exchange part 5310 may use the Peltier effect to exchange heat with air. The heat exchange part 5310 may include a Peltier element.

According to an embodiment, the fan 5320 may deliver air generated in the heat exchange part 5310 to a storage space, and the duct part 5330 may guide the air delivered by the fan 5320 to the storage space through the rotatable duct part 5340.

According to an embodiment, the duct part 5330 may be disposed at an upper side of the storage space and may have a duct provided therein to guide movement of air. The duct part 5330 may be disposed at the upper side of the storage space, and movement of the duct part 5330 may be restricted.

According to an embodiment, the duct part 5330 may be installed continuously with the fan 5320 and may extend in the horizontal direction. Also, the duct part 5330 may have a form that is bent downward. The air introduced into the duct part 5330 after passing through the fan 5320 may be moved into the storage space.

According to an embodiment, the rotatable duct part 5340 may extend to the inside of the storage space by an operation of rotating or longitudinally moving. The rotatable duct part 5340 may rotate due to an operation of a motor 5350 and may be inserted into the duct module 5300 in a case in which a shoe is not present in the storage space.

According to an embodiment, the rotatable duct part 5340 may rotate due to the operation of the motor 5350 in a case in which air is supplied to the storage space.

According to an embodiment, the rotatable duct part 5340 may be rotatably installed in a fixed housing 5370 and may, due to the rotating operation, be inserted into the fixed housing 5370 or expand to the storage space.

According to an embodiment, the motor 5350 may be connected to the rotatable duct part 5340, and various types of driving devices may be used as the motor 5350 within the technical idea that the driving device supplies rotation power for rotating the rotatable duct part 5340 downward (e.g., toward a shoe). The motor 5350 may be axially connected to the center of rotation of the rotatable duct part 5340 and may rotate the rotatable duct part 5340. The motor 5350 may be included in a motor part (the motor part 437 of FIG. 4).

According to an embodiment, the motor 5350 may be directly connected to the center of rotation of the rotatable duct part 5340.

According to an embodiment, a roller 5360 may be rotatably disposed at a lower side of an expandable duct part 5520. Also, in a case in which the roller 5360 comes in contact with the insole of the shoe, the roller 5360 may rotate to reduce a frictional force. The roller 5360 may protrude toward the insole of the shoe and rotate due to coming in contact with the insole of the shoe.

According to an embodiment, in a case in which a shoe is detected in the process (S5210), the processor 470 may control the motor 5350 to rotate the rotatable duct part 5340 downward to where the shoe is placed.

Referring to FIG. 55, in the state of being rotated downward, the rotatable duct part 5340 according to an embodiment of the present invention may discharge the expandable duct part 5520 downward (e.g., in the direction of the rotatable duct part 5340).

According to an embodiment, the expandable duct part 5520 may extend and be discharged in the direction of the rotatable duct part 5340. The rotatable duct part 5340 may include a rotatable duct body 5510 forming an exterior and the expandable duct part 5520 disposed inside the rotatable duct body 5510. The rotatable duct body 5510 has one side and the other side that are open.

According to an embodiment, the expandable duct part 5520 may come in contact with the insole of the shoe stored in the storage space and may, due to malleability of a variable duct part, be bent toward the front of the shoe. The expandable duct part 5520 is disposed inside the rotatable duct part 5340.

According to an embodiment, the expandable duct part 5520 may be formed in a quadrilateral shape but may also be formed in other shapes.

According to an embodiment, the roller 5360 may be disposed at a lower portion of the expandable duct part 5520. Also, a discharge port 5540 through which at least part of air, steam, low-temperature hot air, and water repellent are discharged to the inside of the shoe may be formed at the lower portion of the expandable duct part 5520. The discharge port 5540 is an end portion of the duct formed in the rotatable duct part 5340. Also, at least one light emitting element 5530 (e.g., UVC LED) may be included at the lower portion of the expandable duct part 5520. The at least one light emitting element may be included in a light emitting part (e.g., the light emitting part 439 of FIG. 4).

According to an embodiment, the expandable duct part 5520 may be extended from the rotatable duct part 5340 toward the inside of the shoe.

Referring to FIG. 52, the processor 470 may discharge at least part of air, steam, low-temperature hot air, and water repellent through the lower portion of the rotatable duct part 5340 to treat the shoe (S5214). The processor 470 may discharge at least part of air, steam, low-temperature hot air, and water repellent, which are generated by the treatment part 440, through a duct of the rotatable duct part 5340 to intensively treat the shoe. The duct formed in the rotatable duct part 5340 may be formed to discharge at least part of air, steam, low-temperature hot air, and water repellent, which are generated by the treatment part 440, to the inside of the shoe.

According to an embodiment, the intensive treatment may include at least one of the first function of removing foreign substances adsorbed onto the shoe, the second function of executing at least one of sanitization and deodorization of the shoe, the third function of executing at least one of steaming and sanitization of the shoe, the fourth function of executing at least one of dehumidification and drying of the shoe, and the fifth function of executing at least one of nourishing and water-repellent coating of the shoe.

According to an embodiment, the processor 470 may emit at least one of a photocatalyst and a deodorizer through at least one emitting element (e.g., the UV light emitting part 422, the photocatalyst emitting part 424, the plasma emitting part 426) disposed at the lower portion of the rotatable duct part 5340 (e.g., the lower portion of the expandable duct part 5520 inserted into the rotatable duct part 5340) to sanitize the shoe and/or deodorize the shoe.

According to an embodiment, the processor 470 may sanitize the inside of the shoe through at least one light emitting element disposed at the lower portion of the rotatable duct part (S5216). The processor 470 may sanitize the inside of the shoe through at least one light emitting element 5530 (e.g., UVC LED) disposed at the lower portion of the rotatable duct part 5340 (e.g., the lower portion of the expandable duct part 5520 inserted into the rotatable duct part 5340.

According to an embodiment, the processor 470 may identify whether shoe treatment has ended (S5218). The processor 470 may identify whether the time during which the processes (S5214 and S5216) are performed has exceeded a predetermined amount of time. The predetermined amount of time may be set to different amounts of time according to at least one of the material, function, type, and condition of the shoe. The predetermined amount of time is the time during which intensive treatment is performed on the shoe and may be adjusted on the basis of a user input.

According to an embodiment, the processor 470 may return the rotatable duct part to its normal position (S5220). When intensive treatment on the shoe has ended, the processor 470 may rotate the rotatable duct part to insert the rotatable duct part into the duct module 5300.

Figure 56:
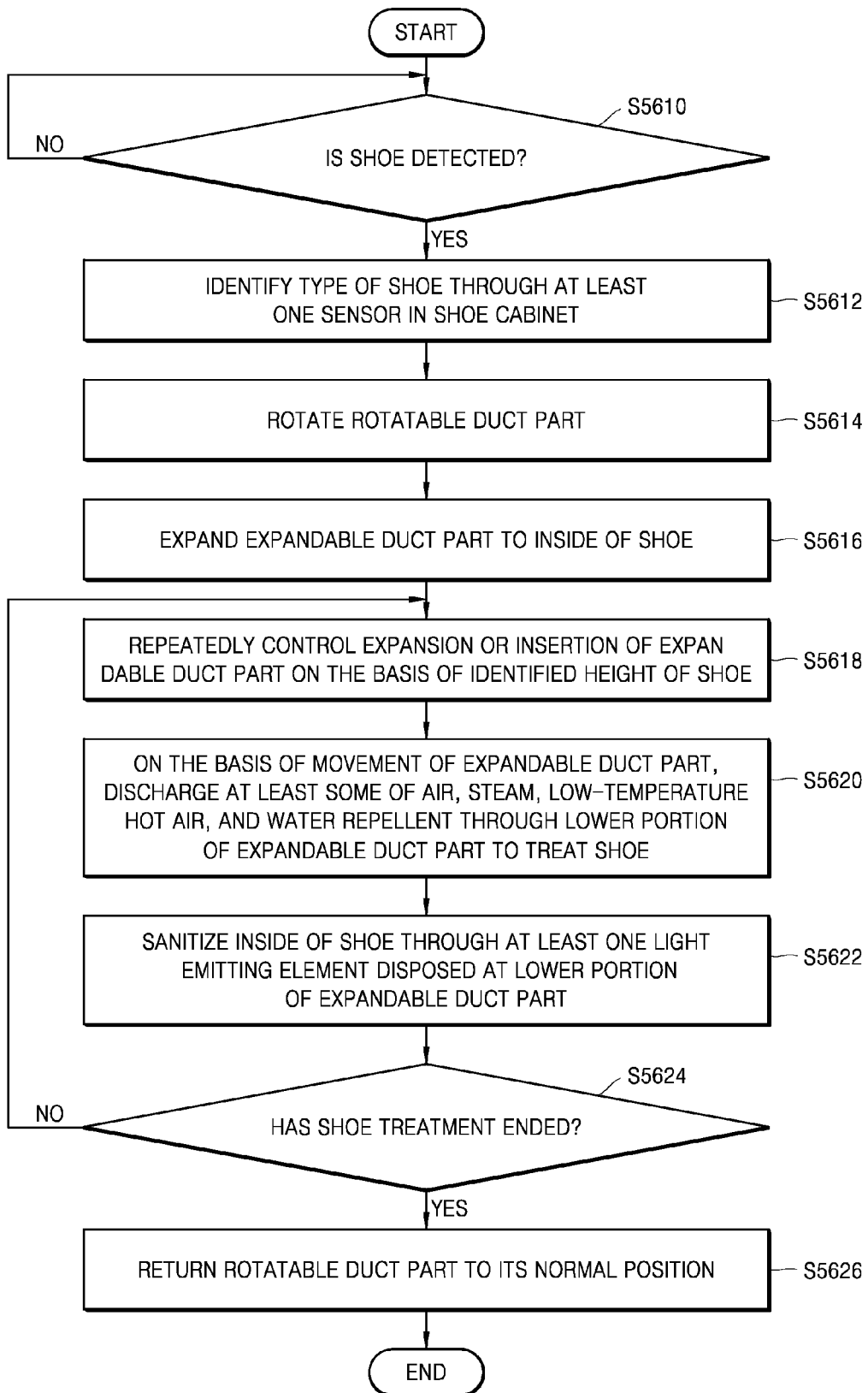
FIG. 56 is a flowchart illustrating a process of controlling an operation of a rotatable duct part disposed in a storage space according to another embodiment of the present invention.
Figure 57:
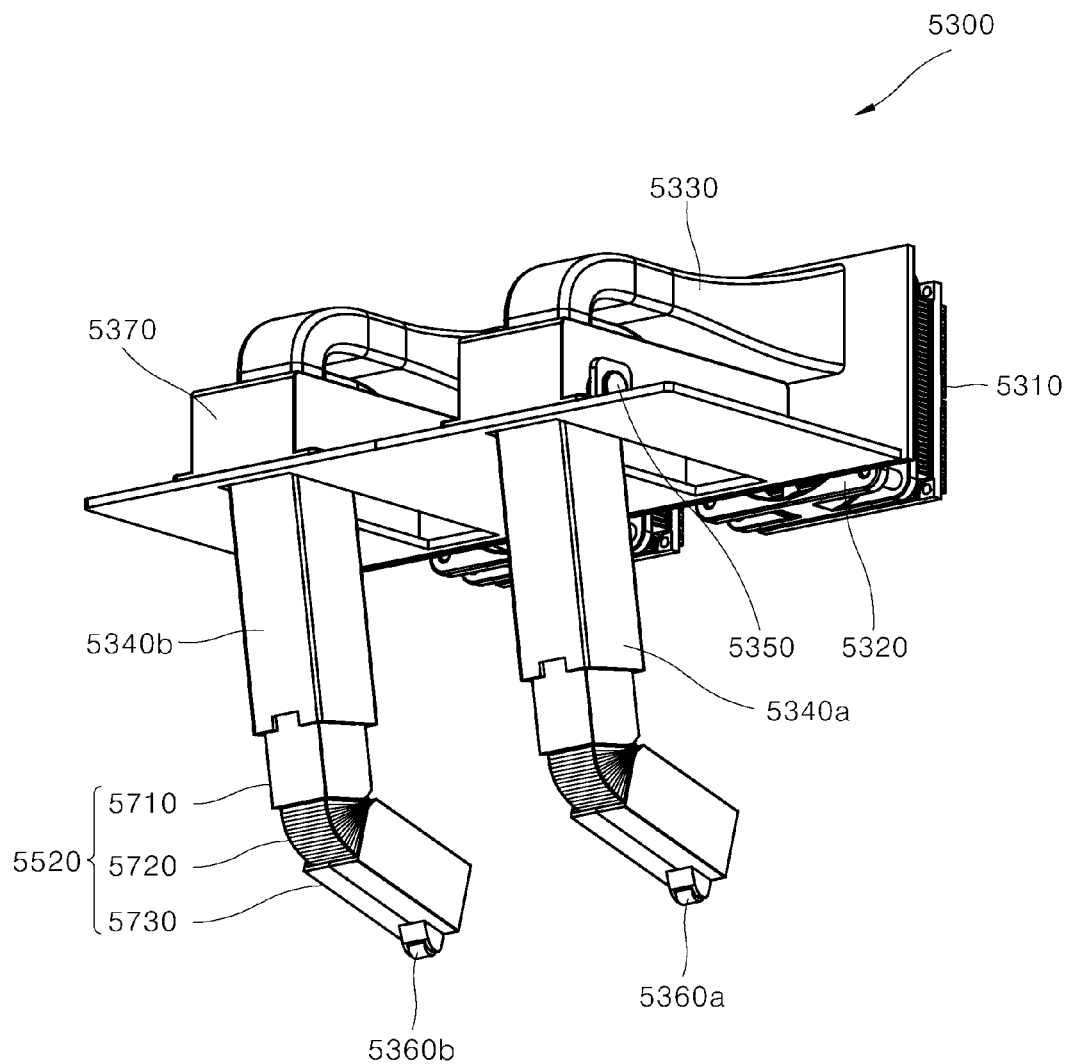
FIG. 57 is a perspective view illustrating a state in which an expandable duct part is bent according to an embodiment of the present invention.
Figure 58A:
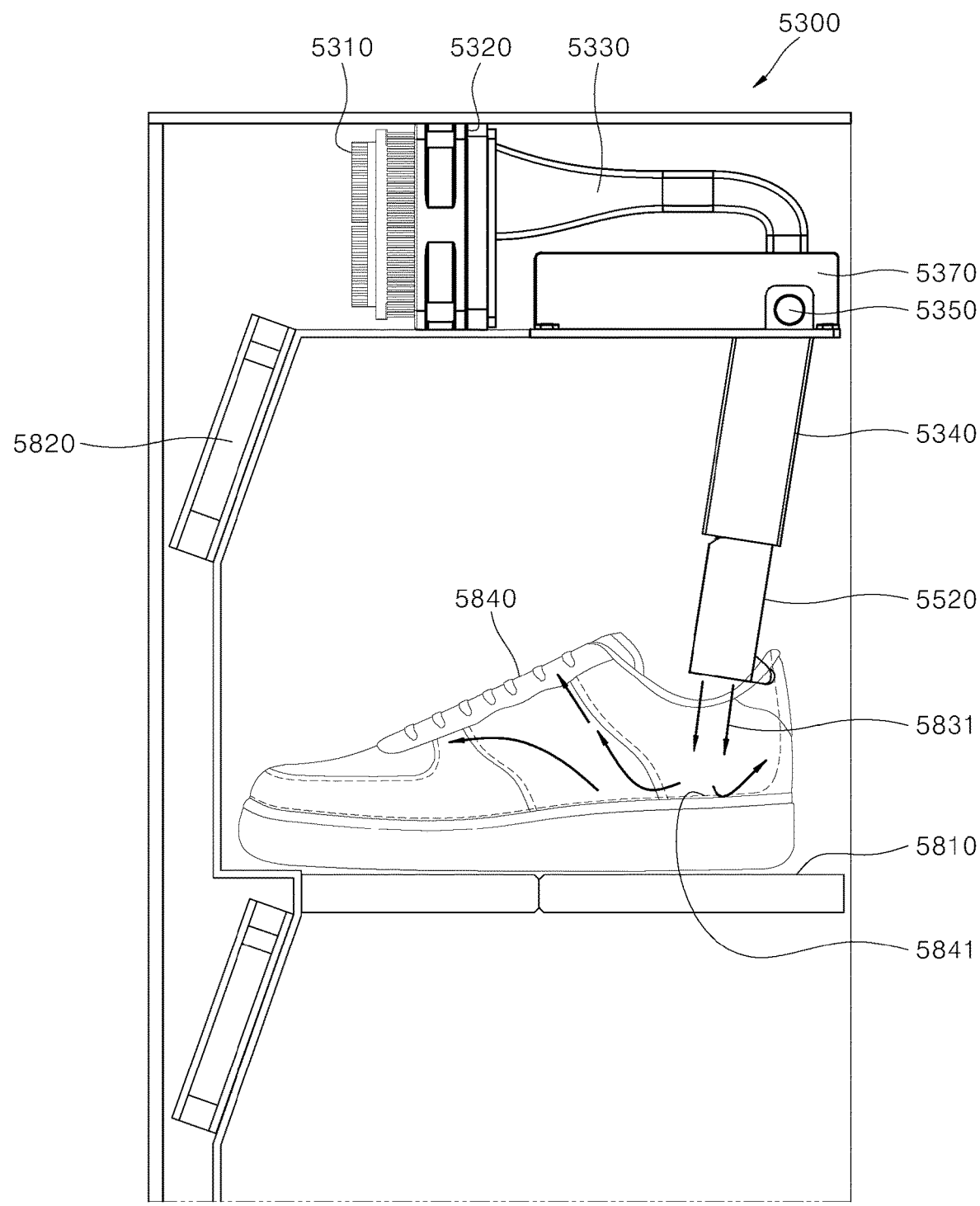
FIG. 58A is an exemplary view illustrating a state in which an expandable duct part faces the inside of a shoe according to an embodiment of the present invention.
Figure 58B:
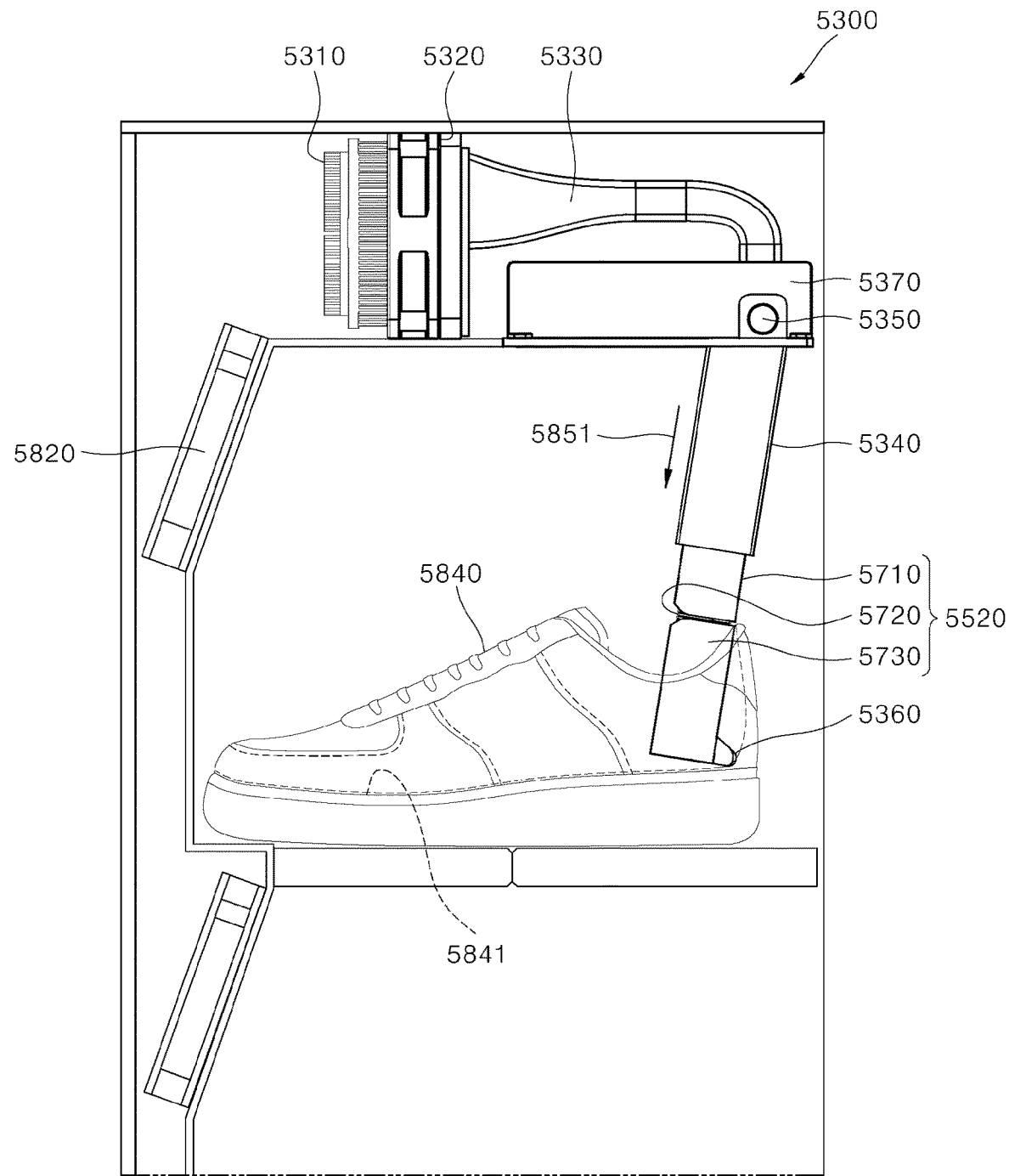
FIG. 58B is an exemplary view illustrating a state in which an expandable duct part comes in contact with an insole of a shoe according to an embodiment of the present invention.
Figure 58C:
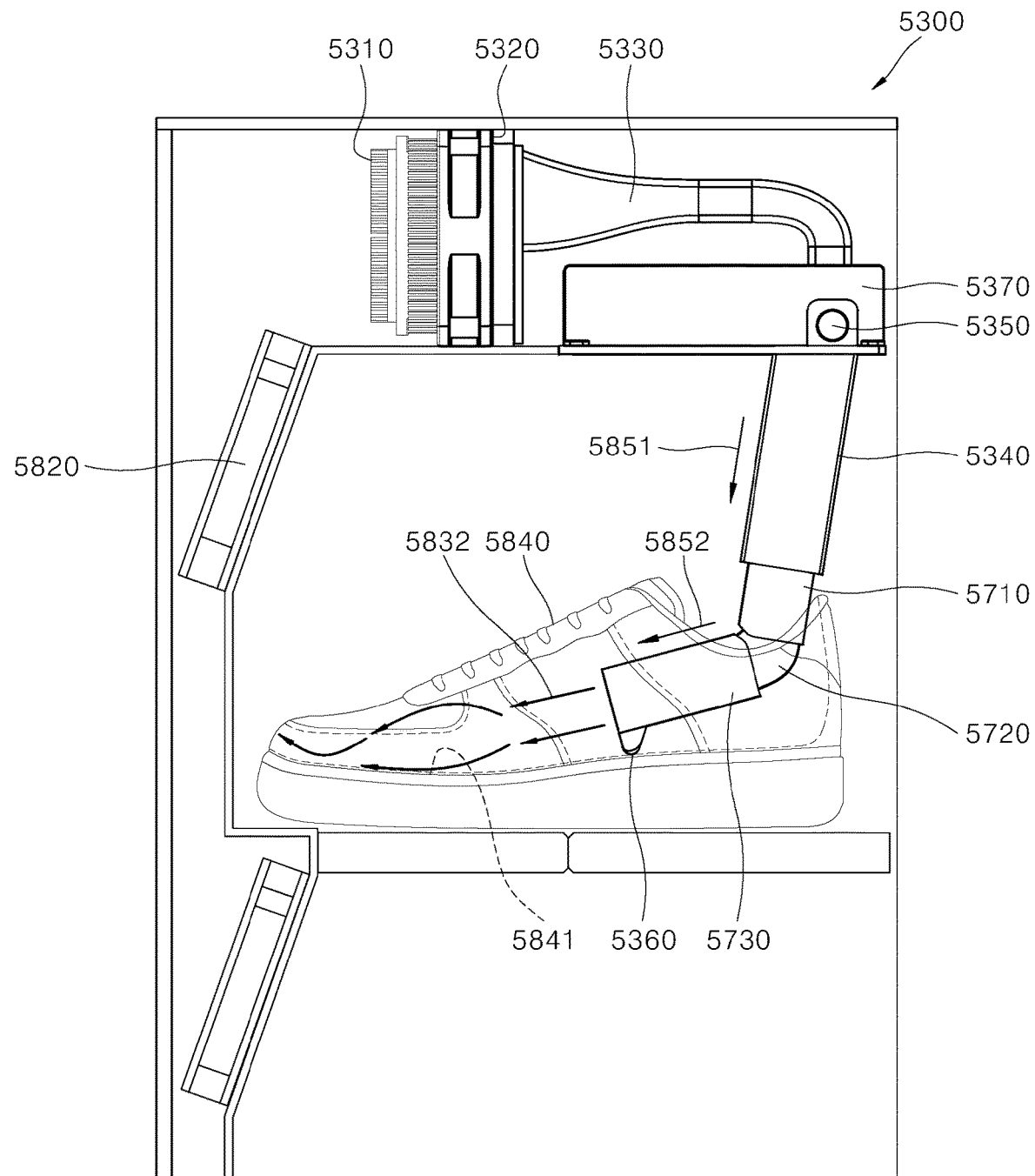
FIG. 58C is an exemplary view illustrating a state in which an expandable duct part faces the inside of a shoe according to an embodiment of the present invention.
Figure 59A:
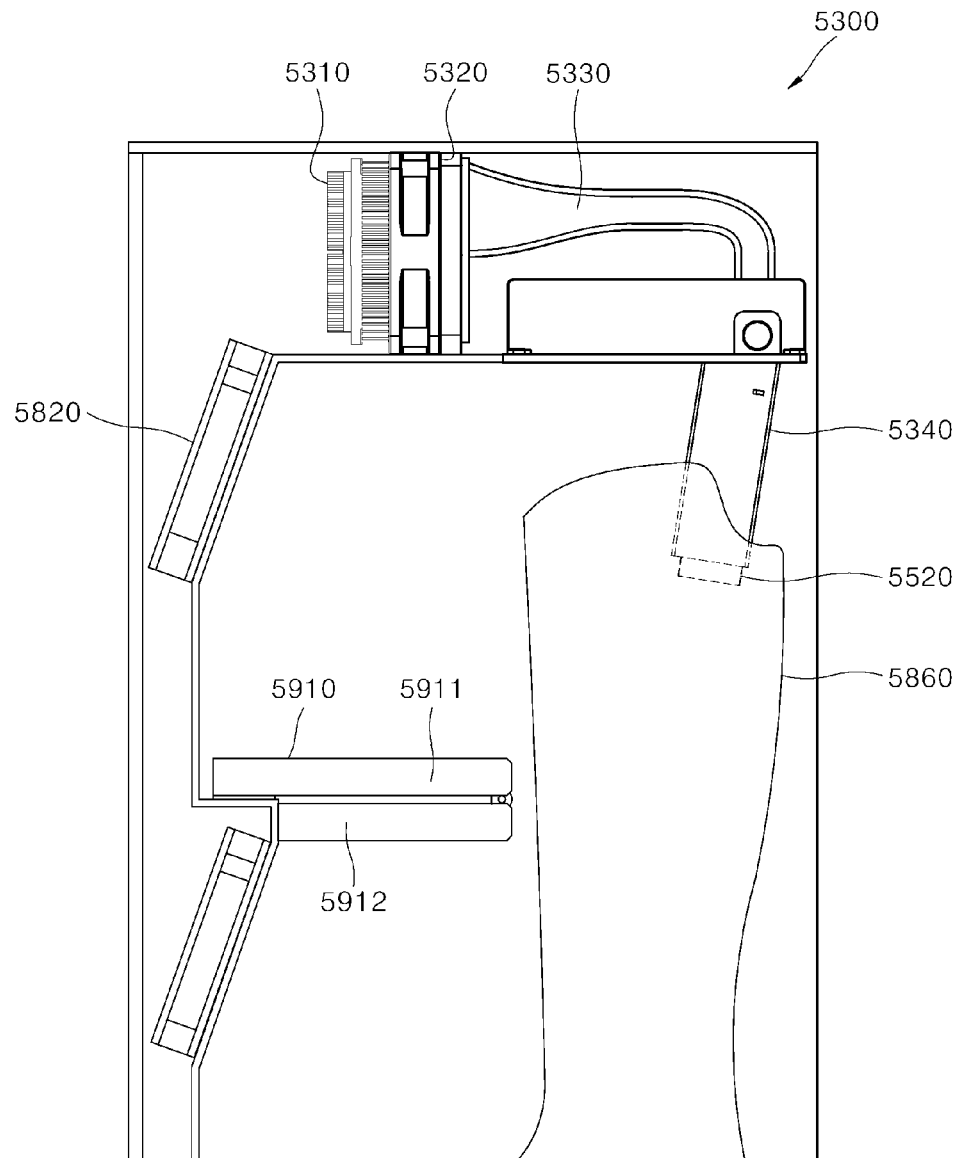
FIG. 59A is an exemplary view illustrating a state in which a rotatable duct part faces the inside of a shoe according to another embodiment of the present invention.
Figure 59B:
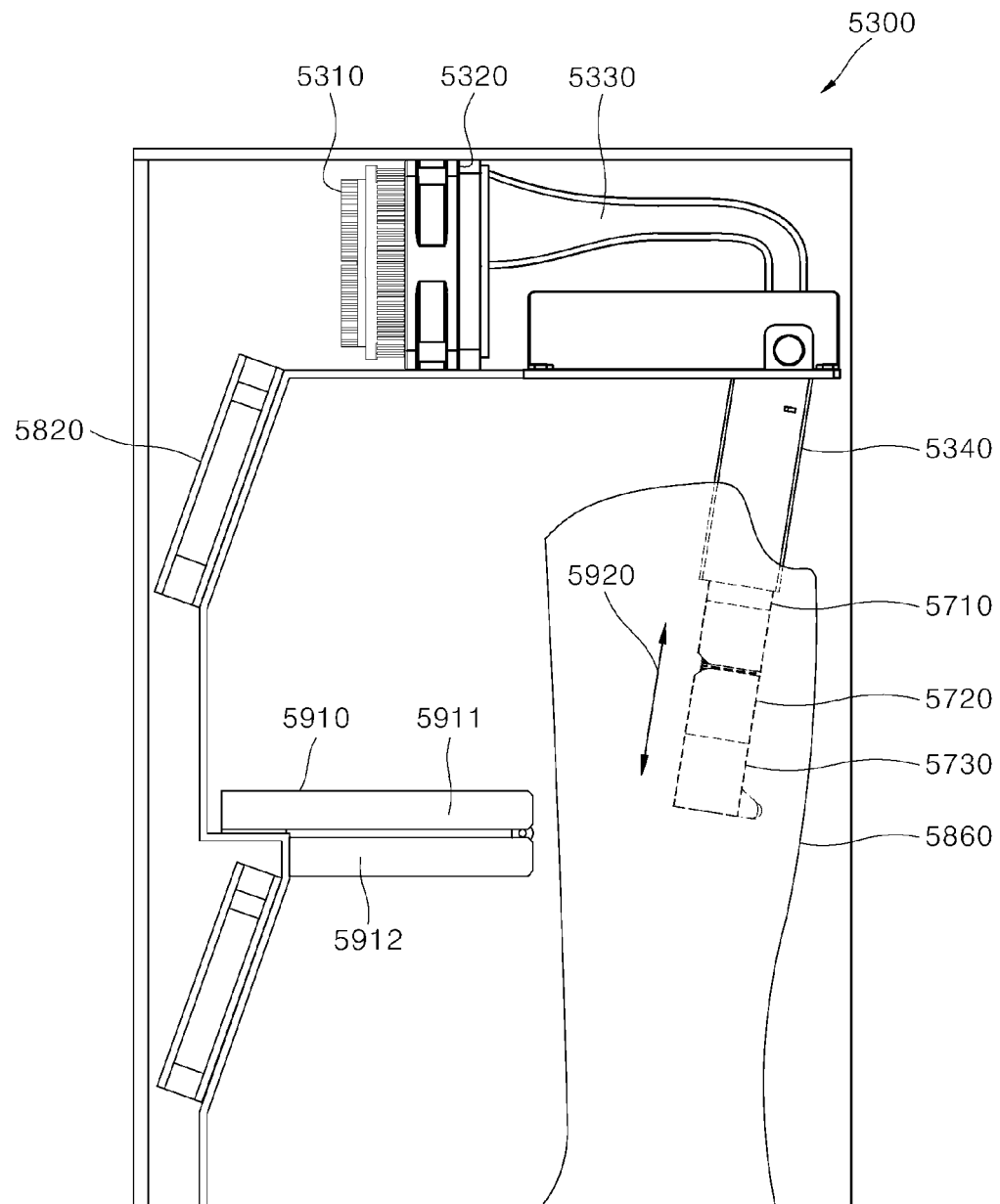
FIG. 59B is an exemplary view illustrating a state in which an expandable duct part faces the inside of a shoe according to another embodiment of the present invention.

FIG. 56 is a flowchart illustrating a process of controlling an operation of a rotatable duct part disposed in a storage space according to another embodiment of the present invention. FIG. 57 is a perspective view illustrating a state in which an expandable duct part is bent according to an embodiment of the present invention. FIG. 58A is an exemplary view illustrating a state in which an expandable duct part faces the inside of a shoe according to an embodiment of the present invention. FIG. 58B is an exemplary view illustrating a state in which an expandable duct part comes in contact with an insole of a shoe according to an embodiment of the present invention. FIG. 58C is an exemplary view illustrating a state in which an expandable duct part faces the inside of a shoe according to an embodiment of the present invention. FIG. 59A is an exemplary view illustrating a state in which a rotatable duct part faces the inside of a shoe according to another embodiment of the present invention. FIG. 59B is an exemplary view illustrating a state in which an expandable duct part faces the inside of a shoe according to another embodiment of the present invention.

Hereinafter, the process of controlling an operation of a rotatable duct part disposed in a storage space according to another embodiment of the present invention will be described in detail with reference to FIGS. 56, 57, 58A, 58B, 58C, 59A, and 59B.

According to an embodiment, the processor 470 may identify whether a shoe is detected (S5610). The process (S5610) may include at least one function or at least one operation performed in the process (S4710) of FIG. 47. According to an embodiment, the processor 470 may identify the type of shoe through at least one sensor in the shoe cabinet (S5612). The processor 470 may identify the type of the shoe placed in the shoe cabinet (e.g., a storage space of the lower cabinet 160) through at least one sensor (e.g., the distance measurement sensor 416, the IR sensor 419, and/or the camera 432) included in the sensor part 410.

According to an embodiment, the processor 470 may, through the at least one sensor (e.g., the distance measurement sensor 416, the IR sensor 419, and/or the camera 432), identify whether the height of the identified shoe is low like sneakers or high like boots.

In this way, the processor 470 may identify the height of the shoe through distance values acquired from each of the plurality of sensors (e.g., the distance measurement sensor 416, the IR sensor 419, and the like) vertically disposed inside the shoe cabinet.

According to an embodiment, the processor 470 may rotate a rotatable duct part (S5614). The processor 470 may rotate the rotatable duct part 5340 of the duct module 5300 toward where the shoe is located (e.g., downward). The processor 470 may, on the basis of identifying the type (or height) of shoe, determine whether to rotate the rotatable duct part 5340.

For example, in a case in which the height of the shoe is less than or equal to a first predetermined height, the processor 470 may rotate the rotatable duct part 5340 toward the shoe. The first predetermined height may be a height at which the height of the shoe does not interfere with rotation of the rotatable duct part.

In this way, in a case in which a shoe is detected in the process (S5610), the processor 470 may control the motor 5350 to control physical movement of the rotatable duct part 5340 so that the rotatable duct part 5340 rotates downward to where the shoe is placed.

According to an embodiment, the processor 470 may expand an expandable duct part to the inside of the shoe (S5616). In a case in which the height of the shoe identified in the process (S5612) is less than or equal to a second predetermined height, the processor 470 may rotate the rotatable duct part 5340 toward the shoe and then may expand the expandable duct part 5520, which is formed in the rotatable duct part 5340, toward the inside of the shoe. The second predetermined height may be less than or equal to the first predetermined height.

For example, in a case in which, when the height of the storage space is 50 cm and the length of the rotatable duct part 5340 is 10 cm, the identified height of the shoe is 38 cm, that is, not greater than a first predetermined height (e.g., a height obtained by subtracting the length of the rotatable duct part 5340 from the height of the storage space (e.g., 40 cm)), the processor 470 may rotate the rotatable duct part 5340. Also, the processor 470 may expand the expandable duct part 5520 formed in the rotatable duct part toward the inside of the shoe.

For example, in a case in which, when the height of the storage space is 50 cm and the length of the rotatable duct part 5340 is 10 cm, the height of the shoe is 30 cm, that is, not greater than a second predetermined height (e.g., a height obtained by subtracting the length of the rotatable duct part 5340 from the height of the storage space (e.g., 40 cm)), the processor 470 may rotate the rotatable duct part and then may expand the expandable duct part 5520 formed in the rotatable duct part 5340 toward the inside of the shoe.

Referring to FIG. 57, the rotatable duct part 5340 according to an embodiment of the present invention may be embedded in the duct module 5300 in a state of being folded upward or may rotate downward. Description of features of the duct module of FIG. 57 that are the same as the above-described features of the duct module of FIG. 53 may be omitted.

Although the term "first" or "second" is omitted (for example, the first duct module 5300*a* and the second duct module 5300*b* are referred to as "duct module 5300") in the following description, the corresponding element may be interpreted as including at least one of "first" and "second."

According to an embodiment, the rotatable duct part 5340 may extend to the inside of the storage space by an operation of rotating or longitudinally moving. The rotatable duct part 5340 may rotate due to an operation of a motor 5350 and may maintain a state of being inserted into the duct module 5300 in a case in which a shoe is not present in the storage space.

According to an embodiment, the motor 5350 may be connected to the rotatable duct part 5340, and various types of driving devices may be used as the motor 5350 within the technical idea that the driving device supplies rotation power for rotating the rotatable duct part 5340 downward (e.g., toward a shoe). The motor 5350 may be axially connected to the center of rotation of the rotatable duct part 5340 and may rotate the rotatable duct part 5340. The motor 5350 may be included in a motor part (the motor part 437 of FIG. 4).

According to an embodiment, the motor 5350 may be directly connected to the center of rotation of the rotatable duct part 5340.

According to an embodiment, the roller 5360 may be rotatably disposed at a lower side of the expandable duct part 5520. Also, in a case in which the roller 5360 comes in contact with the insole of the shoe, the roller 5360 may rotate to reduce a frictional force. The roller 5360 may protrude toward the insole of the shoe and rotate due to coming in contact with the insole of the shoe.

According to an embodiment, in the state of being rotated downward, the rotatable duct part 5340 may extend and discharge the expandable duct part 5520 downward (e.g., in the direction of the rotatable duct part 5340).

According to an embodiment, the rotatable duct part 5340 may include a rotatable duct body 5510 forming an exterior and the expandable duct part 5520 disposed inside the rotatable duct body 5510. The rotatable duct body 5510 has one side and the other side that are open.

According to an embodiment, the expandable duct part 5520 may come in contact with the insole of the shoe stored in the storage space and may, due to malleability of a variable duct part, be bent toward the front of the shoe. The expandable duct part 5520 is disposed inside the rotatable duct part 5340.

According to an embodiment, the expandable duct part 5520 may be formed to include an upper duct part 5710, a variable duct part 5720 which is connected to a lower side of the upper duct part 5710 and has a shape that may be changed by an external force, and a lower duct part 5730 which is connected to a lower side of the variable duct part 5720 and has the roller 5360 disposed on a lower portion.

According to an embodiment, the upper duct part 5710 and the lower duct part 5730 may be coupled through the variable duct part 5720 whose shape may be changed by an external force. Also, the roller 5360 for reducing friction against the bottom of a shoe may be disposed on the lower portion of the lower duct part 5730.

For example, in a case in which the expandable duct part 5520 expands toward the inside of a shoe, the lower portion of the lower duct part 5730 may come in contact with the bottom of the shoe. In this state, in a case in which the expandable duct part 5520 continues to expand to the inside of the shoe, due to the roller 5360 disposed at the lower portion of the lower duct part 5730 and the variable duct part 5720, an expanding direction of the lower duct part 5730 may be a direction (e.g., a direction toward the inside of the shoe) that is different from an expanding direction of the upper duct part 5710.

Referring to FIG. 58A, the expandable duct part 5520 according to an embodiment of the present invention may face the inside of the shoe.

According to an embodiment, due to the processor 470 controlling the motor 5350, the expandable duct part 5520 may be discharged toward the inside of a shoe 5840 (e.g., sneakers) placed on a shelf 5810. Through the discharge port 5540 formed in the lower surface of the expandable duct part 5520, at least part of air, steam, low-temperature hot air, and water repellent may be discharged (5831). Also, at least part of air, steam, low-temperature hot air, and water repellent discharged through the discharge port 5540 may be diffused to the inside of the shoe 5840.

According to an embodiment, a sub-fan 5820 may be additionally disposed in a storage space. The sub-fan 5820 may be used in causing at least part of air, steam, low-temperature hot air, and water repellent, which are discharged to the inside of the storage space, to be diffused in the storage space.

Referring to FIG. 58B, the expandable duct part 5520 according to an embodiment of the present invention may come in contact with an insole 5841 of the shoe.

According to an embodiment, under control of the processor 470 through the motor 5350, the expandable duct part 5520 may be continuously discharged in a direction 5851 toward the inside of the shoe 5840 (e.g., sneakers) placed on the shelf 5810. Also, as a result, the roller 5360 disposed at the lower portion of the expandable duct part 5520 may come in contact with the insole 5841 of the shoe 5840 (e.g., sneakers).

The expandable duct part 5520 may be connected to the rotatable duct part 5340 and may extend downward from the rotatable duct part 5340 which is rotated to face the inside of the storage space. Also, the expandable duct part 5520 may include a second duct connected to a first duct formed in the rotatable duct part 5340, and the expandable duct part 5520 may be formed so that at least part of air, steam, low-temperature hot air, and water repellent introduced through the first duct are discharged in the direction 5851 toward the inside of the shoe 5840 (e.g., sneakers) through the second duct.

Referring to FIG. 58C, when, in a state in which the expandable duct part 5520 according to an embodiment of the present invention is in contact with the insole 5841 of the shoe, the motor 5350 controls the expandable duct part 5520 to continue to move in the downward direction 5851, in the expandable duct part 5520, the variable duct part 5720 whose shape may be changed by an external force may enter in a direction 5852 toward the inside of the shoe 5840. The expandable duct part 5520 may continue to move in the direction 5852 toward the inside of the shoe 5840 (e.g., sneakers).

Also, through the discharge port 5540 formed in the lower surface of the expandable duct part 5520, at least part of air, steam, low-temperature hot air, and water repellent may be discharged (5832) to inside the shoe 5840.

According to an embodiment, the processor 470 may maintain the expandable duct part 5520 in any one of the states shown in FIGS. 58A, 58B, and 58C to discharge at least part of air, steam, low-temperature hot air, and water repellent.

According to an embodiment, the processor 470 may repeatedly control the expansion or insertion of the expandable duct part on the basis of the identified height of the shoe (S5618). On the basis of the height of the shoe, the processor 470 may control the motor 5350 in the rotatable duct part 5340 to allow the expandable duct part 5520 to repeatedly perform expansion to the outside of the rotatable duct part 5340 and insertion into the rotatable duct part 5340.

Referring to FIGS. 59A and 59B, the processor 470 may allow the expandable duct part 5520 to repeatedly perform the expansion and insertion during a shoe treatment process to thoroughly treat the inside of a shoe 5860 (e.g., boots).

According to an embodiment, when the shoe 5860 (e.g., boots) is determined as a type having a height greater than a predetermined height (e.g., boots, rain boots, or the like), the processor 470 may control the motor 5350 in the rotatable duct part 5340 to allow the expandable duct part 5520 to repeatedly perform the expansion to the outside of the rotatable duct part 5340 and insertion into the rotatable duct part 5340 (5920).

According to an embodiment, a shelf 5910 in a storage space may be folded or unfolded on the basis of identifying the height of the shoe 5860. For example, in a case in which the shoe 5860 is a sneaker as in FIGS. 58A to 58C, the shelf 5910 may be operated to be unfolded under control of the processor 470 or may maintain an unfolded state.

Alternatively, in a case in which the shoe 5860 is a boot as in FIG. 59A, the shelf 5910 may be operated to be folded under control of the processor 470. Also, the shelf 5910 may be formed by coupling between a first sub-shelf 5911 and a second sub-shelf 5912.

Although the heat exchange part 5310 and the fan 5320 are illustrated in FIGS. 59A and 59B as being formed in a single storage space, this is merely an embodiment, and a heat exchange part and a fan may be formed at an upper side of each storage space. Also, in a case in which a shelf is folded, the heat exchange part 5310 and the fan 5320 which are disposed at portions above the shoe may be operated while a heat exchange part and a fan which are disposed at portions below the shoe are not operated.

According to an embodiment, on the basis of movement of the expandable duct part, the processor 470 may discharge at least part of air, steam, low-temperature hot air, and water repellent through the lower portion of the expandable duct part to treat the shoe (S5620). The processor 470 may discharge at least part of air, steam, low-temperature hot air, and water repellent, which are provided by the treatment part 440, through a duct of the rotatable duct part 5340 to intensively treat the shoe. The processor 470 may intensively treat the shoe on the basis of at least one of the first to fifth functions.

According to an embodiment, the processor 470 may emit at least one of a photocatalyst and a deodorizer through at least one emitting element (e.g., the UV light emitting part 422, the photocatalyst emitting part 424, the plasma emitting part 426) disposed at the lower portion of the rotatable duct part 5340 (e.g., the lower portion of the expandable duct part 5520 inserted into the rotatable duct part 5340) to sanitize the shoe and/or deodorize the shoe.

According to an embodiment, in a state in which the expandable duct part 5520 is continuously moving in the vertical direction, the processor 470 may discharge at least part of air, steam, low-temperature hot air, and water repellent through the lower portion of the expandable duct part 5520 to treat the shoe. The speed at which the expandable duct part 5520 moves in the vertical direction may be variably adjusted according to the shoe condition (e.g., the degree of foreign substance adsorption, the degree of bacterial infection, or the like) or shoe type (e.g., heels, sneakers, boots, or the like).

According to an embodiment, the processor 470 may sanitize the inside of the shoe through at least one light emitting element disposed at the lower portion of the expandable duct part (S5622). The processor 470 may sanitize the inside of the shoe through at least one light emitting element (e.g., UVC LED) disposed at the lower portion of the rotatable duct part 5340 (e.g., the lower portion of the expandable duct part 5520 inserted into the rotatable duct part 5340).

According to an embodiment, the processor 470 may control expandable duct parts 5520 to move identically or may control the expandable duct parts 5520 to not move identically.

According to an embodiment, the processor 470 may identify whether shoe treatment has ended (S5624). The processor 470 may identify whether the time during which the processes (S5618, S5620, and S5622) are performed has exceeded a predetermined amount of time. The predetermined amount of time may be set to different amounts of time according to at least one of the material, function, type, and condition of the shoe. The predetermined amount of time is the time during which intensive treatment is performed on the shoe and may be adjusted on the basis of a user input.

According to an embodiment, the processor 470 may return the rotatable duct part to its normal position (S5626). When intensive treatment on the shoe has ended, the processor 470 may rotate the rotatable duct part 5340 to insert the rotatable duct part 5340 into the duct module 5300.

Hereinafter, controlling an operation of a rolling brush in a storage space will be described.

[Rolling Brush Control]

Figure 60:
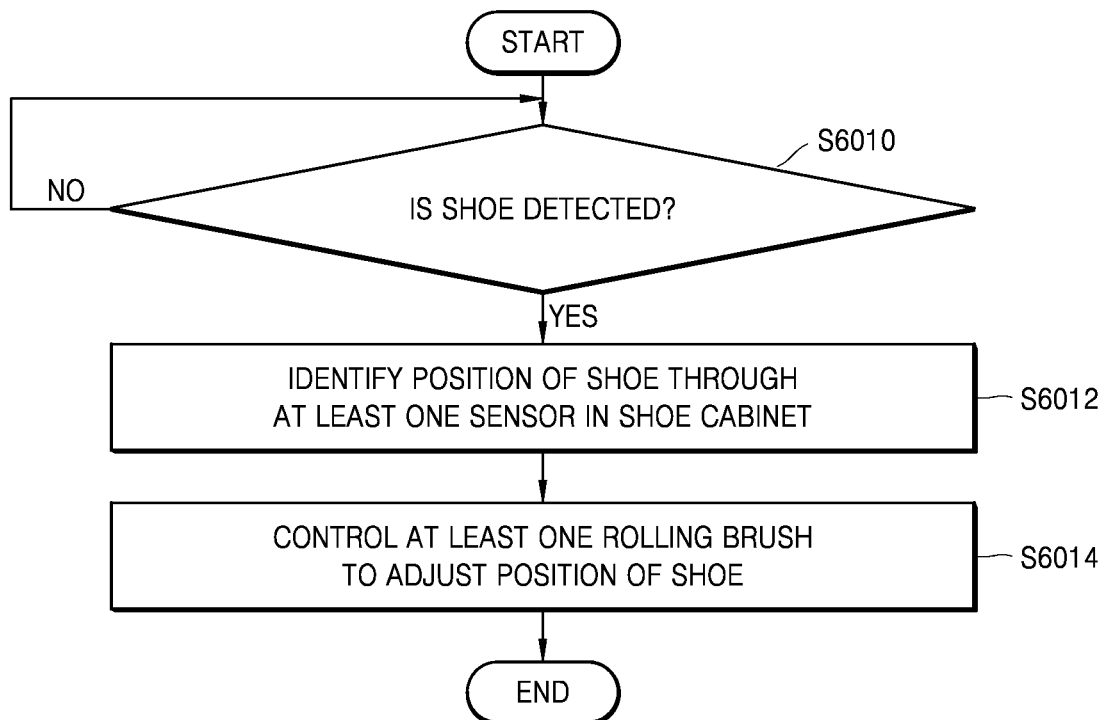
FIG. 60 is a flowchart illustrating a process of adjusting the position of a shoe in a storage space according to an embodiment of the present invention.
Figure 61A:
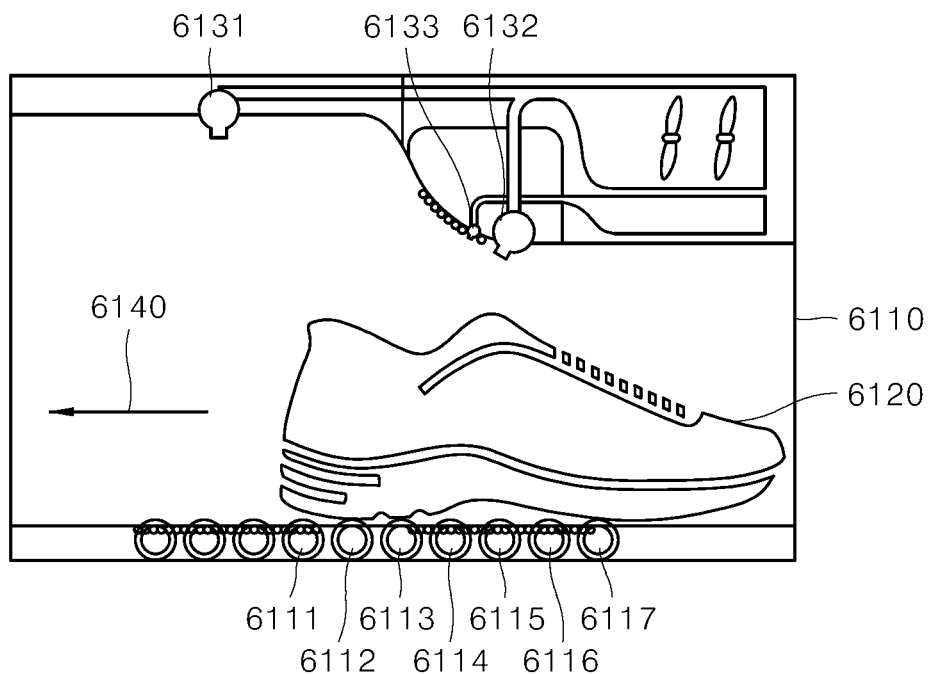
FIG. 61A is an exemplary view of a state before the position of a shoe in a storage space is adjusted according to an embodiment of the present invention.
Figure 61B:
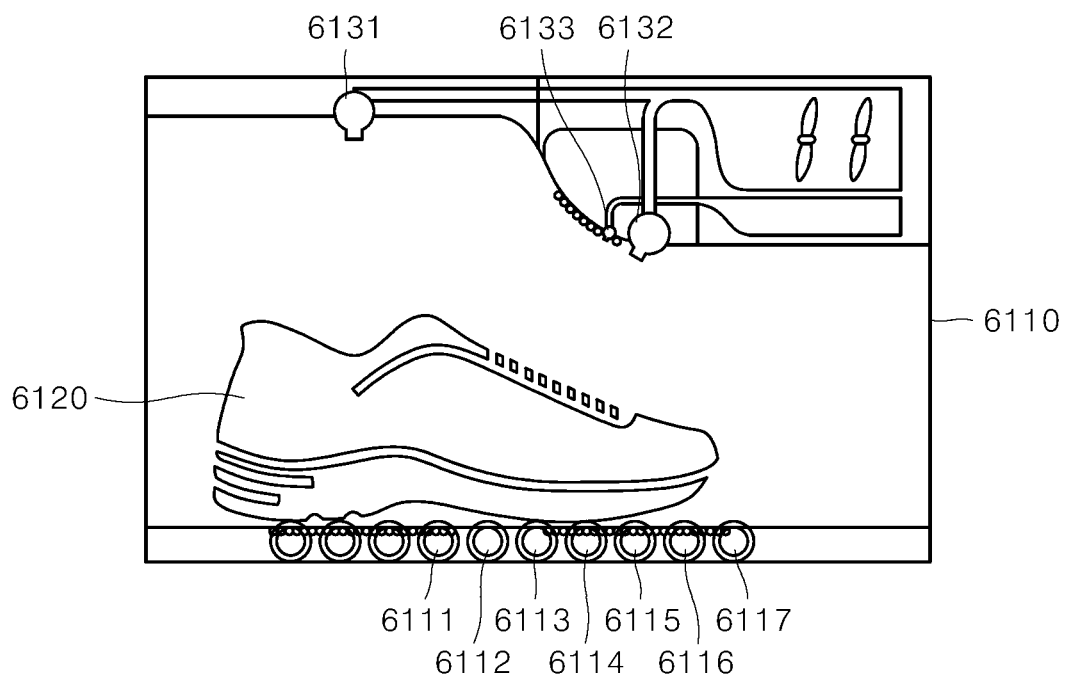
FIG. 61B is an exemplary view of a state after the position of the shoe is adjusted by controlling a rolling brush in the storage space according to an embodiment of the present invention.

FIG. 60 is a flowchart illustrating a process of adjusting the position of a shoe in a storage space according to an embodiment of the present invention. FIG. 61A is an exemplary view of a state before the position of a shoe in a storage space is adjusted according to an embodiment of the present invention. FIG. 61B is an exemplary view of a state after the position of the shoe is adjusted by controlling a rolling brush in the storage space according to an embodiment of the present invention.

Hereinafter, the process of adjusting the position of a shoe in a storage space according to an embodiment of the present invention will be described in detail with reference to FIGS. 60, 61A, and 61B.

According to an embodiment, the processor 470 may identify whether a shoe is detected (S6010). The process (S6010) may include at least one function or at least one operation performed in the process (S4710) of FIG. 47.

According to an embodiment, the processor 470 may identify the position of a shoe through at least one sensor in a shoe cabinet (S6012). The processor 470 may acquire an image of a shoe through the camera 432 and may analyze the acquired image to identify the position of the shoe in a storage space of the shoe cabinet (e.g., the lower cabinet 160).

Alternatively, through values measured by at least one distance measurement sensor 416 and/or at least one IR sensor 419 which are disposed on an inner wall of the shoe cabinet (e.g., the lower cabinet 160), the processor 470 may identify the position of the shoe in the shoe cabinet (e.g., the lower cabinet 160). The at least one distance measurement sensor 416 and at least one IR sensor 419 may be vertically disposed on at least one inner wall of the shoe cabinet (e.g., the lower cabinet 160).

According to an embodiment, the processor 470 may control at least one rolling brush to adjust the position of the shoe (S6014). A rolling brush module 6300 may be disposed in the storage space of the shoe cabinet (e.g., the lower cabinet 160), and the rolling brush module 6300 may be formed to be detachable from the corresponding shoe cabinet.

Referring to FIGS. 61A and 61B, a rolling brush module including a plurality of rolling brushes may be disposed at the lower portion of the shoe cabinet.

According to an embodiment, at least one of the plurality of rolling brushes may rotate clockwise or counterclockwise under control of the processor 470 and the driving part 435. Alternatively, at least one of the plurality of rolling brushes may rotate clockwise or counterclockwise under control of a motor of the motor part 437.

For example, a shoe 6120 is stored in a shoe cabinet 6110. Also, the shoe 6120 may be placed rightward in the shoe cabinet 6110. In this case, the processor 470 may identify one or more rolling brushes 6111, 6112, 6113, 6114, 6115, 6116, and 6117, which correspond to the position, weight, or size of the shoe 6120, and may determine a rotational direction (e.g., counterclockwise) of the identified one or more rolling brushes 6111, 6112, 6113, 6114, 6115, 6116, and 6117.

Also, the processor 470 may rotate the identified one or more rolling brushes 6111, 6112, 6113, 6114, 6115, 6116, and 6117 on the basis of the determined rotational direction (e.g., counterclockwise) to move the shoe 6120 in a leftward direction 6140.

In this way, the processor 470 may adjust the position of the shoe 6120 to correspond to a direction of one or more discharge ports 6131, 6132, and 6133. Alternatively, the processor 470 may adjust the direction or angle of the one or more discharge ports 6131, 6132, and 6133 to correspond to the position of the shoe 6120.

Figure 62:
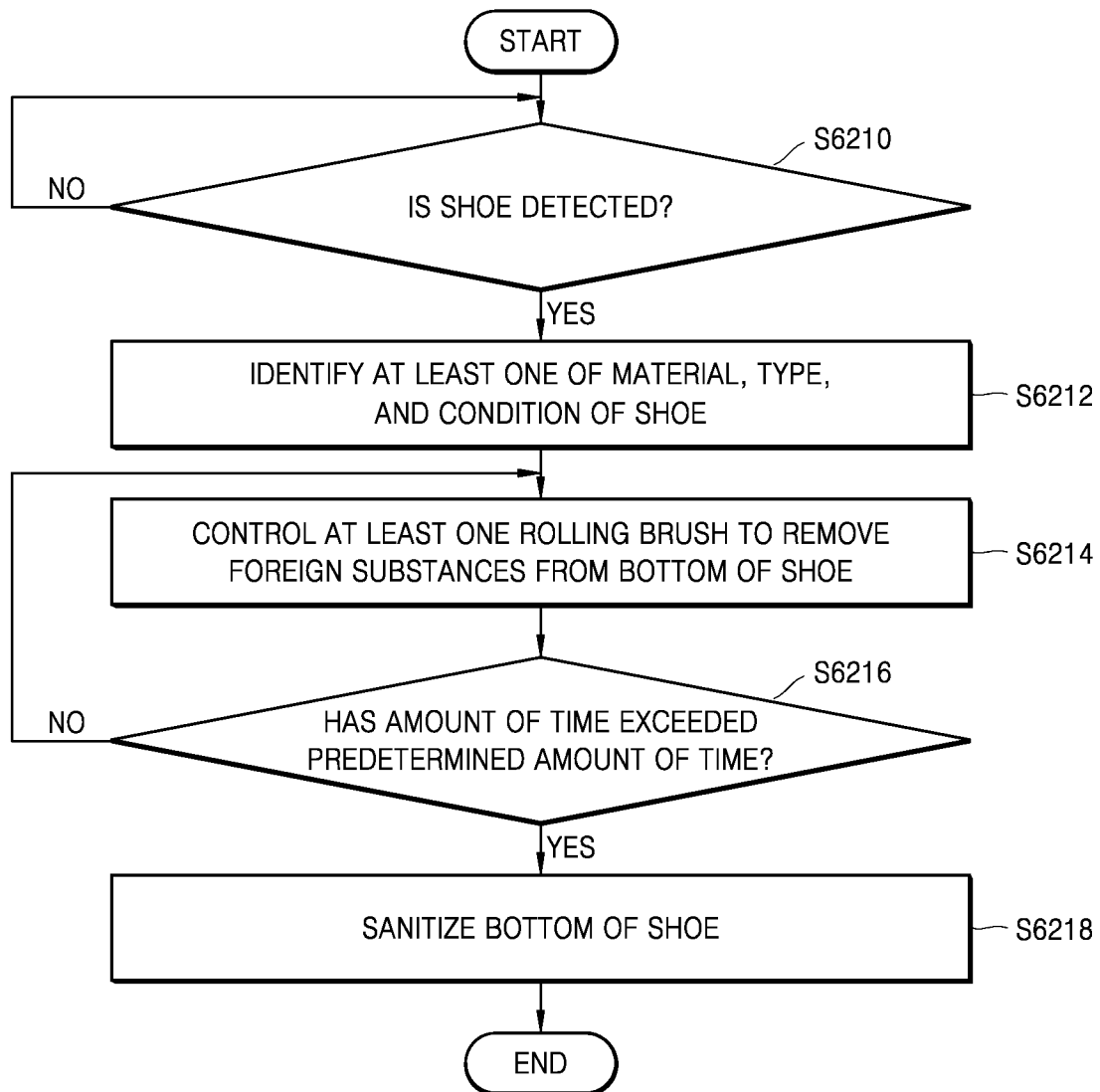
FIG. 62 is a flowchart illustrating a process of treating a shoe in a storage space through a rolling brush module according to an embodiment of the present invention.

FIG. 62 is a flowchart illustrating a process of treating a shoe in a storage space through a rolling brush module according to an embodiment of the present invention. FIG. 63 is a perspective view illustrating a rolling brush module according to an embodiment of the present invention. FIG. 64 is a perspective view illustrating a state in which a shoe is placed on the rolling brush module according to an embodiment of the present invention. FIG. 65 is an exploded view of a rolling brush of the rolling brush module according to the present invention.

Hereinafter, the process of treating a shoe in a storage space through a rolling brush module according to an embodiment of the present invention will be described in detail with reference to FIGS. 62, 63, 64, and 65.

According to an embodiment, the processor 470 may identify whether a shoe is detected (S6210). The process (S6210) may include at least one function or at least one operation performed in the process (S4710) of FIG. 47. According to an embodiment, the processor 470 may identify at least one of the material, type, and condition of the shoe (S6212). The process (S6212) may include at least one operation or at least one function performed in the process (S512) of FIG. 5. According to an embodiment, the memory 434 of the shoe treating apparatus 310 stores data relating to the temperature, humidity, degree of ventilation, and the like according to various materials, functions, types, and conditions of shoes. Also, the processor 470 may acquire the corresponding data according to the material, function, type, and condition of the shoe from the memory 434.

According to an embodiment, the processor 470 may, on the basis of the material, type, and condition of the shoe, set the rotational speed, operation time, and rotational direction of one or more rolling brushes. The processor 470 may, on the basis of the material (e.g., leather, fabric, rubber, or the like), type (e.g., sneakers, heels, or the like), and condition (e.g., cleanliness) of a shoe, set the rotational speed (e.g., RPM), operation time (e.g., ten minutes), and rotational direction (e.g., clockwise/counterclockwise rotation) of the one or more rolling brushes.

According to an embodiment, the processor 470 may, on the basis of identifying at least one of the material, type, and condition of the shoe, set an operation time (e.g., rotation time) of one or more rolling brushes to remove foreign substances from the bottom of the shoe.

For example, in a case in which the amount of foreign substances (e.g., dirt) adsorbed onto a shoe (e.g., the bottom of the shoe) is large, the processor 470 may set the operation time (e.g., rotation time) of the one or more rolling brushes as a first time (e.g., ten minutes).

Alternatively, in a case in which the amount of foreign substances adsorbed onto a shoe (e.g., the bottom of the shoe) is not large, the processor 470 may set the operation time of the one or more rolling brushes as a second time (e.g., five minutes) which is less than the first time (e.g., ten minutes). The time may be variably adjusted according to the amount of foreign substances adsorbed onto the shoe, the material of the shoe, and the type of the shoe.

According to an embodiment, the processor 470 may control one or more rolling brushes to remove foreign substances from the bottom of the shoe (S6214). The processor 470 may operate a motor coupled to each rolling brush of the rolling brush module 6300 during the set operation time to rotate the corresponding rolling brush clockwise or counterclockwise.

Figure 63:
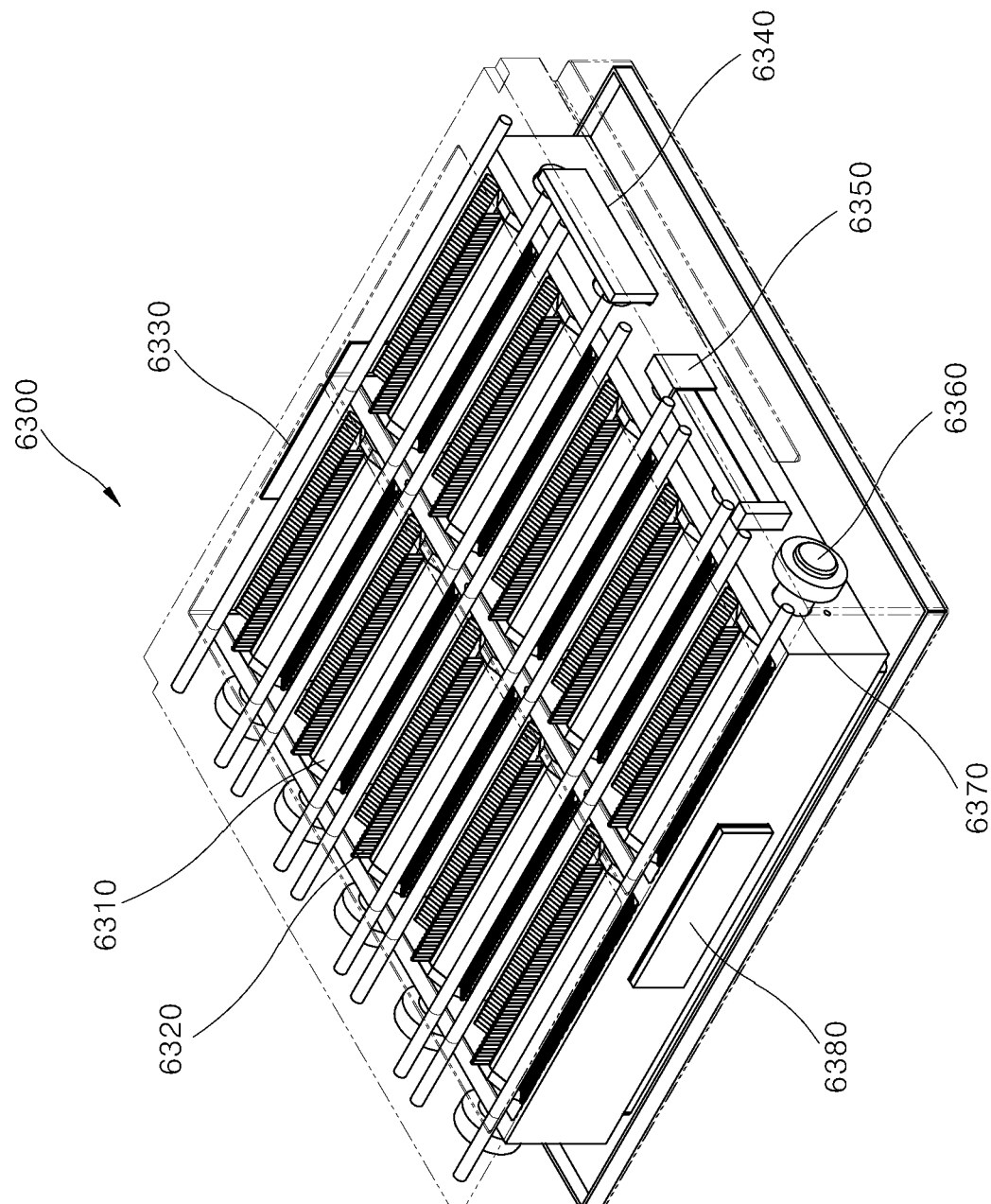
FIG. 63 is a perspective view illustrating a rolling brush module according to an embodiment of the present invention.
Figure 64:
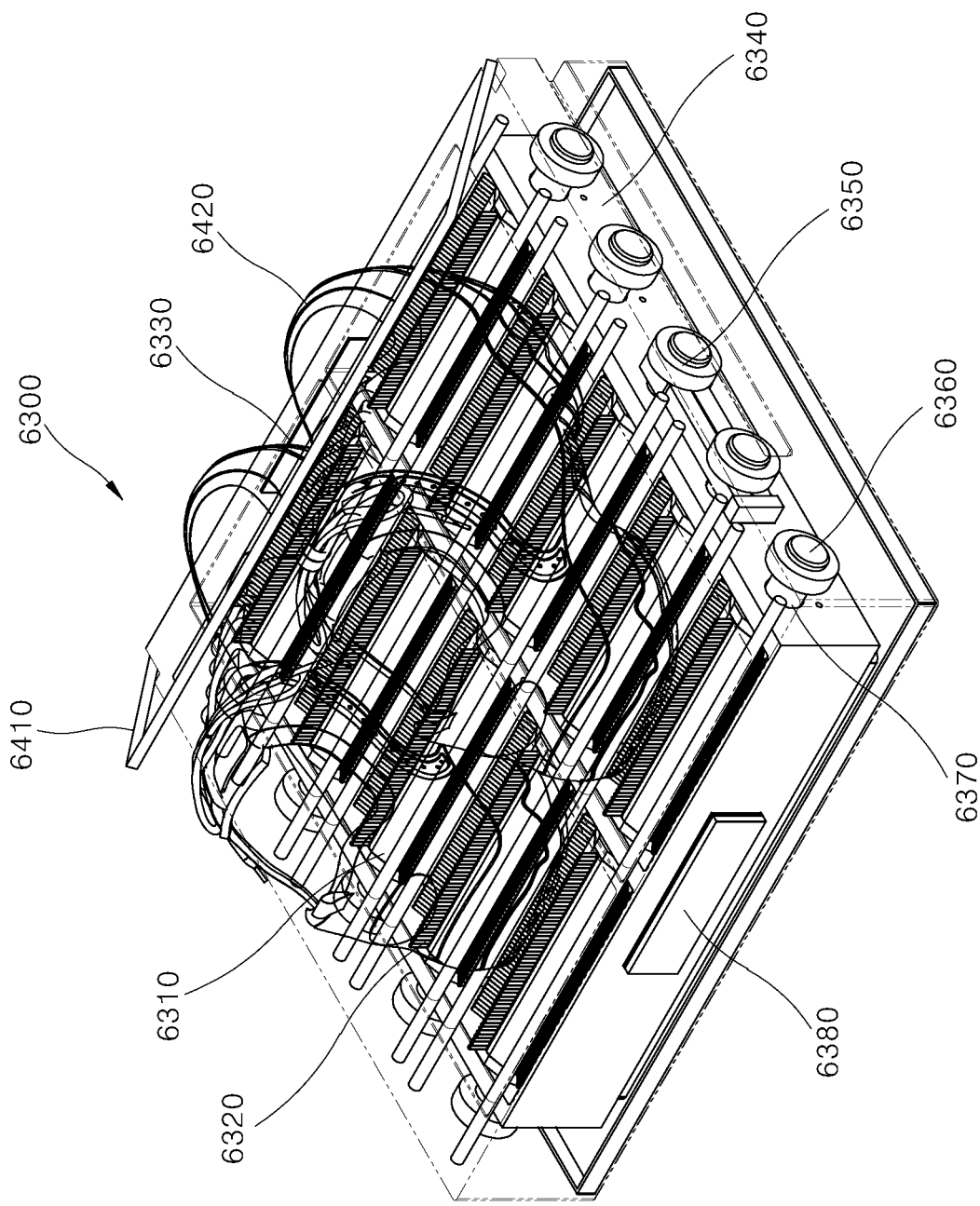
FIG. 64 is a perspective view illustrating a state in which a shoe is placed on the rolling brush module according to an embodiment of the present invention.

Referring to FIGS. 63 and 64, the rolling brush module 6300 according to an embodiment of the present invention may include one or more rolling bodies 6310, one or more brushes 6320 coupled to each rolling body 6310 at predetermined intervals, a wireless charging module 6330 configured to wirelessly receive power from an external device (e.g., wireless charging device), and a battery 6340 configured to charge power.

Also, the rolling brush module 6300 may include an actuator 6350 configured to convert electrical energy to mechanical energy to vibrate the one or more rolling brushes, an ultrasonic vibrator 6360 configured to vibrate the one or more rolling brushes, and a motor 6370 configured to rotate the rolling brush.

Also, the rolling brush module 6300 may include a printed circuit board (PCB) 6380 configured to control the overall operation (e.g., wireless power reception, wireless power charging, rolling brush rotation, actuator control, ultrasonic vibrator control, and the like) of the rolling brush module 6300.

According to an embodiment, an operation performed by the rolling brush module 6300 may be controlled by the PCB or controlled by the processor 470.

For example, when attempting to move a shoe 6420, the processor 470 (or the PCB 6380) may rotate one or more rolling brushes 6500, which correspond to the position of the shoe, in a direction in which the shoe 6420 is desired to move (e.g., clockwise or counterclockwise).

For example, when attempting to remove foreign substances adsorbed onto the shoe 6420, the processor 470 (or the PCB 6380) may rotate each rolling brush (e.g., a first rolling brush) of the plurality of rolling brushes 6500 corresponding to the position of the shoe so that the rotational direction of the rolling brush (e.g., the first rolling brush) is opposite to the rotational direction of another rolling brush (e.g., a second rolling brush) adjacent thereto.

For example, the processor 470 may rotate the first rolling brush clockwise and rotate the second rolling brush, which is adjacent to the first rolling brush, counterclockwise. Also, the processor 470 may rotate a third rolling brush, which is adjacent to the second rolling brush, clockwise.

In this way, the processor 470 may rotate a rolling brush in a direction opposite to a rotational direction of other rolling brushes adjacent to the rolling brush.

In this way, the processor 470 may operate the motor 6370 coupled to each of the identified one or more rolling brushes to rotate the rolling brush (e.g., clockwise and/or counterclockwise).

According to an embodiment, even when the one or more rolling brushes are rotating or not rotating, the processor 470 may vibrate one or more ultrasonic vibrators 6360 disposed at one side of the rolling brush module 6300 to vibrate the one or more rolling brushes.

According to an embodiment, the rolling brush module 6300 may include a holder 6410 for controlling (or preventing) movement of the shoe 6420. The holder 6410 may be bent toward the shoe 6420 and prevent the shoe 6420 from moving.

Figure 65:
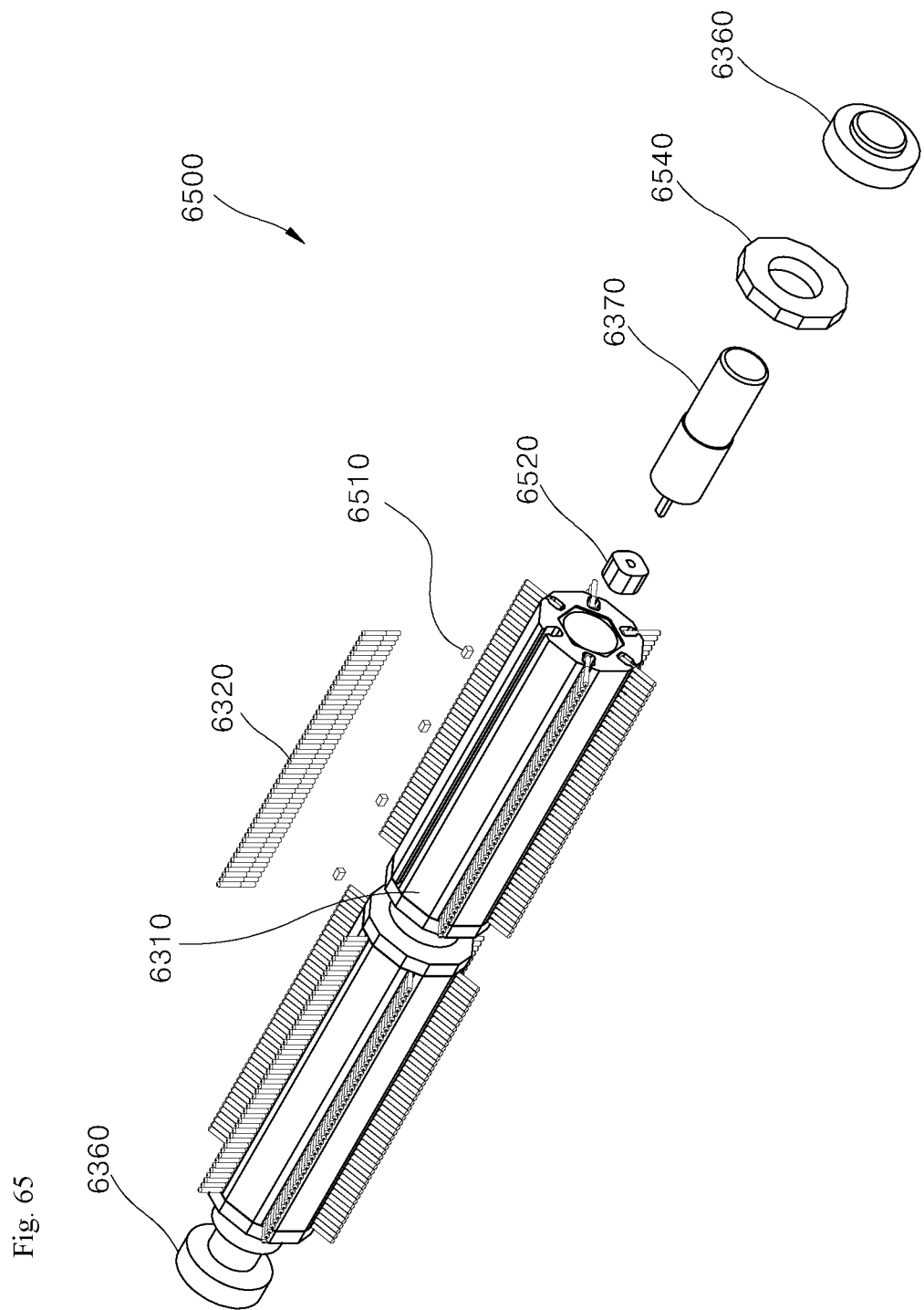
FIG. 65 is an exploded view of a rolling brush of the rolling brush module according to the present invention.

Referring to FIG. 65, a rolling brush 6500 according to an embodiment of the present invention may include one or more ultrasonic vibrators 6360 disposed at both left and right sides to vibrate the rolling brush 6500, a motor 6370 configured to rotate the rolling brush 6500, a brush side decoration 6540 disposed between the ultrasonic vibrator 6360 and the motor 6370, a rolling body 6310, one or more brushes 6320 coupled to the rolling body 6310 at predetermined intervals, one or more light emitting elements 6510 attached to a surface of the rolling body 6310 to output UV light, and a key 6520 inserted into the rolling body 6310 to transmit a rotational force of the motor 6370.

According to an embodiment, the processor 470 may identify whether an amount of time has exceeded a predetermined amount of time (S6216). The processor 470 may, on the basis of identifying the shoe in the process (S6212), identify whether the time during which the process (S6214) is performed has exceeded the predetermined amount of time. For example, the processor 470 may keep track of the time during which foreign substances are removed from the shoe and may identify whether the time has exceeded or not exceeded the predetermined amount of time.

For example, the predetermined amount of time may be variably adjusted according to the shoe condition (e.g., the degree of foreign substance adsorption, the degree of bacterial infection, or the like) or shoe type (e.g., heels, sneakers, boots, or the like). Alternatively, the predetermined amount of time may be adjusted on the basis of a user input.

According to an embodiment, the processor 470 may sanitize the bottom of the shoe (S6218). When the time during which the process (S6214) is performed is identified as exceeding the predetermined amount of time on the basis of identifying the shoe in the process (S6212), the processor 470 may sanitize the bottom of the shoe 6420.

According to an embodiment, the processor 470 may treat the shoe (e.g., perform at least one of the first to fifth functions) during an operation time which is set according to the condition, type, and material of the shoe, and when the set operation time has elapsed, the processor 470 may rotate the rolling brush 6500 through the motor 6370 coupled to each rolling brush 6500 and may cause one or more light emitting elements (e.g., UVC LEDs) 6510 disposed in the rolling brush (e.g., the rolling body) to emit light to sanitize the bottom of the shoe 6420.

The steps in each flowchart described above may be performed regardless of the illustrated order or may be simultaneously performed. Also, one or more elements of the present invention and one or more operations performed by the one or more elements may be implemented with hardware and/or software.

Also, various values mentioned herein are only an embodiment, and the present invention is not limited thereto and may include various other values.

The present invention has been described above with reference to the accompanying drawings, but the present invention is not limited by the embodiments disclosed herein and the drawings, and it is apparent that various modifications may be made by those of ordinary skill in the art to which the present invention pertains. Further, even when the effects according to configurations of the present invention are not explicitly described while describing the embodiments of the present invention, predictable effects of the corresponding configurations should also be recognized.

What is claimed is:

1. A shoe treating apparatus, comprising:
   at least one storage space;
   at least one shelf tiltably mounted in the at least one storage space;
   a motor part configured to control tilting of the at least one shelf;
   at least one sensor; and
   a processor electrically connected to the motor part and the at least one sensor, wherein the processor is configured to:
identify a height of a user by using the at least one sensor,
generate a control signal for adjusting a tilt angle of the at least one shelf based on the identified user height, and
transmit the generated control signal to the motor part to adjust the tilt angle of the at least one shelf based on the identified user height.

2. The shoe treating apparatus of claim 1, further comprising a memory,
wherein the processor is further configured to:
acquire the tilt angle of the at least one shelf corresponding to the height of the identified user from the memory, and
generate the control signal based on the acquired tilt angle of the at least one shelf.

3. The shoe treating apparatus of claim 1, further comprising a door to open and close the at least one storage space,
wherein the processor is further configured to:
identify, by the at least one sensor, whether the door is opened, and
based on the door being opened, stop an operation being performed in the at least one storage space while allowing the at least one shelf to continue tilting.

4. The shoe treating apparatus of claim 1, further comprising a display,
wherein the processor is further configured to:
identify the user through the at least one sensor,
identify a position at which at least one shoe corresponding to the identified user is placed in the at least one storage space, and
display state information of the at least one shoe corresponding to the identified position by the display.

5. The shoe treating apparatus of claim 4, wherein the processor is further configured to display the identified position by the display.

6. The shoe treating apparatus of claim 4, further comprising an upper cabinet,
wherein the at least one storage space is in the upper cabinet, and
wherein the state information comprises a current state of treating the at least one shoe through adjusting at least one of a temperature and a humidity inside the upper cabinet based on at least one of a material, a type, or a condition of the at least one shoe.

7. The shoe treating apparatus of claim 4, wherein the at least one sensor comprises a camera, and
wherein the processor is further configured to:
acquire, by the camera, an image of the at least one shoe, and
compare the acquired image with a pre-stored image to identify the position at which the at least one shoe corresponding to the identified user is placed.

8. The shoe treating apparatus of claim 4, wherein the at least one shelf comprises a plurality of shelves,
wherein the processor is further configured to, through an identifier allocated for each of the plurality of shelves in the shelf part, identify the position at which the at least one shoe corresponding to the identified user is placed, and
wherein the identifier comprises information for distinguishing a shelf on which at least one shoe of each of a plurality of users is placed.

9. The shoe treating apparatus of claim 4, further comprising a door to open and close the at least one storage space,
wherein the at least one sensor comprises at least one of a weight sensor, a camera, or a distance measurement sensor disposed in the at least one storage space, and
wherein the processor is further configured to:
identify the user,
identify whether the door is opened,
when the door is identified as having been opened, identify, by the at least one of the weight sensor, the camera, or the distance measurement sensor, whether the at least one shoe is stored, and
when the at least one shoe is identified as having been stored, determine that the at least one stored shoe is a shoe corresponding to the user.

10. The shoe treating apparatus of claim 1, wherein the at least one sensor comprises at least one of a camera, an infrared (IR) sensor, a door open/close sensor, a knock-on sensor, a weight sensor, a distance measurement sensor, or a fingerprint sensor.

11. The shoe treating apparatus of claim 1, wherein the at least one shelf comprises a plurality of shelves, and
wherein the processor is further configured to control a tilting direction of each shelf of the plurality of shelves to be different from an adjacent shelf of the plurality of shelves.

12. The shoe treating apparatus of claim 1, wherein the at least one shelf comprises a plurality of shelves, and
wherein the processor is further configured to:
control a first shelf which is located at a lowest position among the plurality of shelves to move in a vertical direction by the motor part, and
control at least one second shelf disposed above the first shelf to tilt by the motor part.

13. The shoe treating apparatus of claim 1, further comprising:
a cabinet, the at least one storage space being located in the cabinet; and
a light emitting element disposed in the cabinet,
wherein the processor is further configured to cause the at least one light emitting element to emit light based on the identified user approach.

14. A method of operating a shoe treating apparatus, the method comprising:
identifying a height of a user using at least one sensor;
generating, by a processor, a control signal for adjusting a tilt angle of at least one shelf based on the identified user height in at least one storage space of the shoe treating apparatus; and
transmitting the generated control signal to a motor part to adjust the tilt angle of the at least one shelf based on the identified user height.

15. The method of claim 14, wherein generating the control signal comprises:
acquiring a tilt angle of the at least one shelf corresponding to the identified user height; and
generating the control signal on the basis of the acquired tilt angle of the at least one shelf.

16. The method of claim 14, further comprising:
identifying, by using the at least one sensor, whether a door of the shoe treating apparatus is opened; and
based on opening the door, stopping an operation being performed in the at least one storage space while allowing the at least one shelf to continue tilting.

17. The method of claim 14, wherein the identifying the approach of the user comprises:

identifying the user through the at least one sensor;

identifying a position at which at least one shoe corresponding to the identified user is placed in the at least one storage space; and displaying condition information on the at least one shoe corresponding to the identified position through a display.

18. The method of claim 14, wherein the at least one shelf comprises a plurality of shelves, and wherein transmitting the generated control signal controls a tilting direction of each shelf of the plurality of shelves to be different from an adjacent shelf of the plurality of shelves.

\* \* \* \* \*